US012806291B2

(12) United States Patent
Gray et al.

(10) Patent No.: US 12,806,291 B2
(45) Date of Patent: Nov. 24, 2026

(54) TRANSGENE CASSETTE DESIGNED TO EXPRESS THE HUMAN CODON-OPTIMIZED GENE FMR1

(71) Applicants: THE BOARD OF REGENTS OF THE UNIVERSITY OF TEXAS SYSTEM, Austin, TX (US); THE GOVERNING COUNCIL OF THE UNIVERSITY OF TORONTO, Toronto (CA)

(72) Inventors: Steven J. Gray, Austin, TX (US); David R. Hampson, Austin, TX (US); Hye Ri Kang, Austin, TX (US); Hayes Ga-Hei Wong, Austin, TX (US); Alexander W.M. Hooper, Austin, TX (US)

(73) Assignees: THE BOARD OF REGENTS OF THE UNIVERSITY OF TEXAS SYSTEM, Austin, TX (US); THE GOVERNING COUNCIL OF THE UNIVERSITY OF TORONTO, Ontario (CA)

( * ) Notice: Subject to any disclaimer, the term of this patent is extended or adjusted under 35 U.S.C. 154(b) by 205 days.

(21) Appl. No.: 18/729,389

(22) PCT Filed: Jan. 27, 2023

(86) PCT No.: PCT/US2023/061459
§ 371 (c)(1),
(2) Date: Jul. 16, 2024

(87) PCT Pub. No.: WO2023/147476
PCT Pub. Date: Aug. 3, 2023

(65) Prior Publication Data

US 2025/0082782 A1 Mar. 13, 2025

Related U.S. Application Data

(60) Provisional application No. 63/267,236, filed on Jan. 28, 2022.

(51) Int. Cl.
*C12N 15/86* (2006.01)
*A61K 48/00* (2006.01)

(52) U.S. Cl.
CPC .......... *A61K 48/0058* (2013.01); *C12N 15/86* (2013.01); *C12N 2750/14122* (2013.01); *C12N 2750/14143* (2013.01); *C12N 2750/14145* (2013.01)

(58) Field of Classification Search
CPC ................ A61K 48/0058; C12N 15/86; C12N 2750/14122; C12N 2750/14143; C12N 2750/14145
See application file for complete search history.

(56) References Cited

U.S. PATENT DOCUMENTS

| | | | |
|---|---|---|---|
| 5,958,736 | A | 9/1999 | Stahl et al. |
| 8,795,965 | B2 | 8/2014 | Zhang |
| 8,853,381 | B2 | 10/2014 | Matsui et al. |
| 9,434,928 | B2 | 9/2016 | Medndell et al. |
| 2004/0023517 | A1 | 2/2004 | Yoo |
| 2021/0198692 | A1 | 7/2021 | Hampson et al. |

FOREIGN PATENT DOCUMENTS

| | | | |
|---|---|---|---|
| WO | 0183692 | A2 | 11/2001 |
| WO | 2019227219 | A1 | 12/2019 |

OTHER PUBLICATIONS

Arsenault et al, "FMRP Expression Levels in Mouse Central Nervous System Neurons Determine Behavioral Phenotype", Human Gene Therapy, vol. 27, No. 12, pp. 982-996, (2016).
Ausubel et al, "Short Protocols in Molecular Biology", Jordan University of Science and Technology, 2 pages, (2008).
Becerra et al, "Direct mapping of adeno-associated virus capsid proteins B and C: A possible ACG initiation codon", Proc. Natl. Acad. Sci., vol. 82, pp. 7919-7923, Dec. 1985.
Berns et al, "Parvoviridae and Their Replication", Virology, 2nd Edition, Ch. 62, (1990).
Blacklow, "Adeno-Associated Viruses of Humans", Parvoviruses and Human Disease, pp. 165-173, (1988).
Carter et al, "AAV DNA Replication, Integration, and Genetics", CRC Handbook of Parvoviruses, vol. 1, Ch. 11, pp. 169-197, (1990).
Cassinotti et al, "Organization of the Adeno-Associated Virus (AAV) Capsid Gene: Mapping of a Minor Spliced mRNA Coding for Virus Capsid Protein I", Virology, vol. 167, No. 1, pp. 176-184, Nov. 1998.
Chao et al, "Several Log Increase in Therapeutic Transgene Delivery by Distinct Adeno-Associated Viral Serotype Vectors", Molecular Therapy, vol. 2, No. 6, pp. 619-623, Dec. 2000.
Chao et al, "Sustained and Complete Phenotype Correction of Hemophilia B Mice Following Intramuscular Injection of AAV1 Serotype Vectors", Molecular Therapy, vol. 4, No. 3, pp. 217-222, Sep. 2001.
Clark et al, "Recombinant Adeo-Associated Viral Vectors Mediate Long-Term Transgene Expression in Muscle", Human Gene Therapy, vol. 8, pp. 659-669, Apr. 10, 1997.
De et al, "High Levels of Persistent Expression of a1-Antitrypsin Mediated by the Nonhuman Primate Serotype rh.10 Adeno-associated Virus Despite Preexisting Immunity to Common Human Adeno-associated Viruses", Molecular Therapy, vol. 13, No. 1, pp. 67-76, Nov. 2, 2005.
DiMattia et al, "Structural Insight into the Unique Properties of Adeno-Associated Virus Serotype 9", Journal of Virology, vol. 86, No. 12, pp. 6947-6958, Jun. 2012.
(Continued)

*Primary Examiner* — Tracy Vivlemore
*Assistant Examiner* — Zanna Maria Beharry
(74) *Attorney, Agent, or Firm* — DLA PIPER LLP (US)

(57) ABSTRACT

This technology relates to polynucleotides comprising optimized FMR1 open reading frame (ORF) sequences, viral vectors comprising the same, and methods of using the same for delivery of the ORF to a cell or a subject and to treat disorders associated with aberrant expression of FMR1, such as Fragile X syndrome ("FXS").

12 Claims, 65 Drawing Sheets

Specification includes a Sequence Listing.

(56) References Cited

OTHER PUBLICATIONS

Gao et al , "Clades of Adeno-Associated Viruses are Widely Disseminated in Human Tissues", Journal of Virology, vol. 78, No. 12, pp. 6381-6388, Feb. 13, 2004.
Gholizadeh et al, "Reduced Phenotypic Severity Following Adeno-Associated Virus-Mediated Fmrl Gene Delivery in Fragile X Mice", Neuropsychopharmacology, vol. 39, pp. 3100-3111, (2014).
Gonzalez et al, "Audiogenic Seizures in the Fmrl Knock-Out Mouse Are Induced by Fmrl Deletion in Subcortical, VGlut2-Expressing Excitatory Neurons and Require Deletion in the Inferior Colliculus", The Journal of Neuroscience, vol. 39, No. 49, pp. 9852-9863, Dec. 4, 2019.
Herzog et al, "Stable gene transfer and expression of human blood coagulation factor IX after intramuscular injection of recombinant adeno-associated virus", Proc. Natl. Acad. Sci., No. 94, pp. 5804-5809, May 1997.
Hooper et al, "Gene therapy using an ortholog of human fragile X mental retardation protein partially rescues behavioral abnormalities and EEG activity", Molecular Therapy Methods & Clinical Development, vol. 22, pp. 196-209, Sep. 2021.
Kessler et al, "Gene delivery to skeletal muscle results in sustained expression and systemic delivery of a therapeutic protein", Proc. Natl. Acad. Sci., vol. 93, pp. 14082-14087, Nov. 1996.
Lewis et al, "Generation of Neutralizing Activity against Human Immunodeficiency Virus Type 1 in Serum by Antibody Gene Transfer", Journal of Virology, vol. 76, No. 17, pp. 8769-8775, Sep. 2002.
Lovelace et al, "Translation-relevant EEG phenotypes in a mouse model of Fragile X Syndrome", Neurobiology of Disease, vol. 115, pp. 39-48, (2018).
Marsic et al, "Vector Design Tour de Force: Integrating Combinatorial and Rational Approaches to Derive Novel Adeno-associated Virus Variants", The American Society of Gene & Cell Therapy, vol. 22, No. 11, pp. 1900-1909, Nov. 2014.
Moghaddam, "Virus-Mediated Delivery of the Fmr1 Gene as a Tool for the Treatment of Fragile X Syndrome", Department of Pharmaceutical Sciences, 145 pages, (2016).
Mori et al, "Two novel adeno-associated viruses from cynomolgus monkey: pseudotyping characterization of capsid protein", Virology, vol. 330, pp. 375-383, (2004).
Muralidhar et al, "Site-Directed Mutagenesis of Adeno-Associated Virus Type 2 Structural Protein Initiation Codons: Effects on Regulation of Synthesis and Biological Activity", Journal of Virology, vol. 68, No. 1, pp. 170-176, Jan. 1994.
Murphy et al, "Long-term correction of obesity and diabetes in genetically obese mice by a single intramuscular injection of recombinant adeno-associated virus encoding mouse leptin", Proc. Natl. Acad. Sci., vol. 94, pp. 13921-13926, Dec. 1997.
Pacey et al, "Subchronic Administration and Combination Matabotropic Glutamate and GABAb Receptor Drug Therapy in Fragile X Syndrome", The Journal of Pharmacology and Experimental Therapeutics, vol. 338, No. 3, pp. 897-905, May 31, 2011.
Pack et al, "A Novel Method For High Throughput Phenotyping Of Sleep In Mice", American Physiological Society, 31 pages, (2006).
Paulk et al, "Bioengineered AAV Capsids with Combined High Human Liver Transduction In Vivo and Unique Humoral Seroeactivity", Molecular Therapy, vol. 26, N. 1, pp. 289-303, Jan. 2018.
Pekrun et al, "Using a barcoded AAV capsid library to select for novel clinically relevant gene therapy vectors", 50 pages, (2019).
Rabinowtiz et al, "Building a Better Vector: The Manipulation of AAV Virions", Virology, vol. 278, pp. 301-308, Nov. 22, 2000.
Sare et al, "Deficient Sleep in Mouse Models of Fragile X Syndrome", frontiers in Molecular Neuroscience, vol. 10, Article 280, 7 pages, Sep. 1, 2017.
Sontagg et al, "A viral assembly factor promotes AAV2 capsid formation in the nucleolus", PNAS, vol. 107, No. 22, pp. 10220-10225, Jun. 1, 2010.
Srivastava et al, "Nucleotide Sequence and Organization of the Adeno-Associated Virus 2 Genome", Journal of Virology, vol. 45, No. 2, pp. 555-564, Feb. 1983.
Trempe et al, "Alternate mRNA Splicing Is Required for Synthesis of Adeno-Associated Virus VP1 Capsid Protein", Journal of Virology, No. 62, No. 9, pp. 3356-3363, Sep. 1988.
Wang et al, "A resting EEG study of neocortical hyperexcitability and altered functional connectivity in fragile X syndrome", Journal of Neurodevelopmental Disorders, vol. 9, No. 11, 12 pages, (2017).
Xiao et al, "Efficient Long-Term Gene Transfer into Muscle Tissue of Immunocompetent Mice by Adeno-Associated Virus Vector", Journal of Virology, vol. 70, No. 11, pp. 8098-8108, Nov. 1996.
Ying et al, "Cancer therapy using a self-replicating RNA vaccine", Nat Med., vol. 5, No. 7, pp. 823-827, Jul. 1999.
Gholizadeh et al, "Expression of Fragile X Mental Retardation Protein in Neurons and Glia of The Developing and Adult Mouse Brain," Brain Research, vol. 1596, pp. 22-30, (2015).
Wong et al, "Sexually dimorphic patterns in electroencephalography power spectrum and autism-related behaviors in a rat model of fragile X syndrome," Neurobiology of disease, vol. 146, Dec. 1, 2020.
International Search Report and Written Opinion of the International Searching Authority issued in International Application No. PCT/US2023/061459, 10 pages, dated May 25, 2023.
International Preliminary Report on Patentability issued in International Application No. PCT/US2023/061459, 7 pages, dated Jul. 30, 2024.
Sambrook et al, "Molecular Cloning: A Laboratory Manual," Cold Spring Harbor Laboratory Press, 2nd Edition, vol. 1, pp. 169-228, 1989.

| Version | Promoter | Expression | FMR1 | Poly A |
|---|---|---|---|---|
| 1 | Synthetic JeT | Ubiquitous/weak | Human FMR1 Iso17 | Synthetic pA |
| 2 | Murine MeP229 | Most Neuron/little glial cell | Human FMR1 Iso17 | Synthetic pA |
| 3 | Human FMR1 (244) | Endogenous | Human FMR1 Iso17 | Synthetic pA |

SEQUENCE LISTING

```
Sequence total quantity: 39
SEQ ID NO: 1            moltype = DNA  length = 5838
FEATURE                 Location/Qualifiers
source                  1..5838
                        mol_type = other DNA
                        organism = synthetic construct
SEQUENCE: 1
ctgcgcgctc gctcgctcac tgaggccgcc cgggcaaagc ccgggcgtcg ggcgaccttt  60
ggtcgcccgg cctcagtgag cgagcgagcg cgcagagagg gagtggggtt cggtaccggg  120
cggagttagg gcggagccaa tcagcgtgcg ccgttccgaa agttgccttt tatggctggg  180
cggagaatgg gcggtgaacg ccgatgatta tataaggacg cgccgggtgt ggcacagcta  240
gttccgtcgc agccgggatt tgggtcgcgg ttcttgtttg tggatcctcc ggaaacgcgc  300
gcggccacca tggaagaact ggtggtggaa gtgagaggaa gcaatggagc cttctacaag  360
gcctttgtga aggatgtgca tgaggactcc attactgtgg cttttgaaaa caactggcaa  420
ccagacagac agattccttt ccatgatgtg agattccccc ctcctgtggg gtacaacaag  480
gacatcaatg agtcagatga agtggaagtg tactccagag ccaatgagaa ggaaccatgt  540
tgttggtggc ttgccaaagt gagaatgatc aagggggagt tctatgtgat tgaatatgca  600
gcctgtgatg ctacctacaa tgaaattgtg accattgaga ggcttagatc tgtgaacccc  660
aacaaaccag ccacaaagga caccttccac aagatcaagc tggatgtgcc tgaggatctg  720
aggcagatgt gtgccaagga agctgcccac aaggatttca agaaagctgt gggagccttc  780
tcagtgactt atgaccctga gaattatcag ctggtgatac tgagcatcaa tgaagtgact  840
tccaagagag cccacatgct gattgatatg cattttagaa gccttagaac caaactgagc  900
ctcatcatga ggaatgagga ggccagcaag caactggaaa gctccaggca gttggcttcc  960
agattccatg aacagttcat tgtgagggaa gatctgatgg gcctggcaat tggtactcat  1020
ggagccaaca tccaacaagc caggaaggtc ccaggagtga ctgccattga cctagatgaa  1080
gatacttgta ctttccacat ttatggagaa gatcaggatg ctgtgaagaa ggctagatcc  1140
ttcctggagt ttgcagaaga tgtgatccag gtgcccagaa acctggtggg gaaagtcatt  1200
gggaagaatg ggaagctgat ccaggaaatt gtggacaagt caggtgtggt cagggtcaga  1260
attgaggcag aaaatgaaaa gaatgtgcca caggaggaag aaatcatgcc ccctaactca  1320
ttgccttcca acaactccag ggtgggccca aatgccccag aagaaaagaa gcatcttgac  1380
atcaaggaaa actccaccca tttctcacag cccaacagca ccaaggtgca gagaggaatg  1440
gtgccttttg tctttgtggg aaccaaggac tcaattgcaa atgcaactgt cctgttggac  1500
taccacttga actacctgaa ggaagtggac cagctgagac tggagagatt acaaattgat  1560
gaacagttga ggcagattgg agccagcagc aggccacctc ctaacagaac tgacaaggag  1620
aagtcctatg tgactgatga tggacagggg atgggcaggg gtagcagacc ttacagaaac  1680
agaggacatg gcagaagggg acctggttac acatcaggaa ctaactcaga agcctccaat  1740
gcttcagaga ctgaatcaga ccatagagat gaactgtcag actggagcct ggcccccact  1800
gaagaagaaa gagaaagctt cctgaggaga ggagacggac ggcggcgtgg agggggagga  1860
agaggacaag gaggaagagg acgtggagga ggcttcaagg gaaatgatga tcacagcaga  1920
actgacaaca gacccagaaa ccccagagaa gccaagggca ggaccactga tggaagcctg  1980
cagaacactt cctcagaggg ttccaggctg agaactggga aggatagaaa ccagaagaag  2040
gaaaagcctg actcagtgga tggccagcag cctctggtca atggagtccc ttaagcggcc  2100
gcctcgagaa taaagagctc agatgcatcg atcagagtgt gttggttttt tgtgtgacgc  2160
gtaggaaccc ctagtgatgg agttggccac tccctctctg cgcgctcgct cgctcactga  2220
```

```
ggccgggcga ccaaaggtcg cccgacgccc gggctttgcc cgggcggcct cagtgagcga  2280
gcgagcgcgc agctggcgta atagcgaaga ggcccgcacc gatcgccctt cccaacagtt  2340
gcgcagcctg aatggcgaat ggcgattccg ttgcaatggc tggcggtaat attgttctgg  2400
atattaccag caaggccgat agtttgagtt cttctactca ggcaagtgat gttattacta  2460
atcaaagaag tattgcgaca acggttaatt tgcgtgatgg acagactctt ttactcggtg  2520
gcctcactga ttataaaaac acttctcagg attctggcgt accgttcctg tctaaaatcc  2580
ctttaatcgg cctcctgttt agctcccgct ctgattctaa cgaggaaagc acgttatacg  2640
tgctcgtcaa agcaaccata gtacgcgccc tgtagcggcg cattaagcgc ggcgggtgtg  2700
gtggttacgc gcagcgtgac cgctacactt gccagcgccc tagcgcccgc tcctttcgct  2760
ttcttccctt cctttctcgc cacgttcgcc ggctttcccc gtcaagctct aaatcggggg  2820
ctccctttag ggttccgatt tagtgcttta cggcacctcg accccaaaaa acttgattag  2880
ggtgatggtt cacgtagtgg gccatcgccc tgatagacgg tttttcgccc tttgacgttg  2940
gagtccacgt tctttaatag tggactcttg ttccaaactg gaacaacact caaccctatc  3000
tcggtctatt cttttgattt ataagggatt ttgccgattt cggcctattg gttaaaaaat  3060
gagctgattt aacaaaaatt taacgcgaat tttaacaaaa tattaacgct tacaatttaa  3120
atatttgctt atacaatctt cctgtttttg gggcttttct gattatcaac cggggtacat  3180
atgattgaca tgctagtttt acgattaccg ttcatcgatt ctcttgtttg ctccagactc  3240
tcaggcaatg acctgatagc ctttgtagag acctctcaaa aatagctacc ctctccggca  3300
tgaatttatc agctagaacg gttgaatatc atattgatgg tgatttgact gtctccggcc  3360
tttctcaccc gtttgaatct ttacctacac attactcagg cattgcattt aaaatatatg  3420
agggttctaa aaatttttat ccttgcgttg aaataaaggc ttctcccgca aaagtattac  3480
agggtcataa tgtttttggt acaaccgatt tagctttatg ctctgaggct ttattgctta  3540
atttgctaa ttctttgcct tgcctgtatg atttattgga tgttggaatc gcctgatgcg  3600
gtattttctc cttacgcatc tgtgcggtat ttcacaccgc atatggtgca ctctcagtac  3660
aatctgctct gatgccgcat agttaagcca gccccgacac ccgccaacac ccgctgacgc  3720
gccctgacgg gcttgtctgc tcccggcatc cgcttacaga caagctgtga ccgtctccgg  3780
gagctgcatg tgtcagaggt tttcaccgtc atcaccgaaa cgcgcgagac gaaagggcct  3840
cgtgatacgc ctatttttat aggttaatgt catgataata atggtttctt agacgtcagg  3900
tggcactttt cggggaaatg tgcgcggaac ccctatttgt ttatttttct aaatacattc  3960
aaatatgtat ccgctcatga gacaataacc ctgataaatg cttcaataat attgaaaaag  4020
gaagagtatg agccatattc aacgggaaac gtcttgctct aggccgcgat taaattccaa  4080
catggatgct gatttatatg ggtataaatg ggctcgcgat aatgtcgggc aatcaggtgc  4140
gacaatctat cgattgtatg ggaagcccga tgcgccagag ttgtttctga aacatggcaa  4200
aggtagcgtt gccaatgatg ttacagatga gatggtcaga ctaaactggc tgacggaatt  4260
tatgcctctt ccgaccatca agcattttat ccgtactcct gatgatgcat ggttactcac  4320
cactgcgatc cctgggaaaa cagcattcca ggtattagaa gaatatcctg attcaggtga  4380
aaatattgtt gatgcgctgg cagtgttcct gcgccggttg cattcgattc ctgtttgtaa  4440
ttgtcctttt aacagcgatc gcgtatttcg tctcgctcag gcgcaatcac gaatgaataa  4500
cggtttggtt gatgcgagtg attttgatga cgagcgtaat ggctggcctg ttgaacaagt  4560
ctggaaagaa atgcataaac ttttgccatt ctcaccggat tcagtcgtca ctcatggtga  4620
tttctcactt gataacctta tttttgacga ggggaaatta ataggttgta ttgatgttgg  4680
acgagtcgga atcgcagacc gataccagga tcttgccatc ctatggaact gcctcggtga  4740
gttttctcct tcattacaga aacggctttt tcaaaaatat ggtattgata atcctgatat  4800
gaataaattg cagtttcatt tgatgctcga tgagtttttc taactgtcag accaagttta  4860
ctcatatata ctttagattg atttaaaact tcatttttaa tttaaaagga tctaggtgaa  4920
gatccttttt gataatctca tgaccaaaat cccttaacgt gagttttcgt tccactgagc  4980
gtcagacccc gtagaaaaga tcaaaggatc ttcttgagat cctttttttc tgcgcgtaat  5040
ctgctgcttg caaacaaaaa aaccaccgct accagcggtg gtttgtttgc cggatcaaga  5100
gctaccaact ctttttccga aggtaactgg cttcagcaga gcgcagatac caaatactgt  5160
tcttctagtg tagccgtagt taggccacca cttcaagaac tctgtagcac cgcctacata  5220
cctcgctctg ctaatcctgt taccagtggc tgctgccagt ggcgataagt cgtgtcttac  5280
cgggttggac tcaagacgat agttaccgga taaggcgcag cggtcgggct gaacgggggg  5340
ttcgtgcaca cagcccagct tggagcgaac gacctacacc gaactgagat acctacagcg  5400
tgagctatga gaaagcgcca cgcttcccga agggagaaag gcggacaggt atccggtaag  5460
cggcagggtc ggaacaggag agcgcacgag ggagcttcca gggggaaacg cctggtatct  5520
ttatagtcct gtcgggtttc gccacctctg acttgagcgt cgatttttgt gatgctcgtc  5580
aggggggcgg agcctatgga aaaacgccag caacgcggcc tttttacggt tcctggcctt  5640
ttgctggcct tttgctcaca tgttctttcc tgcgttatcc cctgattctg tggataaccg  5700
tattaccgcc tttgagtgag ctgataccgc tcgccgcagc cgaacgaccg agcgcagcga  5760
gtcagtgagc gaggaagcgg aagagcgccc aatacgcaaa ccgcctctcc ccgcgcgttg  5820
gccgattcat taatgcag                                                5838

SEQ ID NO: 2           moltype = DNA  length = 106
FEATURE                Location/Qualifiers
source                 1..106
                       mol_type = other DNA
                       organism = synthetic construct
SEQUENCE: 2
ctgcgcgctc gctcgctcac tgaggccgcc cgggcaaagc ccgggcgtcg ggcgaccttt  60
ggtcgcccgg cctcagtgag cgagcgagcg cgcagagagg gagtgg                 106

SEQ ID NO: 3           moltype = DNA  length = 164
FEATURE                Location/Qualifiers
source                 1..164
                       mol_type = other DNA
                       organism = synthetic construct
SEQUENCE: 3
gggcggagtt agggcggagc caatcagcgt gcgccgttcc gaaagttgcc ttttatggct  60
gggcggagaa tgggcggtga acgccgatga ttatataagg acgcgccggg tgtggcacag  120
```

```
ctagttccgt cgcagccggg atttgggtcg cggttcttgt ttgt                164

SEQ ID NO: 4           moltype = DNA  length = 1785
FEATURE                Location/Qualifiers
source                 1..1785
                       mol_type = other DNA
                       organism = synthetic construct
SEQUENCE: 4
atggaagaac tggtggtgga agtgagagga agcaatggag ccttctacaa ggcctttgtg  60
aaggatgtgc atgaggactc cattactgtg gcttttgaaa acaactggca accagacaga  120
cagattcctt tccatgatgt gagattcccc cctcctgtgg ggtacaacaa ggacatcaat  180
gagtcagatg aagtggaagt gtactccaga gccaatgaga aggaaccatg ttgttggtgg  240
cttgccaaag tgagaatgat caagggggag ttctatgtga ttgaatatgc agcctgtgat  300
gctacctaca atgaaattgt gaccattgag aggcttagat ctgtgaaccc caacaaacca  360
gccacaaagg acaccttcca caagatcaag ctggatgtgc ctgaggatct gaggcagatg  420
tgtgccaagg aagctgccca caaggatttc aagaaagctg tgggagcctt ctcagtgact  480
tatgaccctg agaattatca gctggtgata ctgagcatca atgaagtgac ttccaagaga  540
gcccacatgc tgattgatat gcattttaga agccttagaa ccaaactgag cctcatcatg  600
aggaatgagg aggccagcaa gcaactggaa agctccaggc agttggcttc cagattccat  660
gaacagttca ttgtgaggga agatctgatg ggcctggcaa ttggtactca tggagccaac  720
atccaacaag ccaggaaggt cccaggagtg actgccattg acctagatga agatacttgt  780
actttccaca tttatggaga agatcaggat gctgtgaaga aggctagatc cttcctggag  840
tttgcagaag atgtgatcca ggtgcccaga aacctggtgg ggaaagtcat tgggaagaat  900
gggaagctga tccaggaaat tgtggacaag tcaggtgtgg tcagggtcag aattgaggca  960
gaaaatgaaa agaatgtgcc acaggaggaa gaaatcatgc cccctaactc attgccttcc  1020
aacaactcca gggtgggccc aaatgcccca gaagaaaaga agcatcttga catcaaggaa  1080
aactccaccc atttctcaca gcccaacagc accaaggtgc agagaggaat ggtgcctttt  1140
gtctttgtgg gaaccaagga ctcaattgca aatgcaactg tcctgttgga ctaccacttg  1200
aactacctga aggaagtgga ccagctgaga ctggagagat tacaaattga tgaacagttg  1260
aggcagattg gagccagcag caggccacct cctaacagaa ctgacaagga gaagtcctat  1320
gtgactgatg atggacaggg gatgggcagg ggtagcagac cttacagaaa cagaggacat  1380
ggcagaaggg gacctggtta cacatcagga actaactcag aagcctccaa tgcttcagag  1440
actgaatcag accatagaga tgaactgtca gactggagcc tggcccccac tgaagaagaa  1500
agagaaagct tcctgaggag aggagacgga cggcggcgtg gagggggagg aagaggacaa  1560
ggaggaagag gacgtggagg aggcttcaag ggaaatgatg atcacagcag aactgacaac  1620
agacccagaa accccagaga agccaagggc aggaccactg atggaagcct gcagaacact  1680
tcctcagagg gttccaggct gagaactggg aaggatagaa accagaagaa ggaaaagcct  1740
gactcagtgg atggccagca gcctctggtc aatggagtcc cttaa              1785

SEQ ID NO: 5           moltype = DNA  length = 62
FEATURE                Location/Qualifiers
source                 1..62
                       mol_type = other DNA
                       organism = synthetic construct
SEQUENCE: 5
gcggccgcct cgagaataaa gagctcagat gcatcgatca gagtgtgttg gtttttgtg  60
tg                                                              62

SEQ ID NO: 6           moltype = DNA  length = 169
FEATURE                Location/Qualifiers
source                 1..169
                       mol_type = other DNA
                       organism = synthetic construct
SEQUENCE: 6
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag ctggcgtaat agcgaagagg cccgcaccga tcgcccttc           169

SEQ ID NO: 7           moltype = DNA  length = 5885
FEATURE                Location/Qualifiers
source                 1..5885
                       mol_type = other DNA
                       organism = synthetic construct
SEQUENCE: 7
ctgcgcgctc gctcgctcac tgaggccgcc cgggcaaagc ccgggcgtcg ggcgaccttt  60
ggtcgcccgg cctcagtgag cgagcgagcg cgcagagagg gagtggggtt cggtacccaa  120
ttgagggcgt caccgctaag gctccgcccc agcctgggct ccacaaccaa tgaagggtaa  180
tctcgacaaa gagcaagggg tggggcgcgg gcgcgcaggt gcagcagcac acaggctggt  240
cgggagggcg gggcgcgacg tctgccgtgc ggggtcccgg catcggttgc gcgcgcgctc  300
cctcctctcg gagagagggc tgtggtaaaa cccgtccgga aacgcgcgcg gccaccatgg  360
aagaactggt ggtggaagtg agaggaagca atggagcctt ctacaaggcc tttgtgaagg  420
atgtgcatga ggactccatt actgtggctt ttgaaaacaa ctggcaacca gacagacaga  480
ttcctttcca tgatgtgaga ttcccccctc ctgtggggta caacaaggac atcaatgagt  540
cagatgaagt ggaagtgtac tccagagcca atgagaagga accatgttgt tggtggcttg  600
ccaaagtgag aatgatcaag ggggagttct atgtgattga atatgcagcc tgtgatgcta  660
cctacaatga aattgtgacc attgagaggc ttagatctgt gaaccccaac aaaccagcca  720
caaaggacac cttccacaag atcaagctgg atgtgcctga ggatctgagg cagatgtgtg  780
ccaaggaagc tgcccacaag gatttcaaga aagctgtggg agccttctca gtgacttatg  840
accctgagaa ttatcagctg gtgatactga gcatcaatga agtgacttcc aagagagccc  900
```

-continued

```
acatgctgat tgatatgcat tttagaagcc ttagaaccaa actgagcctc atcatgagga  960
atgaggaggc cagcaagcaa ctggaaagct ccaggcagtt ggcttccaga ttccatgaac  1020
agttcattgt gagggaagat ctgatgggcc tggcaattgg tactcatgga gccaacatcc  1080
aacaagccag gaaggtccca ggagtgactg ccattgacct agatgaagat acttgtactt  1140
tccacattta tggagaagat caggatgctg tgaagaaggc tagatccttc ctggagtttg  1200
cagaagatgt gatccaggtg cccagaaacc tggtggggaa agtcattggg aagaatggga  1260
agctgatcca ggaaattgtg gacaagtcag gtgtggtcag ggtcagaatt gaggcagaaa  1320
atgaaaagaa tgtgccacag gaggaagaaa tcatgccccc taactcattg ccttccaaca  1380
actccagggt gggcccaaat gccccagaag aaaagaagca tcttgacatc aaggaaaact  1440
ccacccattt ctcacagccc aacagcacca aggtgcagag aggaatggtg ccttttgtct  1500
ttgtgggaac caaggactca attgcaaatg caactgtcct gttggactac cacttgaact  1560
acctgaagga agtggaccag ctgagactgg agagattaca aattgatgaa cagttgaggc  1620
agattggagc cagcagcagg ccacctccta acagaactga caaggagaag tcctatgtga  1680
ctgatgatgg acaggggatg ggcaggggta gcagacctta cagaaacaga ggacatggca  1740
gaaggggacc tggttacaca tcaggaacta actcagaagc ctccaatgct tcagagactg  1800
aatcagacca tagagatgaa ctgtcagact ggagcctggc ccccactgaa gaagaaagag  1860
aaagcttcct gaggagagga gacggacggc ggcgtggagg gggaggaaga ggacaaggag  1920
gaagaggacg tggaggaggc ttcaagggaa atgatgatca cagcagaact gacaacagac  1980
ccagaaaccc cagagaagcc aagggcagga ccactgatgg aagcctgcag aacacttcct  2040
cagagggttc caggctgaga actgggaagg atagaaacca gaagaaggaa aagcctgact  2100
cagtggatgg ccagcagcct ctggtcaatg gagtccctta agcggccgcc tcgagaataa  2160
agagctcaga tgcatcgatc agagtgtgtt ggtttttttgt gtgacgcgta ggaaccccta  2220
gtgatggagt tggccactcc ctctctgcgc gctcgctcgc tcactgaggc cgggcgacca  2280
aaggtcgccc gacgcccggg ctttgcccgg gcggcctcag tgagcgagcg agcgcgcagc  2340
tggcgtaata gcgaagaggc ccgcaccgat cgcccttccc aacagttgcg cagcctgaat  2400
ggcgaatggc gattccgttg caatggctgg cggtaatatt gttctggata ttaccagcaa  2460
ggccgatagt ttgagttctt ctactcaggc aagtgatgtt attactaatc aaagaagtat  2520
tgcgacaacg gttaatttgc gtgatggaca gactctttta ctcggtggcc tcactgatta  2580
taaaaacact tctcaggatt ctggcgtacc gttcctgtct aaaatccctt taatcggcct  2640
cctgtttagc tcccgctctg attctaacga ggaaagcacg ttatacgtgc tcgtcaaagc  2700
aaccatagta cgcgccctgt agcggcgcat taagcgcggc gggtgtggtg gttacgcgca  2760
gcgtgaccgc tacacttgcc agcgccctag cgcccgctcc tttcgctttc ttcccttcct  2820
ttctcgccac gttcgccggc tttccccgtc aagctctaaa tcgggggctc cctttagggt  2880
tccgatttag tgctttacgg cacctcgacc ccaaaaaact tgattagggt gatggttcac  2940
gtagtgggcc atcgccctga tagacggttt ttcgcccttt gacgttggag tccacgttct  3000
ttaatagtgg actcttgttc caaactggaa caacactcaa ccctatctcg gtctattctt  3060
ttgatttata agggattttg ccgatttcgg cctattggtt aaaaaatgag ctgatttaac  3120
aaaaatttaa cgcgaatttt aacaaaatat taacgcttac aatttaaata tttgcttata  3180
caatcttcct gtttttgggg cttttctgat tatcaaccgg ggtacatatg attgacatgc  3240
tagttttacg attaccgttc atcgattctc ttgtttgctc cagactctca ggcaatgacc  3300
tgatagcctt tgtagagacc tctcaaaaat agctaccctc tccggcatga atttatcagc  3360
tagaacggtt gaatatcata ttgatggtga tttgactgtc tccggccttt ctcacccgtt  3420
tgaatcttta cctacacatt actcaggcat tgcatttaaa atatatgagg gttctaaaaa  3480
tttttatcct tgcgttgaaa taaaggcttc tcccgcaaaa gtattacagg gtcataatgt  3540
ttttggtaca accgatttag ctttatgctc tgaggcttta ttgcttaatt ttgctaattc  3600
tttgccttgc ctgtatgatt tattggatgt tggaatcgcc tgatgcggta ttttctcctt  3660
acgcatctgt gcggtatttc acaccgcata tggtgcactc tcagtacaat ctgctctgat  3720
gccgcatagt taagccagcc ccgacacccg ccaacacccg ctgacgcgcc ctgacgggct  3780
tgtctgctcc cggcatccgc ttacagacaa gctgtgaccg tctccgggag ctgcatgtgt  3840
cagaggtttt caccgtcatc accgaaacgc gcgagacgaa agggcctcgt gatacgccta  3900
tttttatagg ttaatgtcat gataataatg gtttcttaga cgtcaggtgg cacttttcgg  3960
ggaaatgtgc gcggaacccc tatttgttta tttttctaaa tacattcaaa tatgtatccg  4020
ctcatgagac aataaccctg ataaatgctt caataatatt gaaaaaggaa gagtatgagc  4080
catattcaac gggaaacgtc ttgctctagg ccgcgattaa attccaacat ggatgctgat  4140
ttatatgggt ataaatgggc tcgcgataat gtcgggcaat caggtgcgac aatctatcga  4200
ttgtatggga agcccgatgc gccagagttg tttctgaaac atggcaaagg tagcgttgcc  4260
aatgatgtta cagatgagat ggtcagacta aactggctga cggaatttat gcctcttccg  4320
accatcaagc attttatccg tactcctgat gatgcatggt tactcaccac tgcgatccct  4380
gggaaaacag cattccaggt attagaagaa tatcctgatt caggtgaaaa tattgttgat  4440
gcgctggcag tgttcctgcg ccggttgcat tcgattcctg tttgtaattg tccttttaac  4500
agcgatcgcg tatttcgtct cgctcaggcg caatcacgaa tgaataacgg tttggttgat  4560
gcgagtgatt ttgatgacga gcgtaatggc tggcctgttg aacaagtctg gaaagaaatg  4620
cataaacttt tgccattctc accggattca gtcgtcactc atggtgattt ctcacttgat  4680
aaccttattt ttgacgaggg gaaattaata ggttgtattg atgttggacg agtcggaatc  4740
gcagaccgat accaggatct tgccatccta tggaactgcc tcggtgagtt ttctccttca  4800
ttacagaaac ggctttttca aaaatatggt attgataatc ctgatatgaa taaattgcag  4860
tttcatttga tgctcgatga gtttttctaa ctgtcagacc aagtttactc atatatactt  4920
tagattgatt taaaacttca tttttaattt aaaaggatct aggtgaagat cctttttgat  4980
aatctcatga ccaaaatccc ttaacgtgag ttttcgttcc actgagcgtc agaccccgta  5040
gaaaagatca aaggatcttc ttgagatcct ttttttctgc gcgtaatctg ctgcttgcaa  5100
acaaaaaaac caccgctacc agcggtggtt tgtttgccgg atcaagagct accaactctt  5160
tttccgaagg taactggctt cagcagagcg cagataccaa atactgttct tctagtgtag  5220
ccgtagttag gccaccactt caagaactct gtagcaccgc ctacatacct cgctctgcta  5280
atcctgttac cagtggctgc tgccagtggc gataagtcgt gtcttaccgg gttggactca  5340
agacgatagt taccggataa ggcgcagcgg tcgggctgaa cggggggttc gtgcacacag  5400
cccagcttgg agcgaacgac ctacaccgaa ctgagatacc tacagcgtga gctatgagaa  5460
agcgccacgc ttcccgaagg gagaaaggcg gacaggtatc cggtaagcgg cagggtcgga  5520
acaggagagc gcacgaggga gcttccaggg ggaaacgcct ggtatcttta tagtcctgtc  5580
gggtttcgcc acctctgact tgagcgtcga tttttgtgat gctcgtcagg ggggcggagc  5640
```

```
ctatggaaaa acgccagcaa cgcggccttt ttacggttcc tggccttttg ctggcctttt  5700
gctcacatgt tctttcctgc gttatcccct gattctgtgg ataaccgtat taccgccttt  5760
gagtgagctg ataccgctcg ccgcagccga acgaccgagc gcagcgagtc agtgagcgag  5820
gaagcggaag agcgcccaat acgcaaaccg cctctccccg cgcgttggcc gattcattaa  5880
tgcag                                                              5885

SEQ ID NO: 8            moltype = DNA  length = 225
FEATURE                 Location/Qualifiers
source                  1..225
                        mol_type = other DNA
                        organism = synthetic construct
SEQUENCE: 8
caattgaggg cgtcaccgct aaggctccgc cccagcctgg gctccacaac caatgaaggg  60
taatctcgac aaagagcaag ggtggggcg cgggcgcgca ggtgcagcag cacacaggct   120
ggtcgggagg gcggggcgcg acgtctgccg tgcggggtcc cggcatcggt tgcgcgcgcg  180
ctccctcctc tcggagagag ggctgtggta aaacccgtcc ggaaa                  225

SEQ ID NO: 9            moltype = DNA  length = 5926
FEATURE                 Location/Qualifiers
source                  1..5926
                        mol_type = other DNA
                        organism = synthetic construct
SEQUENCE: 9
ctgcgcgctc gctcgctcac tgaggccgcc cgggcaaagc ccgggcgtcg ggcgaccttt  60
ggtcgcccgg cctcagtgag cgagcgagcg cgcagagagg gagtggggtt cggtacccgc  120
cggcgccgcc cttcagcctt cccgccctcc accaagcccg cgcacgcccg gcccgcgcgt  180
ctgtctttcg acccggcacc ccggccggtt cccagcagcg cgcatgcgcg cgctcccagg  240
ccacttgaag agagagggcg gggccgaggg gctgagcccg cgggggggagg gaacagcgtt 300
gatcacgtga cgtggtttca gtgtttacac ccgcagcggg ccgggggttc ggcctcagtc  360
aggcgctcag gatcctccgg aaacgcgcgc ggccaccatg gaagaactgg tggtggaagt  420
gagaggaagc aatggagcct tctacaaggc ctttgtgaag gatgtgcatg aggactccat  480
tactgtggct tttgaaaaca actggcaacc agacagacag attcctttcc atgatgtgag  540
attcccccct cctgtggggt acaacaagga catcaatgag tcagatgaag tggaagtgta  600
ctccagagcc aatgagaagg aaccatgttg ttggtggctt gccaaagtga gaatgatcaa  660
gggggagttc tatgtgattg aatatgcagc ctgtgatgct acctacaatg aaattgtgac  720
cattgagagg cttagatctg tgaaccccaa caaaccagcc acaaaggaca ccttccacaa  780
gatcaagctg gatgtgcctg aggatctgag gcagatgtgt gccaaggaag ctgcccacaa  840
ggatttcaag aaagctgtgg gagccttctc agtgacttat gaccctgaga attatcagct  900
ggtgatactg agcatcaatg aagtgacttc caagagagcc cacatgctga ttgatatgca  960
ttttagaagc cttagaacca aactgagcct catcatgagg aatgaggagg ccagcaagca  1020
actggaaagc tccaggcagt tggcttccag attccatgaa cagttcattg tgagggaaga  1080
tctgatgggc ctggcaattg gtactcatgg agccaacatc caacaagcca ggaaggtccc  1140
aggagtgact gccattgacc tagatgaaga tacttgtact ttccacattt atggagaaga  1200
tcaggatgct gtgaagaagg ctagatcctt cctggagttt gcagaagatg tgatccaggt  1260
gcccagaaac ctggtgggga aagtcattgg gaagaatggg aagctgatcc aggaaattgt  1320
ggacaagtca ggtgtggtca gggtcagaat tgaggcagaa aatgaaaaga atgtgccaca  1380
ggaggaagaa atcatgcccc ctaactcatt gccttccaac aactccaggg tgggcccaaa  1440
tgccccagaa gaaaagaagc atcttgacat caaggaaaac tccacccatt tctcacagcc  1500
caacagcacc aaggtgcaga gaggaatggt gccttttgtc tttgtgggaa ccaaggactc  1560
aattgcaaat gcaactgtcc tgttggacta ccacttgaac tacctgaagg aagtggacca  1620
gctgagactg gagagattac aaattgatga acagttgagg cagattggag ccagcagcag  1680
gccacctcct aacagaactg acaaggagaa gtcctatgtg actgatgatg gacaggggat  1740
gggcaggggt agcagacctt acagaaacag aggacatggc agaaggggac ctggttacac  1800
atcaggaact aactcagaag cctccaatgc ttcagagact gaatcagacc atagagatga  1860
actgtcagac tggagcctgg cccccactga agaagaaaga gaaagcttcc tgaggagagg  1920
agacggacgg cggcgtggag ggggaggaag aggacaagga ggaagaggac gtggaggagg  1980
cttcaaggga aatgatgatc acagcagaac tgacaacaga cccagaaacc ccagagaagc  2040
caagggcagg accactgatg gaagcctgca gaacacttcc tcagagggtt ccaggctgag  2100
aactgggaag gatagaaacc agaagaagga aaagcctgac tcagtggatg gccagcagcc  2160
tctggtcaat ggagtccctt aagcggccgc ctcgagaata aagagctcag atgcatcgat  2220
cagagtgtgt tggtttttttg tgtgacgcgt aggaacccct agtgatggag ttggccactc 2280
cctctctgcg cgctcgctcg ctcactgagg ccgggcgacc aaaggtcgcc cgacgcccgg  2340
gctttgcccg ggcggcctca gtgagcgagc gagcgcgcag ctggcgtaat agcgaagagg  2400
cccgcaccga tcgcccttcc caacagttgc gcagcctgaa tggcgaatgg cgattccgtt  2460
gcaatggctg gcggtaatat tgttctggat attaccagca aggccgatag tttgagttct  2520
tctactcagg caagtgatgt tattactaat caaagaagta ttgcgacaac ggttaatttg  2580
cgtgatggac agactctttt actcggtggc ctcactgatt ataaaaacac ttctcaggat  2640
tctggcgtac cgttcctgtc taaaatccct ttaatcggcc tcctgtttag ctcccgctct  2700
gattctaacg aggaaagcac gttatacgtg ctcgtcaaag caaccatagt acgcgccctg  2760
tagcggcgca ttaagcgcgg cgggtgtggt ggttacgcgc agcgtgaccg ctacacttgc  2820
cagcgcccta gcgcccgctc ctttcgcttt cttcccttcc tttctcgcca cgttcgccgg  2880
ctttccccgt caagctctaa atcgggggct ccctttaggg ttccgattta gtgctttacg  2940
gcacctcgac cccaaaaaac ttgattaggg tgatggttca cgtagtgggc catcgccctg  3000
atagacggtt tttcgccctt tgacgttgga gtccacgttc tttaatagtg gactcttgtt  3060
ccaaactgga acaacactca accctatctc ggtctattct tttgatttat aagggatttt  3120
gccgatttcg gcctattggt taaaaaatga gctgatttaa caaaaattta acgcgaattt  3180
taacaaaata ttaacgctta caatttaaat atttgcttat acaatcttcc tgtttttggg  3240
gcttttctga ttatcaaccg ggtacatat gattgacatg ctagttttac gattaccgtt   3300
catcgattct cttgtttgct ccagactctc aggcaatgac ctgatagcct ttgtagagac  3360
```

```
ctctcaaaaa tagctaccct ctccggcatg aatttatcag ctagaacggt tgaatatcat  3420
attgatggtg atttgactgt ctccggcctt tctcacccgt ttgaatcttt acctacacat  3480
tactcaggca ttgcatttaa aatatatgag ggttctaaaa atttttatcc ttgcgttgaa  3540
ataaaggctt ctcccgcaaa agtattacag ggtcataatg tttttggtac aaccgattta  3600
gctttatgct ctgaggcttt attgcttaat tttgctaatt ctttgccttg cctgtatgat  3660
ttattggatg ttggaatcgc ctgatgcggt attttctcct tacgcatctg tgcggtattt  3720
cacaccgcat atggtgcact ctcagtacaa tctgctctga tgccgcatag ttaagccagc  3780
cccgacaccc gccaacaccc gctgacgcgc cctgacgggc ttgtctgctc ccggcatccg  3840
cttacagaca agctgtgacc gtctccggga gctgcatgtg tcagaggttt tcaccgtcat  3900
caccgaaacg cgcgagacga aagggcctcg tgatacgcct atttttatag gttaatgtca  3960
tgataataat ggtttcttag acgtcaggtg gcacttttcg gggaaatgtg cgcggaaccc  4020
ctatttgttt atttttctaa atacattcaa atatgtatcc gctcatgaga caataaccct  4080
gataaatgct tcaataatat tgaaaaagga agagtatgag ccatattcaa cgggaaacgt  4140
cttgctctag gccgcgatta aattccaaca tggatgctga tttatatggg tataaatggg  4200
ctcgcgataa tgtcgggcaa tcaggtgcga caatctatcg attgtatggg aagcccgatg  4260
cgccagagtt gtttctgaaa catggcaaag gtagcgttgc caatgatgtt acagatgaga  4320
tggtcagact aaactggctg acggaattta tgcctcttcc gaccatcaag cattttatcc  4380
gtactcctga tgatgcatgg ttactcacca ctgcgatccc tgggaaaaca gcattccagg  4440
tattagaaga atatcctgat tcaggtgaaa atattgttga tgcgctggca gtgttcctgc  4500
gccggttgca ttcgattcct gtttgtaatt gtccttttaa cagcgatcgc gtatttcgtc  4560
tcgctcaggc gcaatcacga atgaataacg gtttggttga tgcgagtgat tttgatgacg  4620
agcgtaatgg ctggcctgtt gaacaagtct ggaaagaaat gcataaactt ttgccattct  4680
caccggattc agtcgtcact catggtgatt tctcacttga taaccttatt tttgacgagg  4740
ggaaattaat aggttgtatt gatgttggac gagtcggaat cgcagaccga taccaggatc  4800
ttgccatcct atggaactgc ctcggtgagt tttctccttc attacagaaa cggctttttc  4860
aaaaatatgg tattgataat cctgatatga ataaattgca gtttcatttg atgctcgatg  4920
agtttttcta actgtcagac caagtttact catatatact ttagattgat ttaaaacttc  4980
atttttaatt taaaaggatc taggtgaaga tcctttttga taatctcatg accaaaatcc  5040
cttaacgtga gttttcgttc cactgagcgt cagaccccgt agaaaagatc aaaggatctt  5100
cttgagatcc tttttttctg cgcgtaatct gctgcttgca aacaaaaaaa ccaccgctac  5160
cagcggtggt ttgtttgccg gatcaagagc taccaactct ttttccgaag gtaactggct  5220
tcagcagagc gcagatacca aatactgttc ttctagtgta gccgtagtta ggccaccact  5280
tcaagaactc tgtagcaccg cctacatacc tcgctctgct aatcctgtta ccagtggctg  5340
ctgccagtgg cgataagtcg tgtcttaccg ggttggactc aagacgatag ttaccggata  5400
aggcgcagcg gtcgggctga acggggggtt cgtgcacaca gcccagcttg gagcgaacga  5460
cctacaccga actgagatac ctacagcgtg agctatgaga aagcgccacg cttcccgaag  5520
ggagaaaggc ggacaggtat ccggtaagcg gcagggtcgg aacaggagag cgcacgaggg  5580
agcttccagg gggaaacgcc tggtatcttt atagtcctgt cgggtttcgc cacctctgac  5640
ttgagcgtcg atttttgtga tgctcgtcag gggggcggag cctatggaaa aacgccagca  5700
acgcggcctt tttacggttc ctggcctttt gctggccttt tgctcacatg ttctttcctg  5760
cgttatcccc tgattctgtg gataaccgta ttaccgcctt tgagtgagct gataccgctc  5820
gccgcagccg aacgaccgag cgcagcgagt cagtgagcga ggaagcggaa gagcgcccaa  5880
tacgcaaacc gcctctcccc gcgcgttggc cgattcatta atgcag                 5926

SEQ ID NO: 10          moltype = DNA  length = 244
FEATURE                Location/Qualifiers
source                 1..244
                       mol_type = other DNA
                       organism = synthetic construct
SEQUENCE: 10
ccgcccttca gccttcccgc cctccaccaa gcccgcgcac gcccggcccg cgcgtctgtc  60
tttcgacccg gcaccccggc cggttcccag cagcgcgcat gcgcgcgctc ccaggccact  120
tgaagagaga gggcggggcc gaggggctga gcccgcgggg ggagggaaca gcgttgatca  180
cgtgacgtgg tttcagtgtt tacacccgca gcgggccggg ggttcggcct cagtcaggcg  240
ctca                                                              244

SEQ ID NO: 11          moltype = DNA  length = 106
FEATURE                Location/Qualifiers
source                 1..106
                       mol_type = other DNA
                       organism = synthetic construct
SEQUENCE: 11
ctgcgcgctc gctcgctcac tgaggccgcc cgggcaaagc ccgggcgtcg ggcgaccttt  60
ggtcgcccgg cctcagtgag cgagcgagcg cgcagagagg gagtgg                106

SEQ ID NO: 12          moltype = DNA  length = 169
FEATURE                Location/Qualifiers
source                 1..169
                       mol_type = other DNA
                       organism = synthetic construct
SEQUENCE: 12
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag ctggcgtaat agcgaagagg cccgcaccga tcgcccttc             169

SEQ ID NO: 13          moltype = DNA  length = 130
FEATURE                Location/Qualifiers
source                 1..130
                       mol_type = other DNA
```

```
                          organism = synthetic construct
SEQUENCE: 13
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct                                                         130

SEQ ID NO: 14             moltype = DNA  length = 130
FEATURE                   Location/Qualifiers
source                    1..130
                          mol_type = other DNA
                          organism = synthetic construct
SEQUENCE: 14
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag                                                         130

SEQ ID NO: 15             moltype = DNA  length = 168
FEATURE                   Location/Qualifiers
source                    1..168
                          mol_type = other DNA
                          organism = synthetic construct
SEQUENCE: 15
gggggggggg ggggggttg gccactccct ctctgcgcgc tcgctcgctc actgaggccg  60
ggcgaccaaa ggtcgcccga cgcccgggct ttgcccgggc ggcctcagtg agcgagcgag  120
cgcgcagaga gggagtggcc aactccatca ctaggggttc ctagatct               168

SEQ ID NO: 16             moltype = DNA  length = 168
FEATURE                   Location/Qualifiers
source                    1..168
                          mol_type = other DNA
                          organism = synthetic construct
SEQUENCE: 16
agatctagga acccctagtg atggagttgg ccactccctc tctgcgcgct cgctcgctca  60
ctgaggccgc ccgggcaaag cccgggcgtc gggcgacctt tggtcgcccg gcctcagtga  120
gcgagcgagc gcgcagagag ggagtggcca acccccccc cccccccc                168

SEQ ID NO: 17             moltype = DNA  length = 170
FEATURE                   Location/Qualifiers
source                    1..170
                          mol_type = other DNA
                          organism = synthetic construct
SEQUENCE: 17
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcca gctggcgtaa tagcgaagag gcccgcaccg atcgcccttc             170

SEQ ID NO: 18             moltype = DNA  length = 104
FEATURE                   Location/Qualifiers
source                    1..104
                          mol_type = other DNA
                          organism = synthetic construct
SEQUENCE: 18
tgcgcgctcg ctcgctcact gaggccgccc gggcaaagcc cgggcgtcgg gcgacctttg  60
gtcgcccggc ctcagtgagc gagcgagcgc gcagagaggg agtg                   104

SEQ ID NO: 19             moltype = DNA  length = 106
FEATURE                   Location/Qualifiers
source                    1..106
                          mol_type = other DNA
                          organism = synthetic construct
SEQUENCE: 19
ccactccctc tctgcgcgct cgctcgctca ctgaggccgg gcgaccaaag gtcgcccgac  60
gcccgggctt tgcccgggcg gcctcagtga gcgagcgagc gcgcca                 106

SEQ ID NO: 20             moltype = DNA  length = 332
FEATURE                   Location/Qualifiers
source                    1..332
                          mol_type = other DNA
                          organism = synthetic construct
SEQUENCE: 20
ggtaccgggc ggagttaggg cggagccaat cagcgtgcgc cgttccgaaa gttgcctttt  60
atggctgggc ggagaatggg cggtgaacgc cgatgattat ataaggacgc gccgggtgtg  120
gcacagctag ttccgtcgca gccgggattt gggtcgcggt tcttgtttgt ggatccctgt  180
gatcgtcact tggtaagtca ctgactgtct atgcctggga aagggtgggc aggagatggg  240
gcagtgcagg aaaagtggca ctatgaaccc tgcagcccta ggaatgcatc tagacaattg  300
tactaacctt cttctctttc ctctcctgac ag                                332

SEQ ID NO: 21             moltype = DNA  length = 332
FEATURE                   Location/Qualifiers
```

-continued

```
source                 1..332
                       mol_type = other DNA
                       organism = synthetic construct
SEQUENCE: 21
ggtaccgggc ggagttaggg cggagccaat cagcgtgcgc cgttccgaaa gttgcctttt  60
atggctgggc ggagaatggg cggtgaacgc cgatgattat ataaggacgc gccgggtgtg  120
gcacagctag ttccgtcgca gccgggattt gggtcgcggt tcttgtttgt ggatccctgt  180
gatcgtcact tggtaagtca ctgactgtct atgcctggga aagggtgggc aggagatggg  240
gcagtgcagg aaaagtggca ctatgaaccc tgcagcccta ggaatgcatc tagacaattg  300
tactaacctt cttctctttc ctctcctgac ag                                332

SEQ ID NO: 22          moltype = DNA  length = 241
FEATURE                Location/Qualifiers
source                 1..241
                       mol_type = other DNA
                       organism = synthetic construct
SEQUENCE: 22
gagggcctat ttcccatgat tccttcatat ttgcatatac gatacaaggc tgttagagag  60
ataattggaa ttaatttgac tgtaaacaca aagatattag tacaaaatac gtgacgtaga  120
aagtaataat ttcttgggta gtttgcagtt ttaaaattat gttttaaaat ggactatcat  180
atgcttaccg taacttgaaa gtatttcgat ttcttggctt tatatatctt gtggaaagga  240
c                                                                  241

SEQ ID NO: 23          moltype = DNA  length = 448
FEATURE                Location/Qualifiers
source                 1..448
                       mol_type = other DNA
                       organism = synthetic construct
SEQUENCE: 23
agtgcaagtg ggttttagga ccaggatgag gcggggtggg ggtgcctacc tgacgaccga  60
ccccgaccca ctggacaagc acccaacccc cattccccaa attgcgcatc ccctatcaga  120
gagggggagg ggaaacagga tgcggcgagg cgcgtgcgca ctgccagctt cagcaccgcg  180
gacagtgcct tcgcccccgc ctggcggcgc gcgccaccgc cgcctcagca ctgaaggcgc  240
gctgacgtca ctcgccggtc ccccgcaaac tccccttccc ggccaccttg gtcgcgtccg  300
cgccgccgcc ggcccagccg gaccgcacca cgcgaggcgc gagatagggg ggcacgggcg  360
cgaccatctg cgctgcggcg ccggcgactc agcgctgcct cagtctgcgg tgggcagcgg  420
aggagtcgtg tcgtgcctga gagcgcag                                     448

SEQ ID NO: 24          moltype = DNA  length = 469
FEATURE                Location/Qualifiers
source                 1..469
                       mol_type = other DNA
                       organism = synthetic construct
SEQUENCE: 24
ctgcagaggg ccctgcgtat gagtgcaagt gggttttagg accaggatga ggcggggtgg  60
gggtgcctac ctgacgaccg accccgaccc actggacaag cacccaaccc ccattcccca  120
aattgcgcat cccctatcag agagggggag gggaaacagg atgcggcgag gcgcgtgcgc  180
actgccagct tcagcaccgc ggacagtgcc ttcgcccccg cctggcggcg cgcgccaccg  240
ccgcctcagc actgaaggcg cgctgacgtc actcgccggt cccccgcaaa ctccccttcc  300
cggccacctt ggtcgcgtcc gcgccgccgc cggcccagcc ggaccgcacc acgcgaggcg  360
cgagataggg gggcacgggc gcgaccatct gcgctgcggc gccggcgact cagcgctgcc  420
tcagtctgcg gtgggcagcg gaggagtcgt gtcgtgcctg agagcgcag              469

SEQ ID NO: 25          moltype = DNA  length = 302
FEATURE                Location/Qualifiers
source                 1..302
                       mol_type = other DNA
                       organism = synthetic construct
SEQUENCE: 25
acgtattagt catcgctatt accatggtcg aggtgagccc cacgttctgc ttcactctcc  60
ccatctcccc cccctcccca cccccaattt tgtatttatt tattttttaa ttattttgtg  120
cagcgatggg ggcggggggg gggggggggc gcgcgccagg cggggcgggg cggggcgagg  180
ggcggggcgg ggcgaggcgg agaggtgcgg cggcagccaa tcagagcggc gcgctccgaa  240
agtttccttt tatggcgagg cggcggcggc ggcggcccta taaaaagcga agcgcgcggc  300
gg                                                                 302

SEQ ID NO: 26          moltype = DNA  length = 257
FEATURE                Location/Qualifiers
source                 1..257
                       mol_type = other DNA
                       organism = synthetic construct
SEQUENCE: 26
tacataactt acggtaaatg gcccgcctgg ctgaccgccc aacgaccccc gcccattgac  60
gtcaatagta acgccaatag ggactttcca ttgacgtcaa tgggtggagt atttacggta  120
aactgcccac ttggcagtac atcaagtgta tcatatgcca agtacgcccc ctattgacgt  180
caatgacggt aaatggcccg cctggcattg tgcccagtac atgaccttat gggactttcc  240
tacttggcag tacatct                                                 257

SEQ ID NO: 27          moltype = DNA  length = 93
```

```
FEATURE                 Location/Qualifiers
source                  1..93
                        mol_type = other DNA
                        organism = synthetic construct
SEQUENCE: 27
ggagtcgctg cgcgctgcct tcgccccgtg ccccgctccg ccgccgcctc gcgccgcccg  60
ccccggctct gactgaccgc gttactccca cag                               93

SEQ ID NO: 28           moltype = DNA  length = 43
FEATURE                 Location/Qualifiers
source                  1..43
                        mol_type = other DNA
                        organism = synthetic construct
SEQUENCE: 28
gtgagcgggc gggacggccc ttctcctccg ggctgtaatt agc                    43

SEQ ID NO: 29           moltype = DNA  length = 92
FEATURE                 Location/Qualifiers
source                  1..92
                        mol_type = other DNA
                        organism = synthetic construct
SEQUENCE: 29
aagaggtaag ggtttaaggg atggttggtt ggtggggtat taatgtttaa ttacctggag  60
cacctgcctg aaatcacttt ttttcaggtt gg                                92

SEQ ID NO: 30           moltype = DNA  length = 10
FEATURE                 Location/Qualifiers
source                  1..10
                        mol_type = other DNA
                        organism = synthetic construct
SEQUENCE: 30
gccaccatgg                                                         10

SEQ ID NO: 31           moltype = DNA  length = 586
FEATURE                 Location/Qualifiers
source                  1..586
                        mol_type = other DNA
                        organism = synthetic construct
SEQUENCE: 31
tcaacctctg gattacaaaa tttgtgaaag attgactggt attcttaact atgttgctcc  60
ttttacgcta tgtggatacg ctgctttaat gcctttgtat catgctattg cttcccgtat  120
ggctttcatt ttctcctcct tgtataaatc ctggttgctg tctctttatg aggagttgtg  180
gcccgttgtc aggcaacgtg gcgtggtgtg cactgtgttt gctgacgcaa cccccactgg  240
ttggggcatt gccaccacct gtcagctcct ttccgggact ttcgctttcc ccctccctat  300
tgccacggcg gaactcatcg ccgcctgcct tgcccgctgc tggacagggg ctcggctgtt  360
gggcactgac aattccgtgg tgttgtcggg gaaatcatcg tcctttcctt ggctgctcgc  420
ctgtgttgcc acctggattc tgcgcgggac gtccttctgc tacgtccctt cggccctcaa  480
tccagcggac cttccttccc gcggcctgct gccggctctg cggcctcttc cgcgtcttcg  540
ccttcgccct cagacgagtc ggatctccct ttgggccgcc tccccg                 586

SEQ ID NO: 32           moltype = DNA  length = 816
FEATURE                 Location/Qualifiers
source                  1..816
                        mol_type = other DNA
                        organism = synthetic construct
SEQUENCE: 32
atgagccata ttcaacggga aacgtcttgc tctaggccgc gattaaattc caacatggat  60
gctgatttat atgggtataa atgggctcgc gataatgtcg ggcaatcagg tgcgacaatc  120
tatcgattgt atgggaagcc cgatgcgcca gagttgtttc tgaaacatgg caaaggtagc  180
gttgccaatg atgttacaga tgagatggtc agactaaact ggctgacgga atttatgcct  240
cttccgacca tcaagcattt tatccgtact cctgatgatg catggttact caccactgcg  300
atccctggga aaacagcatt ccaggtatta gaagaatatc ctgattcagg tgaaaatatt  360
gttgatgcgc tggcagtgtt cctgcgccgg ttgcattcga ttcctgtttg taattgtcct  420
tttaacagcg atcgcgtatt tcgtctcgct caggcgcaat cacgaatgaa taacggtttg  480
gttgatgcga gtgattttga tgacgagcgt aatggctggc ctgttgaaca agtctggaaa  540
gaaatgcata aacttttgcc attctcaccg gattcagtcg tcactcatgg tgatttctca  600
cttgataacc ttatttttga cgaggggaaa ttaataggtt gtattgatgt tggacgagtc  660
ggaatcgcag accgatacca ggatcttgcc atcctatgga actgcctcgg tgagttttct  720
ccttcattac agaaacggct tttcaaaaa tatggtattg ataatcctga tatgaataaa   780
ttgcagtttc atttgatgct cgatgagttt ttctaa                            816

SEQ ID NO: 33           moltype = DNA  length = 29
FEATURE                 Location/Qualifiers
source                  1..29
                        mol_type = other DNA
                        organism = synthetic construct
SEQUENCE: 33
ttcaaatatg tatccgctca tgagacaat                                    29
```

```
SEQ ID NO: 34          moltype = DNA  length = 105
FEATURE                Location/Qualifiers
source                 1..105
                       mol_type = other DNA
                       organism = synthetic construct
SEQUENCE: 34
cgcggaaccc ctatttgttt atttttctaa atacattcaa atatgtatcc gctcatgaga  60
caataaccct gataaatgct tcaataatat tgaaaaagga agagt                  105

SEQ ID NO: 35          moltype = DNA  length = 732
FEATURE                Location/Qualifiers
source                 1..732
                       mol_type = other DNA
                       organism = synthetic construct
SEQUENCE: 35
catctgattc aacaatgaca gaccgatctc ttatgggctt ggcacacacc atctgcgcat  60
tataaacgtc tgcaaagacc aaggtttgat atgttgattt tactgtcagc cttaagagtg  120
cgacatctgc taatttagtg taataataca attagtagac cctttaaaac aagtcccttg  180
gcttggaaca acgccaggct cctcaacagg caactttgct acttctacag aaaatgataa  240
taaagaaatg ctggtgaagt caaatgctta tcacaatggt gaactactca gcagggaggc  300
tctaataggc gccaagagcc tagacttcct taagcgccag agtccacaag ggcccagtta  360
atcctcaaca ttcaaatgct gcccacaaaa ccagcccctc tgtgccctag ccgcctcttt  420
tttccaagtg acagtagaac tccaccaatc cgcagctgaa tggggtccgc ctcttttccc  480
tgcctaaaca gacaggaact cctgccaatt gagggcgtca ccgctaaggc tccgccccag  540
cctgggctcc acaaccaatg aagggtaatc tcgacaaaga gcaaggggtg gggcgcgggc  600
gcgcaggtgc agcagcacac aggctggtcg ggagggcggg gcgcgacgtc tgccgtgcgg  660
ggtcccggca tcggttgcgc gcgcgctccc tcctctcgga gagagggctg tggtaaaacc  720
cgtccggaaa at                                                      732

SEQ ID NO: 36          moltype = DNA  length = 449
FEATURE                Location/Qualifiers
source                 1..449
                       mol_type = other DNA
                       organism = synthetic construct
SEQUENCE: 36
agtgcaagtg ggttttagga ccaggatgag gcggggtggg ggtgcctacc tgacgaccga  60
ccccgaccca ctggacaagc acccaacccc cattccccaa attgcgcatc ccctatcaga  120
gagggggagg ggaaacagga tgcggcgagg cgcgtgcgca ctgccagctt cagcaccgcg  180
gacagtgcct tcgcccccgc ctggcggcgc gcgccaccgc cgcctcagca ctgaaggcgc  240
gctgacgtca ctcgccggtc ccccgcaaac tcccctcccc ggccaccttg gtcgcgtccg  300
cgccgccgcc ggcccagccg gaccgcacca cgcgaggcgc gagatagggg ggcacgggcg  360
cgaccatctg cgctgcggcg ccggcgactc agcgctgcct cagtctgcgg tgggcagcgg  420
aggagtcgtg tcgtgcctga gagcgcagt                                    449

SEQ ID NO: 37          moltype = DNA  length = 1785
FEATURE                Location/Qualifiers
source                 1..1785
                       mol_type = other DNA
                       organism = synthetic construct
SEQUENCE: 37
atggaggagc tggtggtgga agtgcggggc tccaatggcg ctttctacaa ggcatttgta  60
aaggatgttc atgaagattc aataacagtt gcatttgaaa acaactggca gcctgatagg  120
cagattccat ttcatgatgt cagattccca cctcctgtag gttataataa agatataaat  180
gaaagtgatg aagttgaggt gtattccaga gcaaatgaaa aagagccttg ctgttggtgg  240
ttagctaaag tgaggatgat aaagggtgag ttttatgtga tagaatatgc agcatgtgat  300
gcaacttaca atgaaattgt cacaattgaa cgtctaagat ctgttaatcc caacaaacct  360
gccacaaaag atactttcca taagatcaag ctggatgtgc cagaagactt acggcaaatg  420
tgtgccaaag aggcggcaca taaggatttt aaaaaggcag ttggtgcctt ttctgtaact  480
tatgatccag aaaattatca gcttgtcatt ttgtccatca atgaagtcac ctcaaagcga  540
gcacatatgc tgattgacat gcactttcgg agtctgcgca ctaagttgtc tctgataatg  600
agaaatgaag aagctagtaa gcagctggag agttcaaggc agcttgcctc gagatttcat  660
gaacagttta tcgtaagaga agatctgatg ggtctagcta ttggtactca tggtgctaat  720
attcagcaag ctagaaaagt acctggggtc actgctattg atctagatga agatacctgc  780
acatttcata tttatggaga ggatcaggat gcagtgaaaa aagctagaag ctttctcgaa  840
tttgctgaag atgtaataca agttccaagg aacttagtag gcaaagtaat aggaaaaaat  900
ggaaagctga ttcaggagat tgtggacaag tcaggagttg tgagggtgag gattgaggct  960
gaaaatgaga aaaatgttcc acaagaagag gaaattatgc caccaaattc ccttccttcc  1020
aataattcaa gggttggacc taatgcccca gaagaaaaaa aacatttaga tataaaggaa  1080
aacagcaccc atttttctca acctaacagt acaaaagtcc agaggggtat ggtaccattt  1140
gtttttgtgg gaacaaagga cagcatcgct aatgccactg ttcttttgga ttatcacctg  1200
aactatttaa aggaagtaga ccagttgcgt ttggagagat tacaaattga tgagcagttg  1260
cgacagattg gagctagttc tagaccacca ccaaatcgta cagataagga aaaaagctat  1320
gtgactgatg atggtcaagg aatgggtcga ggtagtagac cttacagaaa tagggggcac  1380
ggcagacgcg gtcctggata tacttcagga actaattctg aagcatcaaa tgcttctgaa  1440
acagaatctg accacagaga cgaactcagt gattggtcat tagctccaac agaggaagag  1500
agggagagct tcctgcgcag aggagacgga cggcggcgtg gagggggagg aagaggacaa  1560
ggaggaagag gacgtggagg aggcttcaaa ggaaacgacg atcactcccg aacagataat  1620
cgtccacgta atccaagaga ggctaaagga agaacaacag atggatccct tcagaatacc  1680
tccagtgaag gtagtcggct gcgcacgggt aaagatcgta accagaagaa agagaagcca  1740
```

-continued

```
gacagcgtgg atggtcagca accactcgtg aatggagtac cctaa                1785

SEQ ID NO: 38          moltype = AA  length = 594
FEATURE                Location/Qualifiers
source                 1..594
                       mol_type = protein
                       organism = Homo sapiens
SEQUENCE: 38
MEELVVEVRG SNGAFYKAFV KDVHEDSITV AFENNWQPDR QIPFHDVRFP PPVGYNKDIN  60
ESDEVEVYSR ANEKEPCCWW LAKVRMIKGE FYVIEYAACD ATYNEIVTIE RLRSVNPNKP  120
ATKDTFHKIK LDVPEDLRQM CAKEAAHKDF KKAVGAFSVT YDPENYQLVI LSINEVTSKR  180
AHMLIDMHFR SLRTKLSLIM RNEEASKQLE SSRQLASRFH EQFIVREDLM GLAIGTHGAN  240
IQQARKVPGV TAIDLDEDTC TFHIYGEDQD AVKKARSFLE FAEDVIQVPR NLVGKVIGKN  300
GKLIQEIVDK SGVVRVRIEA ENEKNVPQEE EIMPPNSLPS NNSRVGPNAP EEKKHLDIKE  360
NSTHFSQPNS TKVQRGMVPF VFVGTKDSIA NATVLLDYHL NYLKEVDQLR LERLQIDEQL  420
RQIGASSRPP PNRTDKEKSY VTDDGQGMGR GSRPYRNRGH GRRGPGYTSG TNSEASNASE  480
TESDHRDELS DWSLAPTEEE RESFLRRGDG RRRGGGGRGQ GGRGRGGGFK GNDDHSRTDN  540
RPRNPREAKG RTTDGSLQNT SSEGSRLRTG KDRNQKKEKP DSVDGQQPLV NGVP        594

SEQ ID NO: 39          moltype = DNA  length = 67
FEATURE                Location/Qualifiers
source                 1..67
                       mol_type = other DNA
                       organism = synthetic construct
SEQUENCE: 39
agaggagacg gacggcggcg tggaggggga ggaagaggac aaggaggaag aggacgtgga  60
ggaggct                                                            67
```

TRANSGENE CASSETTE DESIGNED TO EXPRESS THE HUMAN CODON-OPTIMIZED GENE FMR1

CROSS-REFERENCE TO RELATED APPLICATIONS

The present application is a 371 of International Application No. PCT/US2023/061459, filed Jan. 27, 2023, which claims the benefit of U.S. Provisional Application No. 63/267,236, filed Jan. 28, 2022, the entireties of which are incorporated herein by reference.

INCORPORATION-BY-REFERENCE OF SEQUENCE LISTING

The Sequence Listing XML associated with this application is provided electronically in XML file format and is hereby incorporated by reference into the specification. The name of the XML file containing the Sequence Listing XML is "TAYS-025_001WO_SeqList_ST26". The XML file is 64,081 bytes, created on Jan. 20, 2023, and is being submitted electronically via USPTO Patent Center.

BACKGROUND

Fragile X syndrome ("FXS") is caused by a mutation or mutations in the FMR1 gene, resulting in a Fragile X mental retardation protein (FMRP) protein deficiency. The most common form of single gene inherited intellectual disability and co-morbid autism. A mutation in an FMR1 gene occurs where a DNA segment, known as the CGG triplet repeat, is expanded. Normally, this DNA segment is repeated from 5 to about 40 times. In people with FXS, however, the CGG segment is repeated more than 200 times. The abnormally expanded CGG segment inactivates (silences) the FMR1 gene, which prevents the gene from producing the FMRP protein. Although FXS is typically caused by an expansion of the CGG triplet repeat in FMR1, many different FMR1 mutation types and sequence variations leading to FXS have been reported including missense, nonsense, splicing error, and deletion mutations. The X-linked dominant condition in both male and female children is inherited from carrier parents.

FMRP is an RNA binding protein and it carries mRNAs to the synapse where it typically inhibits translation until stimulation occurs and then it allows translation. In the absence of FMRP there is wide-spread dysregulation of protein production throughout the CNS. FMRP regulates the translation of hundreds of proteins and they include many of the proteins also associated with autism when they are mutated including Neuroligins 3 and 4, Neurorexins, SHANK3, amyloid precursor protein (APP), Arc, MAPKinase, CYFIP 1 and 2 and many more.

There are currently no approved disease-specific treatments available for patients suffering from FXS syndrome. Management of the condition is limited to symptomatic intervention to treat learning disabilities, anxiety, and mood disorders. There remains a need in the art for an effective treatment that targets the cause of the disease, i.e., FMR1 gene mutations.

SUMMARY

The present disclosure is based, in part, on the development of codon-optimized FMR1 genes, expression cassettes, and vectors capable of providing therapeutic levels of FMR1 expression for treating disorders associated with defective FMR1 expression such as FXS syndrome.

Thus, one aspect of the disclosure relates to a polynucleotide comprising a human FMR1 open reading frame, wherein the nucleotide sequence of FMR1 has been codon optimized and has been depleted of CpG dinucleotides for expression in human cells.

A further aspect of the disclosure relates to expression cassettes comprising one or more polynucleotides comprising a human FMR1 open reading frame and vectors, transformed cells, and transgenic animals comprising polynucleotides disclosed herein.

Another aspect of the disclosure relates to a pharmaceutical formulation comprising polynucleotides, expression cassettes, vectors, and/or transformed cells as described herein in a pharmaceutically acceptable carrier.

An additional aspect relates to a method of expressing an FMR1 open reading frame in a cell, comprising contacting the cell with a polynucleotide, expression cassette, and/or vector described herein, thereby expressing an FMR1 open reading frame in the cell.

A further aspect relates to a method of expressing an FMR1 open reading frame in a subject, comprising delivering to the subject the polynucleotide, expression cassette, vector, and/or transformed cell, thereby expressing the FMR1 open reading frame in the subject.

An additional aspect relates to a method of treating a disorder associated with aberrant expression of an FMR1 gene or aberrant activity of an FMR1 gene product in a subject in need thereof, comprising delivering to the subject a therapeutically effective amount of the polynucleotide, expression cassette, vector, and/or transformed cell, thereby treating the disorder associated with aberrant expression of the FMR1 gene in the subject. Another aspect relates to a polynucleotide, expression cassette, vector, and/or transformed cell for use in a method of treating a disorder associated with aberrant expression of an FMR1 gene or aberrant activity of an FMR1 gene product in a subject in need thereof.

Therefore, the methods and compositions described herein can overcome shortcomings in the art by providing a codon-optimized FMR1 coding sequence, expression cassettes, and vectors capable of providing therapeutic levels of FMR1 expression for treating disorders associated with FMR1 expression such as FXS syndrome.

BRIEF DESCRIPTION OF THE DRAWINGS

FIGS. 4A, 4F, 4K), Albumin (ALB; FIGS. 4E, 4J, 4O) are shown in each group. Statistics Ordinary one-way ANOVA $*p<0.05$ FIGS. 5A and 5B show representative images from each group. FIGS. 5C-5E show hFMR1 Iso17 opt mRNA expression in the JeT-FMR1/AAV (FIG. 5C), MeP229-FMR1/AAV (FIG. 5D), and pFMR1-FMR1/AAV (FIG. 5E) groups. Statistics: 2way ANOVA *p<0.05, *p<0.005, *p<0.001, *p<0.0001. Data are shown as mean SEM FIGS. 6A-6**I show results of safety behavior tests to assess anxiety of in wild-type mice.

FIG. 8A shows a western blot of the relative molecular weight of FMRP expressed from the scAAV-JeT-hFMR1iso17 vector co-migrates with the most highly expressed FMRP isoform(s) in the brainstem of the 1-month-old mouse. FIGS. 8B-8E are representative images of FMRP expression in brains of wild-type injected with vehicle and Fmr1 KO mice injected with either vehicle or the scAAV-JeT-hFMR1iso17 vector at PND2-3, and collected at 1 month (FIG. 8B), 3 months (FIG. 8C), or 6 months (FIG. 8D) post-injection. Expression of FMRP from the scAAV-JeT-hFMR1iso17 vector was present in the cerebral cortex, hippocampus, inferior and superior colliculus, thalamus, cerebellum, and brainstem. Scale bars=1 mm. FIG. 8E shows a higher magnification image of KO+FMRP brain in (FIG. 8E), showing extensive staining in the Purkinje and granule cell layers of the cerebellum, and in the brainstem. Scale bar=1 mm.

FIGS. 9A-9E show serum analyses at 6 months. FIG. 9A: blood urea nitrogen (BUN), FIG. 9B: aspartate aminotransferase (AST), FIG. 9C: albumin (ALB), FIG. 9D: total bilirubin (TBIL). FIG. 9E shows percentage of hematoxylin and eosin-stained histological liver samples showing an immune response. There was no indication of abnormal serum levels or liver immune responses from the scAAV-JeT-hFMR1iso17 vector at 6 months post-injection. Bars=mean±SEM; dotted lines=combined 95% male/female reference ranges for C57BL/6 mice 8-10 weeks (Charles River, 2012). n-values (all but AST): WT+vehicle=10; KO+vehicle=10; KO+FMRP=11. n-values (AST, samples with high hemolysis excluded): WT+vehicle=6; KO+vehicle=3; KO+FMRP=7.

FIG. 11A illustrates that both WT+vehicle and KO+FMRP mice had significantly lower incidence of seizure during the audiogenic seizure test, relative to KO+vehicle mice, although KO+FMRP mice showed higher incidence of seizures relative to WT+vehicle mice. Both WT+vehicle and KO+FMRP mice had significantly lower total seizure time (FIG. 11B) and seizure score (FIG. 11C) during audiogenic seizure test relative to KO+vehicle mice, indicating a rescue in seizure severity. n-values: WT+vehicle=25; KO+vehicle=23; KO+FMRP=16. *p<0.05, p<0.01, *p<0.001. Seizure incidence: bars=mean±SEM; Fisher's Exact Test. Seizure time: bars=mean+/−SEM, ANOVA, Tukey's post hoc test. Seizure level; bars=median+/−95% CI, Kruskal-Wallis, Dunn's post hoc test.

FIG. 12A is a schematic of the fear-conditioning protocol. FIGS. 12B-12D show results from the fear conditioning test. No differences were found among genotypes or treatments in response to the conditioned context (FIG. 12B. context A) or a novel context (FIG. 12C. context B). KO+vehicle mice froze significantly more than both WT+vehicle and KO+FMRP mice in the first 30 sec. of exposure to the conditioned stimulus (FIG. 12D). This effect remained after correcting for inherent freezing activity on a per-animal basis (Cond Stim—context B), and KO+vehicle mice also demonstrated a significant higher rate in freezing relative to WT+FMRP mice during the 90-120 sec interval of exposure to the conditioned tone (FIG. 12E). All mice were females. n-values: WT+vehicle=27; KO+vehicle=19; KO+FMRP=14. Bars=mean±SEM. *p<0.05 for one-way ANOVA and Tukey's post hoc test comparing percentage of time frozen between KO+vehicle mice and both WT+vehicle and KO+FMRP mice. #=p<0.05 for one-way ANOVA and Tukey's post hoc test comparing percentage of time frozen between KO+vehicle mice and WT+vehicle mice.

FIGS. 14A and 14B show locomotor activity in the initial 3 hours after being placed in the activity recording apparatus. The KO+vehicle group exhibited hyperactivity which was reduced in the KO+FMRP groups: 2nd hour in the male mice (FIG. 14A) and 3rd hour in the female mice (FIG. 14B). FIGS. 14C and 14D show locomotor activity in the light phase during 3 days of recording. In the male mice, FMRP treatment reduced hyperactivity observed in the 1st and 2nd day compared to the KO+vehicle mice (FIG. 14C). In the female mice, a similar trend was observed in the 1st day but the increase in activity in the KO+vehicle group was not statistically significant (FIG. 14D). FIGS. 14E and 14F show the percent of time sleeping during the light phase. The KO+vehicle and KO+FMRP groups showed significant reductions in sleep in the male mice (FIG. 14E). In the female mice, KO+vehicle group showed significant reduction in the 1st day which was reversed in the KO+FMRP group (FIG. 14F). # and $ denote statistically significant differences ($p<0.05$) among the three treatment groups using two-way repeated measures ANOVA by treatment and by treatment×time, respectively. * denotes statistically significant differences ($p<0.05$) between treatment groups using post hoc Tukey's multiple comparison test. WT+vehicle, n=14 males and 10 females; KO+vehicle, n=14 males and 11 females; KO+FMRP, n=12 males and 10 females.

FIGS. 15A and 15B show FMRP expression scores (mean SEM) correlate with circadian locomotor activity in the light phase (FIG. 15A) and sleep time (FIG. 15B) in the KO+FMRP group (male and female combined). R2 refers to goodness of fit by simple linear regression and P-value refers to whether the slope is significantly non-zero using the F-test. Number of mice with FMRP expression score equals to 0 (n=4), 0.5 (n=5), 1 (n=4), 1.5 (n=1), 2 (n=5), 2.5 (n=3). FIGS. 15C and 15D show that the KO+FMRP group were significantly different from the KO+vehicle group in light phase activity (FIG. 15C) and sleep time (FIG. 15D) during the 1st and 2nd day of recording after mice with no FMRP expression in the KO+FMRP group were excluded from analysis (male and female combined). # and $ denote statistically significant differences ($p<0.05$) among the three treatment groups using two-way repeated measures ANOVA by treatment and by treatment×time, respectively. * denotes statistically significant differences ($p<0.05$) between treatment groups using post hoc Tukey's multiple comparison test. WT+vehicle, n=24; KO+vehicle, n=31; KO+FMRP, n=13.

FIG. 16A shows EEG frequency band comparison between the three treatment groups. FIG. 16B shows a comparison of slow wave power spectrum revealed a significant decrease in the 2-3 Hz delta frequency range in the KO+vehicle group compared to the WT+vehicle group. This deficit was rescued in the KO+FMRP group. +, ^, > represent statistically significant difference ($p<0.05$) between the WT+vehicle and KO+vehicle groups, the WT+vehicle and KO+FMRP groups, and the KO+vehicle and KO+FMRP groups, respectively. FIG. 16C shows a 3D scatterplot of PC1, PC2 and PC3 scores of male mice that underwent both circadian locomotor activity and EEG recording. The FMRP expression score for each mouse in the KO+FMRP group is shown next to each data point.

DETAILED DESCRIPTION

Figure 1:
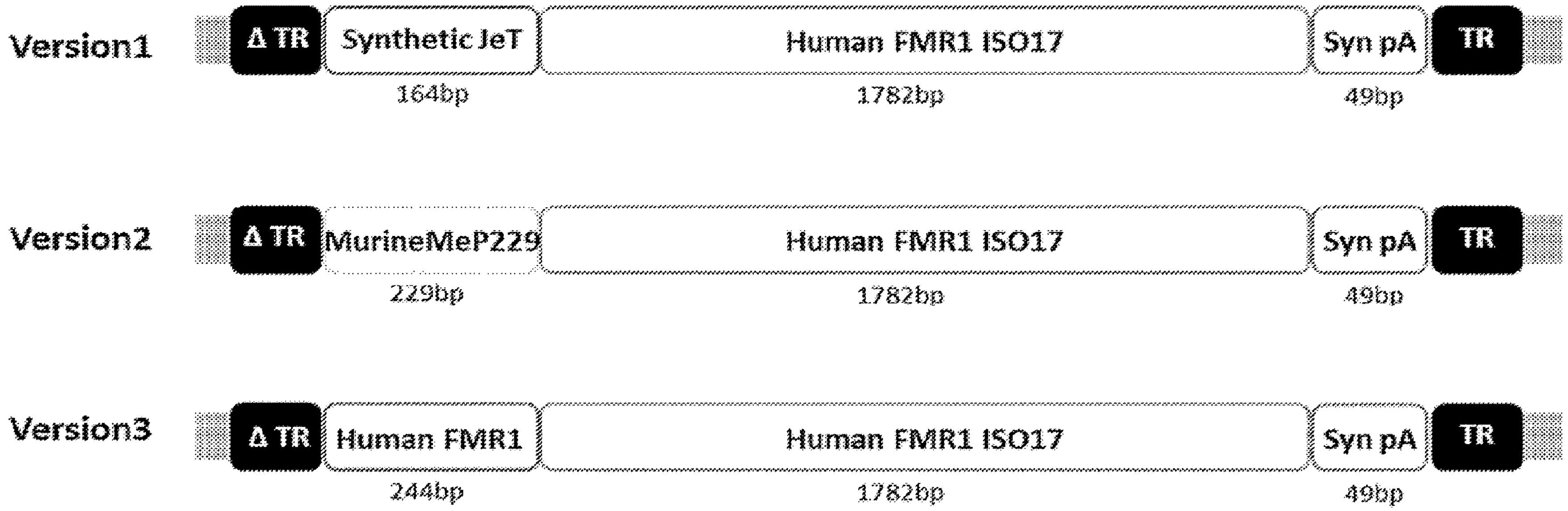
FIG. 1 is a representation of the AAV9-FMR1 vectors.

The present disclosure provides, inter alia, isolated polynucleotides, recombinant adeno-associated virus (rAAV) vectors, and rAAV viral vectors comprising transgene nucleic acid molecules comprising nucleic acid sequences encoding for FMRP polypeptides. The present disclosure also provides methods of manufacturing these isolated polynucleotides, rAAV vectors, and rAAV viral vectors, as well as their use to deliver transgenes to treat or prevent a disease or disorder, including diseases associated with loss, misfunction and/or deficiency of an FMR1 gene.

The term "adeno-associated virus" or "AAV" as used herein refers to a member of the class of viruses associated with this name and belonging to the genus Dependoparvovirus, family Parvoviridae. Adeno-associated virus is a single-stranded DNA virus that grows in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. See, for example, Blacklowe, 1988, pp. 165-174 of Parvoviruses and Human Disease, J. R. Pattison, ed.; and Rose, Comprehensive Virology 3:1-61 (1974). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control. Multiple serotypes of this virus are known to be suitable for gene delivery; all known serotypes can infect cells from various tissue types. At least 11 sequentially numbered AAV serotypes are known in the art. Non-limiting exemplary serotypes useful in the methods disclosed herein include any of the 11 serotypes, e.g., AAV2, AAV8, AAV9, or variant serotypes, e.g., AAV-DJ and AAV PHP.B. The AAV particle comprises, consists essentially of, or consists of three major viral proteins: VP1, VP2 and VP3. In some aspects, AAV refers to the serotype AAV1, AAV2, AAV4, AAV5, AAV6, AAV7, AAV8, AAV9, AAV10, AAV11, AAV12, AAV13, AAVPHP.B, AAVrh74, or AAVrh.10.

Exemplary adeno-associated viruses and recombinant adeno-associated viruses include, but are not limited to all serotypes (e.g., AAV1, AAV2, AAV3, AAV4, AAV5, AAV6, AAV7, AAV8, AAV9, AAV10, AAV11, AAV12, AAV13, AAVPHP.B, AAVrh74, and AAVrh.10). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03, AAV-KP-1 (described in detail in Kerun et al. JCI Insight, 2019; 4(22):e131610) and AAV-NP59 (described in detail in Paulk et al. Molecular Therapy, 2018; 26(1): 289-303).

AAV Structure and Function

AAV is a replication-deficient parvovirus, the single-stranded DNA genome of which is about 4.7 kb in length, including two 145-nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928. U.S. Pat. No. 9,434,928 also provides the sequences of the capsid proteins and a self-complementary genome. In one aspect, an AAV genome is a self-complementary genome. Cis-acting sequences directing viral DNA replication (rep), encapsidation/packaging, and host cell chromosome integration are contained within AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome.

The cap gene is expressed from the p40 promoter and encodes the three capsid proteins, VP1, VP2, and VP3. Alternative splicing and non-consensus translational start sites are responsible for the production of the three related capsid proteins. More specifically, after the single mRNA from which each of the VP1, VP2 and VP3 proteins are translated is transcribed, it can be spliced in two different manners: either a longer or shorter intron can be excised, resulting in the formation of two pools of mRNAs: a 2.3 kb- and a 2.6 kb-long mRNA pool. The longer intron is often preferred and thus the 2.3-kb-long mRNA can be called the major splice variant. This form lacks the first AUG codon, from which the synthesis of VP1 protein starts, resulting in a reduced overall level of VP1 protein synthesis. The first AUG codon that remains in the major splice variant is the initiation codon for the VP3 protein. However, upstream of that codon in the same open reading frame lies an ACG sequence (encoding threonine) which is surrounded by an optimal Kozak (translation initiation) context. This contributes to a low level of synthesis of the VP2 protein, which is actually the VP3 protein with additional N terminal residues, as is VP1, as described in Becerra S P et al., (December 1985). "Direct mapping of adeno-associated virus capsid proteins B and C: a possible ACG initiation codon". Proceedings of the National Academy of Sciences of the United States of America. 82 (23): 7919-23, Cassinotti P et al., (November 1988). "Organization of the adeno-associated virus (AAV) capsid gene: mapping of a minor spliced mRNA coding for virus capsid protein 1". Virology. 167 (1): 176-84, Muralidhar S et al., (January 1994). "Site-directed mutagenesis of adeno-associated virus type 2 structural protein initiation codons: effects on regulation of synthesis and biological activity". Journal of Virology. 68 (1): 170-6, and Trempe J P, Carter B J (September 1988). "Alternate mRNA splicing is required for synthesis of adeno-associated virus VP1 capsid protein". Journal of Virology. 62 (9): 3356-63, each of which is herein incorporated by reference. A single consensus polyA site is located at map position 95 of the AAV genome. The life cycle and genetics of AAV are reviewed in Muzyczka, Current Topics in Microbiology and Immunology, 158: 97-129 (1992).

Each VP1 protein contains a VP1 portion, a VP2 portion, and a VP3 portion. The VP1 portion is the N-terminal portion of the VP1 protein that is unique to the VP1 protein. The VP2 portion is the amino acid sequence present within the VP1 protein that is also found in the N-terminal portion of the VP2 protein. The VP3 portion and the VP3 protein have the same sequence. The VP3 portion is the C-terminal portion of the VP1 protein that is shared with the VP1 and VP2 proteins.

The VP3 protein can be further divided into discrete variable surface regions I-IX (VR-I-IX). Each of the variable surface regions (VRs) can comprise or contain specific amino acid sequences that either alone or in combination with the specific amino acid sequences of each of the other VRs can confer unique infection phenotypes (e.g., decreased antigenicity, improved transduction and/or tissue-specific tropism relative to other AAV serotypes) to a particular serotype as described in DiMatta et al., "Structural Insight into the Unique Properties of Adeno-Associated Virus Serotype 9" J. Virol., Vol. 86 (12): 6947-6958, June 2012, the contents of which are incorporated herein by reference.

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA to generate AAV vectors. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics. Recombinant AAV (rAAV) genomes comprise, consist essentially of, or consist of a nucleic acid molecule encoding a therapeutic protein (e.g., FMRP) and one or more AAV ITRs flanking the nucleic acid molecule. Production of pseudotyped rAAV is disclosed in, for example, WO2001083692. Other types of rAAV variants, for example rAAV with capsid mutations, are also contemplated. See, e.g., Marsic et al., Molecular Therapy, 22(11): 1900-1909 (2014). The nucleotide sequences of the genomes of various AAV serotypes are known in the art.

Isolated Polynucleotides Comprising Transgene Sequences

The present disclosure provides isolated polynucleotides comprising at least one transgene nucleic acid molecule.

In some aspects, a transgene nucleic acid molecule can comprise a nucleic acid sequence encoding an FMRP polypeptide, or at least one fragment thereof. In some aspects, a transgene nucleic acid molecule can comprise a nucleic acid sequence encoding a biological equivalent of an FMRP polypeptide. An AAV-FMRP vector is suitable for use in treating or preventing a Fragile X-associated disorder, such as FXS, in a subject in need thereof.

In an aspect an FMRP polypeptide can be an FMRP human isoform, such as human FMRP isoform 17 (SEQ ID NO:37, 38). Alternative splicing of the FMR1 gene is complex and results in at least 15 mRNA isoforms expressed in human and rodent cells and tissues. Based on mRNA expression experiments, isoform 1 is now known to be a relatively minor isoform. Isoforms lacking exon 12 (which contains part of the sequence for the RNA-binding K homology domain KH2) appear to constitute most of the FMR1 mRNAs in human brain tissue samples. The most highly transcribed of these exon-12-lacking isoforms are isoforms 7 and 17, with isoform 17 having the highest transcript levels. These two isoforms differ in the splicing of exon 17, where a 17 amino acid section is removed from isoform 17. This 17 amino acid region is involved in localizing FMRP to Cajal bodies in isoforms lacking exon 14 (e.g., isoform 6) and is not observed in the mouse or rat. Isoform 17 retains most of the functional domains of FMRP, including the Tudor domains, nuclear localization sequence, K homology domains, nuclear exit sequence, and the RGG domain. Being an evolutionarily conserved isoform, as well as having the most-dominant transcript levels in the brain, isoform 17 is a good candidate for a single isoform expressing the therapeutic vector for FXS treatment, although other isoforms can be used.

In some aspects, an FMRP polypeptide comprises, consists essentially of, or consists of an amino acid sequence at least 65%, 70%, 75%, 80%, 85%, 90%, 95%, 96%, 97%, 98%, 99% or 100% (or any percentage in between) identical to the amino acid sequence set forth in SEQ ID NO:4 or a fragment thereof. In some aspects, an FMRP polypeptide comprises, consists essentially of, or consists of an amino acid sequence at least 65%, 70%, 75%, 80%, 85%, 90%, 95%, 96%, 97%, 98%, 99% or 100% (or any percentage in between) identical to at least one portion of the amino acid sequence set forth in SEQ ID NO:4, or a fragment thereof. In some embodiments, the fragment is a functional fragment, e.g., a fragment that retains at least one function of wildtype FMR1.

In some aspects, a nucleic acid sequence encoding an FMRP polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequence set forth in SEQ ID NO: 1, 7, and 9.

In some aspects, the nucleic acid sequence encoding an FMRP polypeptide can be a codon optimized nucleic acid sequence that encodes for an FMRP polypeptide. A codon optimized nucleic acid sequence encoding an FMRP polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wildtype human nucleic acid sequence encoding the FMRP polypeptide. In one aspect there a region in the FMRP coding sequence that can be left in the natural state, that is, this region is not codon optimized. This region in shown in SEQ ID NO:39. This region is involved with trafficking the FMR1 mRNA. As used herein, the "wildtype human nucleic acid sequence encoding the FMRP polypeptide" refers to the nucleic acid sequence that encodes the FMRP polypeptide in a human genome. Exemplary wildtype human nucleic acid sequences encoding a FMRP peptide include NCBI Entrez Gene number 2332 The gene has about 35 transcripts (splice variants), about 204 orthologues, about 2 paralogues and is associated with about 11 phenotypes. An exemplary codon optimized sequence encoding FMR1 is set forth in SEQ ID NO:4.

In some aspects, a codon optimized nucleic acid sequence encoding an FMRP polypeptide, such as that set forth in SEQ ID NO:4, can comprise no donor splice sites. In some aspects, a codon optimized nucleic acid sequence encoding an FMRP polypeptide can comprise no more than about one, or about two, or about three, or about four, or about five, or about six, or about seven, or about eight, or about nine, or about ten donor splice sites. In some aspects, a codon optimized nucleic acid sequence encoding an FMRP polypeptide comprises at least one, or at least two, or at least three, or at least four, or at least five, or at least six, or at least seven, or at least eight, or at least nine, or at least ten fewer donor splice sites as compared to the wildtype human nucleic acid sequence encoding the FMRP polypeptide. Without wishing to be bound by theory, the removal of donor splice sites in the codon optimized nucleic acid sequence can unexpectedly and unpredictably increase expression of the FMRP polypeptide in vivo, as cryptic splicing is prevented. Moreover, cryptic splicing may vary between different subjects, meaning that the expression level of the FMRP polypeptide comprising donor splice sites may unpredictably vary between different subjects.

Codon-optimization can, in some aspects, enable clear discrimination of the transgene from the endogenous FMRP sequence by standard molecular methods, since the sequences are different. This provides an advantage in the development of drugs and detection in preclinical or clinical specimens. For example, detection of the transgene in biopsied tissue or in blood, feces, urine, saliva, or tears.

In some aspects, a codon optimized nucleic acid sequence encoding an FMRP polypeptide, such as that set forth in SEQ ID NO:4, can have a GC content that differs from the GC content of the wildtype human nucleic acid sequence encoding the FMRP polypeptide. In some aspects, the GC content of a codon optimized nucleic acid sequence encoding an FMR1polypeptide is more evenly distributed across the entire nucleic acid sequence, as compared to the wildtype human nucleic acid sequence encoding the FMRP polypeptide. Without wishing to be bound by theory, by more evenly distributing the GC content across the entire nucleic acid sequence, the codon optimized nucleic acid sequence exhibits a more uniform melting temperature ("Tm") across the length of the transcript. The uniformity of melting temperature results unexpectedly in increased expression of the codon optimized nucleic acid in a human subject, as transcription and/or translation of the nucleic acid sequence occurs with less stalling of the polymerase and/or ribosome.

Furthermore, in another aspect, a CG-depleted genome can be less immunogenic when delivered in vivo. This can lead to lower immunogenicity, increased safety, and enhanced transgene expression.

In some aspects, the codon optimized nucleic acid sequence encoding an FMRP polypeptide, such as that set forth in SEQ ID NO:4, exhibits at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence encoding an FMRP polypeptide.

In some aspects, a nucleic acid sequence encoding a FMRP polypeptide can have the number of CpG dinucleotides reduced by 1, 2, 3, 4, 5, 10 or more CpG dinucleotides. CpG nucleotides are located within regions of DNA where a cytosine nucleotide is followed by a guanine nucleotide in the linear sequence of bases along its 5'→3' direction. A nucleic acid sequence that encodes for a FMRP polypeptide but has had the number of CpG dinucleotides reduced is a CpG dinucleotide optimized FMR1 nucleic acid sequence. A CpG dinucleotide optimized FMR1 nucleic acid sequence can comprise, consist essentially of, or consist of a nucleic acid sequence that is no more than 65%, 70%, 75%, 80%, 85%, 90%, 95%, 96%, 97%, 98%, 99% (or any percentage in between) identical to a wildtype human nucleic acid sequence encoding a FMRP polypeptide. As used herein, a "wildtype human nucleic acid sequence encoding a FMRP polypeptide" refers to a nucleic acid sequence that encodes a healthy FMRP polypeptide in a human genome. An exemplary CpG dinucleotide optimized FMR1 nucleic acid sequence is set forth in SEQ ID NO:4.

In some aspects, a CpG dinucleotide optimized FMR1 nucleic acid sequence encoding a FMRP polypeptide, such as shown in SEQ ID NO:4, can comprise no donor splice sites. In some aspects, a CpG dinucleotide optimized FMR1 nucleic acid sequence encoding a FMRP polypeptide can comprise no more than about one, or about two, or about three, or about four, or about five, or about six, or about seven, or about eight, or about nine, or about ten donor splice sites. In some aspects, a CpG dinucleotide optimized FMR1 nucleic acid sequence encoding a FMRP polypeptide comprises at least one, or at least two, or at least three, or at least four, or at least five, or at least six, or at least seven, or at least eight, or at least nine, or at least ten fewer donor splice sites as compared to a wildtype human nucleic acid sequence encoding a FMRP polypeptide. Without wishing to be bound by theory, the removal of donor splice sites in the optimized nucleic acid sequence can unexpectedly and unpredictably increase expression of the FMRP polypeptide in vivo, as cryptic splicing is prevented. Moreover, cryptic splicing may vary between different subjects, meaning that the expression level of the FMRP polypeptide comprising donor splice sites may unpredictably vary between different subjects.

In some aspects, the CpG dinucleotide optimized FMR1 nucleic acid sequence encoding a FMRP polypeptide, such as shown SEQ ID NO:4, has increased potency and increased safety, because it reduces overexpression of the FMR1 gene.

In some aspects, an FMRP polypeptide can further comprise a protein tag. Without wishing to be bound by theory, the inclusion of a protein tag can allow for the detection and/or visualization of the exogenous FMRP polypeptide. As would be appreciated by the skilled artisan, non-limiting examples of protein tags include Myc tags, poly-histidine tags, FLAG-tags, HA-tags, SBP-tags or any other protein tag known in the art.

AAV Vectors

In some aspects, the isolated polynucleotides comprising at least one transgene nucleic acid molecule described herein can be a recombinant AAV (rAAV) vector.

As used herein, the term "vector" refers to a nucleic acid comprising, consisting essentially of, or consisting of an intact replicon such that the vector may be replicated when placed within a cell, for example by a process of transfection, infection, or transformation. A vector can comprise a signal peptide or signal polypeptide. It is understood in the art that once inside a cell, a vector may replicate as an extrachromosomal (episomal) element or may be integrated into a host cell chromosome. Vectors may include nucleic acids derived from retroviruses, adenoviruses, herpesvirus, baculoviruses, modified baculoviruses, papovaviruses, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising, consisting essentially of, or consisting of DNA condensed with cationic polymers such as heterogeneous polylysine, defined-length oligopeptides, and polyethyleneimine, in some cases contained in liposomes; and the use of ternary complexes comprising, consisting essentially of, or consisting of a virus and polylysine-DNA.

With respect to general recombinant techniques, vectors that contain both a promoter and a cloning site into which a polynucleotide can be operatively linked are well known in the art. Such vectors are capable of transcribing RNA in vitro or in vivo and are commercially available from sources such as Agilent Technologies (Santa Clara, Calif) and Promega Biotech (Madison, Wis.). In order to optimize expression and/or in vitro transcription, it may be necessary to remove, add or alter 5' and/or 3' untranslated portions of cloned transgenes to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

An "rAAV vector" as used herein refers to a vector comprising, consisting essentially of, or consisting of one or more transgene nucleic acid molecules and one or more AAV inverted terminal repeat sequences (ITRs). Such AAV vectors can be replicated and packaged into infectious viral particles when present in a host cell that provides the functionality of rep and cap gene products; for example, by transfection of the host cell. In some aspects, AAV vectors contain a promoter, at least one nucleic acid that may encode at least one protein or RNA, and/or an enhancer and/or a terminator within the flanking ITRs that is packaged into the infectious AAV particle. The encapsidated nucleic acid portion may be referred to as the AAV vector genome. Plasmids containing rAAV vectors may also contain elements for manufacturing purposes, e.g., antibiotic resistance genes, origin of replication sequences etc., but these are not encapsidated and thus do not form part of the AAV particle.

In some aspects, an rAAV vector can comprise at least one transgene nucleic acid molecule. In some aspects, an rAAV vector can comprise at least one AAV inverted terminal (ITR) sequence. In some aspects, an rAAV vector can comprise at least one promoter sequence. In some aspects, an rAAV vector can comprise at least one enhancer sequence. In some aspects, an rAAV vector can comprise at least one polyA sequence. In some aspects, an rAAV vector can comprise a RepCap sequence.

In some aspects, an rAAV vector can comprise a first AAV ITR sequence, a promoter sequence, a transgene nucleic acid molecule and a second AAV ITR sequence. In some aspects, an rAAV vector can comprise, in the 5' to 3' direction, a first AAV ITR sequence, a promoter sequence, a transgene nucleic acid molecule and a second AAV ITR sequence.

In some aspects, an rAAV vector can comprise a first AAV ITR sequence, a promoter sequence, a transgene nucleic acid molecule, a polyA sequence and a second AAV ITR sequence. In some aspects, an rAAV vector can comprise, in the 5' to 3' direction, a first AAV ITR sequence, a promoter sequence, a transgene nucleic acid molecule, a polyA sequence and a second AAV ITR sequence.

In some aspects, an rAAV vector can comprise more than one transgene nucleic acid molecule. In some aspects, an rAAV vector can comprise at least two transgene nucleic acid molecules, such that the rAAV vector comprises a first transgene nucleic acid molecule and an at least second transgene nucleic acid molecule. In some aspects, the first and the at least second transgene nucleic acid molecule can comprise the same nucleic acid sequence. In some aspects, the first and the at least second transgene nucleic acid molecules can comprise different nucleic acid sequences. In some aspects, the first and the at least second transgene nucleic acid sequences can be adjacent to each other.

In some aspects, an rAAV vector can comprise more than one promoter sequence. In some aspects, an rAAV vector can comprise at least two promoter sequences, such that the rAAV vector comprises a first promoter sequence and an at least second promoter sequence. In some aspects, the first and the at least second promoter sequences can comprise the same sequence. In some aspects, the first and the at least second promoter sequences can comprise different sequences. In some aspects, the first and the at least second promoter sequences can be adjacent to each other. In some aspects wherein an rAAV vector also comprises a first transgene nucleic acid molecule and an at least second transgene nucleic acid molecule, the first promoter can be located upstream (5') of the first transgene nucleic acid molecule and the at least second promoter can be located between the first transgene nucleic acid molecule and the at least second transgene nucleic acid molecule, such that the at least second promoter is downstream (3') of the first transgene nucleic acid molecule and upstream (5') of the at least second transgene nucleic acid molecule.

Any of the preceding rAAV vectors can further comprise at least one enhancer. The at least one enhancer can be located anywhere in the rAAV vector. In some aspects, the at least one enhancer can be located immediately upstream (5') of a promoter. Thus, an rAAV vector can comprise, in the 5' to 3' direction, a first AAV ITR sequence, an enhancer, a promoter sequence, a transgene nucleic acid molecule, a polyA sequence, and a second AAV ITR sequence. In some aspects, the at least one enhancer can be located immediately downstream (3') of a promoter. Thus, an rAAV vector can comprise, in the 5' to 3' direction, a first AAV ITR sequence, a promoter sequence, an enhancer, a transgene nucleic acid molecule, a polyA sequence, and a second AAV ITR sequence. In some aspects, the at least one enhancer can be located immediately downstream of a transgene nucleic acid molecule. Thus, an rAAV vector can comprise, in the 5' to 3' direction, a first AAV ITR sequence, a promoter sequence, a transgene nucleic acid molecule, an enhancer, a polyA sequence, and a second AAV ITR sequence.

AAV ITR Sequences

In some aspects, an AAV ITR sequence can comprise any AAV ITR sequence known in the art. In some aspects, an AAV ITR sequence can be an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence or an AAVrh.10 ITR sequence.

Thus, in some aspects, an AAV ITR sequence can comprise, consist essentially of, or consist of an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence, or an AAVrh.10 ITR sequence. In some embodiments, an AAV ITR sequence is a wildtype AAV ITR sequence. In some embodiments, an AAV ITR sequence is modified (e.g., mutated) AAV ITR sequence. In some embodiments, an rAAV vector described herein comprises one mutated AAV ITR and one wildtype AAV ITR.

In some aspects, an AAV ITR can comprise consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in any one of SEQ ID NOs:2 or 6.

In some aspects, an AAV ITR can comprise consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:2 or 6-14.

In some aspects, an AAV ITR can comprise consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:2, or 6-19.

In some aspects, an rAAV provided herein comprises a first and a second AAV ITR sequence, wherein the first AAV ITR sequence comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:2 and the second AAV ITR sequence comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:6.

Promoter Sequence and Enhancers

The term "promoter" and "promoter sequence" as used herein means a control sequence that is a region of a polynucleotide sequence at which the initiation and rate of transcription of a coding sequence, such as a gene or a transgene, are controlled. Promoters can be constitutive, inducible, repressible, or tissue-specific, for example. Promoters can contain genetic elements at which regulatory proteins and molecules such as RNA polymerase and transcription factors may bind. Non-limiting exemplary promoters include Rous sarcoma virus (RSV) LTR promoter (optionally with the RSV enhancer), a cytomegalovirus (CMV) promoter, an SV40 promoter, a dihydrofolate reductase promoter, a β-actin promoter, a phosphoglycerol kinase (PGK) promoter, a U6 promoter, a synapsin promoter, an H1 promoter, a hybrid chicken beta-actin (CBA) promoter, a ubiquitous chicken β-actin hybrid (CBh) promoter, a small nuclear RNA (U1a or U1b) promoter, an MECP2 promoter, an MeP418 promoter, an MeP426 promoter, a human variant of the MeP426 promoter, a minimal MECP2 promoter, a VMD2 promoter, an mRho promoter, or an EF1 promoter.

Additional non-limiting exemplary promoters provided herein include, but are not limited to EFla, Ubc, human β-actin, CAG, TRE, Ac5, Polyhedrin, CaMKIIa, Gall, TEF1, GDS, ADH1, Ubi, and α-1-antitrypsin (hAAT). Nucleotide sequences of promoters can be modified to increase or decrease the efficiency of mRNA transcription. For example, the TATA box of 7SK, U6 and H1 promoters can be modified to abolish RNA polymerase III transcription and stimulate RNA polymerase II-dependent mRNA transcription. Synthetically-derived promoters can be used for ubiquitous or tissue specific expression. Furthermore, virus-derived promoters, some of which are noted above, can be useful in the methods disclosed herein, e.g., CMV, HIV, adenovirus, and AAV promoters. In some aspects, a promoter is used together with at least one enhancer to increase the transcription efficiency. Non-limiting examples of enhancers include an interstitial retinoid-binding protein (IRBP) enhancer, an RSV enhancer or a CMV enhancer.

In some aspects, a promoter sequence can comprise, consist essentially of, or consist of a Rous sarcoma virus (RSV) LTR promoter sequence (optionally with the RSV enhancer), a cytomegalovirus (CMV) promoter sequence, an SV40 promoter sequence, a dihydrofolate reductase promoter sequence, a JeT promoter sequence (SEQ ID NO:3), a MeP229 promoter (SEQ ID NO:8), a pFMR1 (244) promoter (SEQ ID NO:10), a β-actin promoter sequence, a phosphoglycerol kinase (PGK) promoter sequence, a U6 promoter sequence (SEQ ID NO:22), synapsin I promoter (SEQ ID NO:23), synapsin II promoter (SEQ ID NO:24), an H1 promoter sequence, a hybrid chicken beta-actin (CBA) promoter sequence (SEQ ID NO:25), a ubiquitous chicken β-actin hybrid (CBh) promoter sequence (SEQ ID NO:21), a shortened synapsin promoter (hSyn) (SEQ ID NO:36) a small nuclear RNA (U1a or U1b) promoter sequence, an MECP2 promoter sequence, an MeP418 promoter, an MeP426 promoter sequence, a small ubiquitous promoter sequence (also known as a Jet+I promoter sequence (SEQ ID NO:20)MECP2 promoter sequence, a VMD2 promoter sequence, an mRho promoter sequence, an EFI promoter sequence, an EFla promoter sequence, a Ubc promoter sequence, a human β-actin promoter sequence, a CAG promoter sequence, a TRE promoter sequence, an Ac5 promoter sequence, a Polyhedrin promoter sequence, a CaMKIIa promoter sequence, a Gall promoter sequence, a TEF1 promoter sequence, a GDS promoter sequence, an ADH1 promoter sequence, a Ubi promoter sequence, a MeP426 promoter, or an α-1-antitrypsin (hAAT) promoter sequence.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) or synthetic techniques such that transcription of that gene is directed by the linked enhancer/promoter. Non-limiting examples of linked enhancer/promoter for use in the methods, compositions and constructs provided herein include a PDE promoter plus IRBP enhancer or a CMV enhancer plus U1a promoter. It is understood in the art that enhancers can operate from a distance and irrespective of their orientation relative to the location of an endogenous or heterologous promoter. It is thus further understood that an enhancer operating at a distance from a promoter is thus "operably linked" to that promoter irrespective of its location in the vector or its orientation relative to the location of the promoter.

As used throughout the disclosure, the term "operably linked" refers to the expression of a gene (i.e. a transgene) that is under the control of a promoter with which it is spatially connected. A promoter can be positioned 5' (upstream) or 3' (downstream) of a gene under its control. A promoter can be positioned 5'(upstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

In some aspects, a promoter sequence can comprise, consist essentially of, or consist of a JeT promoter sequence (e.g., SEQ ID NO:3). A JeT promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:3.

In some aspects, a promoter sequence can comprise, consist essentially of, or consist of a JeT+I promoter sequence. A Jet+I promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:20.

In some aspects, a promoter sequence can comprise, consist essentially of, or consist of a hybrid chicken β-actin promoter sequence. A hybrid chicken β-actin promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:21.

A hybrid chicken β-actin promoter sequence can comprise a CMV sequence (e.g., SEQ ID NO:26), a chicken β-actin promoter sequence, a chicken β-actin exon 1 sequence (e.g., SEQ ID NO:27), a chicken β-actin intron 1 sequence (e.g., SEQ ID NO:28), a minute virus of mice (MVM) intron sequence (e.g., SEQ ID NO:29), or any combination thereof. In some aspects, a hybrid chicken β-actin promoter sequence can comprise, in the 5' to 3' direction, a CMV sequence (e.g., SEQ ID NO:26), a chicken β-actin promoter sequence, chicken β-actin exon 1 sequence, a chicken β-actin intron 1 sequence and a minute virus of mice (MVM) intron sequence.

In some aspects, a CMV sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:26. The β-actin exon 1 sequence may comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:27. The chicken β-actin intron 1 sequence may comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:28. The MVM intron sequence may comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:29.

In some aspects, a promoter sequence can comprise, consist essentially of, or consist of a U6 promoter sequence. A U6 promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:22.

In some aspects, a promoter sequence can comprise a shortened version of a synapsin promoter sequence (hSyn promoter) (SEQ ID NO:36) or a rat MeCP2 promoter SEQ ID NO:35. The Hampson Lab has previously published on AAV9-Fmr1 mouse isoform 1 using a short version of the synapsin promoter (SEQ ID NO:36), and also on the rat version of human isoform 17 using a version of the rat MeCP2 promoter (SEQ ID NO:35). A synapsin promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:23. A synapsin promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO:24.

Transgene Nucleic Acid Molecules

Transgene nucleic acid molecules can comprise, consist essentially of, or consist of any of the transgene nucleic acid molecules described above under the heading "isolated polynucleotides comprising transgene sequences".

In some aspects, a transgene nucleic acid molecule present in an rAAV vector can be under transcriptional control of a promoter sequence also present in the same rAAV vector.

polyA Sequences

In some aspects, a polyadenylation (polyA) sequence can comprise any polyA sequence known in the art. The polyA sequence may be a synthetic polyA sequence or a polyA sequence derived from a naturally occurring protein. Non-limiting examples of polyA sequences include, but are not limited to, an MECP2 polyA sequence, a retinol dehydrogenase 1 (RDH1) polyA sequence, a bovine growth hormone (BGH) polyA sequence, an SV40 polyA sequence (e.g., SEQ ID NO:5), a SPA49 polyA sequence, a sNRP-TK65 polyA sequence, a sNRP polyA sequence, or a TK65 polyA sequence.

Thus, a polyA sequence can comprise, consist essentially of, or consist of an MeCP2 polyA sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

In some aspects, a polyA sequence can comprise, consist essentially of, or consist of an SV40 pA sequence. In some aspects, an SV40 pA sequence can comprise, consist essentially of, or consist of a nucleic acid sequence at least 65%, 70%, 75%, 80%, 85%, 90%, 95%, 96%, 97%, 98%, 99% or 100% (or any percentage in between) identical the sequence set forth in SEQ ID NO:5.

In certain embodiments, an rAAV vector disclosed herein comprises a Kozak sequence. In some aspects, an Kozak sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the sequence set forth in SEQ ID NO:30.

In certain embodiments, an rAAV vector disclosed herein comprises a Woodchuck Hepatitis Virus (WHV) Posttranscriptional Regulatory Element (WPRE). In some aspects, a WPRE sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the sequence set forth in SEQ ID NO:31.

In certain embodiments, an rAAV vector described herein comprises, in 5' to 3' order, a first AAV2 ITR of SEQ ID NO:2; a Jet promoter of SEQ ID NO:3; a codon-optimized hsaFMR1Iso17opt sequence of SEQ ID NO:4; an SV40 polyA sequence of SEQ ID NO:5; and a second AAV2 ITR of SEQ ID NO:6.

In certain embodiments, an rAAV vector described herein comprises, in 5' to 3' order, a first AAV2 ITR of SEQ ID NO:2; a MeP229 promoter of SEQ ID NO:8; a codon-optimized hsaFMR1Iso17opt sequence of SEQ ID NO:4; an SV40 polyA sequence of SEQ ID NO:5; and a second AAV2 ITR of SEQ ID NO:6.

In certain embodiments, an rAAV vector described herein comprises, in 5' to 3' order, a first AAV2 ITR of SEQ ID NO:2; a pFMR1(244) promoter of SEQ ID NO: 10; a codon-optimized hsaFMR1Iso17opt sequence of SEQ ID NO:4; an SV40 polyA sequence of SEQ ID NO:5; and a second AAV2 ITR of SEQ ID NO:6.

Bacterial Plasmids

In some aspects, the rAAV vectors of the present disclosure can be contained within a bacterial plasmid to allow for propagation of the rAAV vector in vitro. Thus, the present disclosure provides bacterial plasmids comprising any of the rAAV vectors described herein. A bacterial plasmid can further comprise an origin of replication sequence. A bacterial plasmid can further comprise an antibiotic resistance gene. A bacterial plasmid can further comprise a resistance gene promoter. A bacterial plasmid can further comprise a prokaryotic promoter. In some aspects, a bacterial plasmid of the present disclosure can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the nucleic acid sequence put forth in SEQ ID NOs:1, 7, or 9.

Origin of Replication Sequence

In some aspects, an origin of replication sequence can comprise, consist essentially of, or consist of any origin of replication sequence known in the art. The origin of replication sequence can be a bacterial origin of replication sequence, thereby allowing the rAAV vector comprising said bacterial origin of replication sequence to be produced, propagated and maintained in bacteria, using methods standard in the art.

Antibiotic Resistance Genes

In some aspects, bacterial plasmids, rAAV vectors and/or rAAV viral vectors of the disclosure can comprise an antibiotic resistance gene.

In some aspects, an antibiotic resistance gene can comprise, consist essentially of, or consist of any antibiotic resistance genes known in the art. Examples of antibiotic resistance genes known in the art include, but are not limited to kanamycin resistance genes, spectinomycin resistance genes, streptomycin resistance genes, ampicillin resistance genes, carbenicillin resistance genes, bleomycin resistance genes, erythromycin resistance genes, polymyxin B resistance genes, tetracycline resistance genes and chloramphenicol resistance genes.

In some aspects, an antibiotic resistance gene can be a kanamycin resistance gene. In some aspects, a kanamycin resistance gene can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the nucleic acid sequence put forth in SEQ ID NO:32.

Resistance Gene Promoter

In some aspects, bacterial plasmids, rAAV vectors and/or rAAV viral vectors of the disclosure can comprise a resistance gene promoter. In some aspects, a resistance gene promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the nucleic acid sequence put forth in SEQ ID NO:33.

AAV Viral Vectors

A "viral vector" is defined as a recombinantly produced virus or viral particle that contains a polynucleotide to be delivered into a host cell, either in vivo, ex vivo or in vitro. Examples of viral vectors include retroviral vectors, AAV vectors, lentiviral vectors, adenovirus vectors, alphavirus vectors and the like. Alphavirus vectors, such as Semliki Forest virus-based vectors and Sindbis virus-based vectors, have also been developed for use in gene therapy and immunotherapy. See, e.g., Schlesinger and Dubensky (1999) Curr. Opin. Biotechnol. 5:434-439 and Ying, et al. (1999) Nat. Med. 5(7):823-827.

An "AAV virion" or "AAV viral particle" or "AAV viral vector" or "rAAV viral vector" or "AAV vector particle" or "AAV particle" refers to a viral particle composed of at least one AAV capsid protein and an encapsidated polynucleotide rAAV vector. Thus, production of an rAAV viral vector necessarily includes production of an rAAV vector, as such a vector is contained within an rAAV vector.

As used herein, the term "viral capsid" or "capsid" refers to the proteinaceous shell or coat of a viral particle. Capsids function to encapsidate, protect, transport, and release into the host cell a viral genome. Capsids are generally comprised of oligomeric structural subunits of protein ("capsid proteins"). As used herein, the term "encapsidated" means enclosed within a viral capsid. The viral capsid of AAV is composed of a mixture of three viral capsid proteins: VP1, VP2, and VP3. The mixture of VP1, VP2 and VP3 contains 60 monomers that are arranged in a T=1 icosahedral symmetry in a ratio of 1:1:10 (VP1:VP2:VP3) or 1:1:20 (VP1:VP2:VP3) as described in Sonntag F et al., (June 2010). "A viral assembly factor promotes AAV2 capsid formation in the nucleolus". Proceedings of the National Academy of Sciences of the United States of America. 107 (22): 10220-5, and Rabinowitz J E, Samulski R J (December 2000). "Building a better vector: the manipulation of AAV virions". Virology. 278 (2): 301-8, each of which is incorporated herein by reference in its entirety.

The present disclosure provides an rAAV viral vector comprising: a) any of the rAAV vectors described herein, or complement thereof; and b) an AAV capsid protein.

The present disclosure provides an rAAV viral vector comprising: a) any of the rAAV vectors described herein; and b) an AAV capsid protein.

An AAV capsid protein can be any AAV capsid protein known in the art. An AAV capsid protein can be an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

Alternative rAAV Vector and rAAV Viral Vector Embodiments

1. A recombinant adeno-associated virus (rAAV) vector comprising in 5' to 3' direction:
   a) a first AAV ITR sequence;
   b) a promoter sequence;
   c) a transgene nucleic acid molecule, wherein the transgene nucleic acid molecule comprises a nucleic acid sequence encoding an FMRP polypeptide;
   d) a polyA sequence; and
   e) a second AAV ITR sequence.
2. The rAAV vector of embodiment 1, wherein the transgene nucleic acid molecule comprises the nucleic acid sequence set forth in SEQ ID NO:4.
3. The rAAV vector of embodiment 1, wherein the vector comprises SEQ ID NO: 1, 7, or 9.
4. The rAAV vector of any one of the preceding embodiments, wherein the transgene nucleic acid sequence encoding for an FMRP polypeptide exhibits at least 5%, at least 10%, at least 20%, at least 30%, at least 50%, at least 75%, at least 100%, at least 200%, at least 300%, at least 500%, or at least 1000% increased expression in a human subject relative to a mutated FMR1 nucleic acid sequence.
5. The rAAV vector of any one of the preceding embodiments, wherein the first AAV ITR sequence comprises the nucleic acid sequence set forth in SEQ ID NO:2.
6. The rAAV vector of any one of the preceding embodiments, wherein the second AAV ITR sequence comprises the nucleic acid sequence set forth in SEQ ID NO:6.
7. The rAAV vector of any one of the preceding embodiments, wherein the promoter sequence comprises a Rous sarcoma virus (RSV) LTR promoter (optionally with an RSV enhancer), a cytomegalovirus (CMV) promoter, an SV40 promoter, a dihydrofolate reductase promoter, a beta-actin promoter, a phosphoglycerol kinase (PGK) promoter, a U6 promoter, a JetI promoter, an H1 promoter, a CAG promoter, a hybrid chicken beta-actin (CBA) promoter, an MeCP2 promoter, an EF1 promoter, a ubiquitous chicken β-actin hybrid (CBh) promoter, a U1a promoter, a U1b promoter, an MeCP2 promoter, an MeP418 promoter, an MeP426 promoter, a minimal MeCP2 promoter, a VMD2 promoter, an mRho promoter, EFla promoter, Ubc promoter, human β-actin promoter, a synapsin (hSyn) promoter sequence, TRE promoter, Ac5 promoter, Polyhedrin promoter, CaMKIIa promoter, Gall promoter, TEF1 promoter, GDS promoter, ADH1 promoter, Ubi promoter, or α-1-antitrypsin (hAAT) promoter.
8. The rAAV vector of any one of the preceding embodiments, wherein the promoter sequence comprises the nucleic acid sequence set forth in SEQ ID NO:3, 8, 10, 35, or 36.
9. The rAAV vector of any one of the preceding embodiments, wherein the polyA sequence comprises the nucleic acid sequence set forth in SEQ ID NO:5.
10. An rAAV vector of any one of the preceding embodiments, comprising, in the 5' to 3' direction:

a) a first AAV ITR sequence comprising the nucleic acid sequence set forth in SEQ ID NO:2;

b) a promoter sequence comprising the nucleic acid sequence set forth in SEQ ID NO:3, 7, 10, 35, or 36;

c) a transgene nucleic acid molecule, wherein the transgene nucleic acid molecule comprises a nucleic acid sequence encoding for an FMRP polypeptide, wherein the nucleic acid sequence encoding for an FMRP polypeptide comprises the nucleic acid sequence set forth in SEQ ID NO:4;

d) a polyA sequence comprising the nucleic acid sequence set forth in SEQ ID NO:5; and e) a second AAV ITR sequence comprising the nucleic acid sequence set forth in SEQ ID NO:6.

11. An rAAV viral vector comprising:

(i) an AAV capsid protein; and (ii) an rAAV vector of any one of the preceding embodiments.

12. The rAAV viral vector of embodiment 11, wherein the AAV capsid protein is an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

13. The rAAV viral vector of embodiment 12, wherein the AAV capsid protein is an AAV9 capsid protein.

14. A pharmaceutical composition comprising:

a) the rAAV viral vector of any one of embodiments 11-13; and at least one pharmaceutically acceptable excipient and/or additive.

15. A method for treating a subject having a disease and/or disorder involving an FMR1 gene, the method comprising administering to the subject at least one therapeutically effective amount of the rAAV viral vector of any one of embodiments 11-13 or the pharmaceutical composition of embodiment 14.

16. The method of embodiment 15, wherein the disease and/or disorder involving an FMR1 gene is Fragile X syndrome.

17. The method of claim embodiment 15 or embodiment 16, wherein the rAAV viral vector or the pharmaceutical composition is administered to the subject at a dose ranging from about $10^{11}$ to about $10^{18}$ viral vector particles.

18. The method of embodiment 17, wherein the rAAV viral vector or the pharmaceutical composition is administered to the subject at a dose ranging from about $10^{13}$ to about $10^{16}$ viral vector particles.

19. The method of any one of embodiments 15-18, wherein the rAAV viral vector or the pharmaceutical composition is administered to the subject intravenously, intrathecally, intracisterna-magna, intracerebrally, intraventricularly, intranasally, intratrache ally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve.

20. The method of embodiment 19, wherein the rAAV viral vector or pharmaceutical composition is administered intrathecally.

21. The method of embodiment 19, wherein the rAAV viral vector or pharmaceutical composition is administered intracisternal-magna.

22. The rAAV viral vector of any one of embodiments 11-13 or the pharmaceutical composition of embodiment 14 for use in treating a disease and/or disorder involving an FMR1 gene in a subject in need thereof.

23. The use of embodiment 22, wherein the disease and/or disorder involving an FMR1 gene is FXS, a FMR1 premutation with or without Fragile X-associated tremor/ataxia, or X-related Premature Ovarian Insufficiency.

24. The use of embodiment 22 or embodiment 23, wherein the rAAV viral vector or the pharmaceutical composition is for administration to the subject at a dose ranging from about $10^{11}$ to about $10^{18}$ viral vector particles.

25. The use of any of embodiments 22-24, wherein the rAAV viral vector or the pharmaceutical composition is for administration to the subject at a dose ranging from about $10^{13}$ to about $10^{16}$ viral vector particles.

26. The use of any one of embodiments 22-25, wherein the rAAV viral vector or the pharmaceutical composition is for administration to the subject intravenously, intrathecally, intracisterna-magna, intracerebrally, intraventricularly, intranasally, intratrache ally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve.

27. The use of embodiment 26, wherein the rAAV viral vector or pharmaceutical composition is for administration intrathecally.

28. The use of embodiment 26, wherein the rAAV viral vector or pharmaceutical composition is for administration intracisterna-magna.

Compositions and Pharmaceutical Compositions

The present disclosure provides compositions comprising any of the isolated polynucleotides, rAAV vectors, and/or rAAV viral vectors described herein. In some aspects, the compositions can be pharmaceutical compositions. Accordingly, the present disclosure provides pharmaceutical compositions comprising any of the isolated polynucleotides, rAAV vectors, and/or rAAV viral vectors described herein.

The pharmaceutical composition, as described herein, may be formulated by any methods known or developed in the art of pharmacology, which include but are not limited to contacting the active ingredients (e.g., viral particles or recombinant vectors) with an excipient and/or additive and/or other accessory ingredient, dividing or packaging the product to a dose unit. The viral particles of this disclosure may be formulated with desirable features, e.g., increased stability, increased cell transfection, sustained or delayed release, biodistributions or tropisms, modulated or enhanced translation of encoded protein in vivo, and the release profile of encoded protein in vivo.

As such, the pharmaceutical composition may further comprise saline, lipidoids, liposomes, lipid nanoparticles, polymers, lipoplexes, core-shell nanoparticles, peptides, proteins, cells transfected with viral vectors (e.g., for transplantation into a subject), nanoparticle mimics or combinations thereof. In some aspects, the pharmaceutical composition is formulated as a nanoparticle. In some aspects, the nanoparticle is a self-assembled nucleic acid nanoparticle.

A pharmaceutical composition in accordance with the present disclosure may be prepared, packaged, and/or sold in bulk, as a single unit dose, and/or as a plurality of single unit doses. The amount of the active ingredient is generally equal to the dosage of the active ingredient which would be administered to a subject and/or a convenient fraction of such a dosage such as, for example, one-half or one-third of such a dosage. The formulations can include one or more excipients and/or additives, each in an amount that together increases the stability of the viral vector, increases cell transfection or transduction by the viral vector, increases the expression of viral vector encoded protein, and/or alters the release profile of viral vector encoded proteins. In some aspects, the pharmaceutical composition comprises an excipient and/or additive. Non limiting examples of excipients and/or additives include solvents, dispersion media, diluents, or other liquid vehicles, dispersion or suspension aids, surface active agents, isotonic agents, thickening or emulsifying agents, preservatives, or combination thereof.

In some aspects, the pharmaceutical composition comprises a cryoprotectant. The term “cryoprotectant” refers to an agent capable of reducing or eliminating damage to a substance during freezing. Non-limiting examples of cryoprotectants include sucrose, trehalose, lactose, glycerol, dextrose, raffinose and/or mannitol.

As used herein, the term “pharmaceutically acceptable carrier” encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington’s Pharm. Sci., 15th Ed. (Mack Publ. Co., Easton).

In some aspects, a pharmaceutical composition of the present disclosure can comprise phosphate-buffered saline (PBS), D-sorbitol or any combination thereof.

In some aspects, a pharmaceutical composition can comprise PBS, wherein the PBS is present at a concentration of about 100 mM to about 500 mM, or about 200 mM to about 400 mM, or about 300 mM to about 400 mM. In some aspects, the sodium chloride can be present at a concentration of about 350 mM.

In some aspects, a pharmaceutical composition can comprise D-sorbitol, wherein the D-sorbitol is present at a concentration of about 1% to about 10%, or about 2.5% to about 7.5%. In some aspects, the D-sorbitol can be present at a concentration of about 5%.

Thus, the present disclosure provides a pharmaceutical composition comprising an rAAV vector and/or rAAV viral vector of the present disclosure in a 350 mM phosphate-buffered saline solution comprising D-sorbitol at a concentration of 5%.

Methods of Using the Compositions of the Disclosure

The present disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In one aspect, the subject is a mammal. The subject can be human.

This disclosure provides methods of preventing or treating a disease and/or disorder, comprising, consisting essentially of, or consisting of administering to a subject a therapeutically effective amount of any one of the rAAV vectors, rAAV viral vectors, compositions and/or pharmaceutical compositions disclosed herein.

In some aspects, the disease and/or disorder can be a genetic disorder involving the FMR1 gene. A genetic disorder involving the FMR1 gene can be FMR1 loss, misfunction and/or deficiency. Genetic disorders involving the FMR1 gene include, but are not limited to, FXS Syndrome, FXS Premutation, Fragile X-associated Tremor/Ataxia Syndrome (FXTAS) and Fragile X-related Premature Ovarian Insufficiency (POI).

In some aspects, the disease can be a disorder involving the FMRP protein. A genetic disorder involving an FMRP protein can be FMR1 loss, misfunction and/or deficiency.

In some aspects, a disease can be a disease that is characterized by the loss-of-function of at least one copy of the FMR1 gene in the genome of a subject. In some aspects, a disease can be a disease that is characterized by a decrease in function of at least one copy of the FMR1 gene in the genome of a subject. In some aspects, a disease can be a disease that is characterized by at least one mutation in at least one mutation in at least one copy of the FMR1 gene in the genome of the subject.

A subject in the methods provided herein can be deficient in FMR1. As used herein, “FMR1 deficiency” means that a subject can have one or more mutations in the FMR1 gene or lacks a functional FMR1 gene. As used herein, “FMR1 deficiency” means that a subject can have one or more mutations in the FMR1 gene or lacks a functional FMR1 protein.

A mutation in an FMR1 gene or FMRP protein can be any type of mutation that is known in the art. Non-limiting examples of mutations include somatic mutations, single nucleotide variants (SNVs), nonsense mutations, insertions, deletions, duplications, frameshift mutations, repeat expansions, short insertions and deletions (INDELs), long INDELs, alternative splicing, the products of alternative splicing, altered initiation of translation, the products of altered initiation of translation, proteomic cleavage, the products of proteomic cleavage. Many cases of Fragile X are due to expansion of CGG trinucleotides in the FMR1 promoter or a mutation in an FMR1 gene, which leads to silencing of FMR1 expression. These CGG expansions are not within the FMR1 gene coding sequence. Therefore, a mutation in an FMR1 gene includes expansion of CGG trinucleotides in the FMR1 promoter.

In some aspects, a disease can be a disease that is characterized by a decrease in expression of the FMR1 gene in a subject as compared to a control subject that does not have the disease. In some aspects, the decrease in expression can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the amount of FMR1 protein in a subject as compared to a control subject that does not have the disease. In some aspects, the decrease in the amount of FMR1 protein can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the activity of FMRP protein in a subject as compared to a control subject that does not have the disease. In some aspects, the decrease in the activity of FMR1 protein can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

Methods of treatment can alleviate one or more symptoms of a disease and/or disorder described herein. In an embodiment, delivery of compositions described herein can prevent or delay development of detectable symptoms, if administered to a subject carrying a mutation in the FMR1 gene before symptoms become detectable. Therefore, treatment can be therapeutic or prophylactic. Therapy refers to inhibition or reversal of established symptoms or phenotype. Therapy can also mean delay of onset of symptoms or phenotype. Prophylaxis means inhibiting or preventing development of symptoms in subjects not already displaying overt symptoms. Subjects not displaying overt symptoms can be identified early in life as carrying a loss of function mutation in the FMR1 gene by appropriate genetic testing performed before 18 months, 12 months, or 6 months of age.

A subject to be treated using the methods, compositions, pharmaceutical compositions, rAAV vectors or rAAV viral vectors of the present disclosure can have any of the diseases and/or symptoms described herein.

In some aspects, a subject can be less than 0.5 years of age, or less than 1 year of age, or less than 1.5 years of age, or less than 2 years of age, or at less than 2.5 years of age, or less than 3 years of age, or less than 3.5 years of age, or less than 3.5 years of age, or less than 4 years of age, or less than 4.5 years of age, or less than 5 years of age, or less than 5.5 years of age, or less than 6 years of age, or less than 6.5 years of age, or less than 7 years of age, or less than 7.5 years of age, or less than 8 years of age, or less than 8.5 years of age, or less than 9 years of age, or less than 9.5 years of age, or less than 10 years of age. In some aspects the subject can be less than 11 years of age, less than 12 years of age, less than 13 years of age, less than 14 years of age, less than 15 years of age, less than 20 years of age, less than 30 years of age, less than 40 years of age, less than 50 years of age, less than 60 years of age, less than 70 years of age, less than 80 years of age, less than 90 years of age, less than 100 years of age, less than 110 years of age, or less than 120 years of age. In some aspects, a subject can be less than 0.5 years of age. In some aspects, a subject can be less than 4 years of age. In some aspects, a subject can be less than 10 years of age.

The methods of treatment and prevention disclosed herein may be combined with appropriate diagnostic techniques to identify and select patients for the therapy or prevention.

The disclosure provides methods of increasing the level of a protein in a host cell, comprising contacting the host cell with any one of the rAAV viral vectors disclosed herein, wherein the rAAV viral vectors comprises any one of the rAAV vectors disclosed herein, comprising a transgene nucleic acid molecule encoding the protein. In some aspects, the protein is a therapeutic protein. In some aspects, the host cell is in vitro, in vivo, or ex vivo. In some aspects, the host cell is derived from a subject. In some aspects, the subject suffers from a disorder, which results in a reduced level and/or functionality of the protein, as compared to the level and/or functionality of the protein in a normal subject.

In some aspects, the level of the protein is increased to level of about $1\times10^{-7}$ ng, about $3\times10^{-7}$ ng, about $5\times10^{-7}$ ng, about $7\times10^{-7}$ ng, about $9\times10^{-7}$ ng, about $1\times10^{-6}$ ng, about $2\times10^{-6}$ ng, about $3\times10^{-6}$ ng, about $4\times10^{-6}$ ng, about $6\times10^{-6}$ ng, about $7\times10^{-6}$ ng, about $8\times10^{-6}$ ng, about $9\times10^{-6}$ ng, about $10\times10^{-6}$ ng, about $12\times10^{-6}$ ng, about $14\times10^{-6}$ ng, about $16\times10^{-6}$ ng, about $18\times10^{-6}$ ng, about $20\times10^{-6}$ ng, about $25\times10^{-6}$ ng, about $30\times10^{-6}$ ng, about $35\times10^{-6}$ ng, about $40\times10^{-6}$ ng, about $45\times10^{-6}$ ng, about $50\times10^{-6}$ ng, about $55\times10^{-6}$ ng, about $60\times10^{-6}$ ng, about $65\times10^{-6}$ ng, about $70\times10^{-6}$ ng, about $75\times10^{-6}$ ng, about $80\times10^{-6}$ ng, about $85\times10^{-6}$ ng, about $90\times10^{-6}$ ng, about $95\times10^{-6}$ ng, about $10\times10^{-5}$ ng, about $20\times10^{-5}$ ng, about $30\times10^{-5}$ ng, about $40\times10^{-5}$ ng, about $50\times10^{-5}$ ng, about $60\times10^{-5}$ ng, about $70\times10^{-5}$ ng, about $80\times10^{-5}$ ng, or about $90\times10^{-5}$ ng in the host cell.

The expression levels of a gene (e.g., FMR1) or a protein (e.g., FMRP) may be determined by any suitable method known in the art or described herein. Protein levels may be determined, for example, by western Blotting, immunohistochemistry and flow cytometry. Gene expression may be determined, for example, by quantitative PCR, gene sequencing, and RNA sequencing.

The disclosure provides methods of introducing a gene of interest to a cell in a subject comprising contacting the cell with an effective amount of any one of the rAAV viral vectors disclosed herein, wherein the rAAV viral vectors contain any one of the rAAV vectors disclosed herein, comprising the gene of interest.

In some aspects of the methods of the present disclosure, a subject can also be administered a prophylactic immunosuppressant treatment regimen in addition to being administered an rAAV vector or rAAV viral vector of the present disclosure. In some aspects, an immunosuppressant treatment regimen can comprise administering at least one immunosuppressive therapeutic. Non limiting examples of immunosuppressive therapeutics include, but are not limited to, Sirolimus (rapamycin), acetaminophen, diphenhydramine, IV methylprednisolone, prednisone, or any combination thereof. An immunosuppressive therapeutic can be administered prior to the day of administration of the rAAV vector and/or rAAV viral vector, on the same day as the administration of the rAAV vector and/or rAAV viral vector, or any day following the administration of the rAAV vector and/or rAAV viral vector.

A "subject" of diagnosis or treatment is a cell or an animal such as a mammal, or a human. The terms "subject" and "patient" are used interchangeably herein. A subject is not limited to a specific species and includes non-human animals subject to diagnosis or treatment and those subject to infections or animal models, including, without limitation, simian, murine, rat, canine, or leporid species, as well as other livestock, sport animals, or pets. In some aspects, the subject is a human. In some embodiments, the subject is a human child, e.g., a child of less than five years of age. In some embodiments, the subject is a human newborn, e.g., a newborn of less than one month, less than two months, less than three months, or less than four months of age.

As used herein, "treating" or "treatment" of a disease in a subject refers to (1) inhibiting the disease or arresting its development; or (2) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In some embodiments, the symptom is a symptom of fragile X syndrome FXS), e.g., speech impediments, learning disabilities, anxiety, depression, seizures, or sleep problems. In some embodiments, the symptom is a symptom of X-related Premature Ovarian Insufficiency.

As used herein, "preventing" or "prevention" of a disease refers to preventing the symptoms or disease from occurring in a subject that is predisposed or does not yet display symptoms of the disease.

In some aspects, the effective amount will depend on the size and nature of the application in question. It will also depend on the nature and sensitivity of the target subject and the methods in use. The skilled artisan will be able to determine the effective amount based on these and other considerations. The effective amount may comprise, consist essentially of, or consist of one or more administrations of a composition depending on the embodiment.

As used herein, the term "administer" or "administration" intends to mean delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and other animals, treating veterinarian.

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage may be impacted by the route of administration. Suitable dosage formulations and methods of administering the agents are known in the art. Non-limiting examples of such suitable dosages may be as low as $10^9$ vector genomes to as much as $10^{17}$ vector genomes per administration.

In some aspects of the methods described herein, the number of viral particles (e.g., rAAV viral vectors) administered to the subject ranges from about $10^9$ to about $10^{17}$. In some aspects, about $10^{10}$ to about $10^{12}$, about $10^{11}$ to about $10^{13}$, about $10^{11}$ to about $10^{12}$, about $10^{11}$ to about $10^{14}$, about $10^{12}$ to about $10^{16}$, about $10^{13}$ to about $10^{16}$, about $10^{14}$ to about $10^{15}$, about $5\times10^{11}$ to about $5\times10^{12}$, about $10^{11}$ to about $10^{18}$, about $10^{13}$ to about $10^{16}$, or about $10^{12}$ to about $10^{13}$ viral particles are administered to the subject.

In some aspects of the methods described herein, the number of viral particles (e.g., rAAV viral vectors) administered to the subject is at least about $10^{10}$, or at least about $10^{11}$, or at least about $10^{12}$, or at least about $10^{13}$, or at least about $10^{14}$, or at least about $10^{15}$, or at least about $10^{16}$, or at least about $10^{17}$ viral particles.

In some aspects of the methods described herein, the number of viral particles (e.g., rAAV viral vectors) administered to the subject can depend on the age of the subject. In non-limiting examples, a subject that is 7 years of age or older can be administered about $10\times10^{14}$ viral particles, a subject that is about 4 years of age to about 7 years of age can be administered about $10\times10^{14}$ viral particles, a subject that is about 3 years of age to about 4 years of age can be administered about $9\times10^{14}$ viral particles, a subject that is about 2 years of age to about 3 years of age can be about $8.2\times10^{14}$ viral particles, a subject that is about 1 year of age to about 2 years of age can be administered about $7.3\times10^{14}$ viral particles, a subject that is about 0.5 years of age to about 1 year of age can be administered about $4\times10^{14}$ viral particles, or a subject that is less than 0.5 years of age can be administered $3\times10^{14}$ viral particles.

In some aspects, the amounts of viral particles in a composition, pharmaceutical composition, or the amount of viral particles administered to a patient can calculated based on the percentage of viral particles that are predicted to contain viral genomes.

In some aspects, rAAV viral vectors of the present disclosure can be introduced to the subject intravenously, intrathecally (IT), intracisterna-magna (ICM) intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally; such introduction may also be intra-arterial, intracardiac, subventricular, epidural, intracerebral, intracerebroventricular, sub-retinal, intravitreal, intraarticular, intraperitoneal, intrauterine, intranerve or any combination thereof. In some aspects, the viral particles are delivered to a desired target tissue, e.g., to the lung, eye, or CNS, as non-limiting examples. In some aspects, delivery of viral particles is systemic. The intracisternal route of administration involves administration of a drug directly into the cerebrospinal fluid of the brain ventricles. It could be performed by direct injection into the cisterna magna or via a permanently positioned tube. In some aspects, the rAAV viral vectors of the present disclosure are administered intrathecally (IT). In some aspects, the rAAV viral vectors of the present disclosure are administered intracisterna-manga (ICM). In some aspects, the rAAV viral vectors of the present disclosure are administered into the cerebrospinal fluid (intra-cerebrospinal fluid).

In some aspects, the rAAV viral vectors of the present disclosure repair a gene deficiency in a subject. In some aspects, the ratio of repaired target polynucleotide or polypeptide to unrepaired target polynucleotide or polypeptide in a successfully treated cell, tissue, organ or subject is at least about 1.5:1, about 2:1, about 3:1, about 4:1, about 5:1, about 6:1, about 7:1, about 8:1, about 9:1, about 10:1, about 20:1, about 50:1, about 100:1, about 1000:1, about 10,000:1, about 100,000:1, or about 1,000,000:1. The amount or ratio of repaired target polynucleotide or polypeptide can be determined by any method known in the art, including but not limited to western blot, northern blot, Southern blot, PCR, sequencing, mass spectrometry, flow cytometry, immunohistochemistry, immunofluorescence, fluorescence in situ hybridization, next generation sequencing, immunoblot, and ELISA.

Administration of the rAAV vectors, rAAV viral vectors, compositions or pharmaceutical compositions of this disclosure can be effected in one dose, continuously or intermittently throughout the course of treatment. In some aspects, the rAAV vectors, rAAV viral vectors, compositions, or pharmaceutical compositions of this disclosure are parenterally administered by injection, infusion, or implantation.

In some embodiments, the subject is administered one single dose of a recombinant rAAV provided herein in its lifetime. In some embodiments, the subject is administered repeat doses of the recombinant rAAV provided herein. The form or serotype of rAAV can differ in subsequent doses versus the initial dose. These repeat doses may contain the same amount of rAAV particles or they may contain different amounts of rAAV particles. In some embodiments, the subject is administered repeat doses of the rAAV about every 6 months, about every 9 months, about every 12 months, about every 15 months, about every 18 months, about every 2 years, about every 3 years, about every 4 years, about every 5 years, about every 6 years, about every 7 years, about every 8 years, about every 9 years, or about every 10 years.

In some embodiments, administration of an rAAV vector described here results in increased expression of FMR1 protein in the brain of the subject. In some embodiments, administration of an rAAV vector described herein results in increased FMR1 protein expression in the cerebral cortex, hippocampus, inferior and superior colliculus, thalamus, the Purkinje and granule cell layers of the cerebellum, and/or brainstem of the subject. In some embodiments, administration of an rAAV vector described herein increases expression of FMR1 protein by about 10%, about 20%, about 30%, about 40%, about 50%, about 60%, about 70%, about 80%, about 90%, about 2-fold, about 3-fold, about 4-fold, about 5-fold, or about 10-fold. In some embodiments, administration of an rAAV vector described herein does not result in expression of FMR1 protein in the glia of the subject. The expression may be detected at any suitable point in time, e.g., 1 month, 3 months, 6 months, 9 months, or 12 months post injection.

Methods of Manufacture

A variety of approaches may be used to produce rAAV viral vectors of the present disclosure. In some aspects, packaging is achieved by using a helper virus or helper plasmid and a cell line. The helper virus or helper plasmid contains elements and sequences that facilitate viral vector production. In another aspect, the helper plasmid is stably incorporated into the genome of a packaging cell line, such that the packaging cell line does not require additional transfection with a helper plasmid.

In some aspects, the cell is a packaging or helper cell line. In some aspects, the helper cell line is eukaryotic cell; for example, an HEK 293 cell or 293T cell. In some aspects, the helper cell is a yeast cell or an insect cell.

In some aspects, the cell comprises a nucleic acid encoding a tetracycline activator protein; and a promoter that regulates expression of the tetracycline activator protein. In some aspects, the promoter that regulates expression of the tetracycline activator protein is a constitutive promoter. In some aspects, the promoter is a phosphoglycerate kinase promoter (PGK) or a CMV promoter.

A helper plasmid can comprise, for example, at least one viral helper DNA sequence derived from a replication-incompetent viral genome encoding in trans all virion proteins required to package a replication incompetent AAV, and for producing virion proteins capable of packaging the replication-incompetent AAV at high titer, without the production of replication-competent AAV.

Helper plasmids for packaging AAV are known in the art, see, e.g., U.S. Patent Pub. No. 2004/0235174 A1, incorporated herein by reference. As stated therein, an AAV helper plasmid may contain as helper virus DNA sequences, by way of non-limiting example, the Ad5 genes E2A, E4 and VA, controlled by their respective original promoters or by heterologous promoters. AAV helper plasmids may additionally contain an expression cassette for the expression of a marker protein such as a fluorescent protein to permit the simple detection of transfection of a desired target cell.

The disclosure provides methods of producing rAAV viral vectors comprising transfecting a packaging cell line with any one of the AAV helper plasmids disclosed herein; and any one of the rAAV vectors disclosed herein. In some aspects, the AAV helper plasmid and rAAV vector are co-transfected into the packaging cell line. In some aspects, the cell line is a mammalian cell line, for example, human embryonic kidney (HEK) 293 cell line. The disclosure provides cells comprising any one of the rAAV vectors and/or rAAV viral vectors disclosed herein.

As used herein, the term "helper" in reference to a virus or plasmid refers to a virus or plasmid used to provide the additional components necessary for replication and packaging of any one of the rAAV vectors disclosed herein. The components encoded by a helper virus may include any genes required for virion assembly, encapsidation, genome replication, and/or packaging. For example, the helper virus or plasmid may encode necessary enzymes for the replication of the viral genome. Non-limiting examples of helper viruses and plasmids suitable for use with AAV constructs include pHELP (plasmid), adenovirus (virus), or herpesvirus (virus). In some aspects, the pHELP plasmid may be the pHELPK plasmid, wherein the ampicillin expression cassette is exchanged with a kanamycin expression cassette.

As used herein, a packaging cell (or a helper cell) is a cell used to produce viral vectors. Producing recombinant AAV viral vectors requires Rep and Cap proteins provided in trans as well as gene sequences from Adenovirus that help AAV replicate. In some aspects, Packaging/helper cells contain a plasmid is stably incorporated into the genome of the cell. In other aspects, the packaging cell may be transiently transfected. Typically, a packaging cell is a eukaryotic cell, such as a mammalian cell or an insect cell.

Kits

The isolated polynucleotides, rAAV vectors, rAAV viral vectors, compositions, and/or pharmaceutical compositions described herein may be assembled into pharmaceutical or diagnostic or research kits to facilitate their use in therapeutic, diagnostic, or research applications. In some aspects, the kits of the present disclosure include any one of the isolated polynucleotides, rAAV vectors, rAAV viral vectors, compositions, pharmaceutical compositions, host cells, isolated tissues, as described herein.

In some aspects, a kit further comprises instructions for use. Specifically, such kits may include one or more agents described herein, along with instructions describing the intended application and the proper use of these agents. In some aspects, the kit may include instructions for mixing one or more components of the kit and/or isolating and mixing a sample and applying to a subject. In some aspects, agents in a kit are in a pharmaceutical formulation and dosage suitable for a particular application and for a method of administration of the agents. Kits for research purposes can contain the components in appropriate concentrations or quantities for running various experiments.

The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. In some aspects, the compositions may be provided in a preservation solution (e.g., cryopreservation solution). Non-limiting examples of preservation solutions include DMSO, paraformaldehyde, and CryoStor® (Stem Cell Technologies, Vancouver, Canada). In some aspects, the preservation solution contains an amount of metalloprotease inhibitors.

In some aspects, the kit contains any one or more of the components described herein in one or more containers. Thus, in some aspects, the kit may include a container housing agents described herein. The agents may be in the form of a liquid, gel or solid (powder). The agents may be prepared sterilely, packaged in a syringe and shipped refrigerated. Alternatively, they may be housed in a vial or other container for storage. A second container can have other agents prepared sterilely. Alternatively, the kit can include the active agents premixed and shipped in a syringe, vial, tube, or other container. The kit can have one or more or all of the components required to administer the agents to a subject, such as a syringe, topical application devices, or IV needle tubing and bag.

Further Definitions

Unless the context indicates otherwise, it is specifically intended that the various features described herein can be used in any combination. Moreover, the disclosure also contemplates that, in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified aspects, embodiments, features, and terms intend to include both the recited aspect, embodiment, feature, or term and biological equivalents thereof.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2nd edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (RI. Freshney, ed. (1987)).

All numerical designations, e.g., pH, temperature, time, concentration, and molecular weight, including ranges, are approximations which are varied (+) or (−) by increments of 1.0 or 0.1, as appropriate, or, alternatively, by a variation of +/−15%, 10%, 5%, 2%. It is to be understood, although not always explicitly stated, that all numerical designations are preceded by the term "about". It also is to be understood, although not always explicitly stated, that the reagents described herein are merely exemplary and that equivalents of such are known in the art. The term "about," as used herein when referring to a measurable value such as an amount or concentration and the like, is meant to encompass variations of 20%, 10%, 5%, 1%, 0.5%, or even 0.1% of the specified amount.

The terms "acceptable" or "effective," when used to describe the selection of any components, ranges, dose forms, etc. disclosed herein intend that said component, range, dose form, etc. is suitable for the disclosed purpose.

Also, as used herein, "and/or" refers to and encompasses any and all possible combinations of one or more of the associated listed items, as well as the lack of combinations when interpreted in the alternative ("or").

Unless specifically recited, the term "host cell" includes a eukaryotic host cell, including, for example, fungal cells, yeast cells, higher plant cells, insect cells and mammalian cells. Non-limiting examples of eukaryotic host cells include simian, bovine, porcine, murine, rat, avian, reptilian and human, e.g., HEK293 cells and 293T cells.

The term "isolated" as used herein refers to molecules or biologicals or cellular materials being substantially free from other materials.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising, consisting essentially of, or consisting of purine and pyrimidine bases or other natural, chemically or biochemically modified, non-natural, or derivatized nucleotide bases.

A "gene" refers to a polynucleotide containing at least one open reading frame (ORF) that is capable of encoding a particular polypeptide or protein. A "gene product" or, alternatively, a "gene expression product" refers to the amino acid sequence (e.g., peptide or polypeptide) generated when a gene is transcribed and translated.

As used herein, "expression" refers to the two-step process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell.

"Under transcriptional control" is a term well understood in the art and indicates that transcription of a polynucleotide sequence, usually a DNA sequence, depends on its being operatively linked to an element that contributes to the initiation of, or promotes, transcription. "Operatively linked" intends that the polynucleotides are arranged in a manner that allows them to function in a cell. In one aspect, promoters can be operatively linked to the downstream sequences.

The term "encode" as it is applied to polynucleotides and/or nucleic acid sequences refers to a polynucleotide and/or nucleic acid sequence which is said to "encode" a polypeptide if its base sequence is identical to the base sequence of the RNA transcript (e.g. mRNA transcript) that is translated into the polypeptide and/or a fragment thereof. The antisense strand is the complement of such a nucleic acid, and the encoding sequence can be deduced therefrom.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise, consist essentially of, or consist of a protein's or peptide's sequence. As used herein the term "amino acid" refers to either natural and/or unnatural or synthetic amino acids, including glycine and both the D and L optical isomers, amino acid analogs and peptidomimetics.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g. across a cell membrane, into a cell membrane, or into the nucleus. In some aspects, the signal peptide is removed following localization. Examples of signal peptides are well known in the art. Non-limiting examples are those described in U.S. Pat. Nos. 8,853,381, 5,958,736, and 8,795,965. In some aspects, the signal peptide can be an IDUA signal peptide.

The terms "equivalent" or "biological equivalent" are used interchangeably when referring to a particular molecule, biological material, or cellular material and intend those having minimal homology while still maintaining desired structure or functionality. Non-limiting examples of equivalent polypeptides include a polypeptide having at least about 60%, at least about 65%, at least about 70%, at least about 75%, at least about 80%, at least about 85%, at least about 90%, at least about 95% identity or at least about 99% identity to a reference polypeptide (for instance, a wild-type polypeptide); or a polypeptide which is encoded by a polynucleotide having at least about 70%, at least about 75%, at least about 80%, at least about 85%, at least about 90%, at least about 95% identity, at least about 97% sequence identity or at least about 99% sequence identity to the reference polynucleotide (for instance, a wild-type polynucleotide).

"Homology" or "identity" or "similarity" refers to sequence similarity between two peptides or between two nucleic acid molecules. Percent identity can be determined by comparing a position in each sequence that may be aligned for purposes of comparison. When a position in the compared sequence is occupied by the same base or amino acid, then the molecules are identical at that position. A degree of identity between sequences is a function of the number of matching positions shared by the sequences. "Unrelated" or "non-homologous" sequences share less than 40% identity, less than 25% identity, with one of the sequences of the present disclosure. Alignment and percent sequence identity may be determined for the nucleic acid or amino acid sequences provided herein by importing said nucleic acid or amino acid sequences into and using ClustalW (available at https://genome.jp/tools-bin/clustalw/). For example, the ClustalW parameters used for performing the protein sequence alignments found herein were generated using the Gonnet (for protein) weight matrix. In some aspects, the ClustalW parameters used for performing nucleic acid sequence alignments using the nucleic acid sequences found herein are generated using the ClustalW (for DNA) weight matrix.

As used herein, amino acid modifications may be amino acid substitutions, amino acid deletions or amino acid insertions. Amino acid substitutions may be conservative amino acid substitutions or non-conservative amino acid substitutions. A conservative replacement (also called a conservative mutation, a conservative substitution or a conservative variation) is an amino acid replacement in a protein that changes a given amino acid to a different amino acid with similar biochemical properties (e.g., charge, hydrophobicity or size). As used herein, "conservative variations" refer to the replacement of an amino acid residue by another, biologically similar residue. Examples of conservative variations include the substitution of one hydrophobic residue such as isoleucine, valine, leucine or methionine for another; or the substitution of one charged or polar residue for another, such as the substitution of arginine for lysine, glutamic acid for aspartic acid, glutamine for asparagine, and the like. Other illustrative examples of conservative substitutions include the changes of: alanine to serine; asparagine to glutamine or histidine; aspartate to glutamate; cysteine to serine; glycine to proline; histidine to asparagine or glutamine; lysine to arginine, glutamine, or glutamate; phenylalanine to tyrosine, serine to threonine; threonine to serine; tryptophan to tyrosine; tyrosine to tryptophan or phenylalanine; and the like.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is a DNA molecule that is typically separate from and capable of replicating independently of the chromosomal DNA. In many cases, it is circular and double-stranded. Plasmids provide a mechanism for horizontal gene transfer within a population of microbes and typically. provide a selective advantage under a given environmental state. Plasmids may carry genes that provide resistance to naturally occurring antibiotics in a competitive environmental niche, or, alternatively, the proteins produced may act as toxins under similar circumstances. It is known in the art that while plasmid vectors often exist as extrachromosomal circular DNA molecules, plasmid vectors may also be designed to be stably integrated into a host chromosome either randomly or in a targeted manner, and such integration may be accomplished using either a circular plasmid or a plasmid that has been linearized prior to introduction into the host cell.

"Plasmids" used in genetic engineering are called "plasmid vectors". Many plasmids are commercially available for such uses. The gene to be replicated is inserted into copies of a plasmid containing genes that make cells resistant to particular antibiotics, and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria or eukaryotic cells containing a plasmid harboring the gene of interest, which can be induced to produce large amounts of proteins from the inserted gene.

In aspects where gene transfer is mediated by a DNA viral vector, such as an adenovirus (Ad) or adeno-associated virus (AAV), a vector construct refers to the polynucleotide comprising, consisting essentially of, or consisting of the viral genome or part thereof, and a transgene.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected), or a group of tissues making up an organ or part or region of the body of an organism. The tissue may comprise, consist essentially of, or consist of a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term “and/or” includes any and all combinations of one or more of the associated listed items. As used in the description herein and throughout the claims that follow, the meaning of “a”, “an”, and “the” includes plural reference as well as the singular reference unless the context clearly dictates otherwise.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms “comprising,” “consisting essentially of,” and “consisting of” can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

EXAMPLES

The following are provided for exemplification purposes only and are not intended to limit the scope of the embodiments described in broad terms above.

Example 1

AAV vectors were designed with codon-optimized and CpG depleted human FMR1 Isoform 17 cDNA (hFMR1Iso17opt) under control of either JeT, MeP229, or human FMR1 promoters, including a synthetic poly(A) tail (SpA) (FIG. 1). Expression cassettes were flanked by an ITR sequence for packing into AAV9.

Figure 2A:
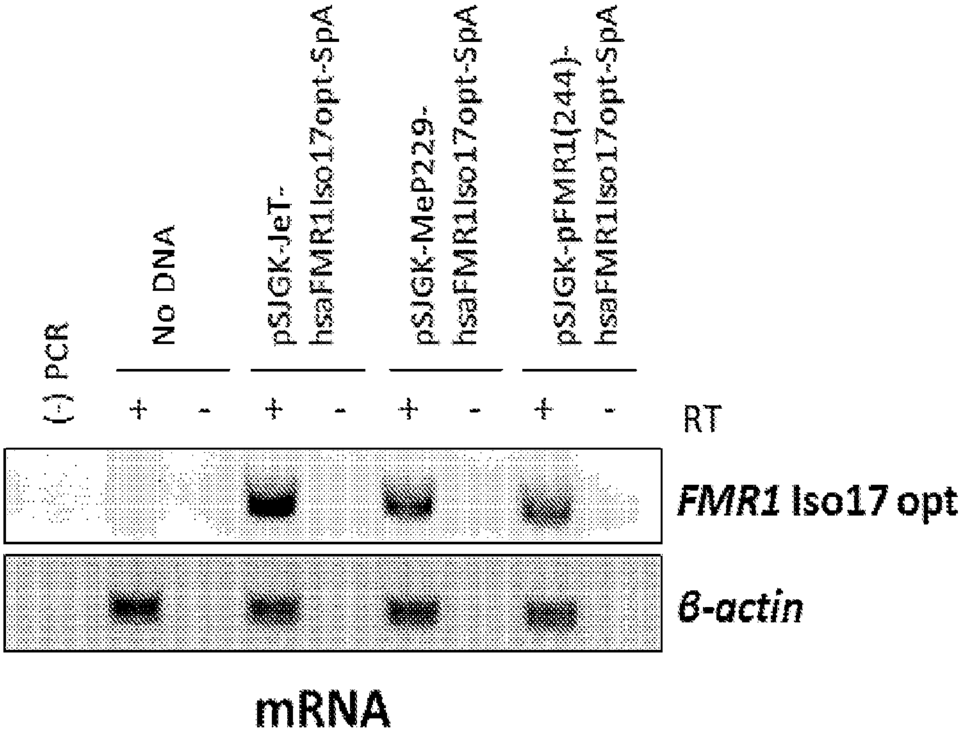
FIGS. 2A-2C show the mRNA and protein expression by AAV-FMR1 vectors.
Figure 2B:
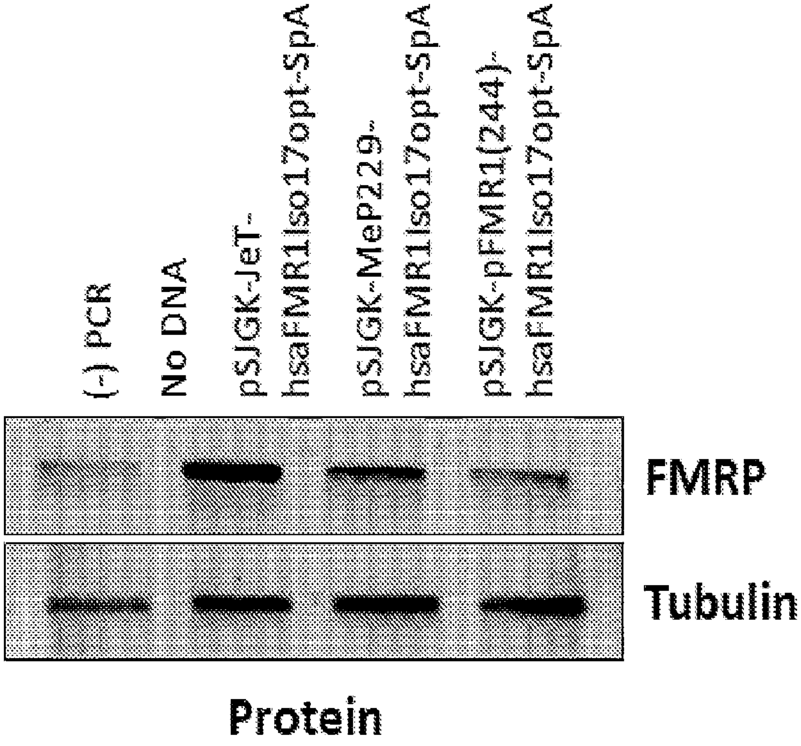
Figure 2C:
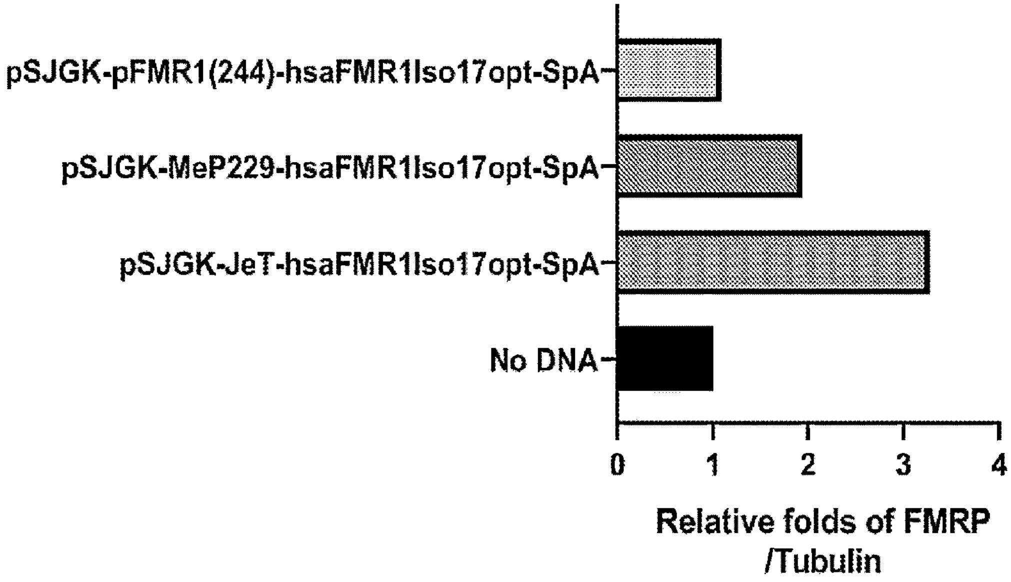

The 3 plasmids were transfected with PEI into HEK293T cells and cells were lysed at 48 hrs (FIG. 2A-2C). mRNA expression was analyzed using RT-PCR (FIG. 2A) and protein expression was analyzed using western blotting (FIG. 2B). Relative protein expression was quantified using Image J (FIG. 2C). The order of the graph is same as (B).

Figure 3A:
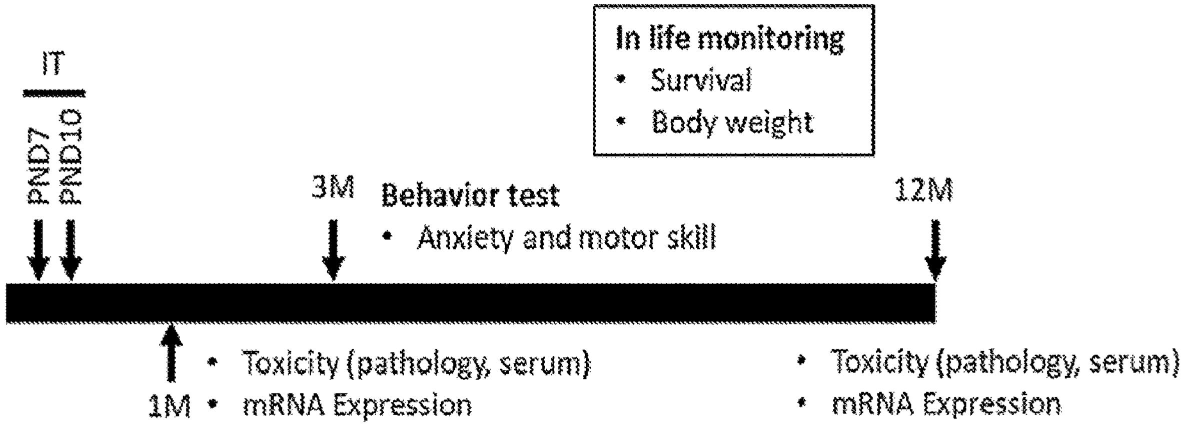
FIG. 3A show an outline of toxicity studies.
Figure 3B:
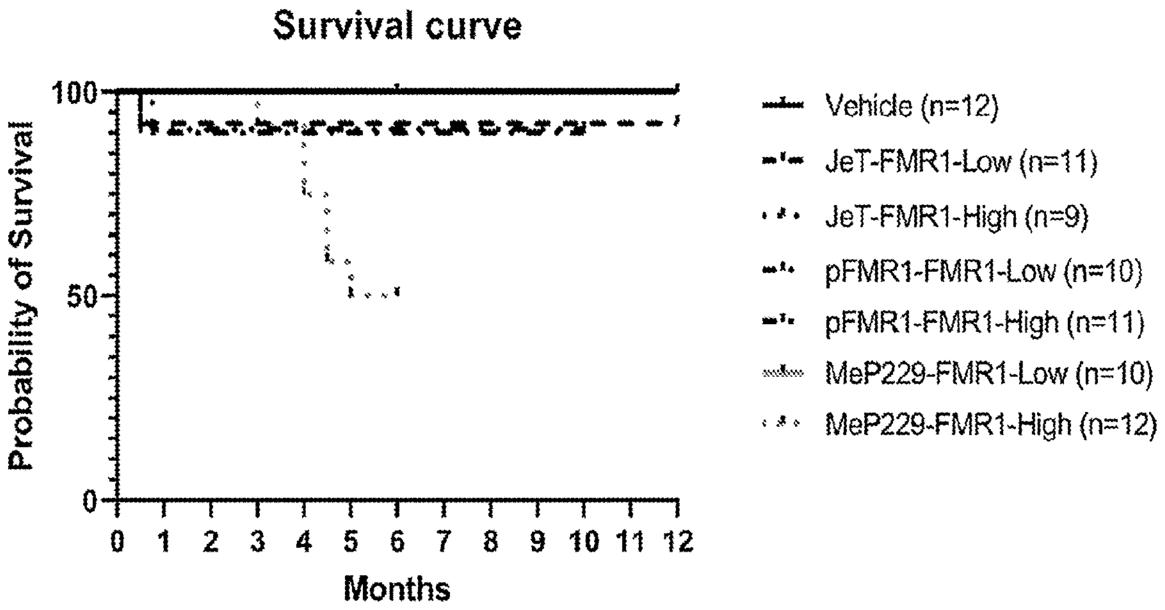
FIGS. 3B-3D shows the results of safety studies in wild-type mice treated with FMR1/AAVs.
Figure 3C:
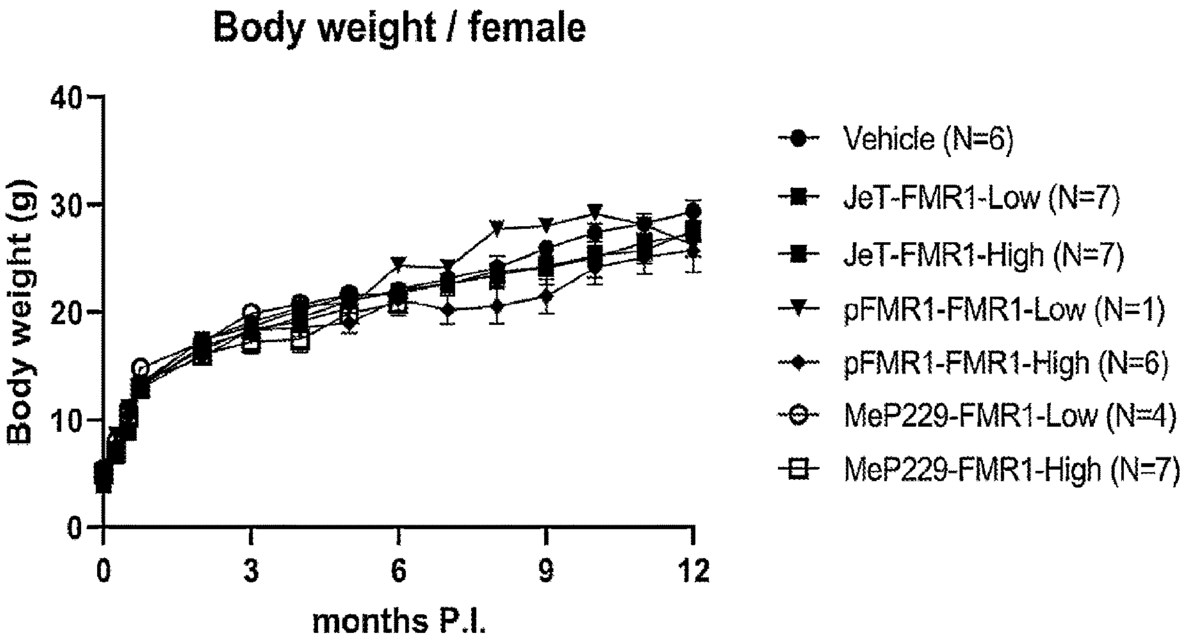
Figure 3D:
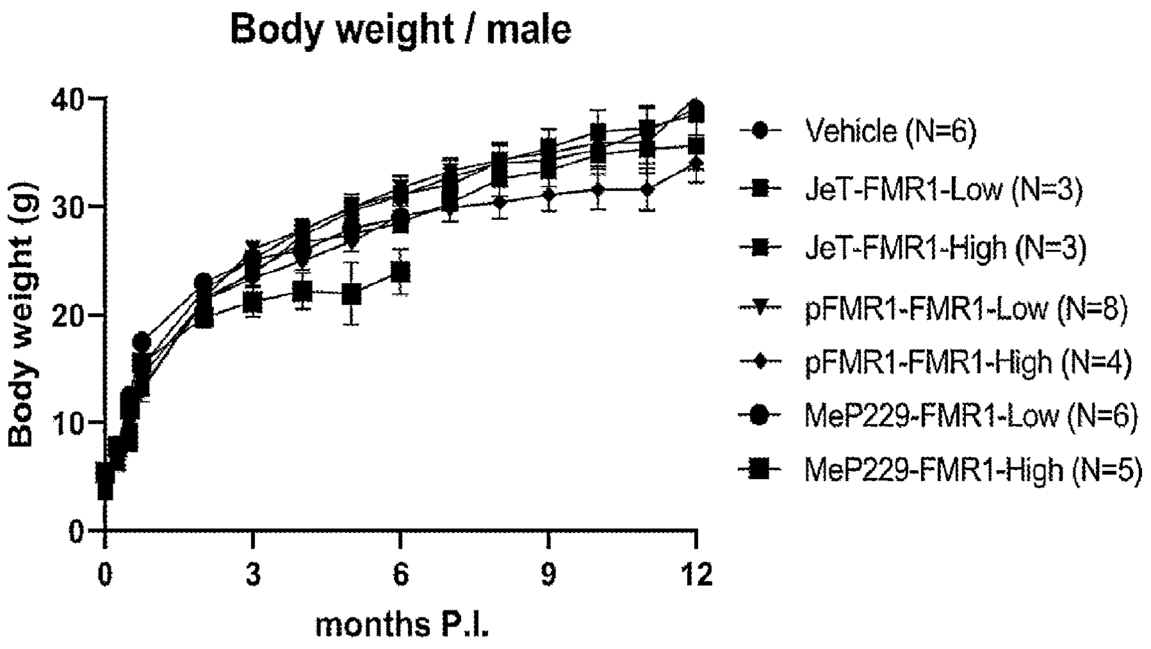

Toxicity was evaluated using wild-type mice with FMR1/AAVs (FIG. 3A-3D). FIG. 3A shows an outline of the safe study to toxicity evaluation. Wild-type mice were treated by i.t. injection at P7-P10 with AAV9-JeT-FMR1, AAV9-MeP229-FMR1, and AAV9-pFMR1-FMR1 at the dose of low (1.25E+11 vg) and high (5.0E+11 vg). Vehicle was treated as a control group in wild-type mice. All mice were monitored for body weight and survival. At 1 month, 4 mice from each group were sacrificed for evaluating the pathological toxicity, serum toxicity and FMR1 mRNA expression. At 3-months, behavior tests were performed. The experiment will terminate at 12 months. However, AAV9-MeP229-FMR1 low and high dose group will terminate at the 6-month time point because of the decreasing survival. Survival (FIG. 3B) and average body weight of each sex (FIG. 3C-3D) are shown. These results indicate that constructs utilizing the JeT or FMR1 promoter are tolerated well, but use of the MeP229 promoter results in dose-dependent early mortality.

Figure 4A:
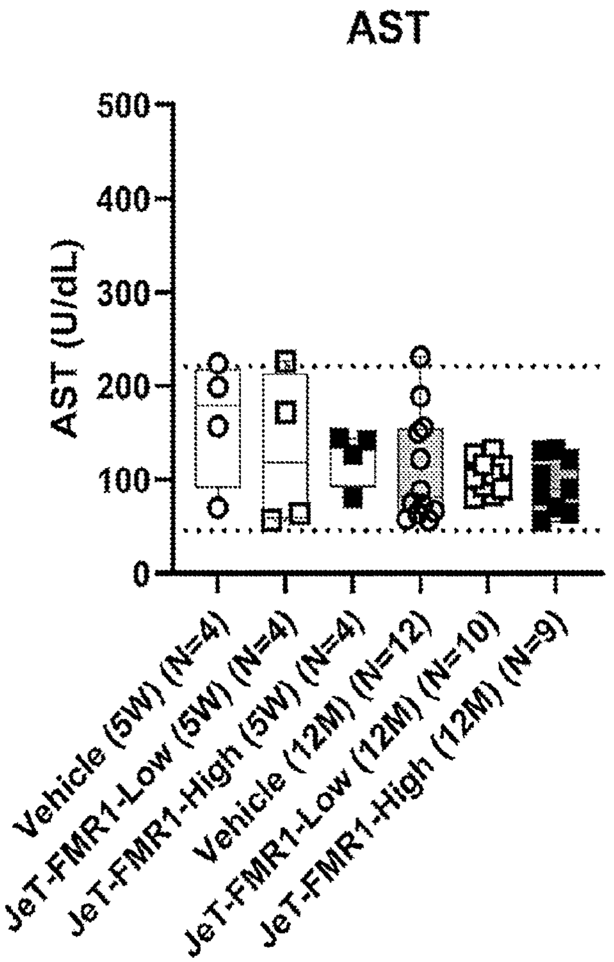
FIGS. 4A-4O show serum toxicity in wild-type mice with FMR1/AAVs. At 4 weeks and 12 months after vector administration, Serum was isolated from the mice blood and each indicator that shows liver, kidney, and muscle toxicity was analyzed using VITROS 350 microslide technology. The level of Aspartate Aminotransferase (AST.
Figure 4B:
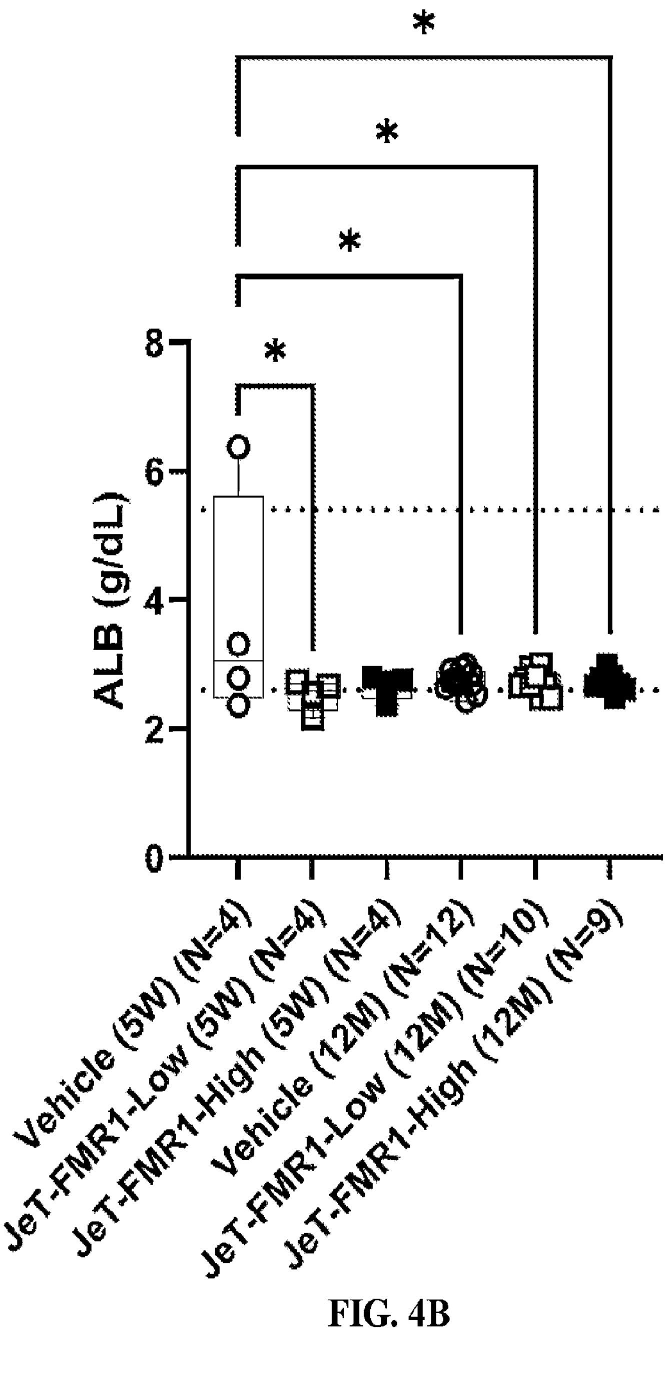
FIGS. 4B, 4G, 4L), Total bilirubin (TBIL.
Figure 4C:
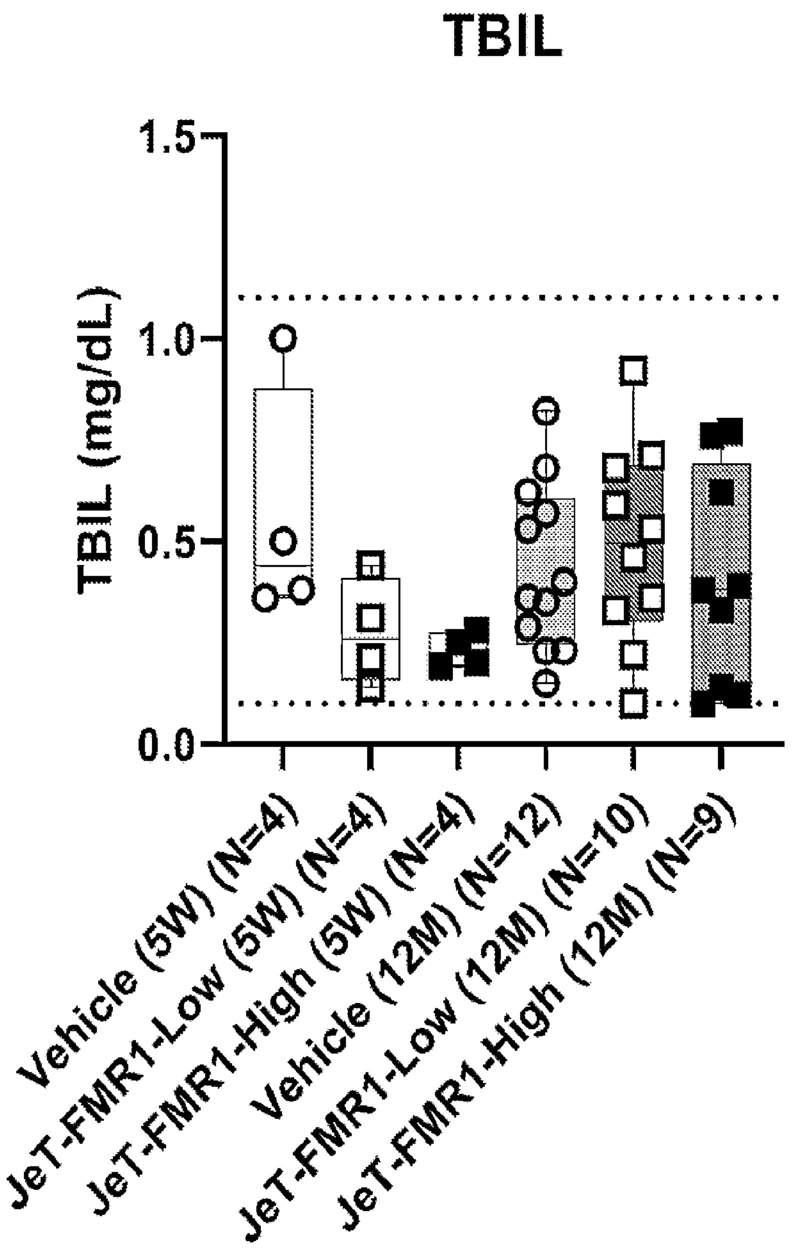
FIGS. 4C, 4H, 4M), Blood urea nitrogen (BUN.
Figure 4D:
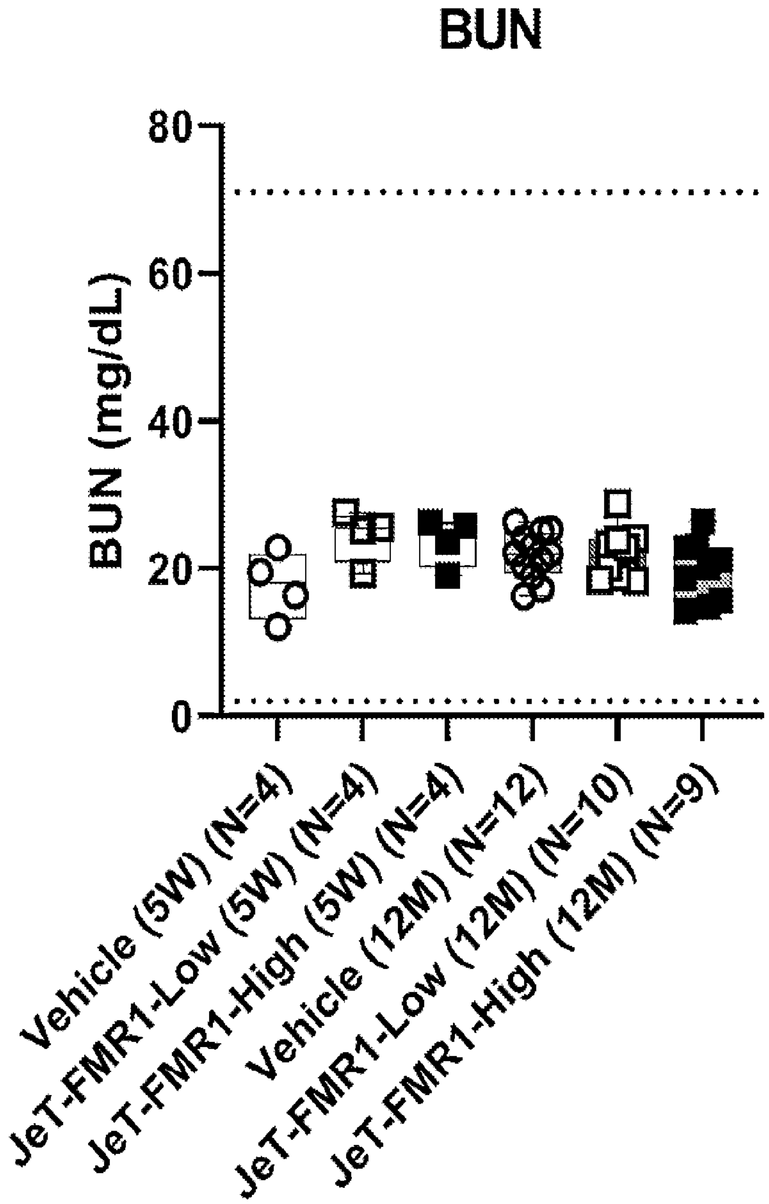
FIGS. 4D, 4I, 4N) and Creatine Kinase (CK.
Figure 4E:
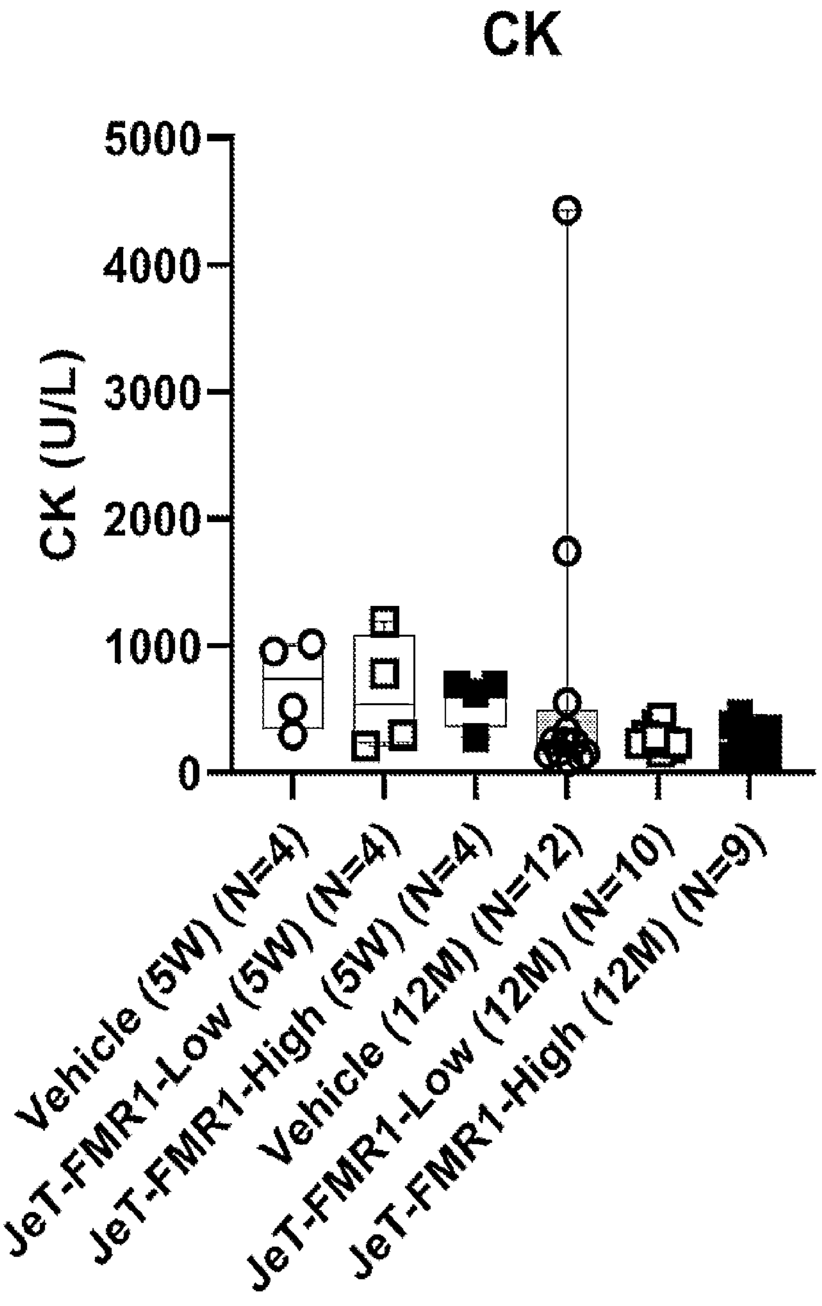
Figure 4F:
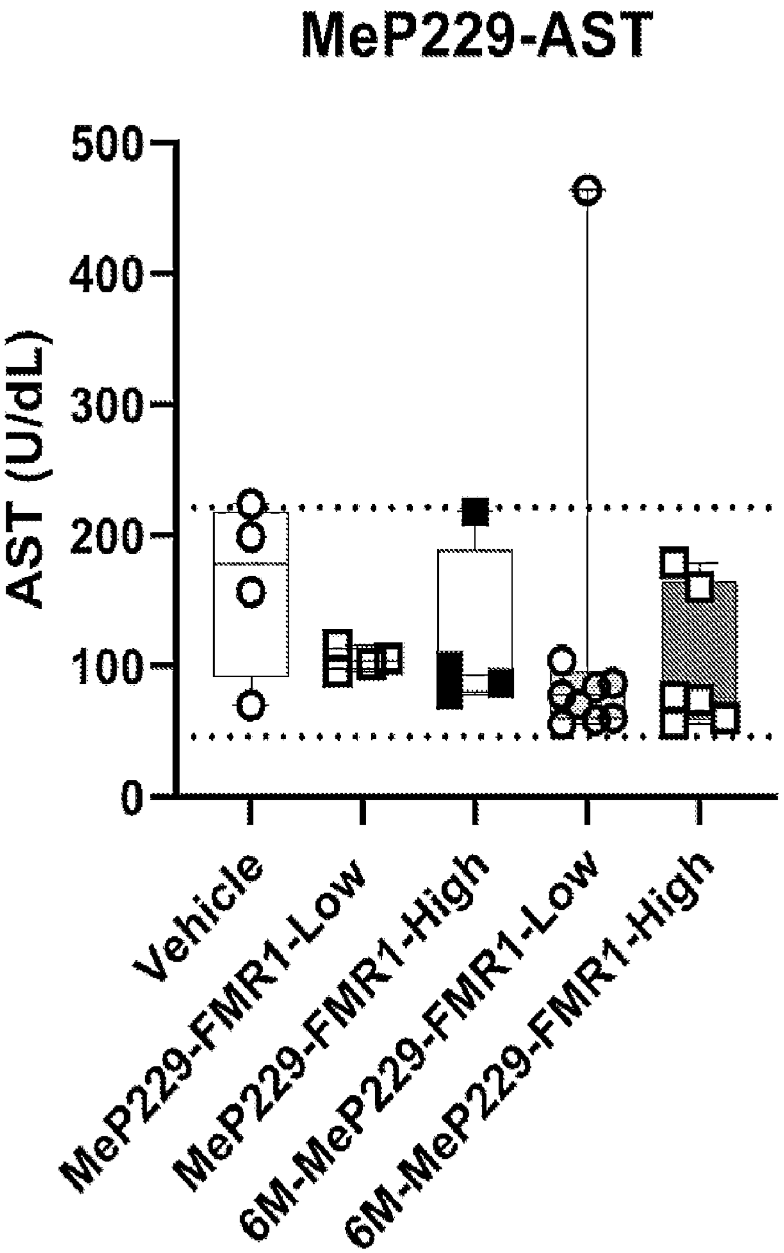
Figure 4G:
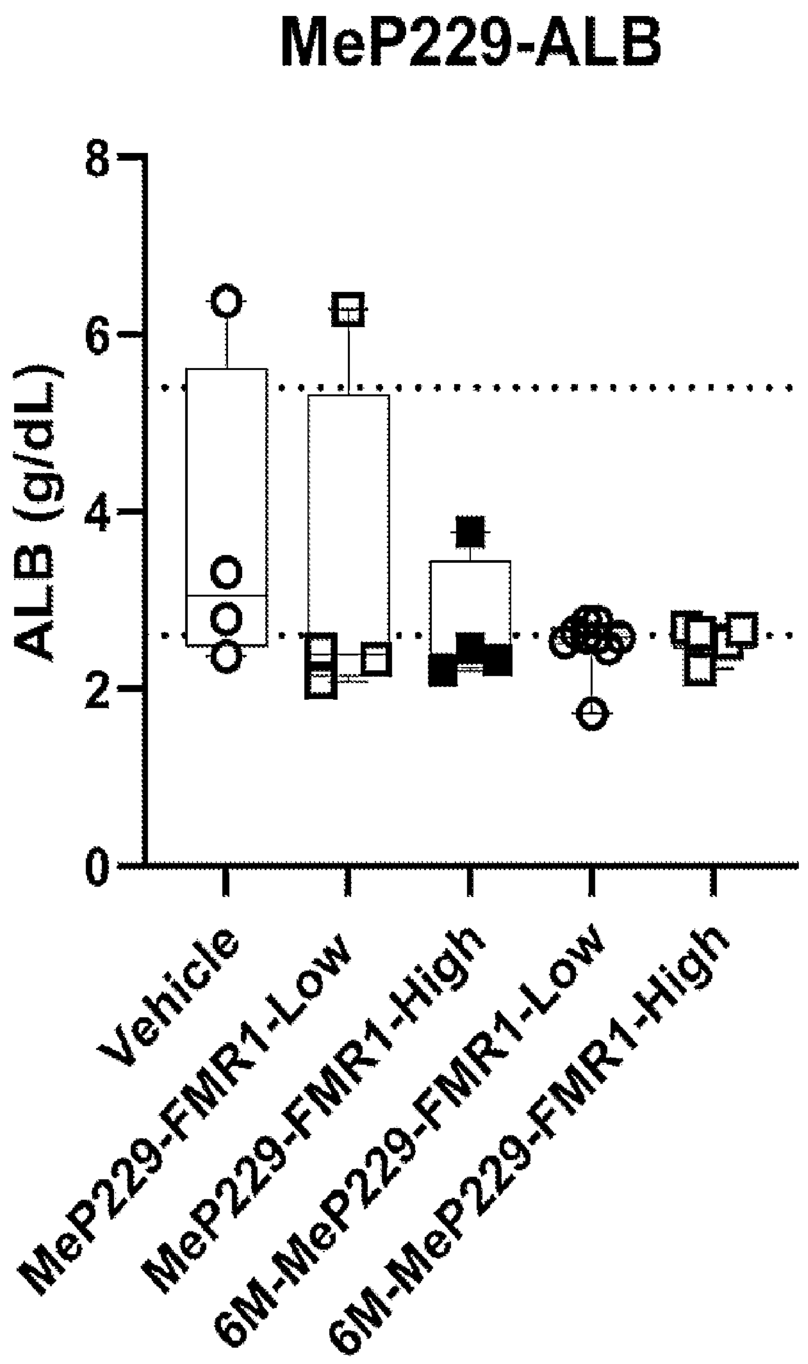
Figure 4H:
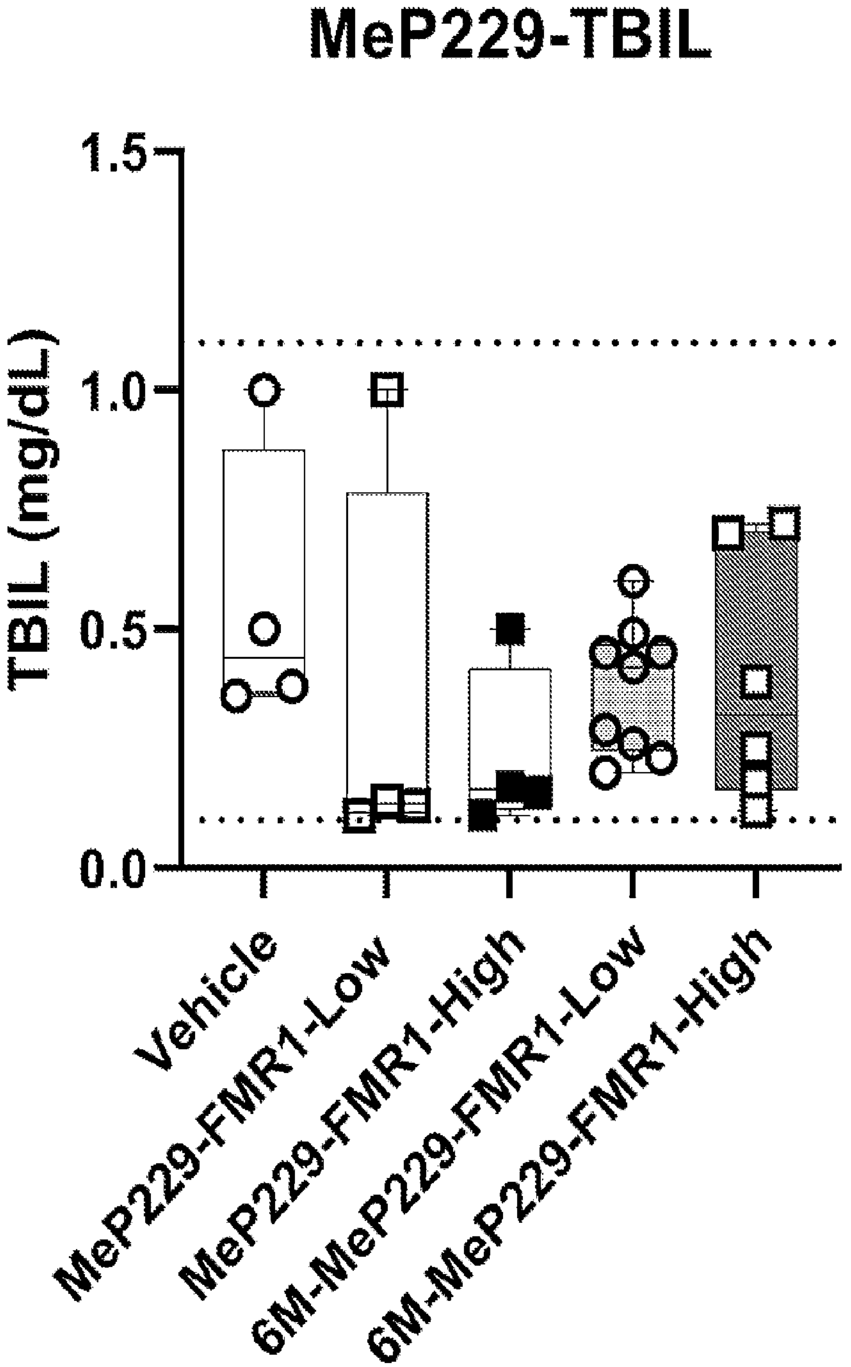
Figure 4I:
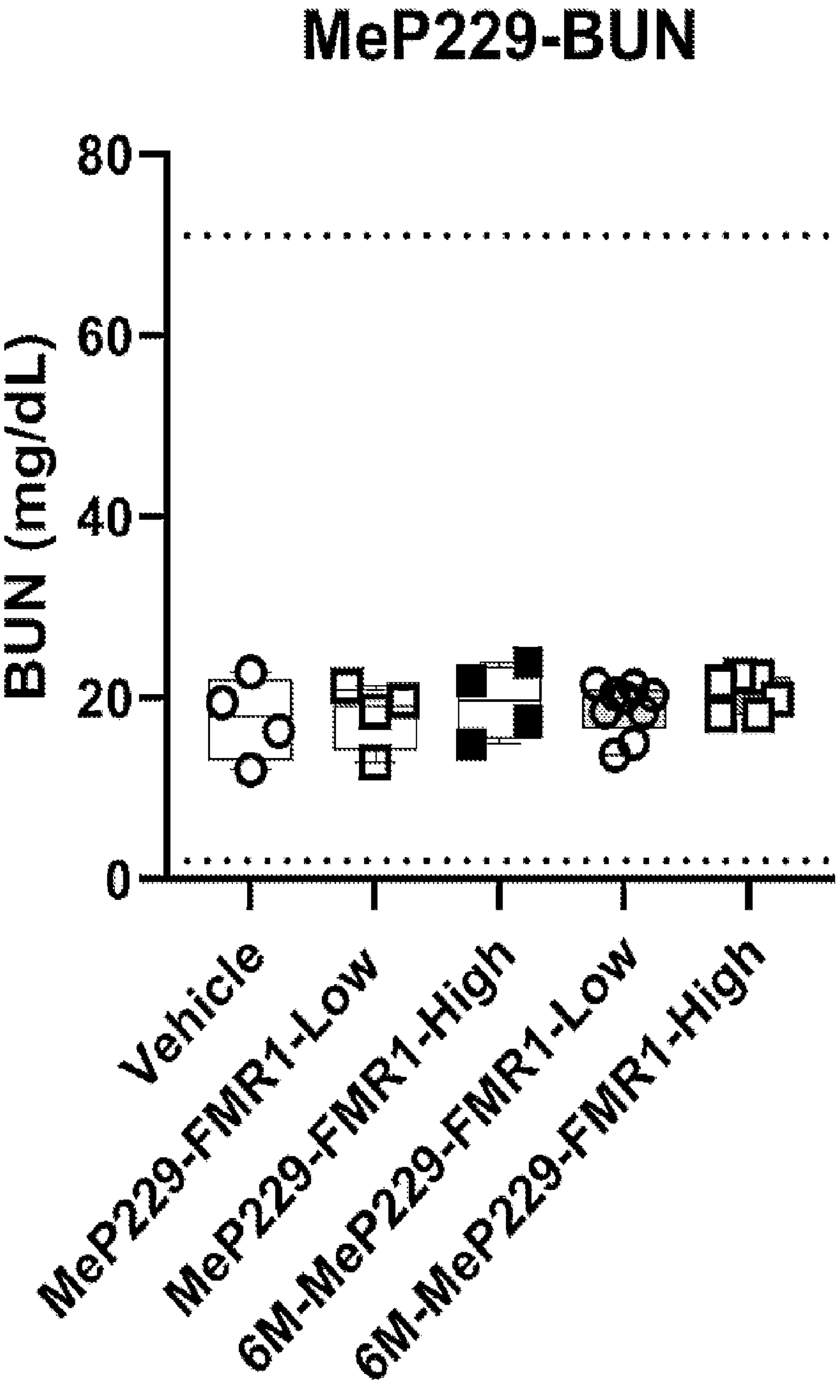
Figure 4J:
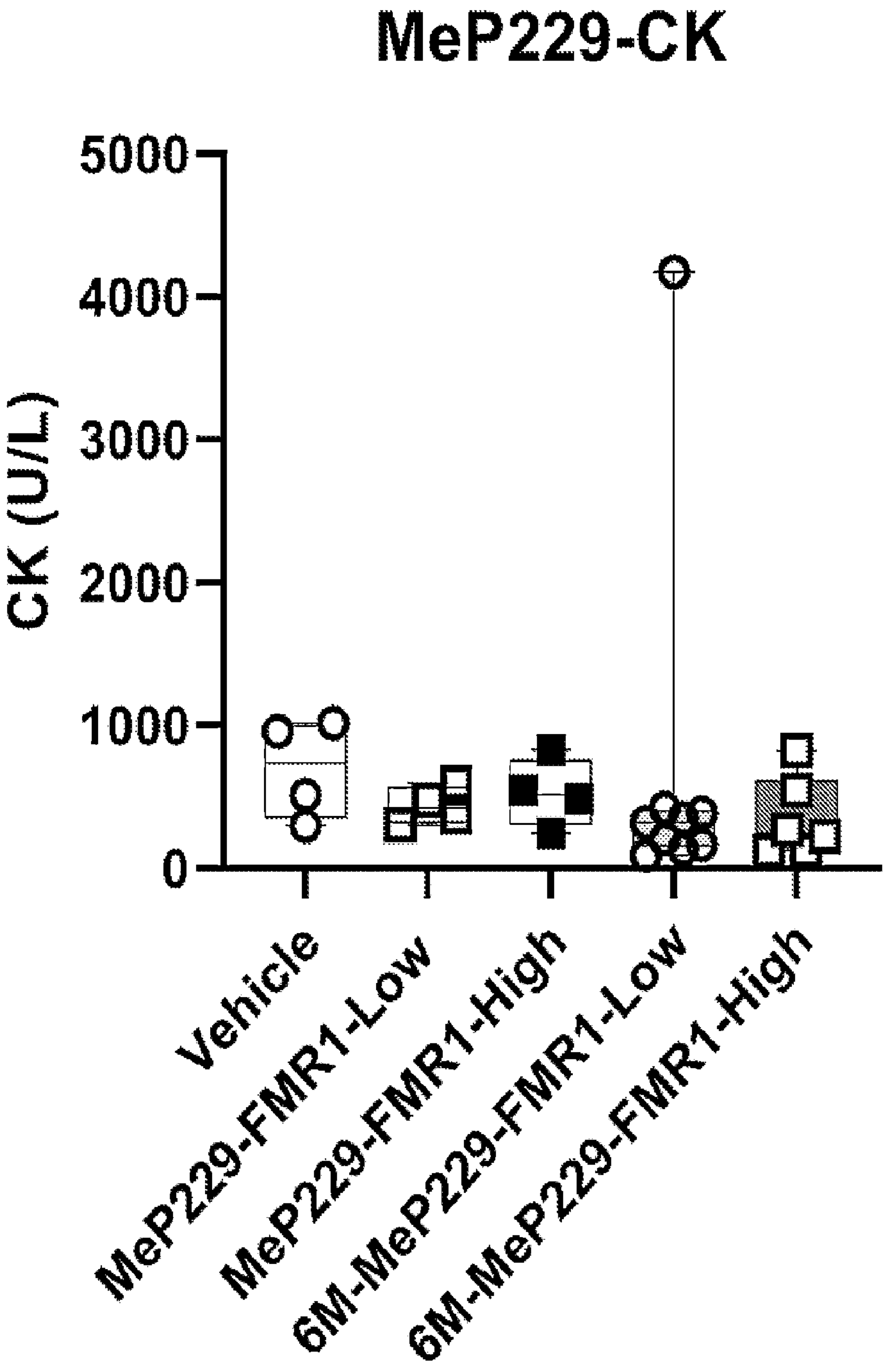
Figure 4K:
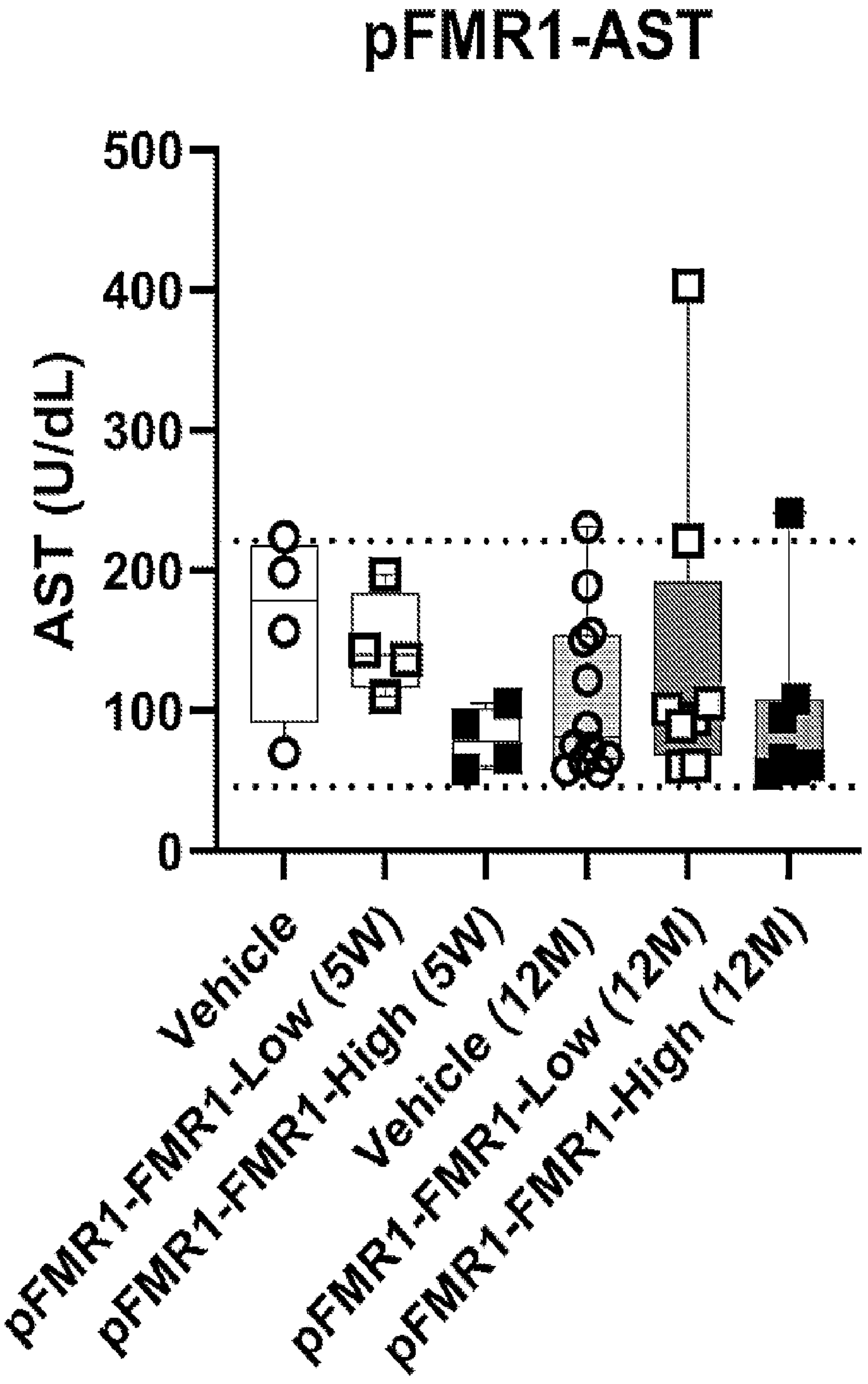
Figure 4L:
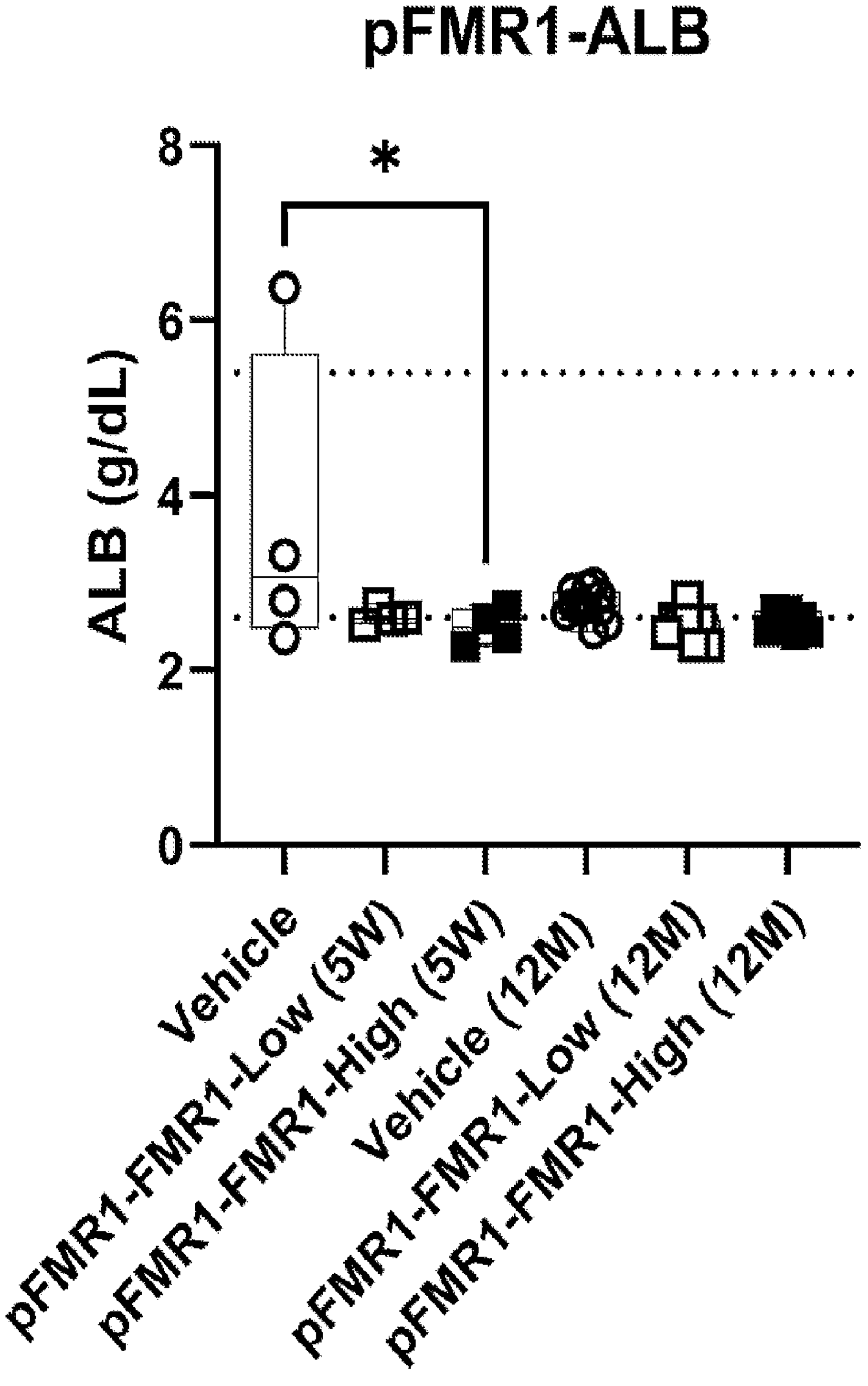
Figure 4M:
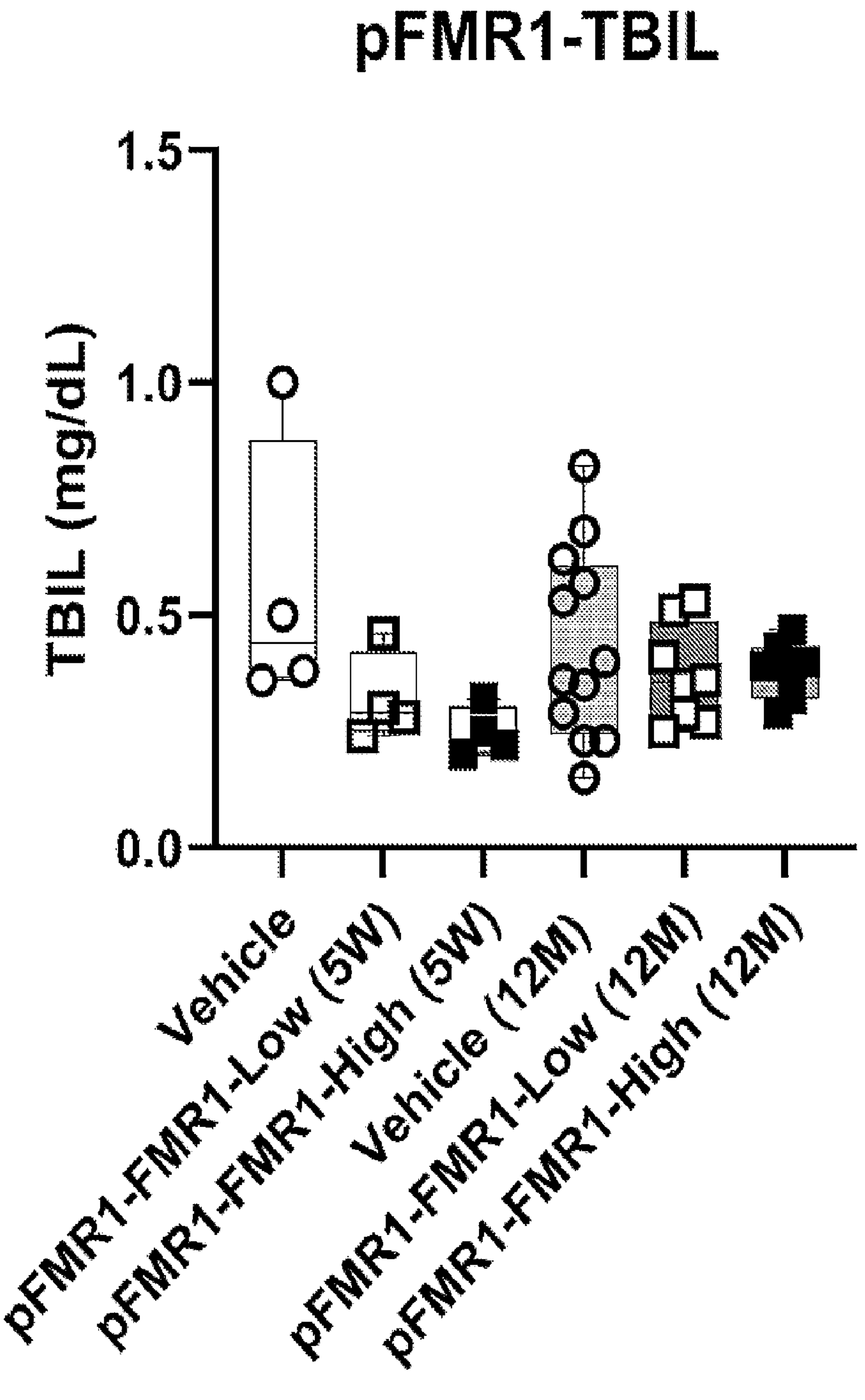
Figure 4N:
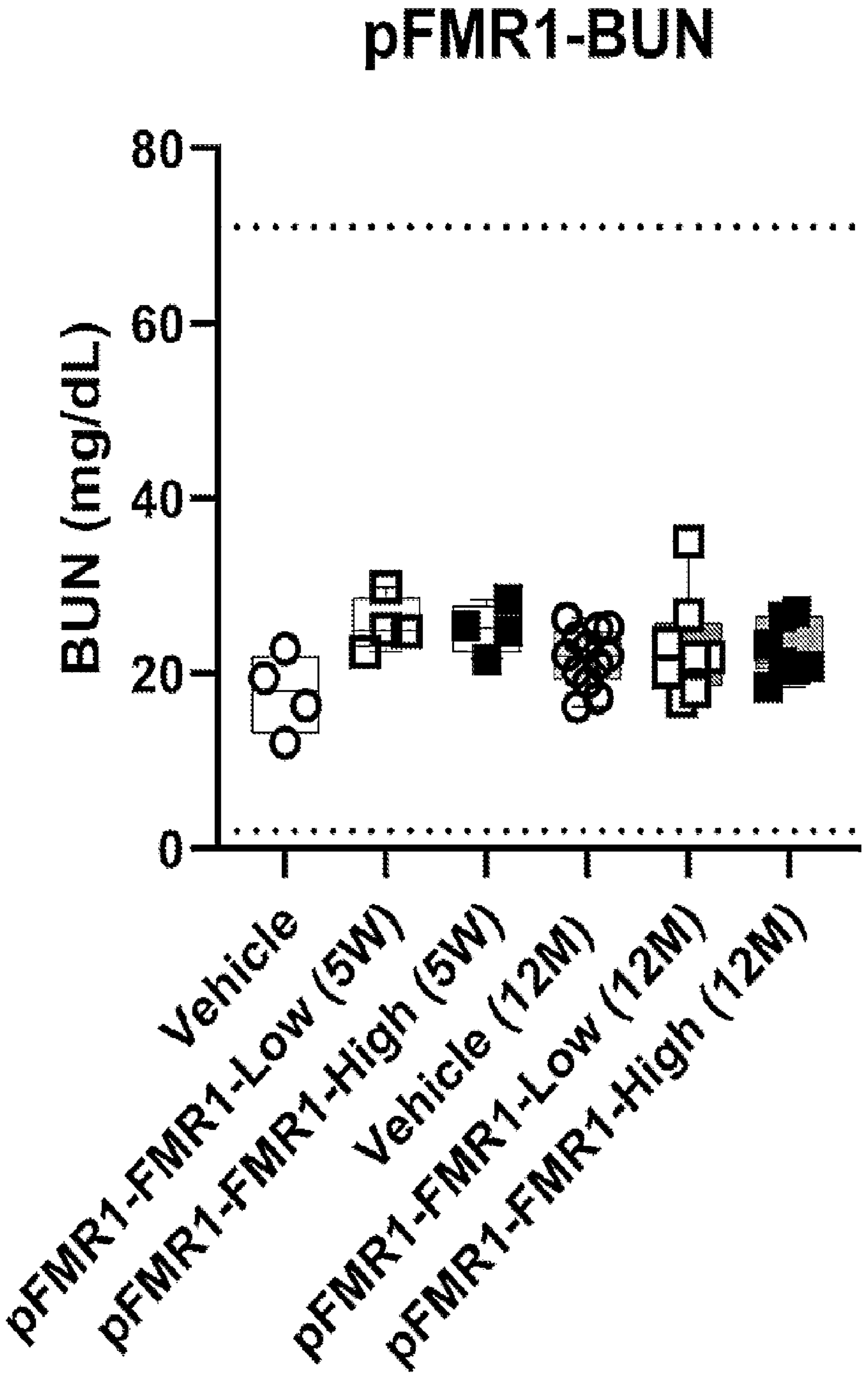
Figure 4O:
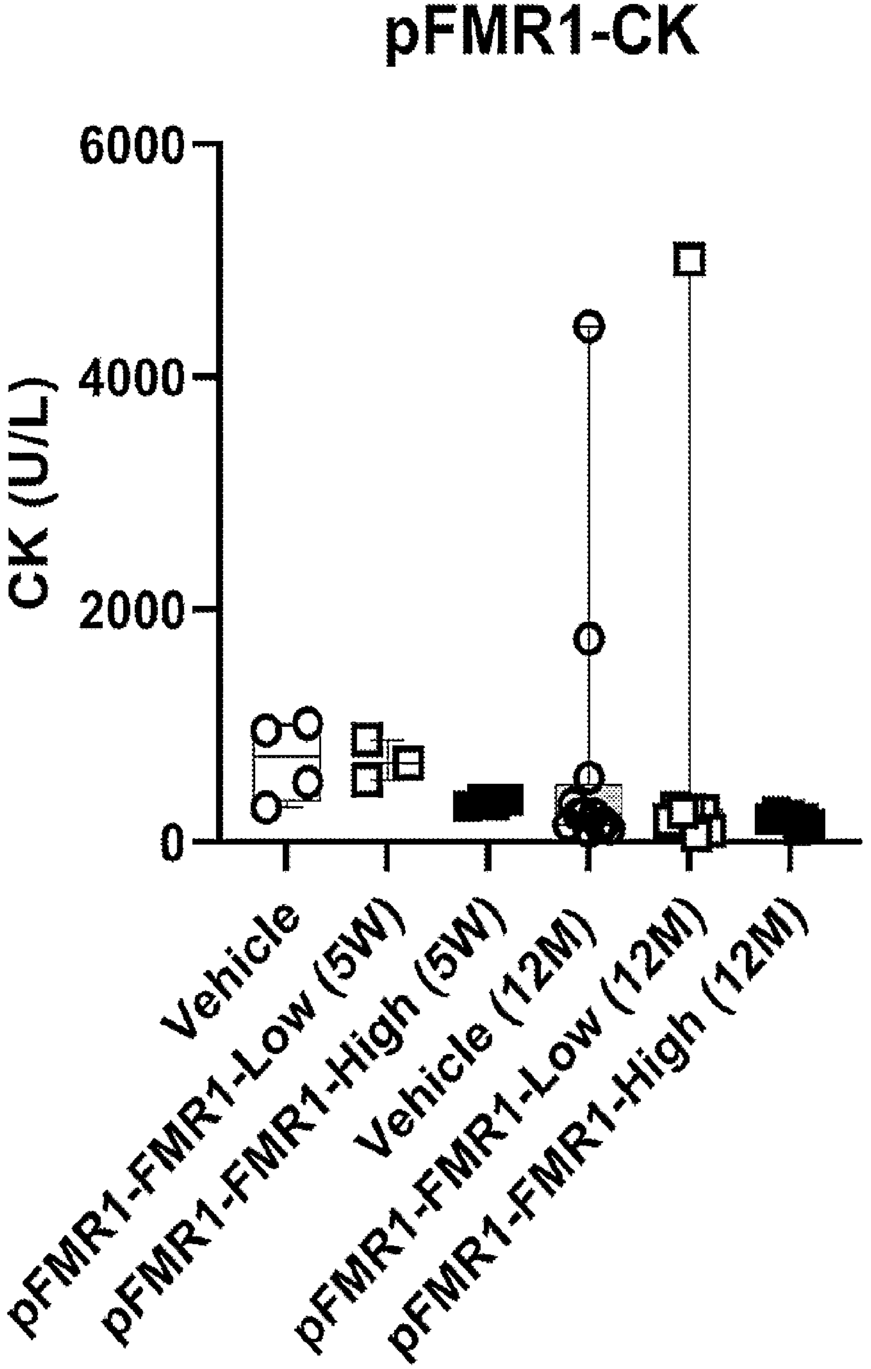

At 4 weeks after vector administration, Serum was isolated from blood and each indicator which shows liver, kidney, and muscle toxicity was analyzed VITROS 350 microslide technology (UTSW metabolic phenotyping core facility). The level of aspartate aminotransferase (AST) (FIGS. 4A, 4F, 4K), albumin (ALB) (FIGS. 4B, 4G, 4L), total bilirubin (TBIL) (FIGS. 4C, 4H, 4M), blood urea nitrogen (BUN) (FIGS. 4D, 4I, 4N) and creatine kinase (CK) (FIGS. 4E, 4J, 4O) were shown in each group. No significant differences were shown among groups, suggesting general short-term safety by these indicators.

Figure 5A:
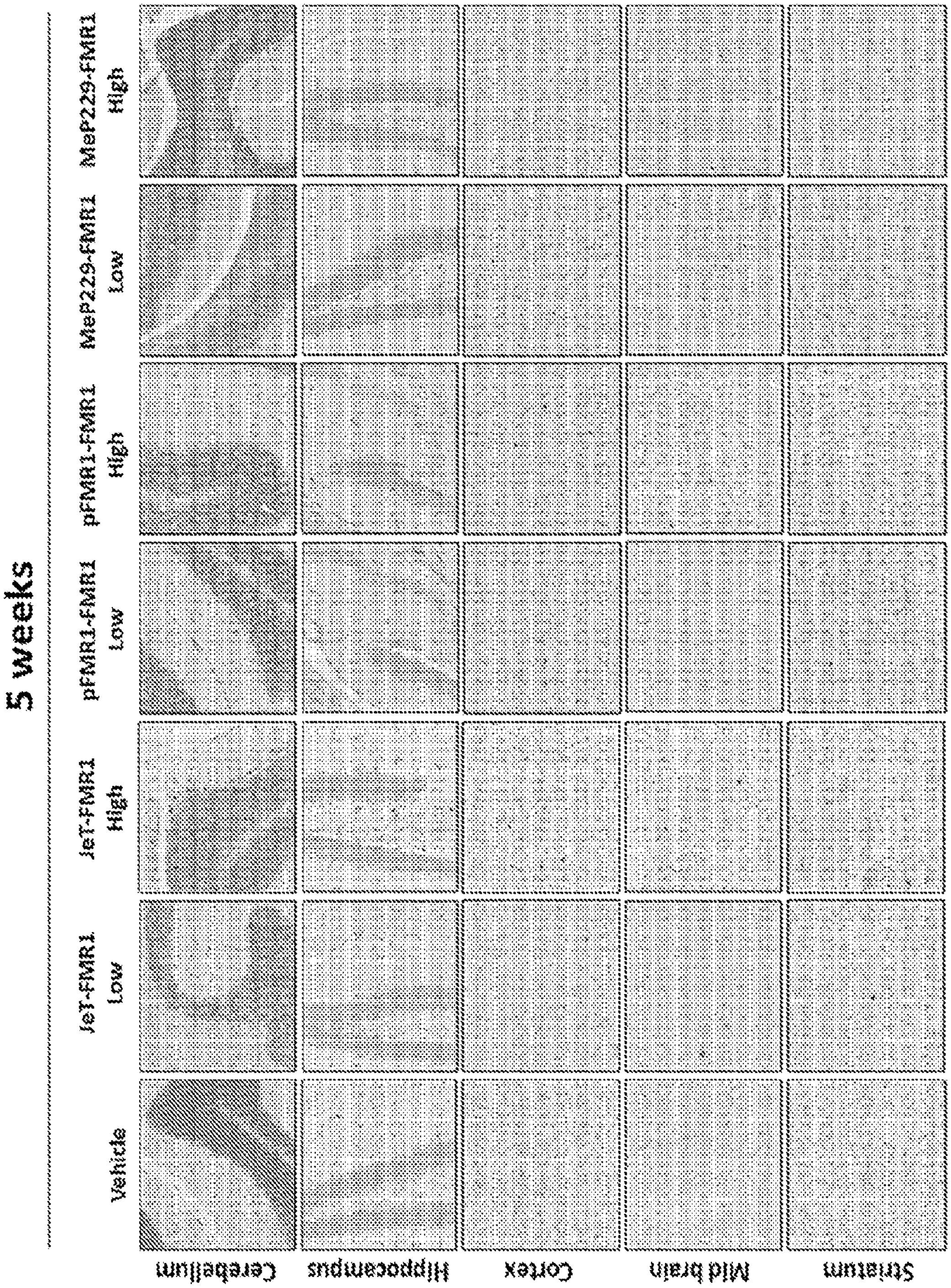
FIGS. 5A-5D show hFMR1 Iso17 opt mRNA expression in the mouse brain. The wild-type mouse brain was fixed at 5 weeks and 12 months. RNAscope was performed with specific probes for hFMR1 Iso17 opt mRNA. Histology images were analyzed using custom analysis settings in the HALO image analysis platform to quantify the signals.
Figure 5B:
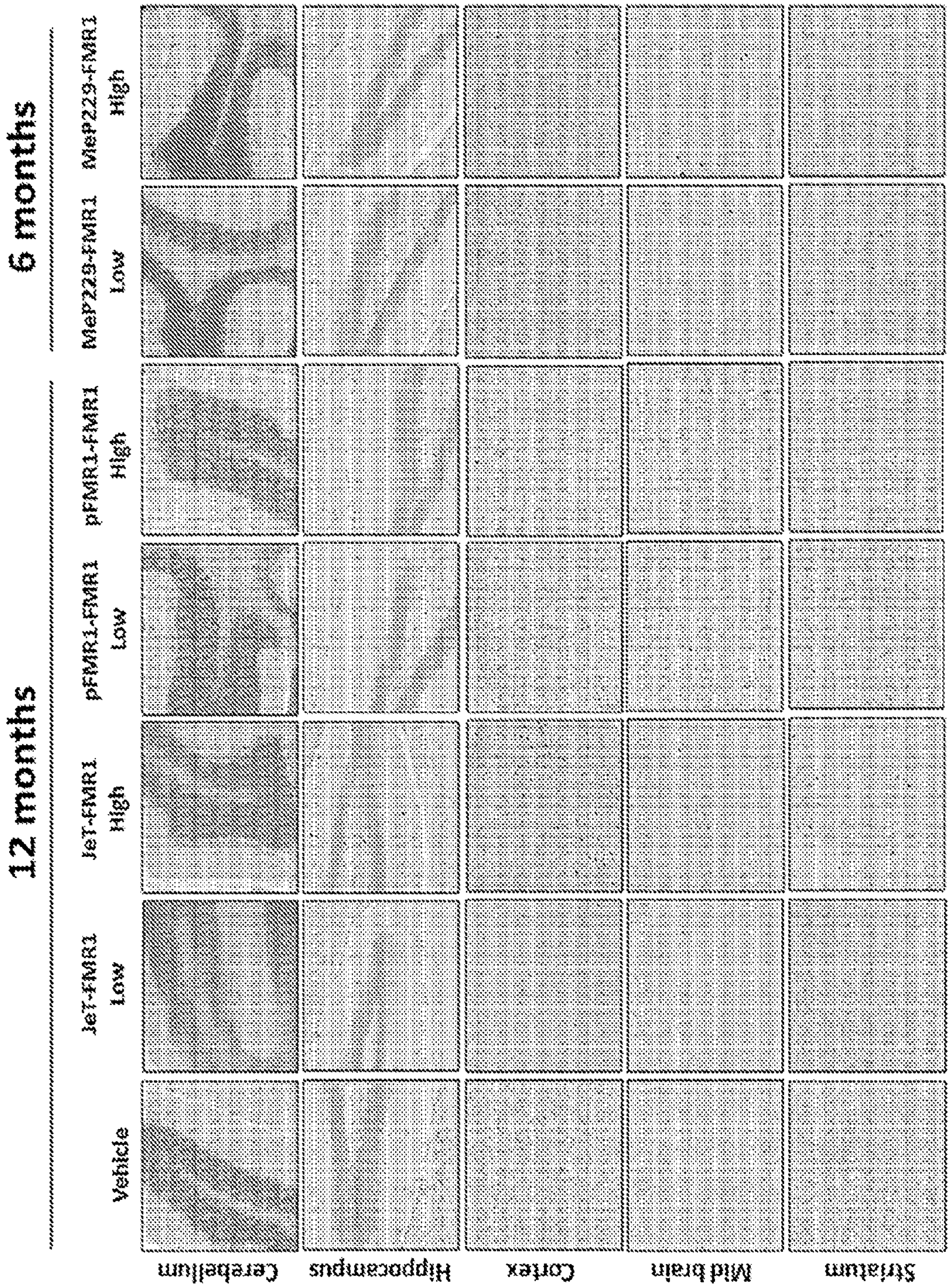
Figure 5C:
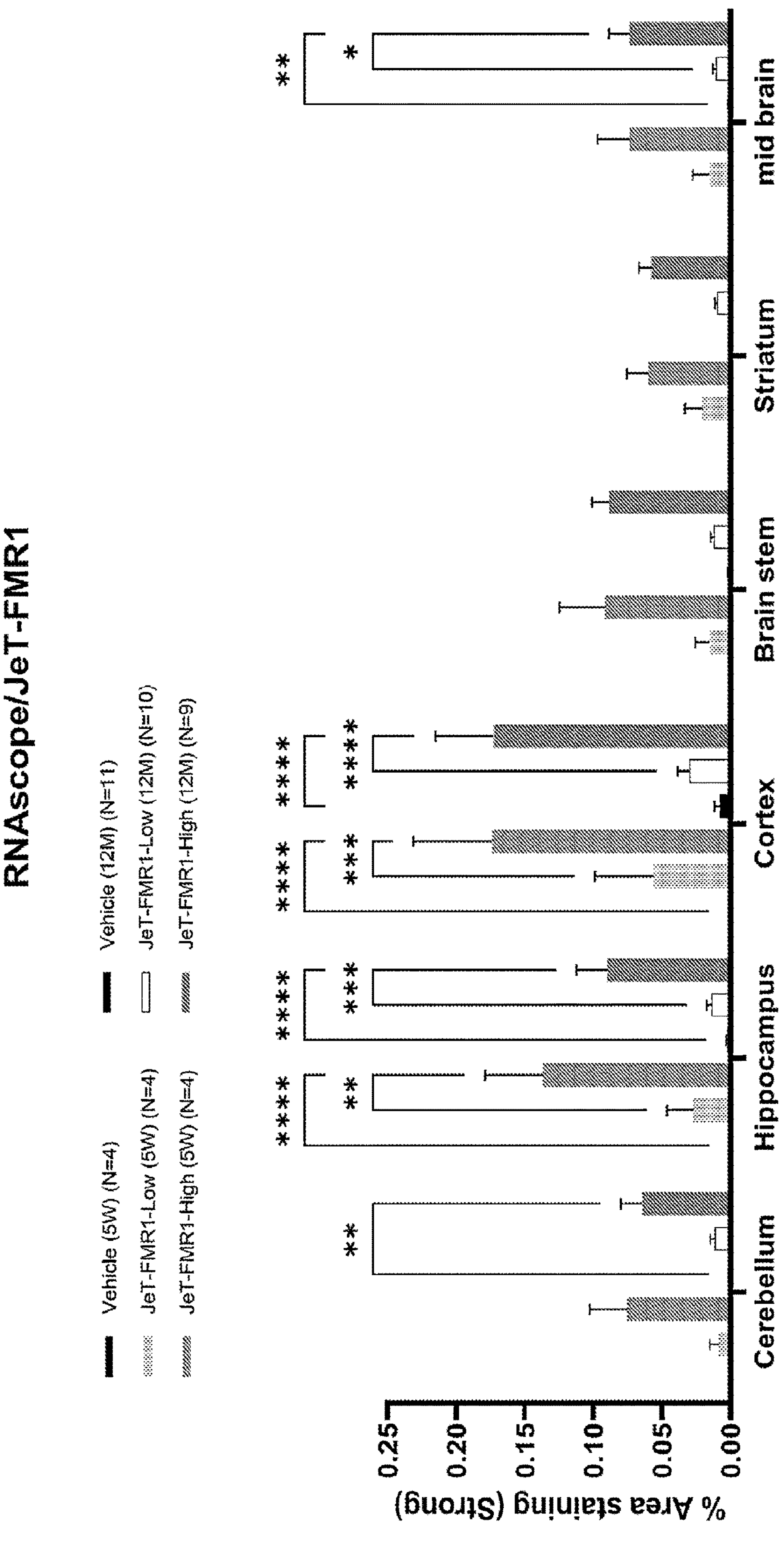
Figure 5D:
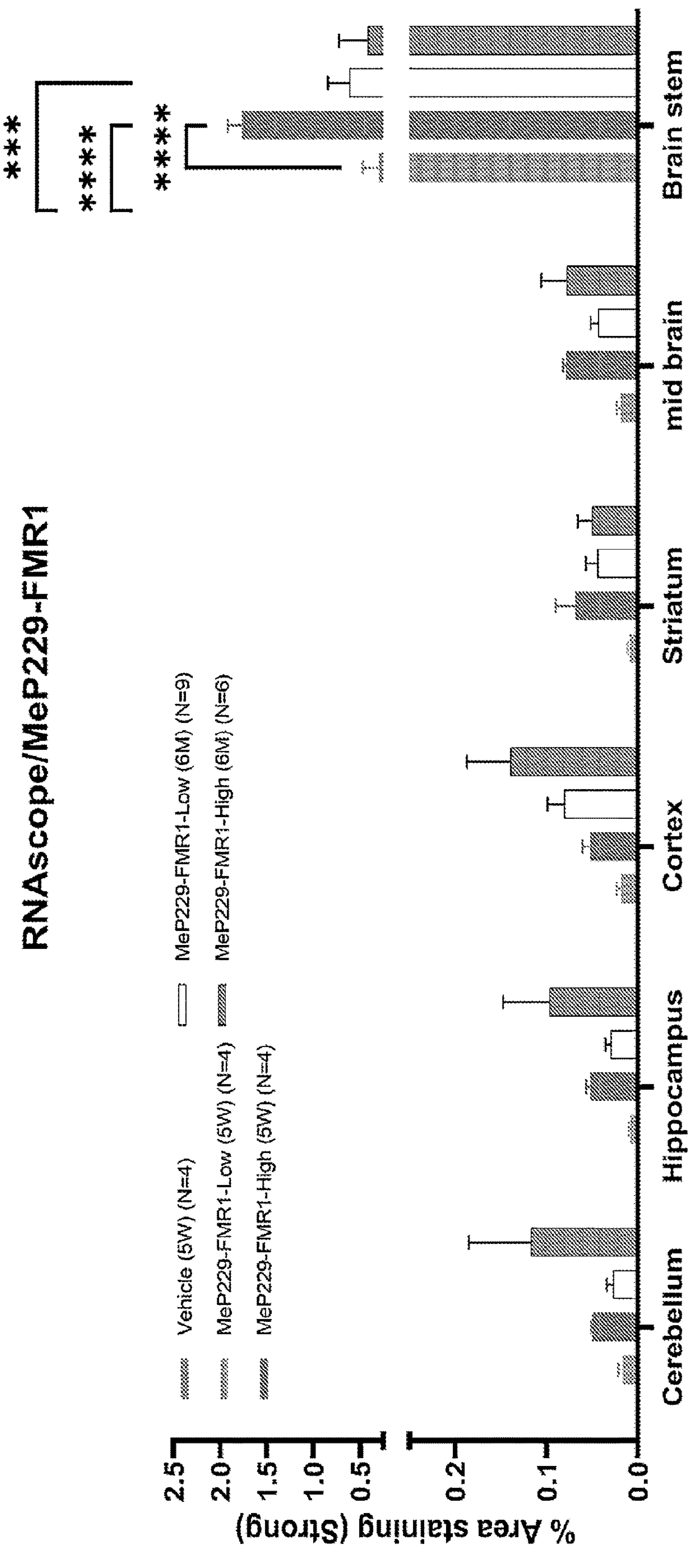
Figure 5E:
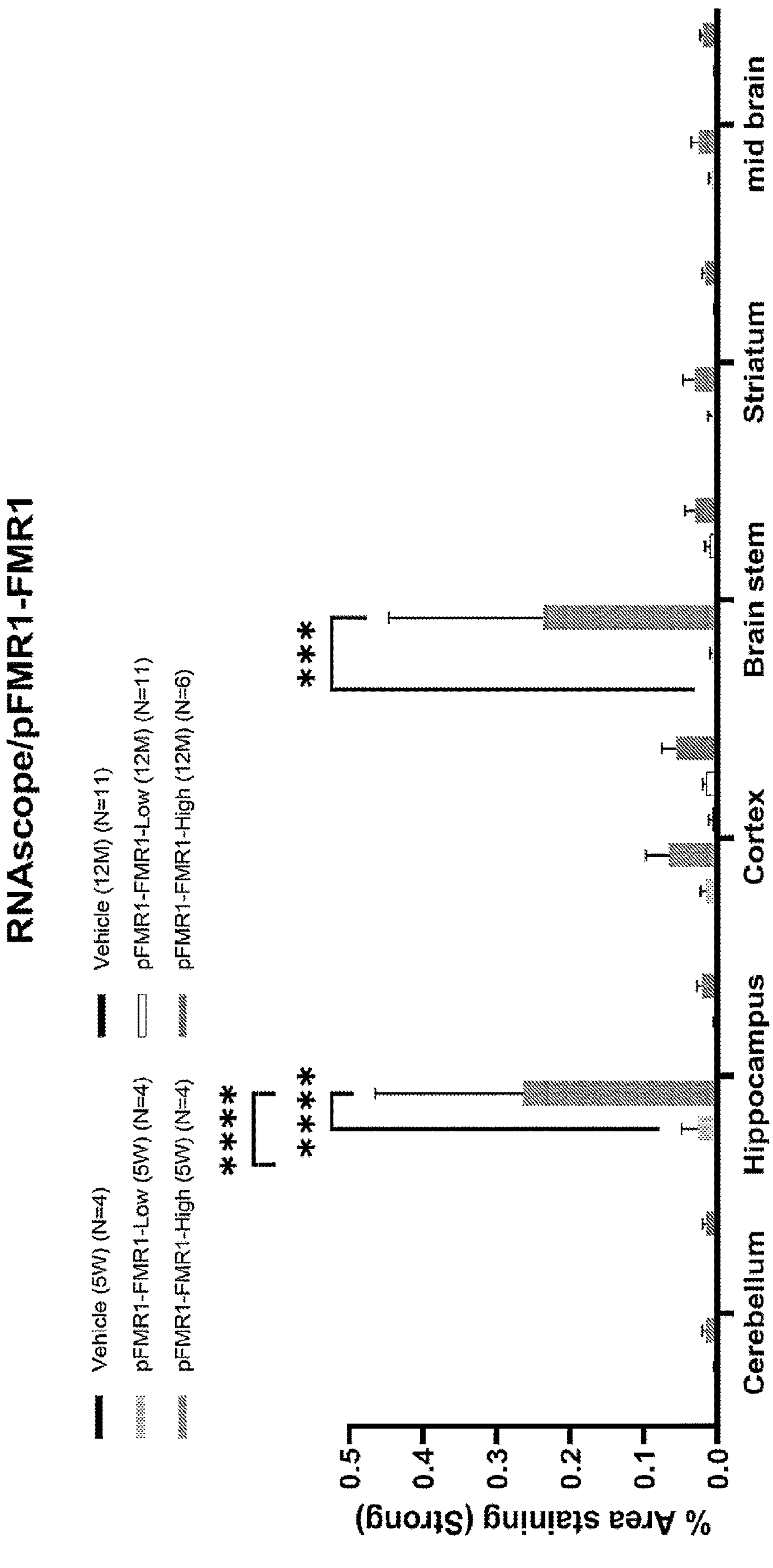

At 4 weeks after AAV administration, for a subset of mice the brain was fixed with formaldehyde and embedded with paraffin (FIGS. 5A-5E). RNAscope was performed with specific probes for FMR1 mRNA (RNAscope 2.5 HD assay kit (Advanced Cell Diagnostics). FIGS. 5A and 5B show representative images of each group, in which RED signal indicates positive staining of FMR1 gene. Histology images were analyzed using custom analysis settings in the HALO image analysis platform to quantify the signals from the JeT-FMR1/AAV (FIG. 5C), MeP229-FMR1/AAV (FIG. 5D), and pFMR1-FMR1/AAV (FIG. 5E) groups. Statistics one-way ANOVA $*p<0.05$, $**p<0.001$. The JeT and MeP229 promoters permit widespread expression of the FMR1 transgene across the nervous system, whereas the FMR1 promoter fragment does not support broad FMR1 transgene expression across the brain.

Figure 6A:
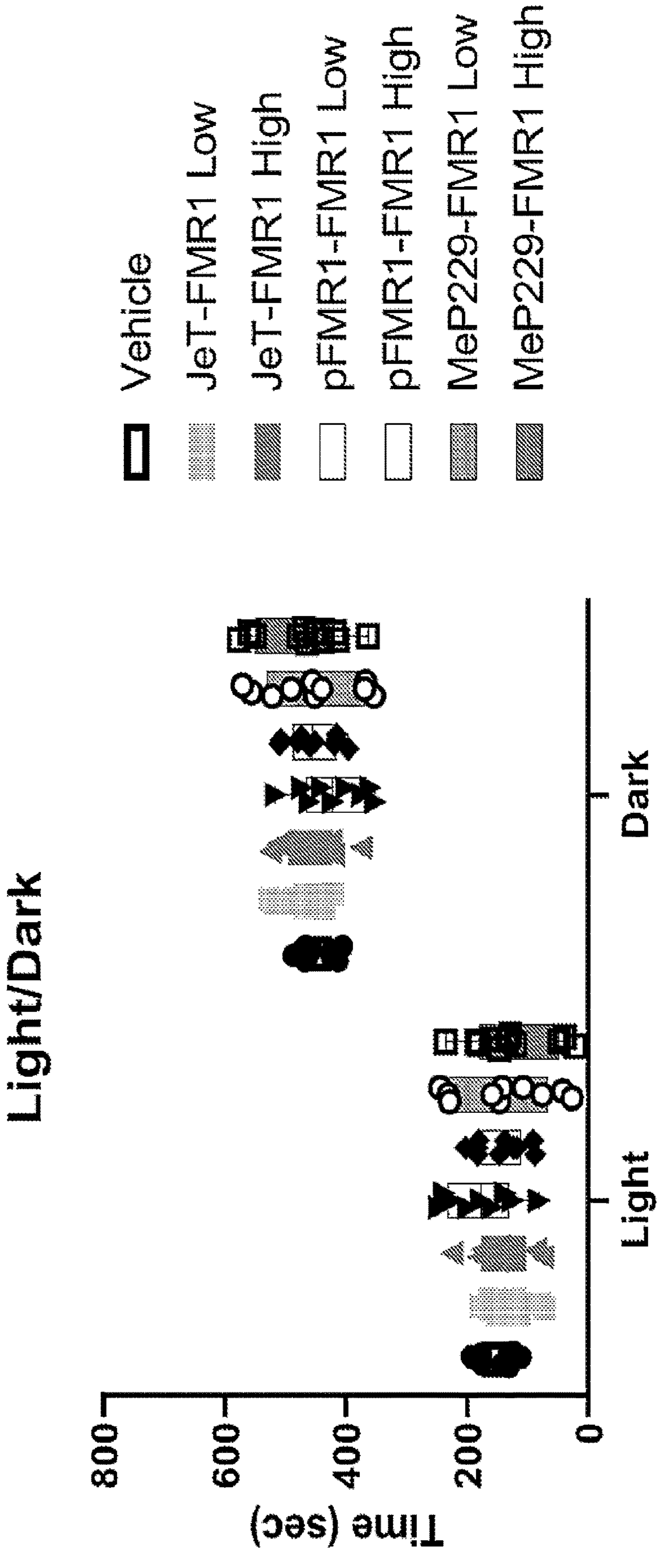
Figure 6B:
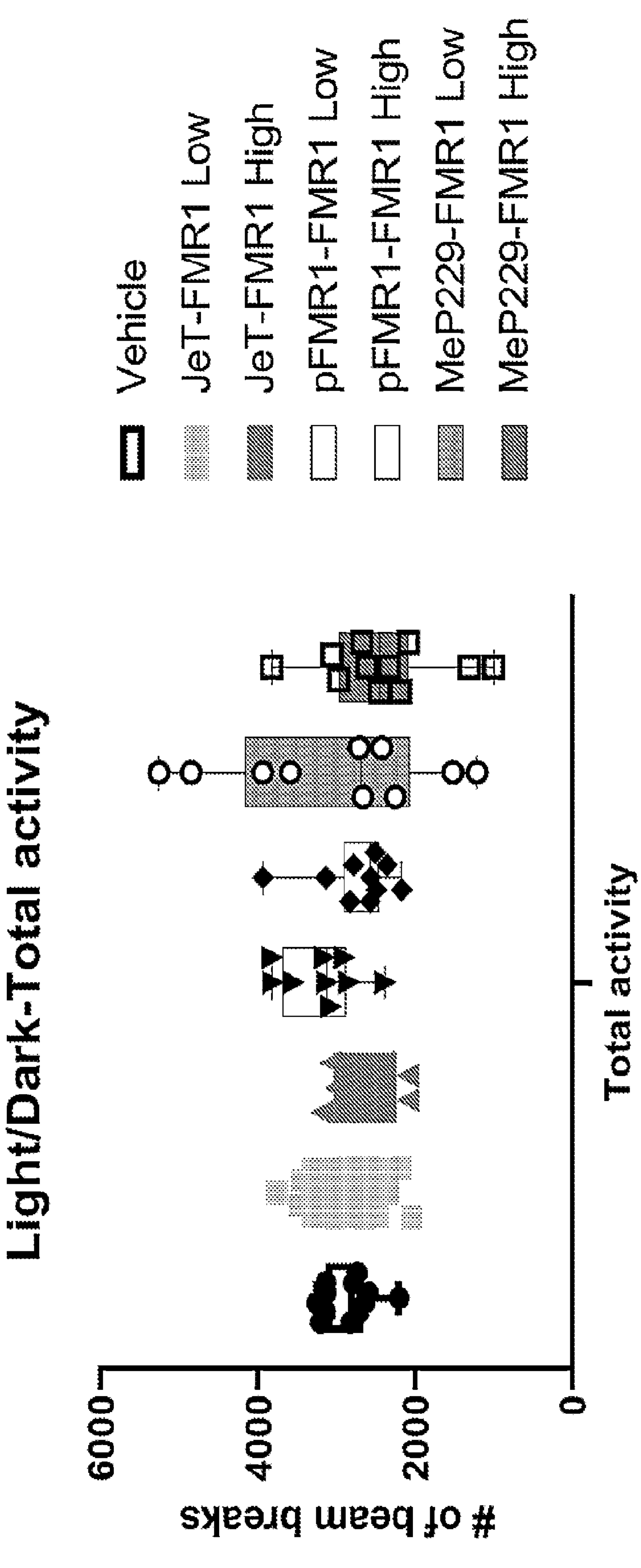
Figure 6C:
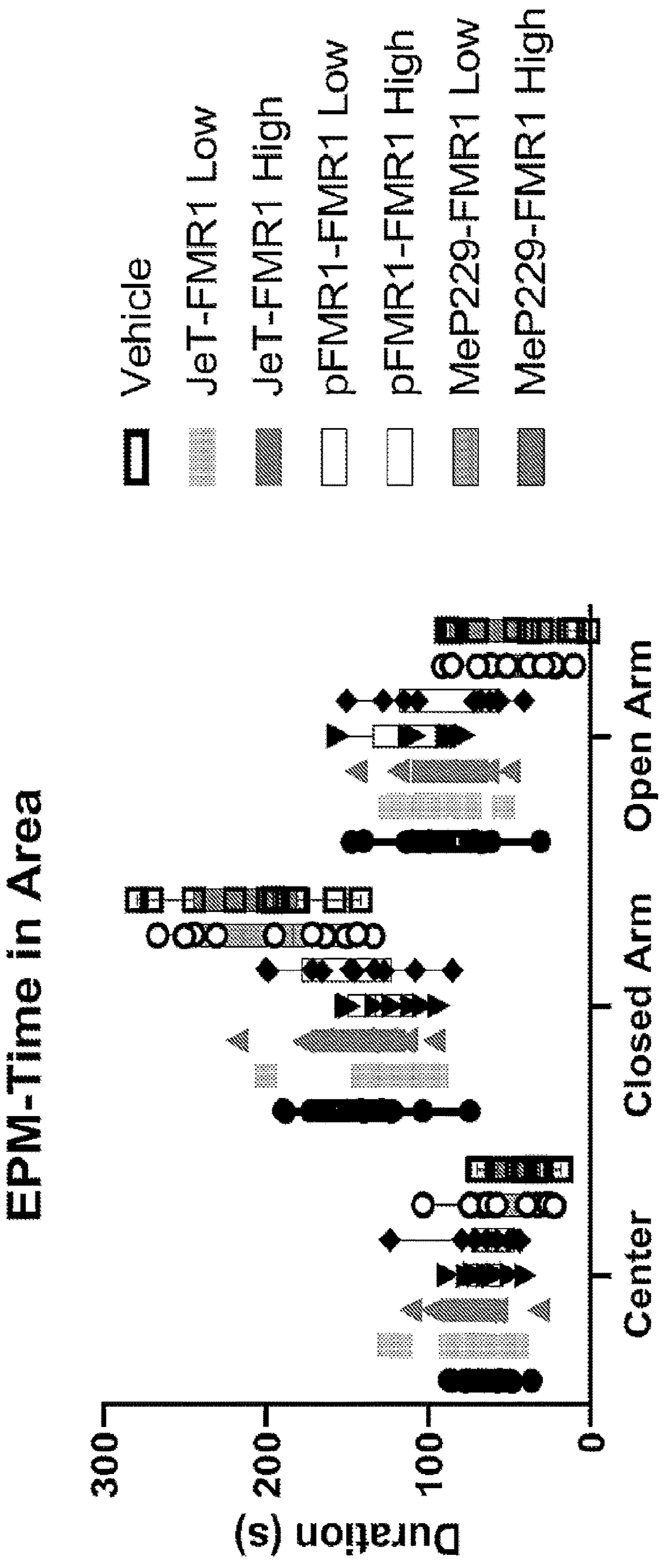
Figure 6D:
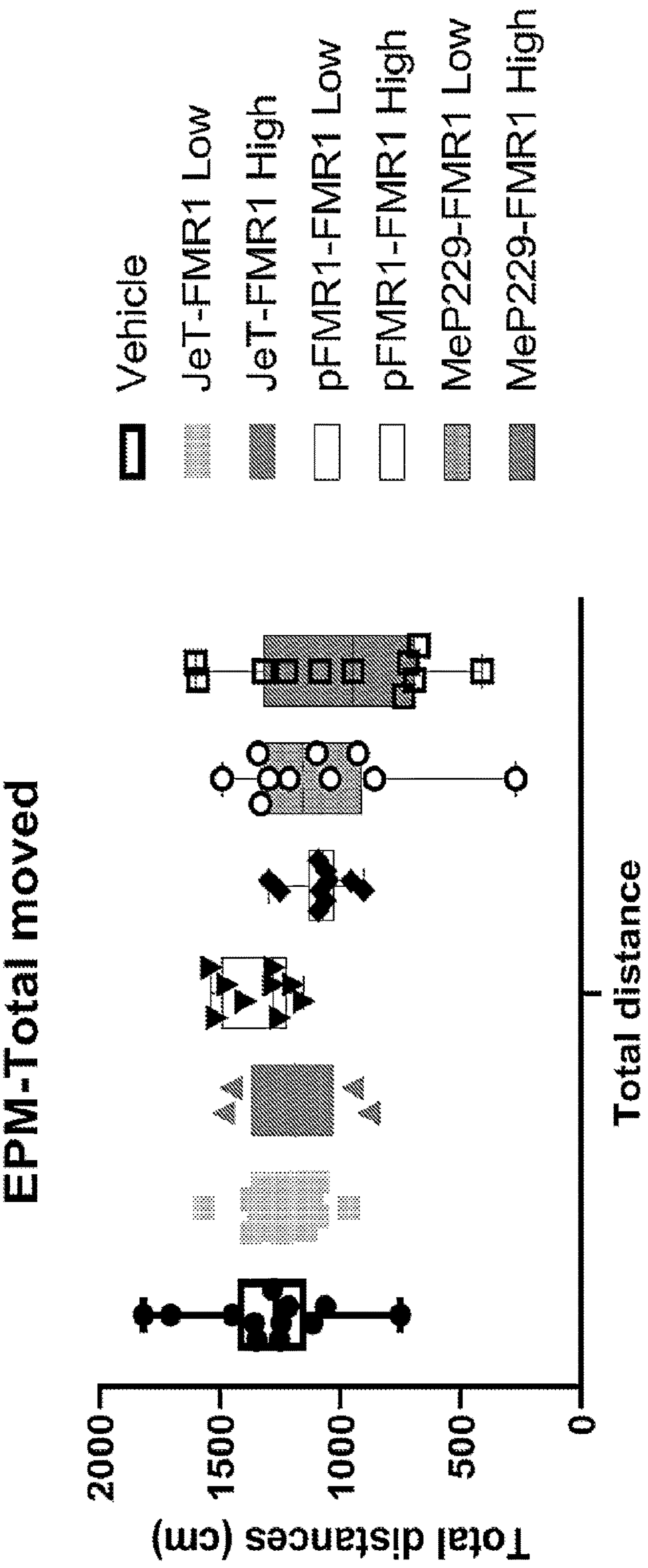
Figure 6E:
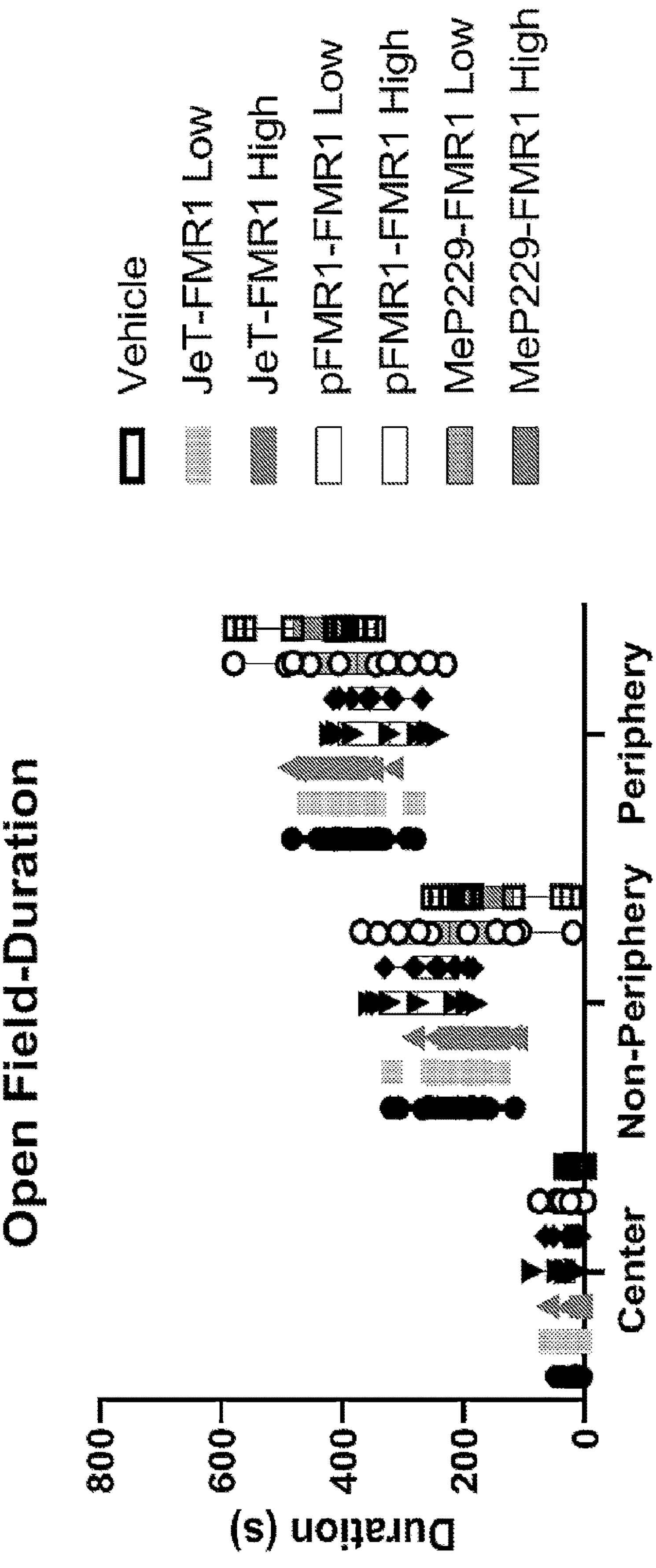
Figure 6F:
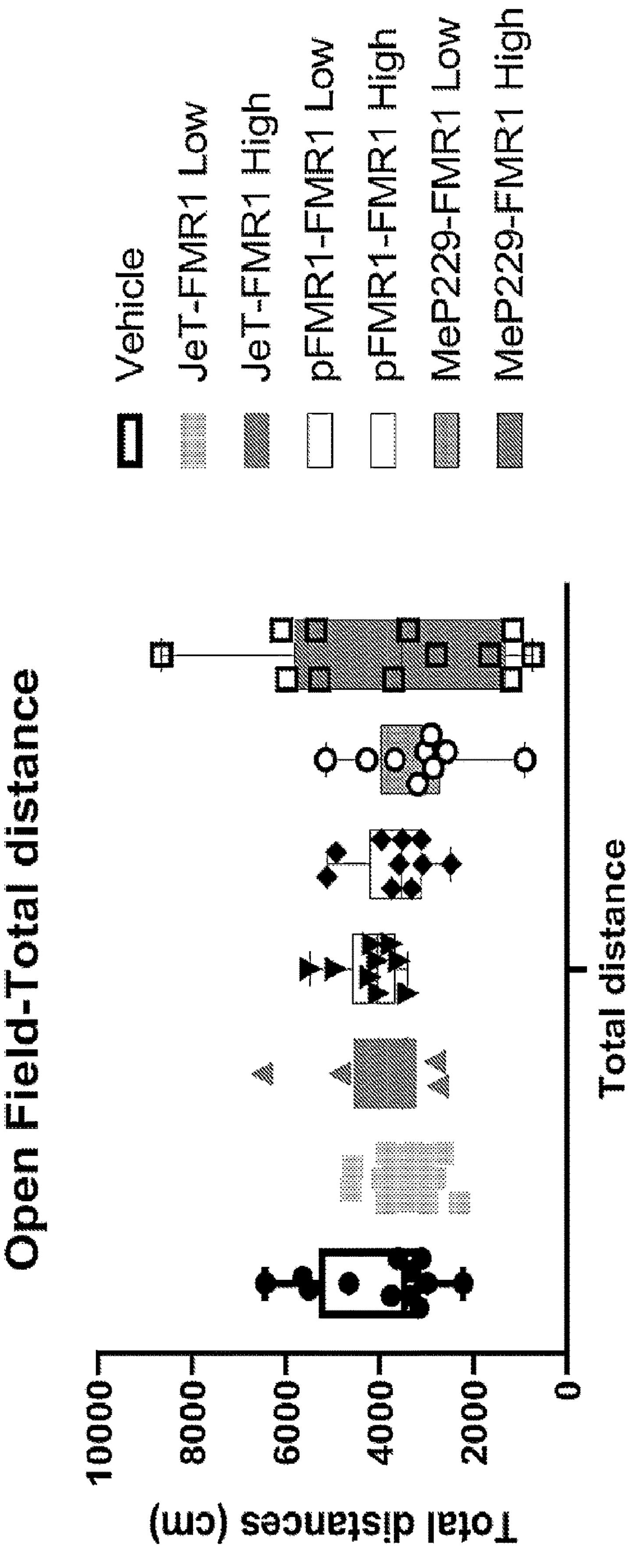
Figure 6G:
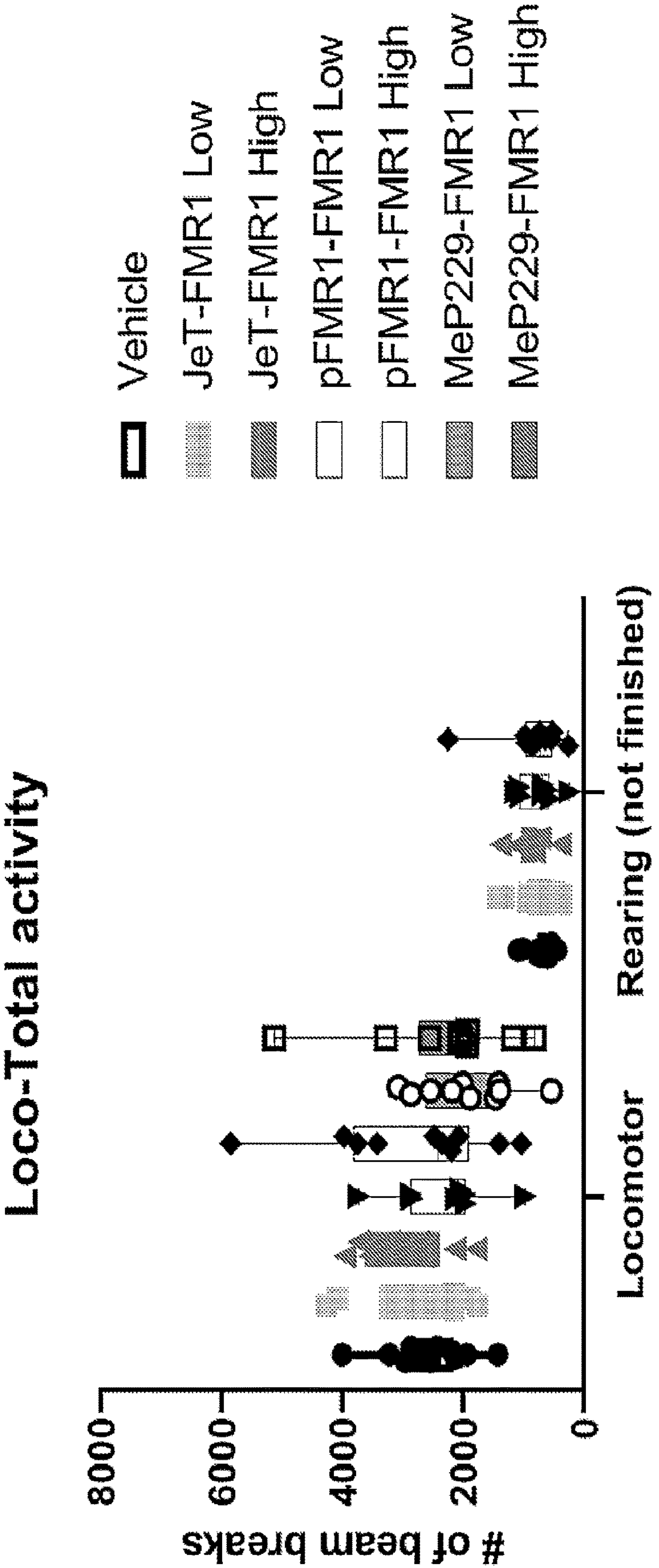
Figure 6H:
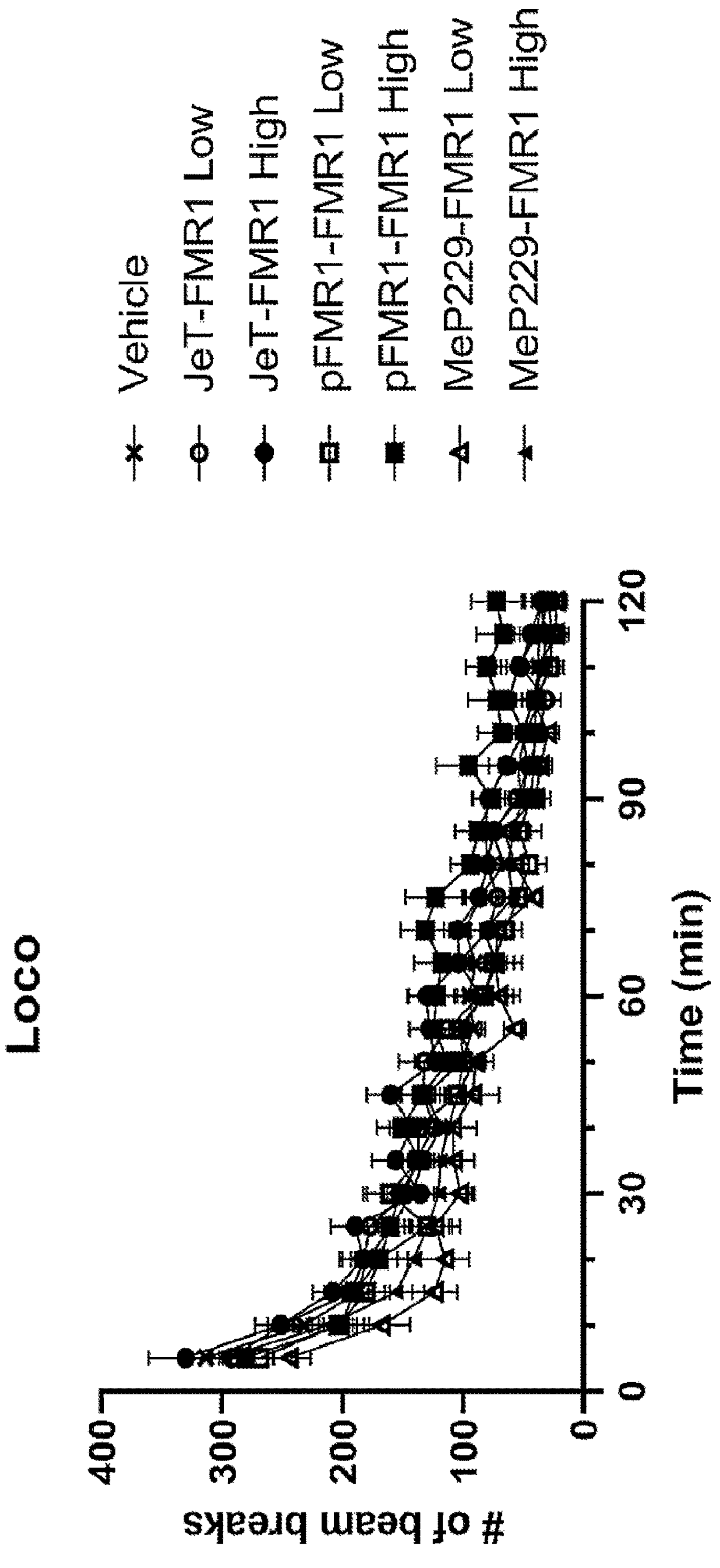
Figure 6I:
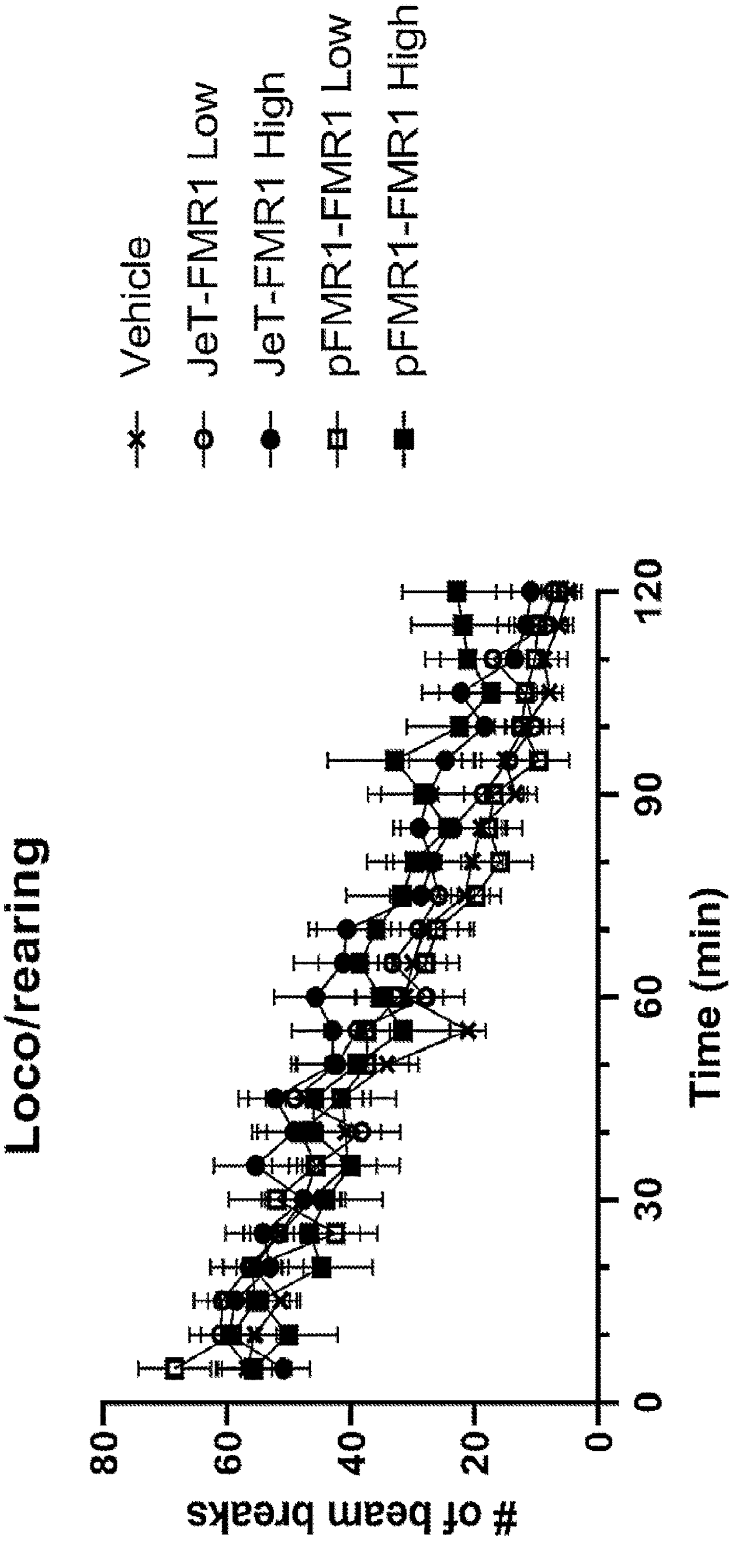

At 3 months after vector administration, Light and Dark transition (FIG. 6A-6B), Elevated plus maze (FIG. 6C-6D), Open field (FIG. 6E-6F), and Locomotor (FIG. 6G-6I) were tested to evaluate the anxiety among groups of normal mice dosed IT with each of the FMR1 expression vector designs. Importantly, there was not a significant difference between any of the groups, indicating that by these tests examining locomotion and anxiety, there was no indication of altered behavior after treatment with any of the FMR1 vectors.

Figure 7:
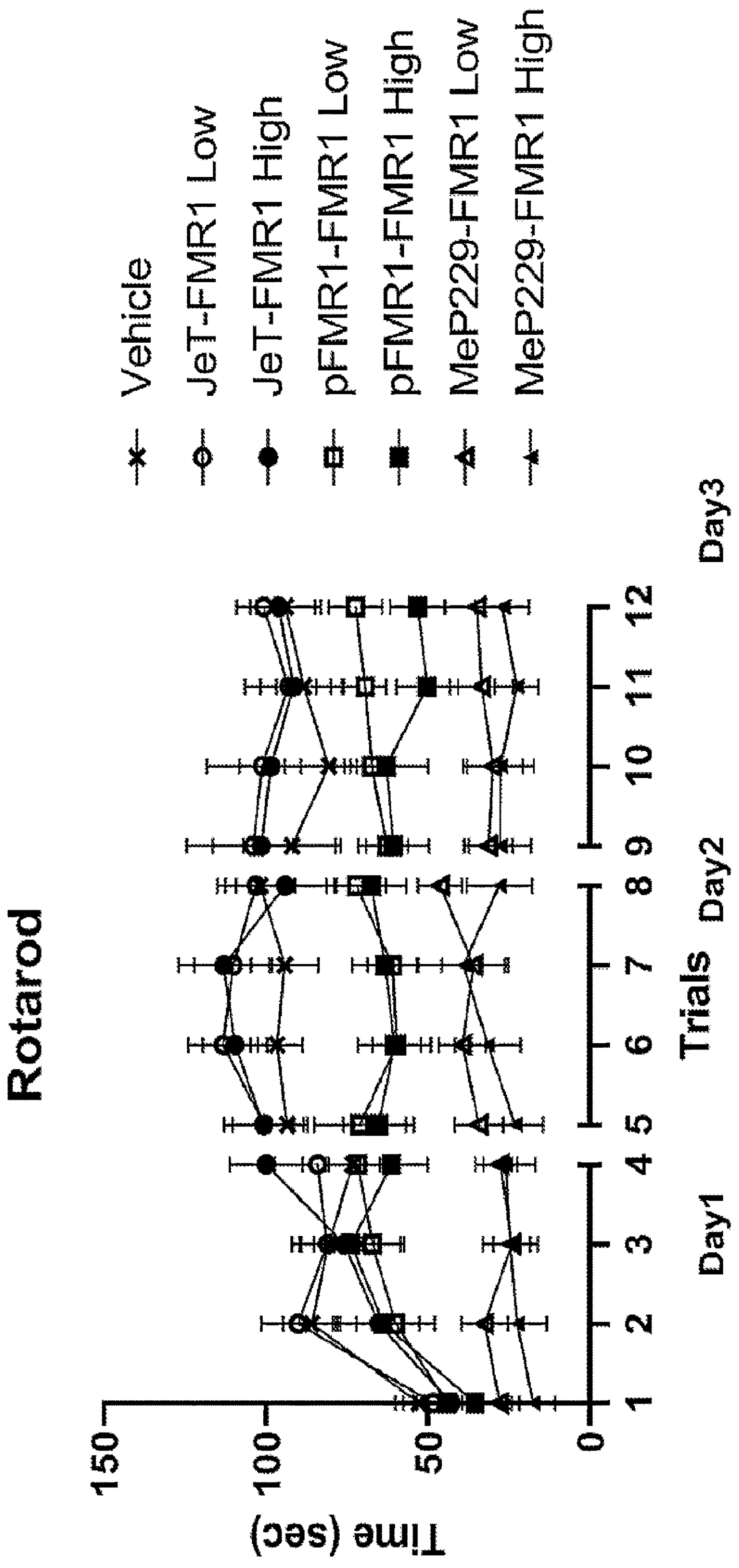
FIG. 7 shows the results of a safety Rotarod test to evaluate wild-type mice motor function and safety.

At 3 months after vector administration, Rotarod was tested to evaluate the motor function of normal mice dosed IT with each of the FMR1 expression vector designs (FIG. 7). The vector design utilizing the MeP229 promoter caused an apparent deficit in motor function in treated mice by this test, whereas the design utilizing the JeT promoter was tolerated well with mice performing equivalent to those injected with vehicle. The construct utilizing the FMR1 promoter fragment showed a trend of decreased motor function by this test.

Example 2

Tissues were analyzed from 5 week-old mice that received an IT injection at day 7-10 days. The animals were perfused with IX PBS with heparin. Tissues were collected and drop fixed in 10% neutral buffered formalin for 24 hours and then placed in 70% ethanol for storage. The tissues were trimmed into cassettes, embedded in paraffin and one hematoxylin and eosin stained slide was produced from each cassette. Tissues and the corresponding slides were labeled with the following ID's: 20, 23, 27, and 29 (injected with vehicle); 3, 4, 11, and 22 (injected with a low dose of JeT-FMR1); and 7, 13, 16, and 26 (injected with a high dose of JeT-FMR1). Brain, heart, skeletal muscle, liver, lung, gonad, spleen, kidney, and spinal cord were analyzed for all animals.

The brain was microscopically normal for all animals. There were no abnormalities found in the spinal cord of all mice.

The testes for 4, 7, 16, 20, 22 and 27 were microscopically normal. Ovaries were present for 3, 11, 13, 23, 26 and 29. All of the ovaries that were present were normal and the structures within the ovaries were consistent with various points in the estrus cycle The hearts were microscopically normal in all animals except animal ID 11. The heart for ID 11 contained a small focal area of mineralization. This is considered an incidental finding as there was no evidence of necrosis or inflammation associated with the mineral. The skeletal muscle was microscopically normal in all animals.

The kidneys of mouse ID 3, 4, 7, 11, 13, 20, 22, 23, 26 and 29 contained no abnormalities. The kidney on animal ID 16 contained a single cyst that compressed adjacent tubules in medulla. One part of the pole of the kidney of animal ID 27 contained interstitial fibrosis and loose connective tissue. There were markedly decreased numbers of tubules in this area and normal glomeruli toward the periphery. These lesions were most likely congenital defects due to the age of the mouse.

The livers of mouse 3, 7, 13, 16 and 27 contained no microscopic abnormalities. The livers of mouse ID 4, 11, 20, 22, 23, 26 and 29 contained multifocal small islands of extramedullary hematopoiesis. Extramedullary hematopoiesis occurs more frequently in young mice and is an expected finding.

The lungs of all mice were microscopically normal.

The spleens of all mice were normal and contained various amounts of extramedullary hematopoiesis in the red pulp. Mouse IDs 26 and 29 had variable amounts of hemosiderin within the macrophages of the red pulp. This is considered normal in mice and the incidence increases as mice age.

Example 3

Tissues were analyzed from 5 week-old mice that received an IT injection between day 7-10 days of age. The animals were perfused with 1×PBS with heparin. Tissues were collected and drop fixed in 10% neutral buffered formalin for 24 hours and then placed in 70% ethanol for storage. The tissues were trimmed into cassettes, embedded in paraffin and one hematoxylin and eosin stained slide was produced from each cassette. Tissues and the corresponding slides were labeled with the following IDs: 64, 66, 68, and 70 (for low dose of pFMR1-FMR1) and 43, 45, 63, and 65 (for high dose of pFMR1-FMR1). Brain, heart, skeletal muscle, liver, lung, gonad, spleen, kidney, and spinal cord were submitted for all animals.

The brain was microscopically normal for all animals. There were no abnormalities found in the spinal cord of all mice.

The testes for 43, 63, and 68 were microscopically normal. The testes for animal ID 63 had a few tubules that only contained sertoli cells and no germ cells (atrophy). There was no evidence of germ cell degeneration in the tubules. The presence of a few atrophic tubules is considered a common, incidental finding in mice.

Ovaries were present for 45, 65 and 66. The ovaries for these animals were normal and the structures within the ovaries were consistent with various points in the estrus cycle. There was no ovary present for animal ID 70 but the fallopian tubes were normal.

The hearts and skeletal muscle were microscopically normal in all animals.

The kidneys of mouse ID 45, 63, 64, 65, 66, 68, and 70 contained no abnormalities. The distal medulla of kidney of animal ID 43 contained two tubules with intra-tubular calcification. This is a common spontaneous finding in mice.

The livers of mouse 65, 66 and 68 contained no microscopic abnormalities. The livers of mouse ID 43, 45, 63, 64, and 70 contained multifocal small islands of extramedullary hematopoiesis. Extramedullary hematopoiesis occurs more frequently in young mice and is an expected finding.

The lungs of all mice were microscopically normal. The spleens of all mice were normal and contained various amounts of extramedullary hematopoiesis in the red pulp. Mouse ID 64 had variable amounts of hemosiderin within the macrophages of the red pulp. This is considered normal in mice and the incidence increases as mice age.

The livers of mouse ID 75, 72, 76, and 78 were normal. The livers of mouse IDs 71 and 73 contained few mitotic figures. This is expected in young mice. The livers of mouse IDs 95 and 98 exhibited single cell necrosis with infiltrates of small numbers of inflammatory cells, mild focal and multifocal. Areas with 1-2 cell hepatocyte necrosis accompanied by inflammatory cells can occur spontaneously in the mouse liver. The spleens of mouse IDs 75, 71, 73, 95 and 98 exhibited extramedullary hematopoiesis. This is expected in young mice. No spleen was present for mouse ID 72. The hearts of mouse IDs 75, 71, 73, 72, 95, 76, 78, and 98 were all microscopically normal. The skeletal muscle of mouse IDs 75, 73, 95, 72, 76, 78, and 98 were all microscopically normal. No skeletal muscle was present for mouse ID 71.

The kidneys of mouse IDs 75, 71, 73, 95, 72, 78, and 98 were all microscopically normal. The kidneys of mouse ID 76 contained minerals in tubule-mild focal. This is an incidental findings as mineralized tubules can occur occasionally in non-treated mice. The lungs of mouse IDs 75, 71, 73, 95, 72, 76, 78, and 98 were all microscopically normal. The ovaries of mouse IDs 75, 95, and 98 were microscopically normal. No ovaries were present for mouse ID 72. The brains of mouse IDs 75, 71, 73, 95, 72, 76, 78, 98, 102, and 103 were all microscopically normal. The spinal cords of mouse IDs 75, 71, 73, 95, 72, 76, 78, 98 and 102 were microscopically normal. The spinal cord of mouse ID 103 contained a single swollen axon adjacent to the ventral median fissure. This may be due to degeneration of this axon or an artifact from collection. Seeing as only one spinal cord was affected and no gitter cells were evident it is most likely an artifact.

Example 4

These examples present updated data for the studies described in Examples 1-3.

Introduction

Fragile X Syndrome is a neurodevelopmental disorder caused by the absence of Fragile X Mental Retardation Protein (FMRP). Because FMRP is a highly pleotropic protein controlling the expression of hundreds of genes, and directly regulating intracellular trafficking of ion channels and other key intracellular proteins, viral vector-mediated gene replacement therapy is viewed as a potential viable treatment to restore the fundamental underlying molecular pathology inherent in the disorder. This Example describes the safety profile and therapeutic effects of a clinically relevant dose of a self-complementary adeno-associated viral (AAV) vector containing a major human brain isoform of FMRP after intrathecal injection into neonatal wild-type and Fragile X knockout (KO) mice.

Results

Expression of the scAAV-JeT-hFMRPiso17 Vector

Figure 8A:
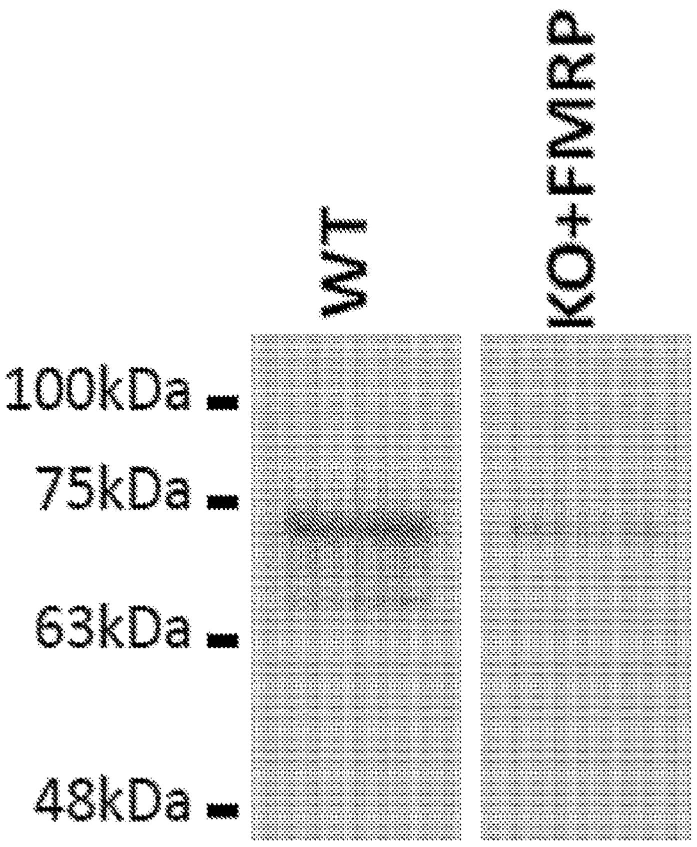
FIGS. 8A-8E show the CNS expression profile of scAAV-JeT-hFMR1iso17 vector after intrathecal injection into the Fmr1 knockout (KO) mouse.
Figure 8B:
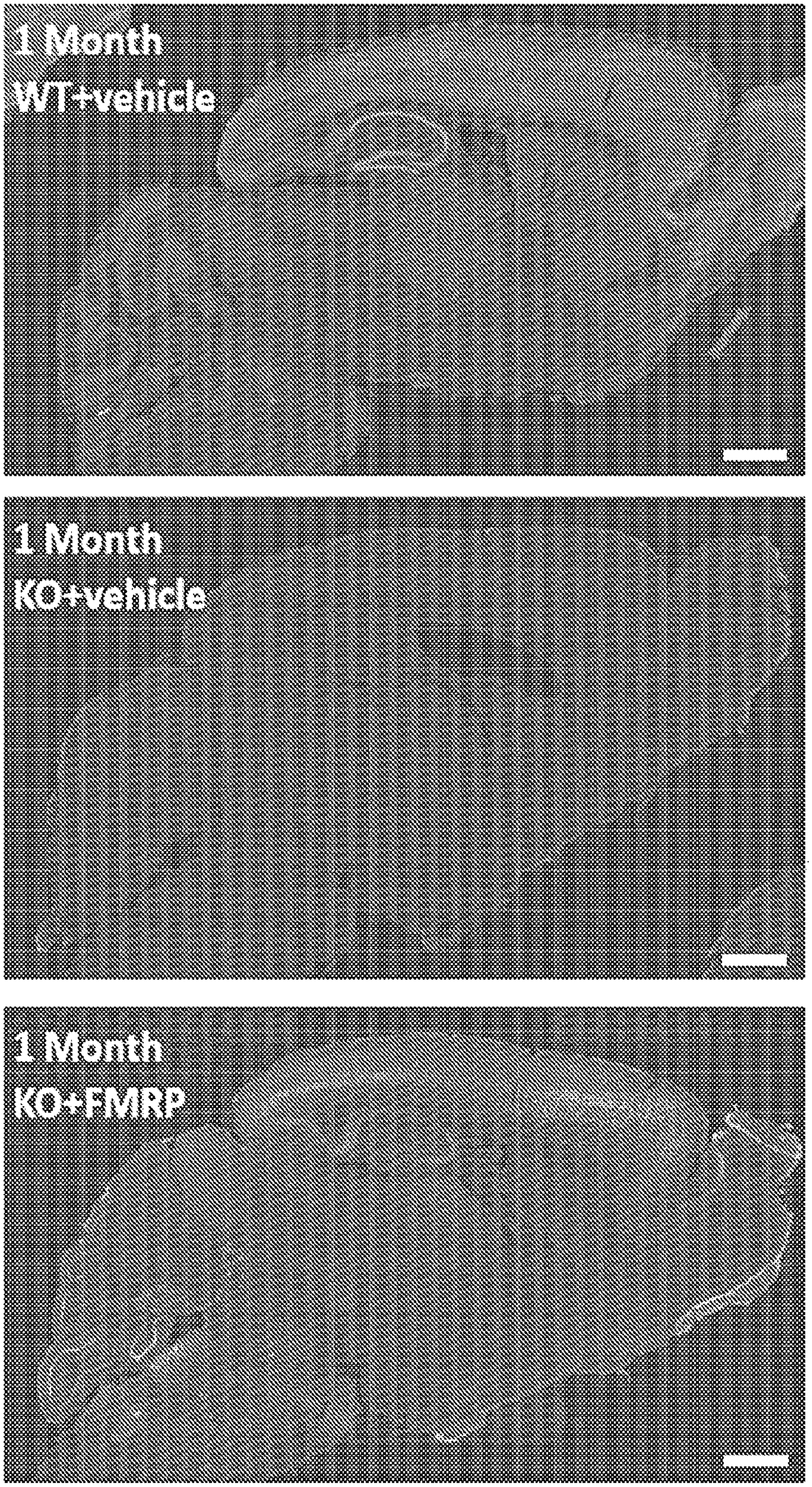
Figure 8C:
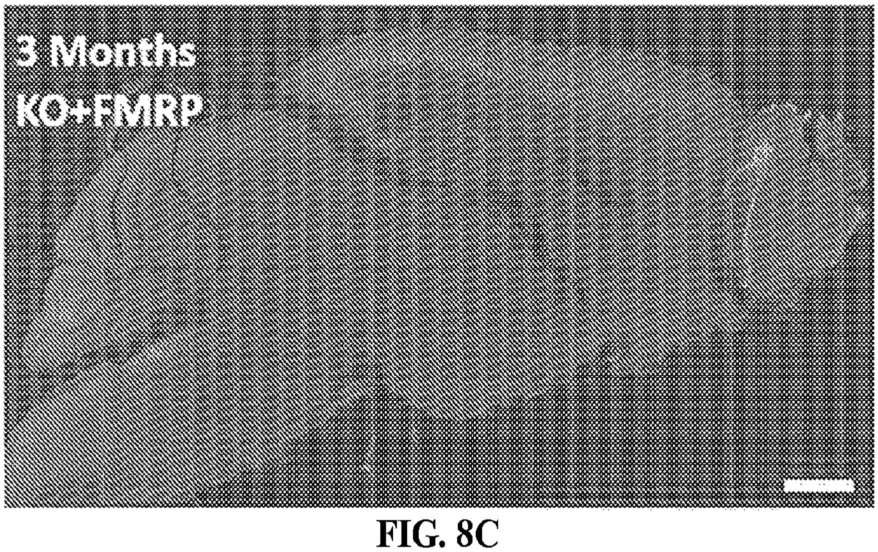
Figure 8D:
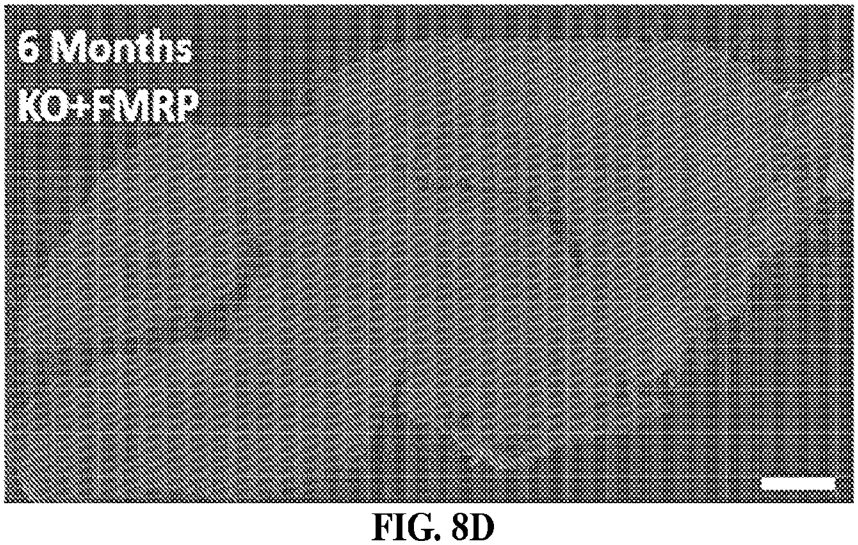
Figure 8E:
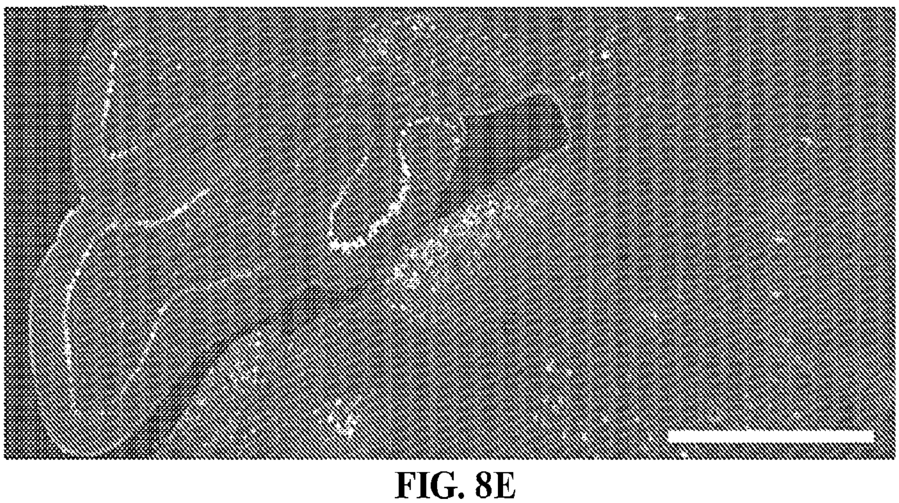
Figure 9A:
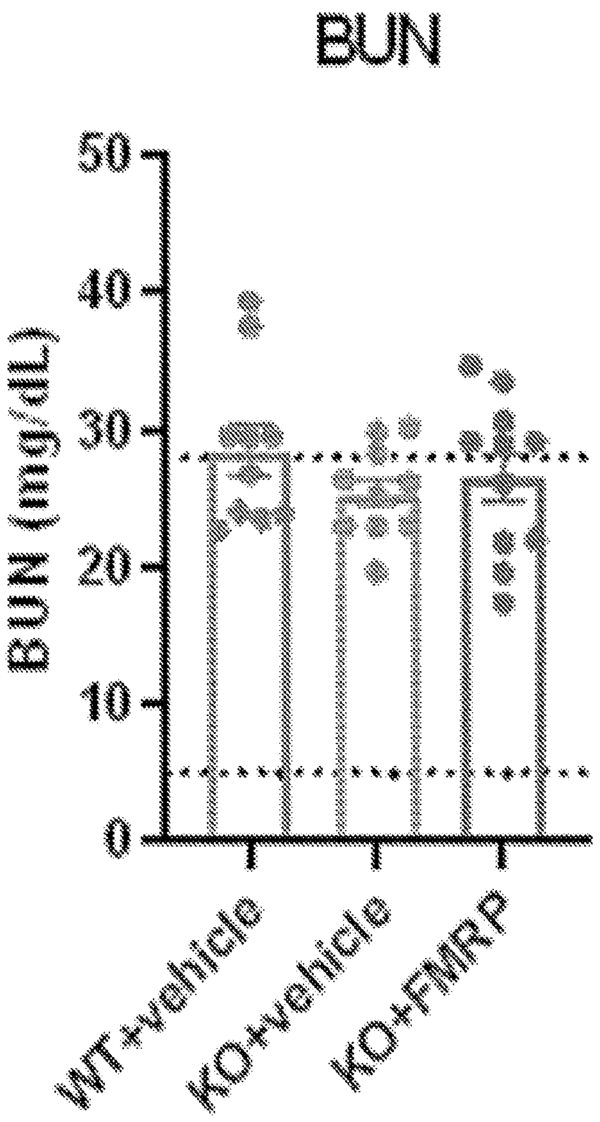
FIGS. 9A-9E show a comparison of blood and liver safety profiles from three treatment cohorts. Wild-type mice were injected at postnatal day (PND) 2 or 3 with vehicle and Fmr1 KO mice were injected at PND 2 or 3 with either vehicle or scAAV-JeT-hFMR1iso17 (2.3E+11 vg) by i.t. injection, and serum and tissue samples were collected at 6 months of age.
Figure 9C:
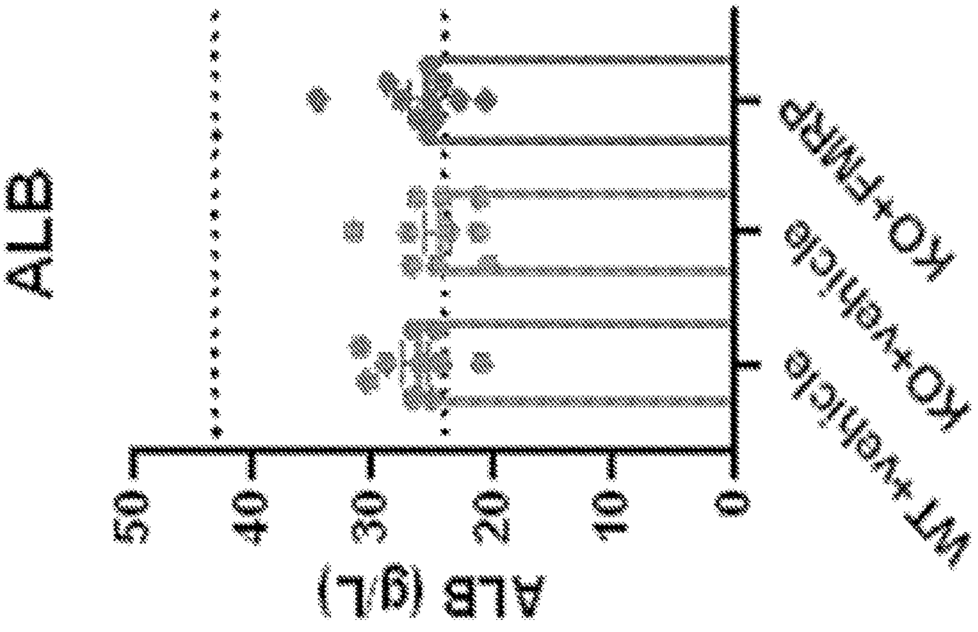
Figure 9B:
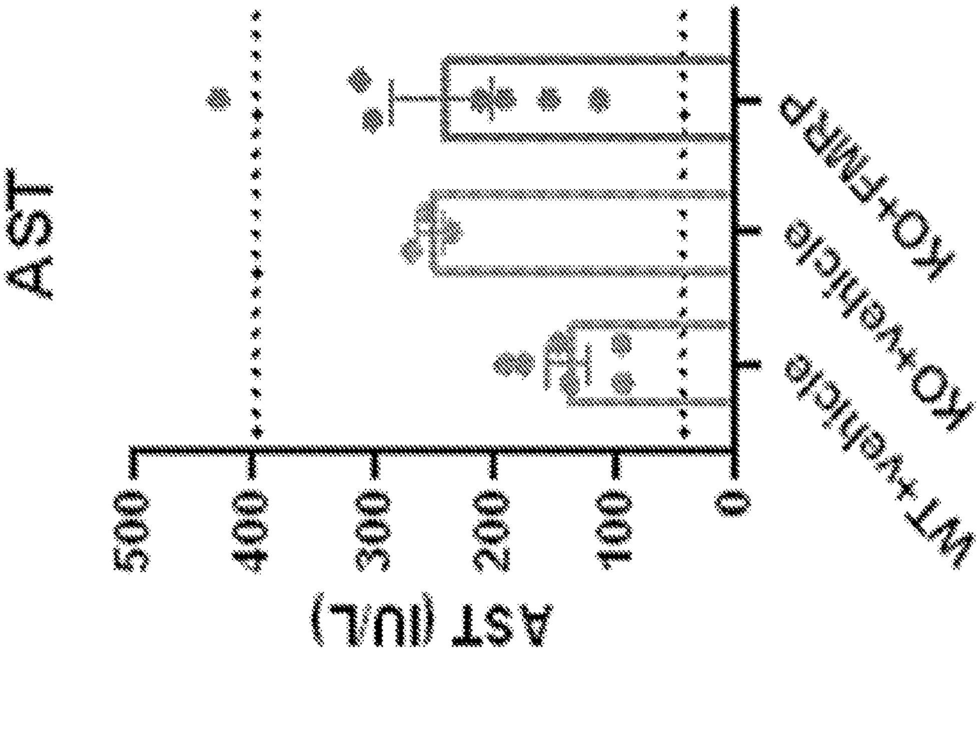
Figure 9D:
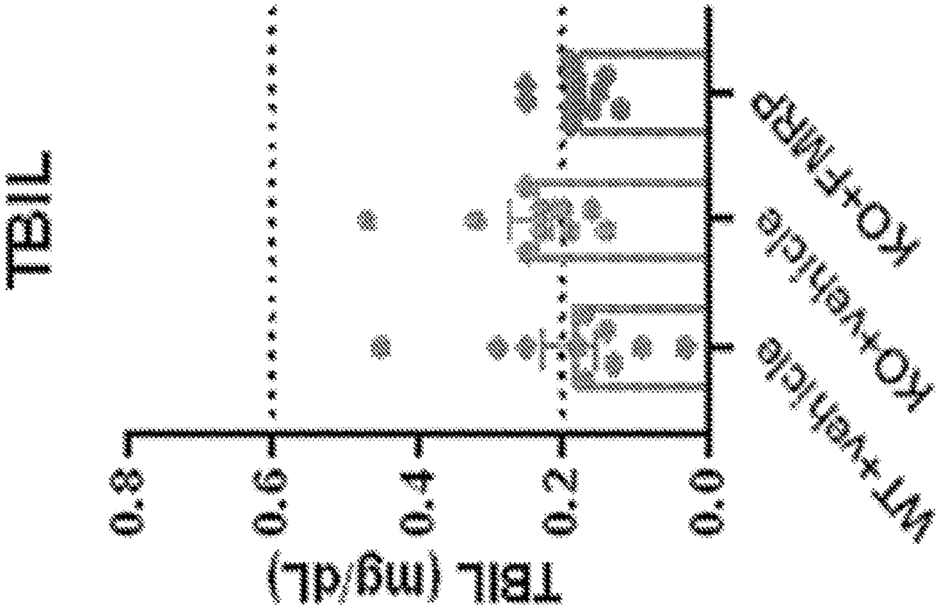
Figure 9E:
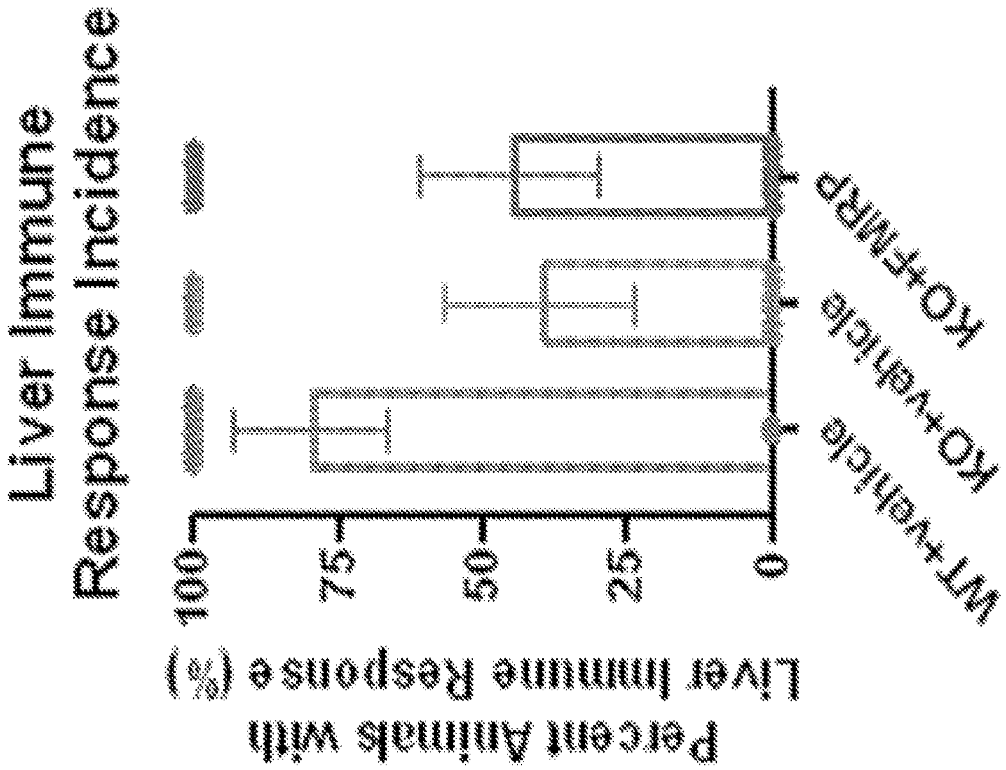

The decision to use human isoform 17 of FMRP in this vector was based on isoform 17 and its rodent orthologues being the most commonly expressed isoforms of FMRP in the human, mouse and rat CNS. To further verify that the AAV-JeT-hFMRPiso17 vector was expressing the desired isoform, a western blot was performed comparing the endogenous FMRP expressed in the WT mouse against the gene product of the AAV vector from an Fmr1-KO mouse. The AAV-generated FMRP transgene co-migrated with the mostly highly expressed FMRP isoform in the WT mouse brain (FIG. 8A).

Fragile X mental retardation protein is endogenously expressed throughout the CNS of humans and mice at all ages, and so the aim was to transduce the brain as widespread as possible with persistent expression. To examine the distribution of the FMRP transgene in mice injected at PND 2, we performed immunofluorescent staining of KO+FMRP mouse brains at 1-month (FIGS. 8B and 8E), 3 months (FIG. 8C), and 6 months (FIG. 8D) timepoints which corresponded with testing ages of our battery of behavioral and safety testing. Expression of FMRP was observed in the cerebral cortex, hippocampus, inferior and superior colliculus, thalamus, the Purkinje and granule cell layers of the cerebellum, and brainstem of KO+FMRP mice 1 month, 3 months, and 6 months post injection (FIGS. 8B-8E). No negative behavioral, serological or pathohistological outcomes were observed after injection of AAV-FMRP into WT (injected at PND 7-10, behavior at 3 months post-injection, serum collected at 5 weeks and 12 months of age) or Fmr1-KO mice (injected at PND 2, serum and tissue samples collected at 6 months of age)(FIGS. 9A-9E). These analyses demonstrate that the AAV-JeT-hFMRPiso17 vector is capable of persistently mediating protein expression of the most abundantly expressed human/rodent isoform of FMRP across multiple brain regions.

Cell-Type Specificity and Coverage of FMRP

Figure 10A:
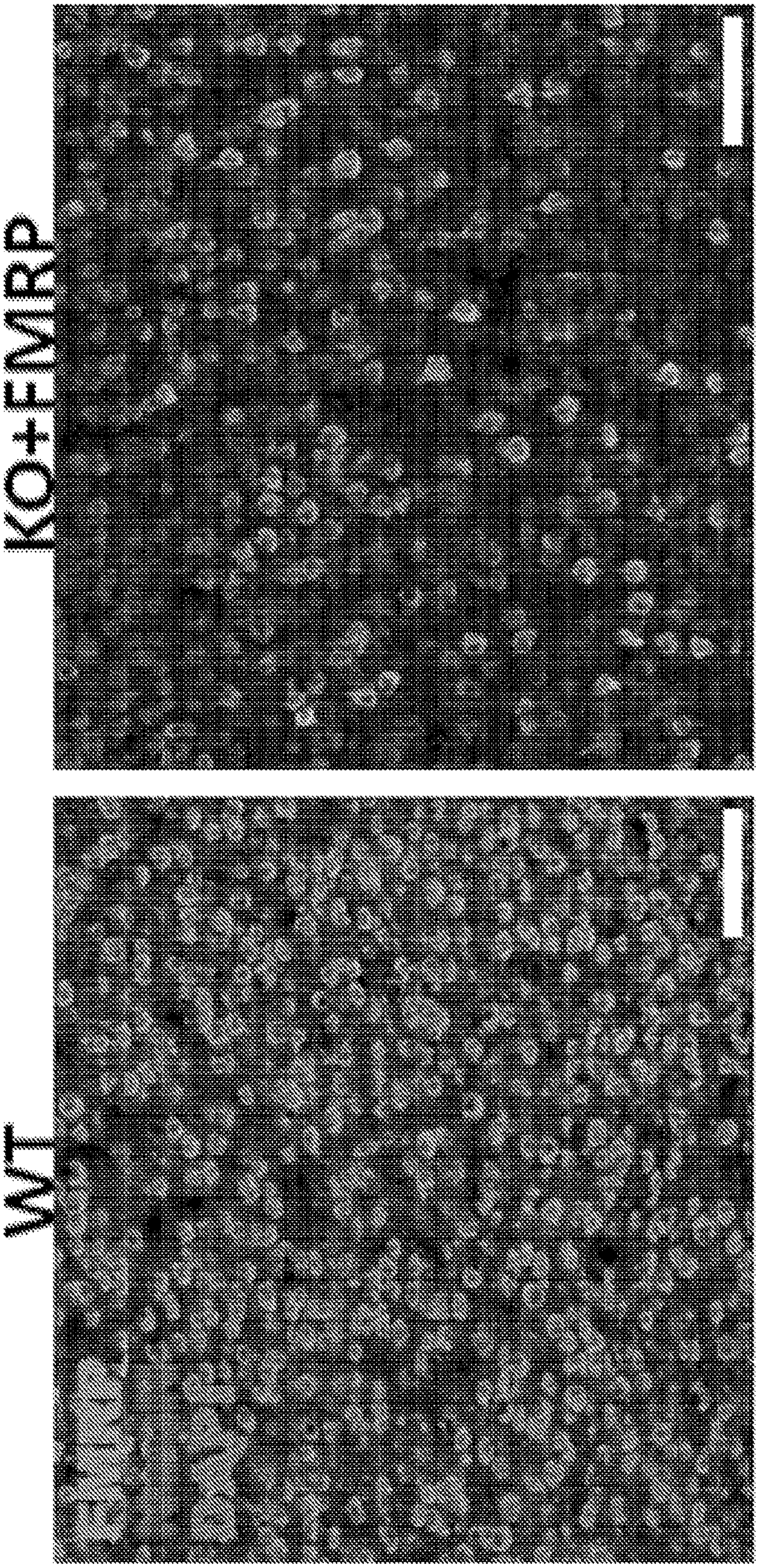
FIGS. 10A-10H show cell-type expression of the scAAV-JeT-hFMR1iso17 vector. The motor cortices of WT+vehicle and KO+FMRP mice were immunolabeled and quantified at 2-weeks of age for colocalization of FMRP and either NeuN (FIG. 10A, all neurons), GAD65/67 (FIG. 10B, GABAergic inhibitory neurons), Sox9 (FIG. 10C, astrocytes), or S100β (FIG. 10D, astrocytes, oligodendrocytes, oligodendroglial progenitor cells). Scale bars=100 μm. The cell-type specificity of FMRP from the scAAV-JeT-hFMR1iso17 vector was similar to endogenous FMRP expression in WT+vehicle mice. Coverage of cell-types with FMRP from the scAAV-JeT-hFMR1iso17 vector is significantly lower than the endogenous FMRP in WT+vehicle mice for NeuN-, GAD65/67-, and Sox9-positive cells, and it likely due to physical distribution of the AAV. n-values, 6 mice for each group. *p<0.05, t-test. Bars=mean±SEM.
Figure 10B:
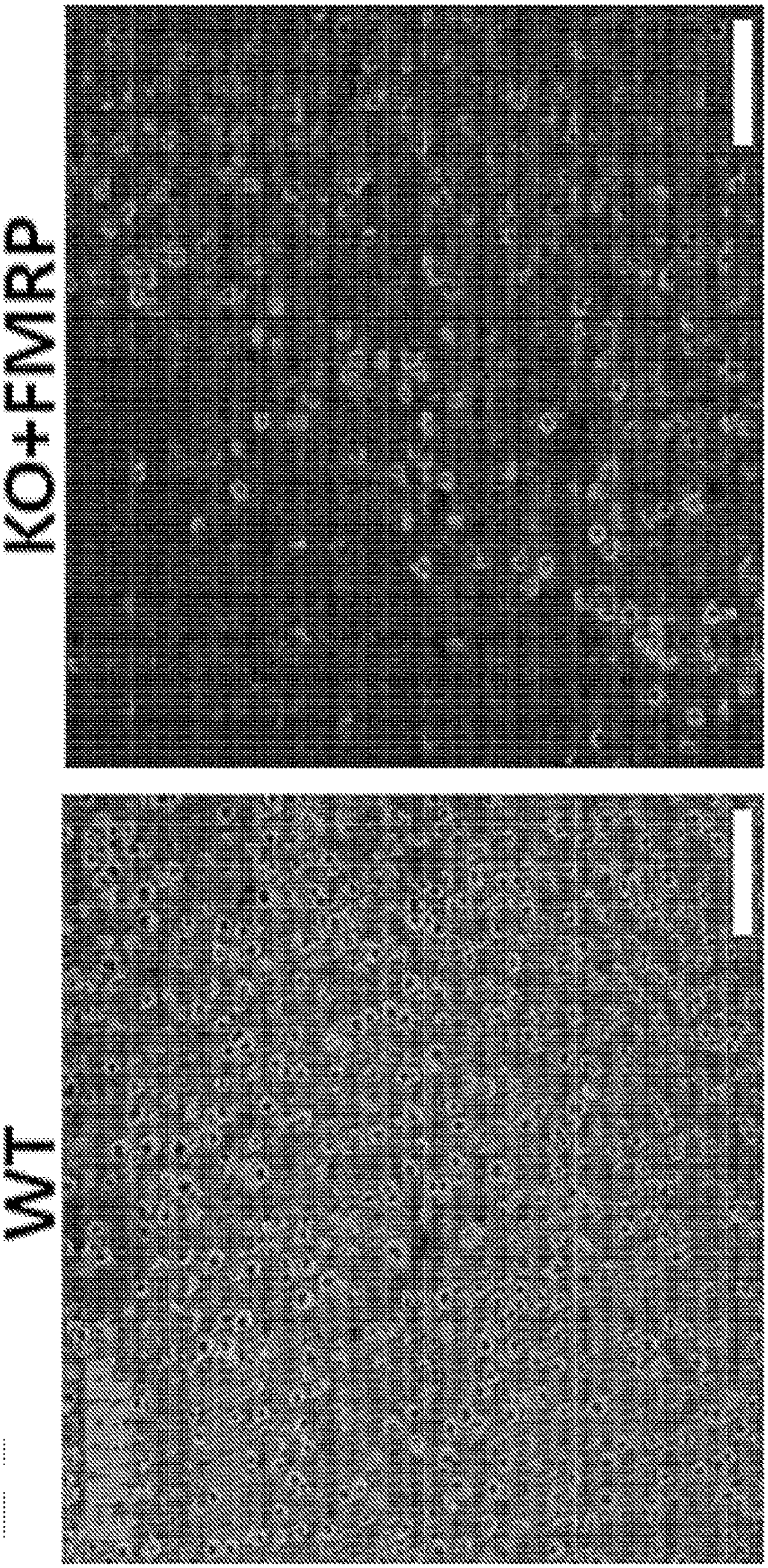
Figure 10C:
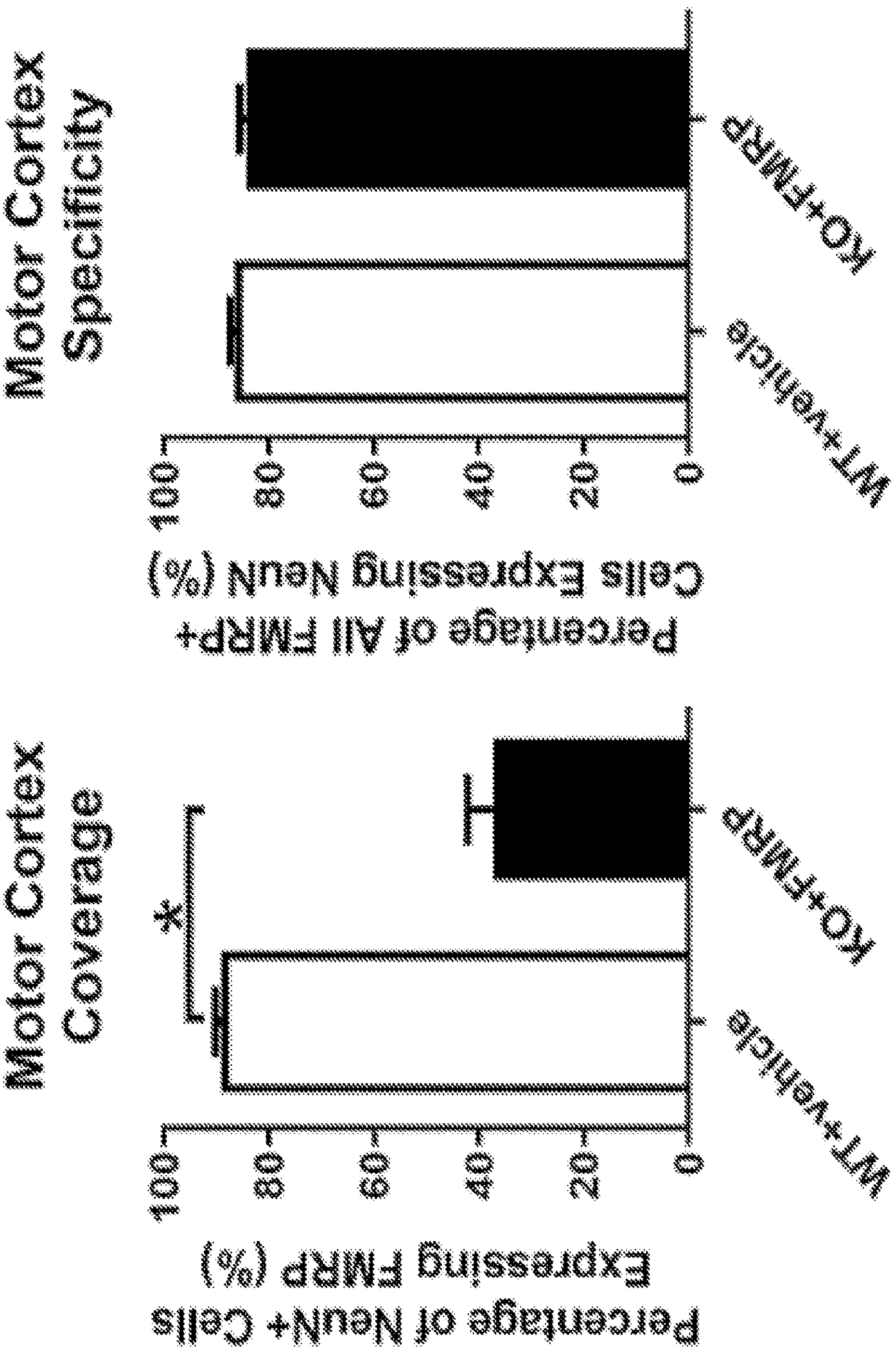
Figure 10D:
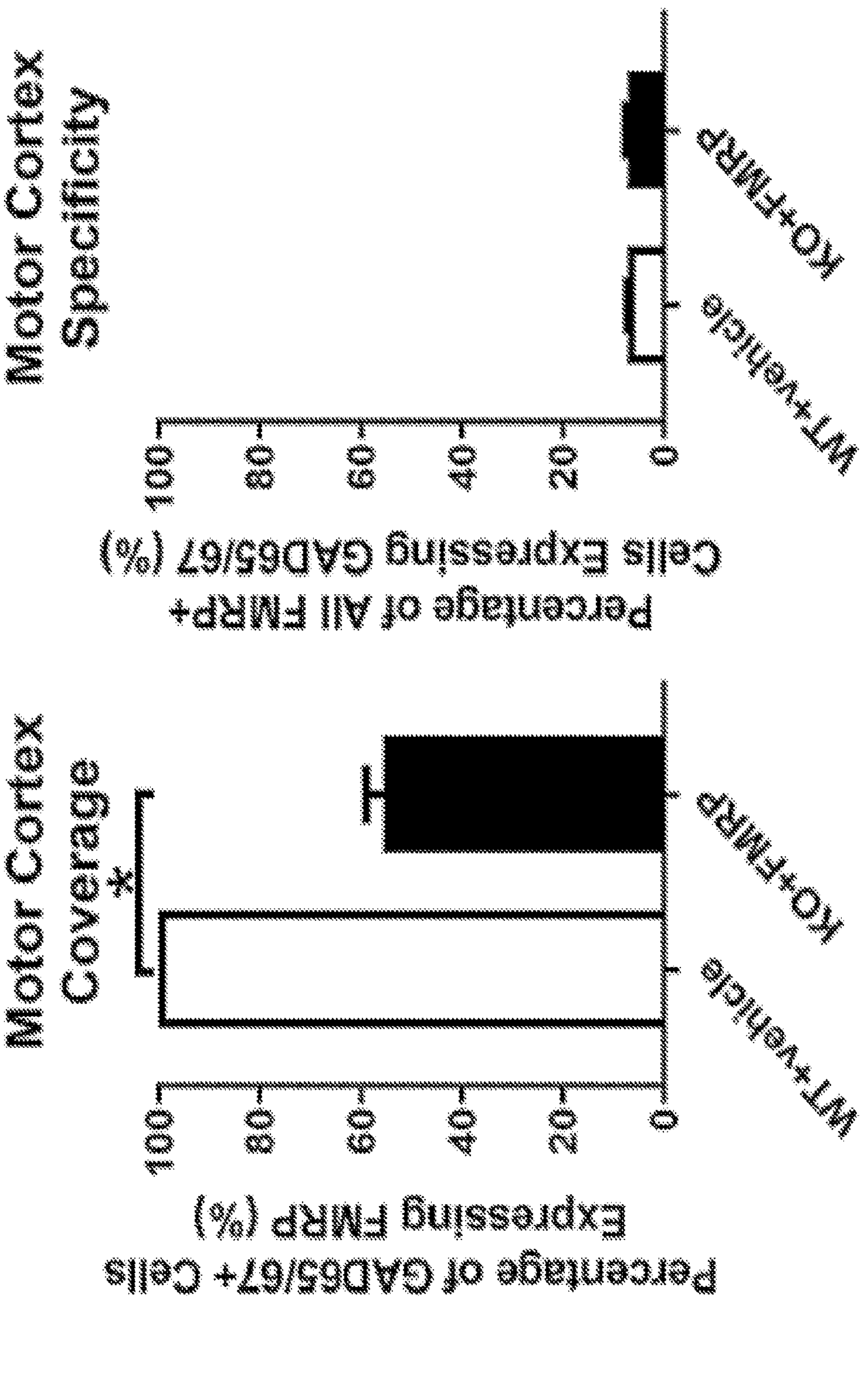
Figure 10E:
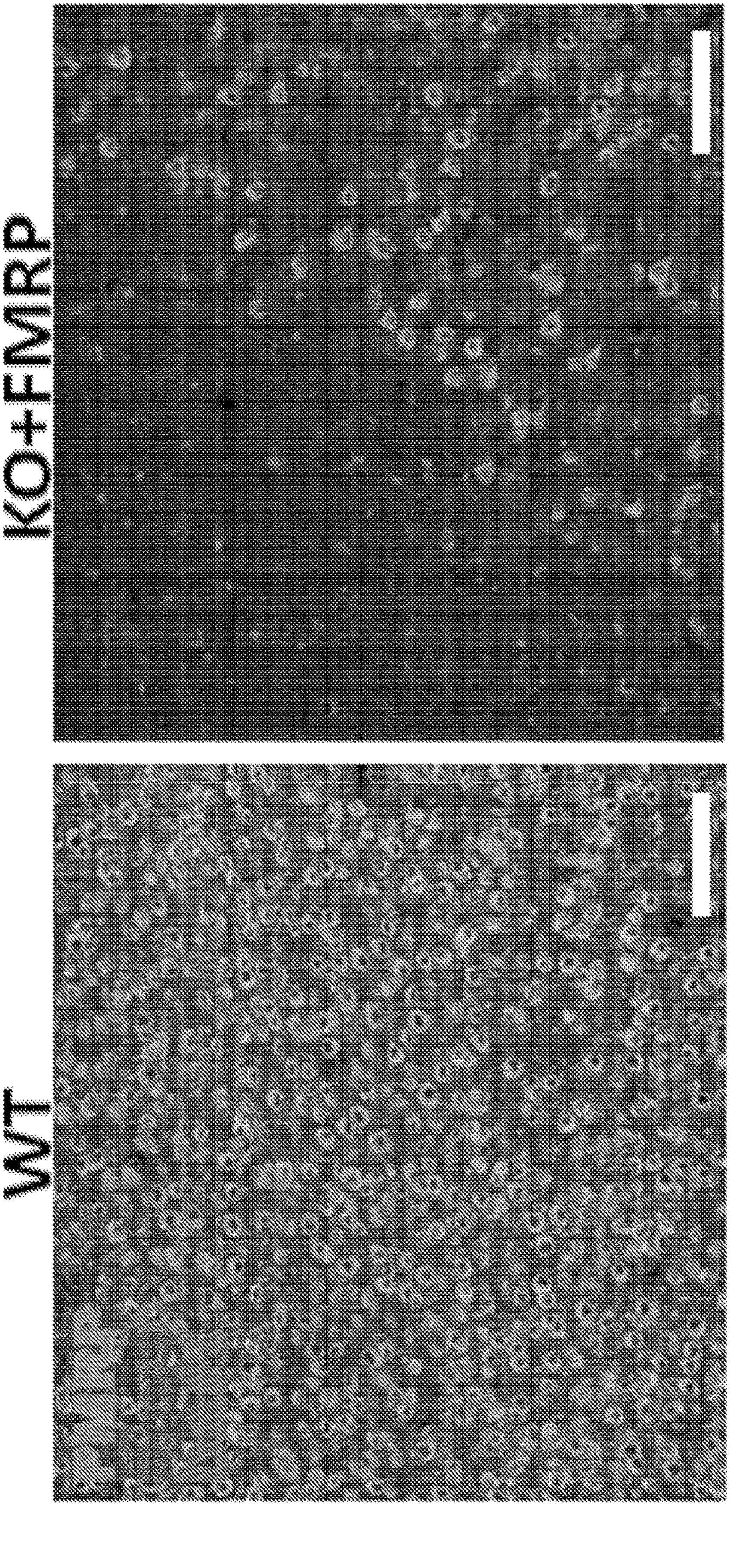
Figure 10F:
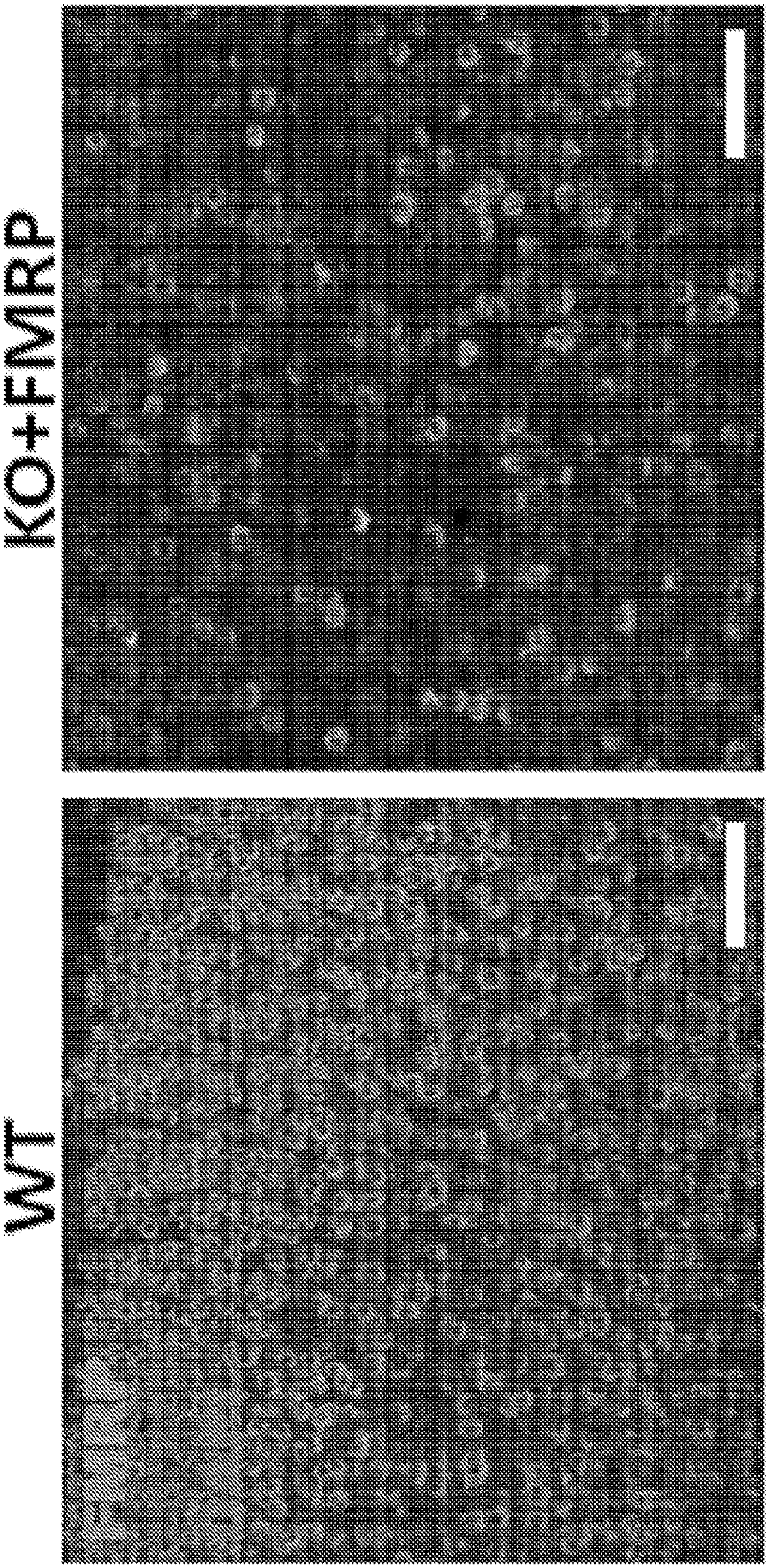
Figure 10G:
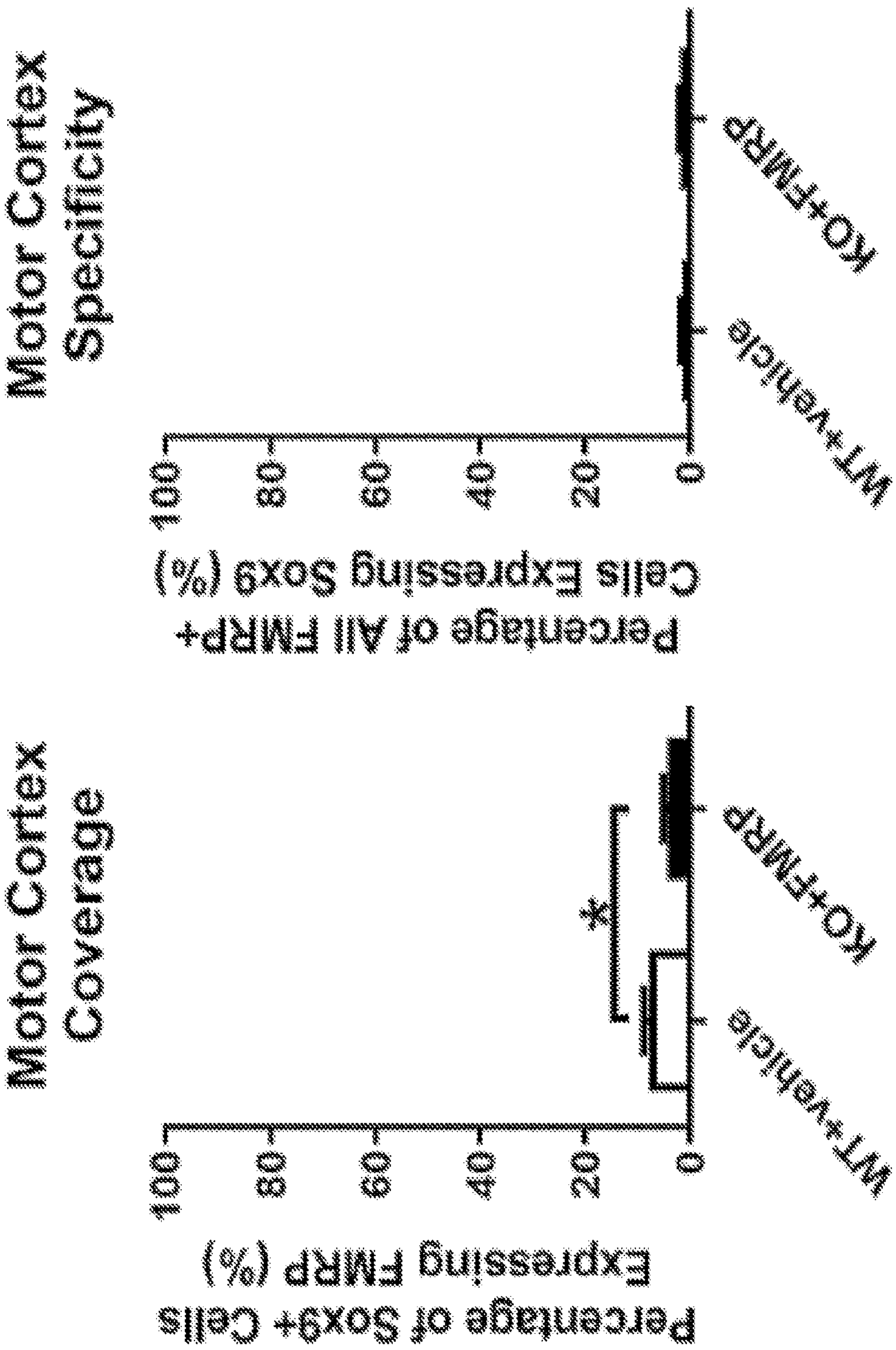
Figure 10H:
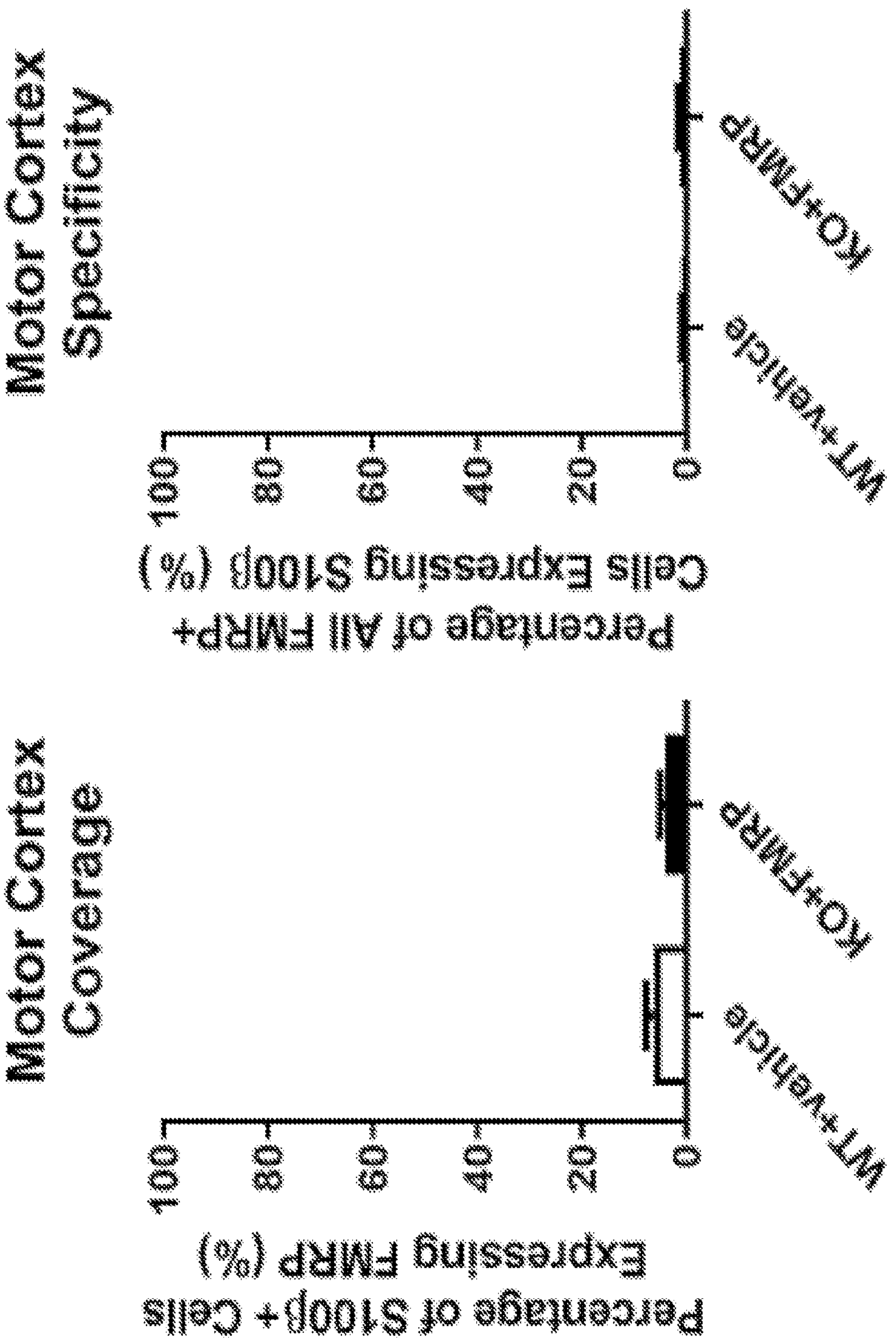

In order to as closely reproduce the wild type expression profile of FMRP as possible, a vector was designed to transduce as many neuronal populations as possible, while limiting expression in glia, as glial expression of FMRP is low in adult wild type (WT) mice (Gholizadeh, S., et al., 2015. Expression of fragile X mental retardation protein in neurons and glia of the developing and adult mouse brain. Brain Res. 1596, 22-30.). Analysis of the cell-type specificity (the percentage of FMRP+ cells expressing a given cell-type marker) of the FMRP transgene in the motor cortex of 2 week-old KO+FMRP mice revealed a cell-type specificity profile very similar to that of WT+vehicle mice, with a mean specificity of the vector for NeuN+ neurons of 84%, and 86%, respectively (FIG. 10C). Both the WT+vehicle and KO+FMRP treatment groups had low FMRP specificity for GAD65/67+ GABAergic neurons (FIG. 10D), with mean specificities of approximately 7%. WT+vehicle and KO+FMRP mice also both showed low specificity of FMRP expression in astrocytes, with mean specificities for Sox9+ cells of approximately 2% in both cases (FIG. 10G). There was similar low specificity of the vector for S100β+ cells (a marker for astrocytes, oligodendrocytes, and oligodendroglial progenitor cells), with a mean specificity of 0.7% in WT+vehicle mice, and 1.2% in KO+FMRP mice (FIG. 10H). The mean coverage (the percentage of cells of a given cell-type expressing FMRP) of FMRP expression in NeuN+ cells was significantly lower in KO+FMRP cortices, than in WT+vehicle mice (88% vs. 37%, $P<0.05$, FIG. 10C), as was coverage of GAD65/67 (100% vs 56%, $P<0.05$, FIG. 10D) and Sox9 (7% vs. 4%, $P<0.05$, FIG. 10G), though in the case of Sox9, the effect size was very small. Based on the transduction pattern after it. AAV injection (FIGS. 8A-8E) compared to previous work with intracerebroventricular AAV-FMRP-injected mice, it is likely the difference in coverage of neurons, GABAergic neurons, and astrocytes between WT+vehicle and KO+FMRP is due to limitations of the movement of AAVs through the CNS (Gholizadeh et al., 2014. Reduced Phenotypic Severity Following Adeno-Associated Virus Mediated Fmr1 Gene Delivery in Fragile X Knockout Mice. Neuropsychopharmacology 39, 3100-11; Hooper, A. W. M., et al., 2021. Gene therapy using an ortholog of human fragile X mental retardation protein partially rescues behavioral abnormalities and EEG activity. Mol Ther Methods Clin Dev. 22, 196-209; Arsenault, J., et al., 2016. FMRP Expression Levels in Mouse Central Nervous System Neurons Determine Behavioral Phenotype. Hum Gene Ther. 27, 982-996). No significant difference was found the in the coverage of S100β+ cells between WT+vehicle and KO+FMRP mice (FIG. 10H). Together these CNS distribution and cell specificity results demonstrate that the combination of the JeT promotor and the AAV9 capsid is capable of producing the desired cell-type expression profile for FMRP in KO+FMRP mice, similar to that of WT+vehicle mice.

Audiogenic Seizure Testing

Figure 11A:
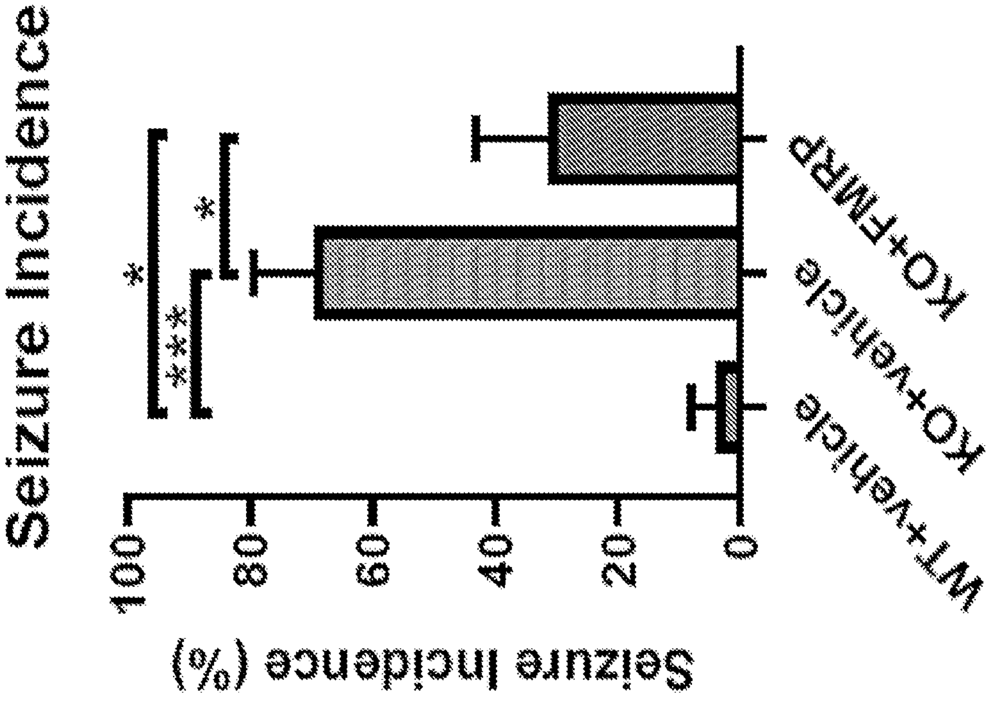
FIGS. 11A-11C show the rescue of audiogenic seizures in Fmr1 KO mice.
Figure 11B:
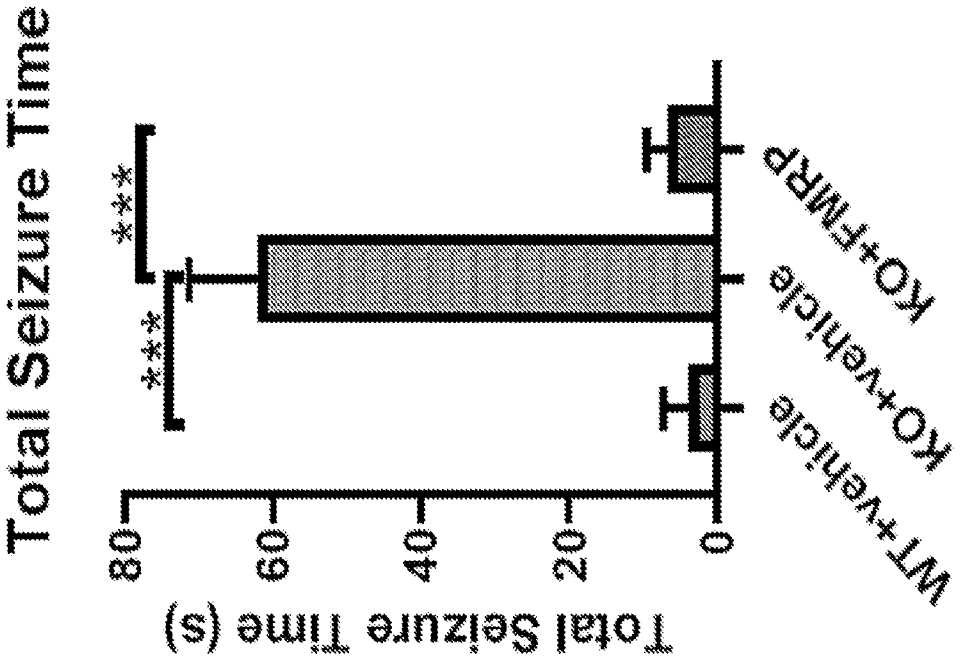
Figure 11C:
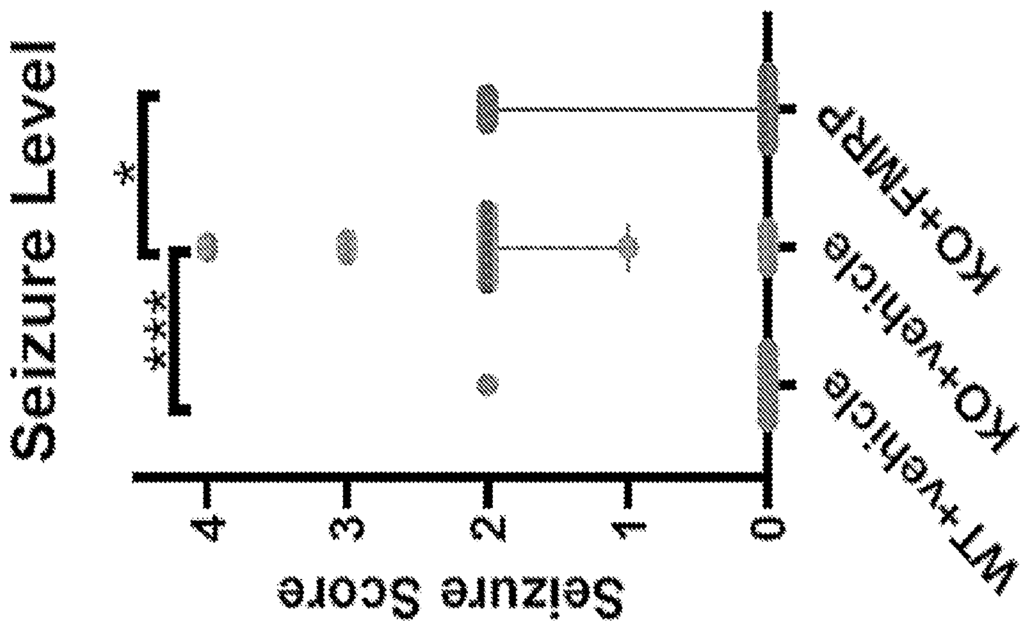

Increased susceptibility to audiogenic seizures (AGS) is a robust endophenotype of Fmr1-KO mice (Gonzalez, D., et al., 2019. Audiogenic Seizures in the Fmr1 Knock-Out Mouse Are Induced by Fmr1 Deletion in Subcortical, VGlut2-Expressing Excitatory Neurons and Require Deletion in the Inferior Colliculus. Journal of Neuroscience. 39, 9852-9863; Pacey, L. K., et al., 2011. Subchronic administration and combination metabotropic glutamate and GABAB receptor drug therapy in fragile X syndrome. J Pharmacol Exp Ther. 338, 897-905.). To date, no gene therapy treatments have successfully rescued this behavior. To test the effectiveness of the AAV-FMRP vector, injected mice were exposed to a high-decibel sound for 3 min (FIGS. 11A-11C). As expected, KO+vehicle mice had a greatly increased seizure incidence, total seizure time, and seizure level, relative to WT+vehicle mice, with only a single tested WT+vehicle mouse (4%) experiencing a seizure, with a mean total seizure time of less than 4 sec, while a significantly higher ($p<0.0001$) 70% of KO+vehicle mice had seizures, with a mean total seizure time of 62 seconds. The sole WT+vehicle mouse who experienced a seizure had a seizure score of 2 (clonic seizure), while the KO+vehicle mice had a maximum score of 4 (status epilepticus/death). Treatment with AAV-FMRP caused a striking significant reduction in seizure incidence (31%), mean total seizure time (7 sec), and maximum seizure score (2–clonic seizure) in Fmr1KO mice, relative to KO+vehicle mice. As with the WT+vehicle mice, no KO+FMRP mice died as a result of AGS during testing. In summary, this is the first demonstration of rescue of AGS susceptibility in Fmr1-KO mice via gene therapy, and demonstrates the utility of this treatment in protection against CNS hyperactivity.

Fear Conditioning

Figure 12A:
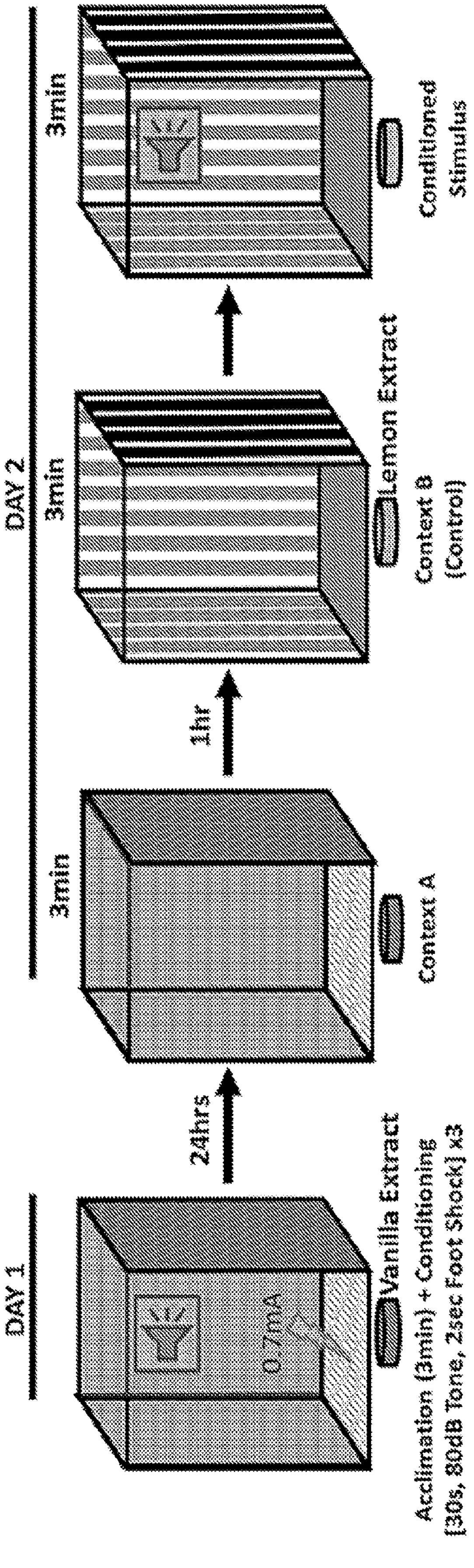
FIGS. 12A-12E show normalization of fear memory response to conditioned stimulus in mice treated with scAAV-JeT-hFMR1iso17 vector.
Figure 12B:
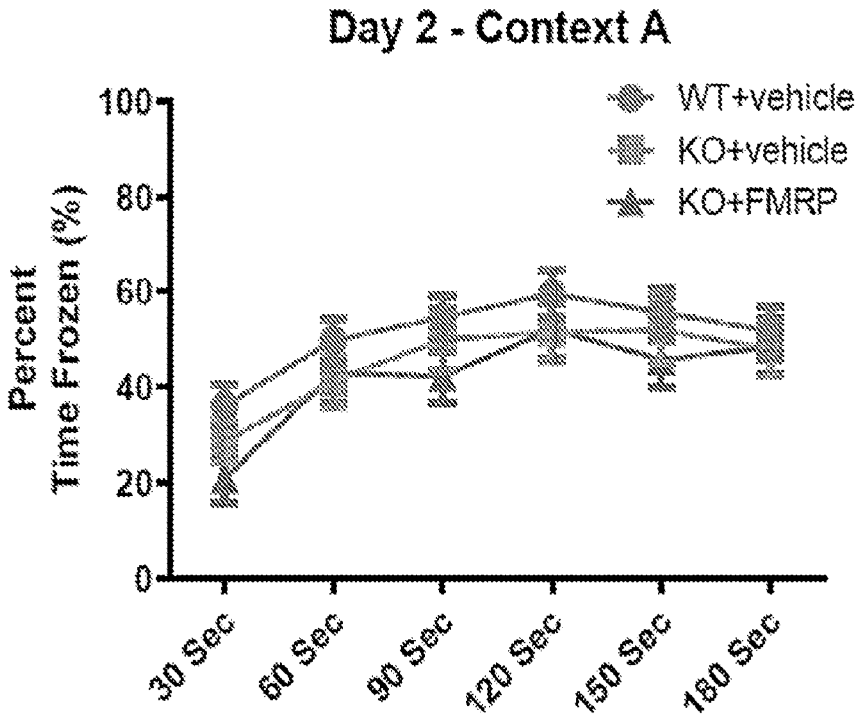
Figure 12C:
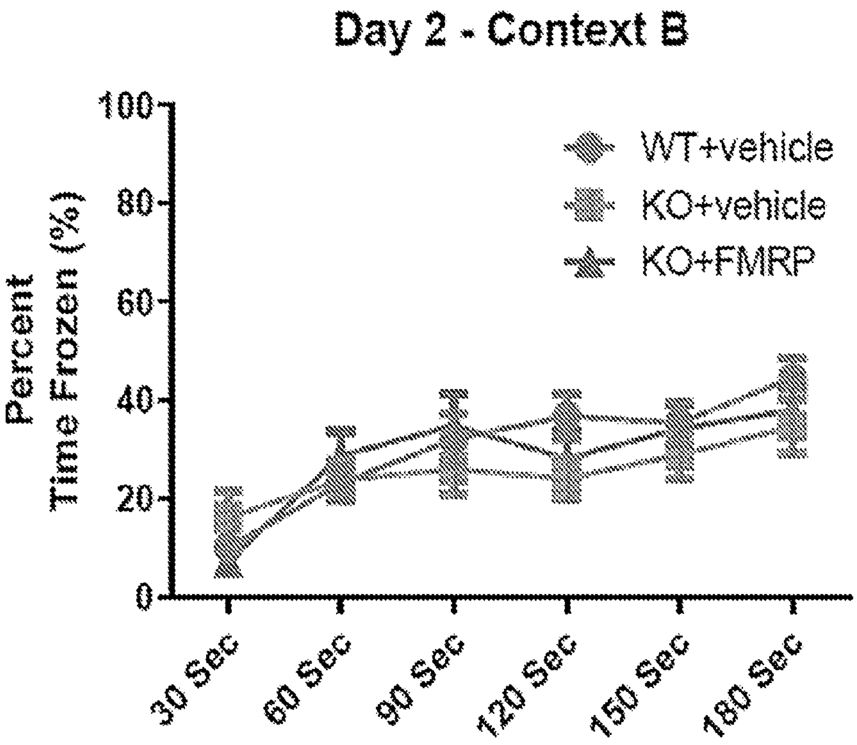
Figure 12D:
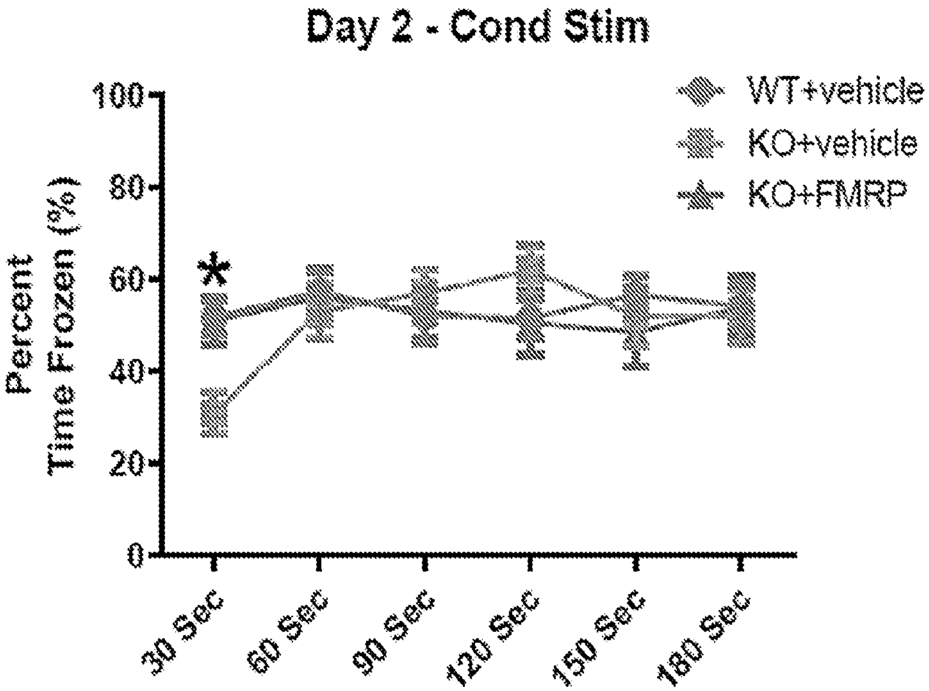
Figure 12E:
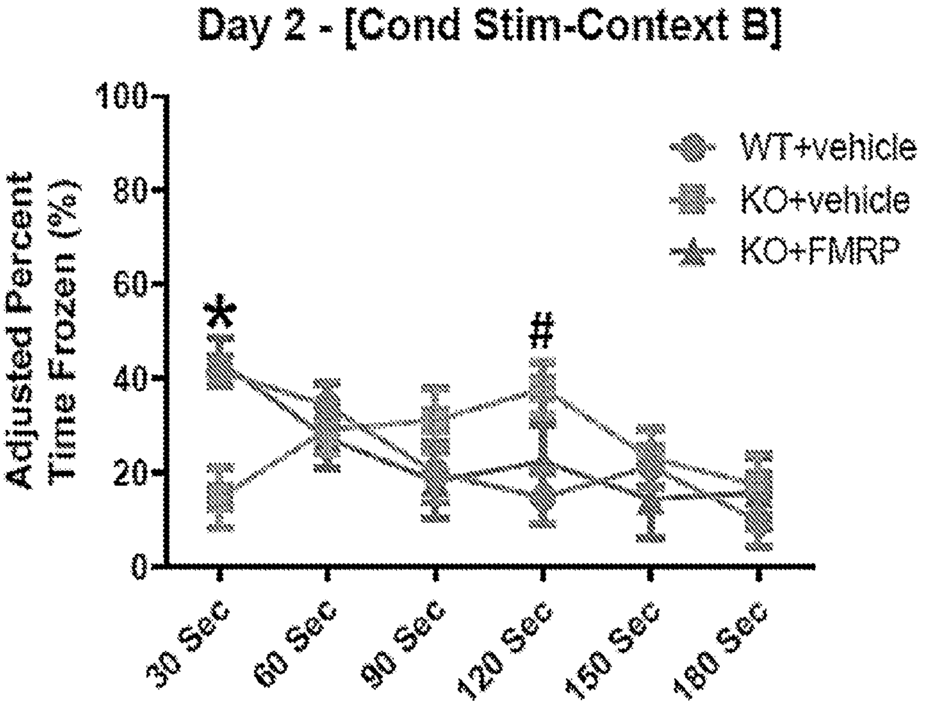
Figure 13:
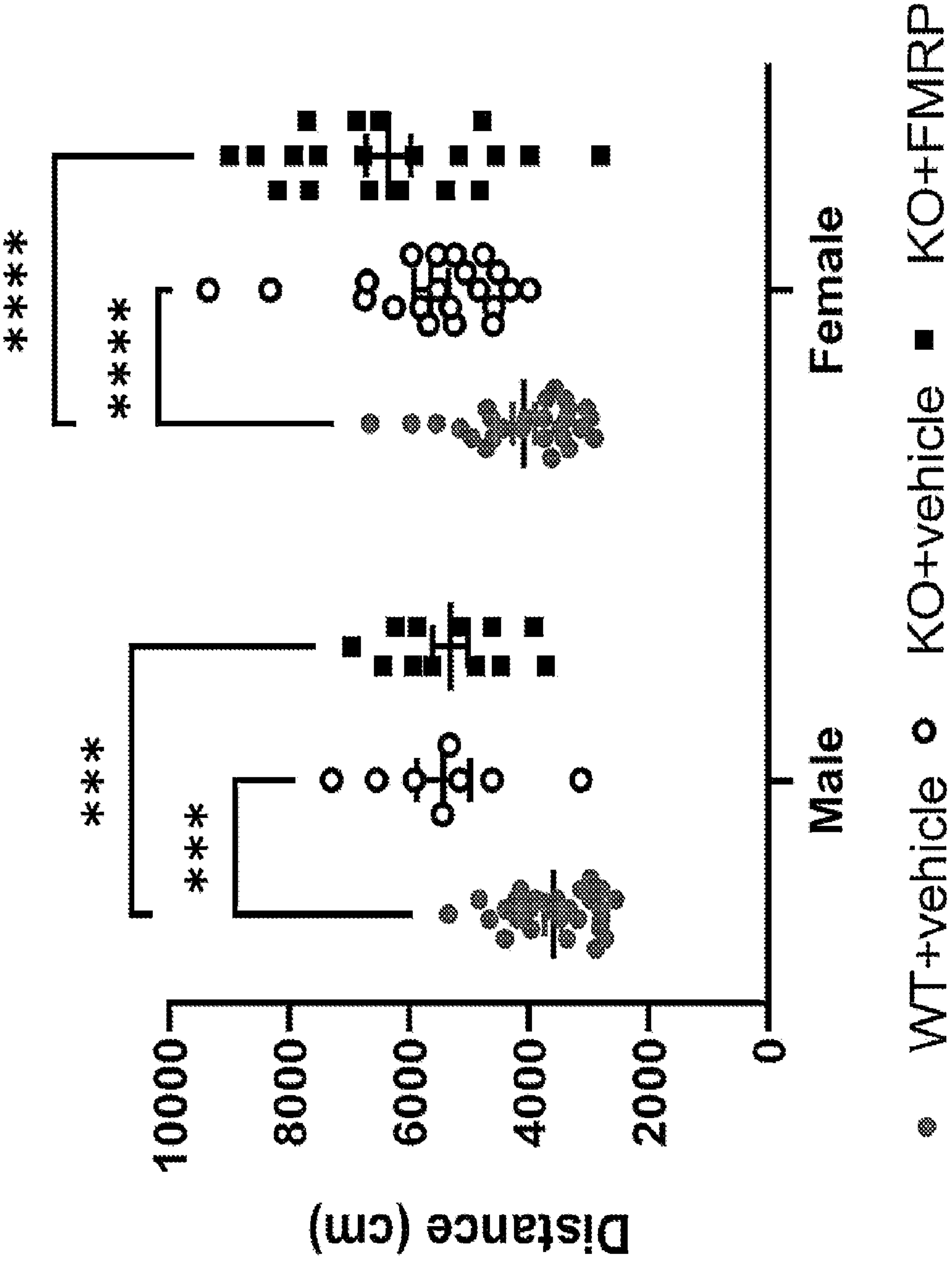
FIG. 13 shows results of the open field test. Total distance travelled in 20 min. by male and female mice in the KO+vehicle and KO+FMRP groups were significantly higher compared to their respective WT+vehicle groups. * denotes statistically significant differences (p<0.05) between treatment groups using post hoc Tukey's multiple comparison test. Male: WT+vehicle (n=27 males and 27 females), KO+vehicle, n=8 males and 21 females; KO+FMRP, n=12 males and 20 females.

To test fear-memory behavior of KO+FMRP mice to contextual and conditioned stimulus cues, mice underwent a fear conditioning test (FIG. 12A). There were no significant differences among WT+vehicle, KO+vehicle, or KO+FMRP treated mice in the freezing time when exposed to a fear-conditioned context (FIG. 12B). There was also no difference in freezing time between WT+vehicle, KO+vehicle, or KO+FMRP mice, when placed into a novel context (FIG. 12C). However, KO+vehicle mice froze significantly less than both WT+vehicle mice in the first 30 sec of exposure to a fear-conditioned tone, indicating that KO+vehicle mice have either a reduced fear-memory to the conditioned stimulus, increased fearlessness, or an alternative non-freezing behavioral response to fear, and that FMRP is important to this endophenotype (FIG. 12D). This altered freezing behavior was not present in KO+FMRP mice, indicating that AAV-FMRP treatment is sufficient to rescue this behavior. The reduced freezing in KO+vehicle mice and the rescue of freezing in KO+FMRP mice remained after correcting for the endogenous freezing rate of the mice on a per mouse basis (FIG. 12E). Interestingly, after this correction was made, it was noted that the percent time frozen in KO+vehicle mice was significantly higher than WT+vehicle mice in the 90-120 see interval. This could indicate a delayed freezing response to the conditioned tone. While the fear conditioning test is a complex measurement of many overlapping endophenotypes, these results demonstrate that i.t. treatment with AAV-FMRP is capable of fully restoring these behaviors to WT levels.

Circadian Locomotor Activity and Sleep Analyses

Figure 14A:
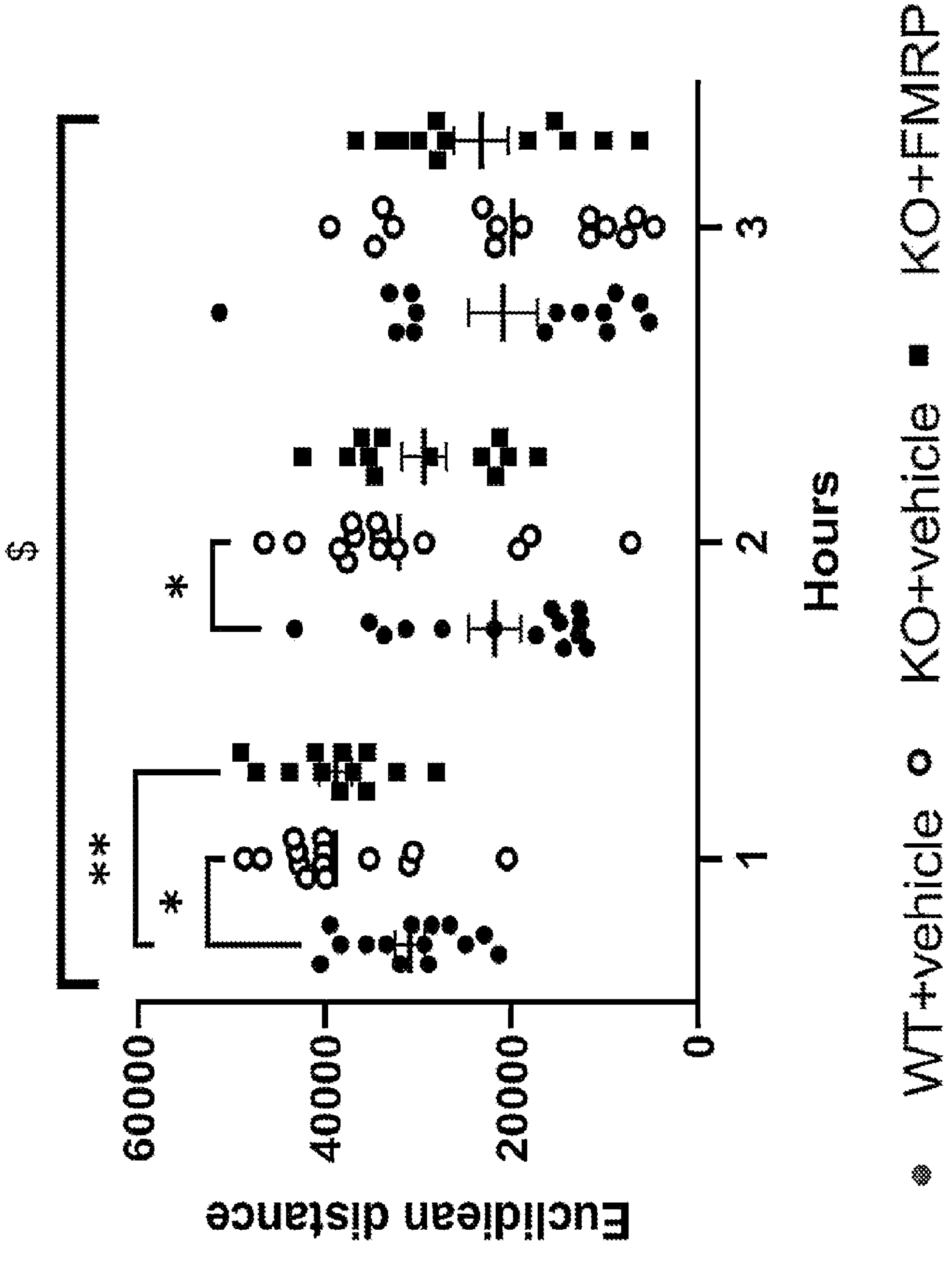
FIGS. 14A-14F show the effect of AAV-JeT-FMRP treatment on circadian locomotor activity of Fmr1 KO mice.
Figure 14B:
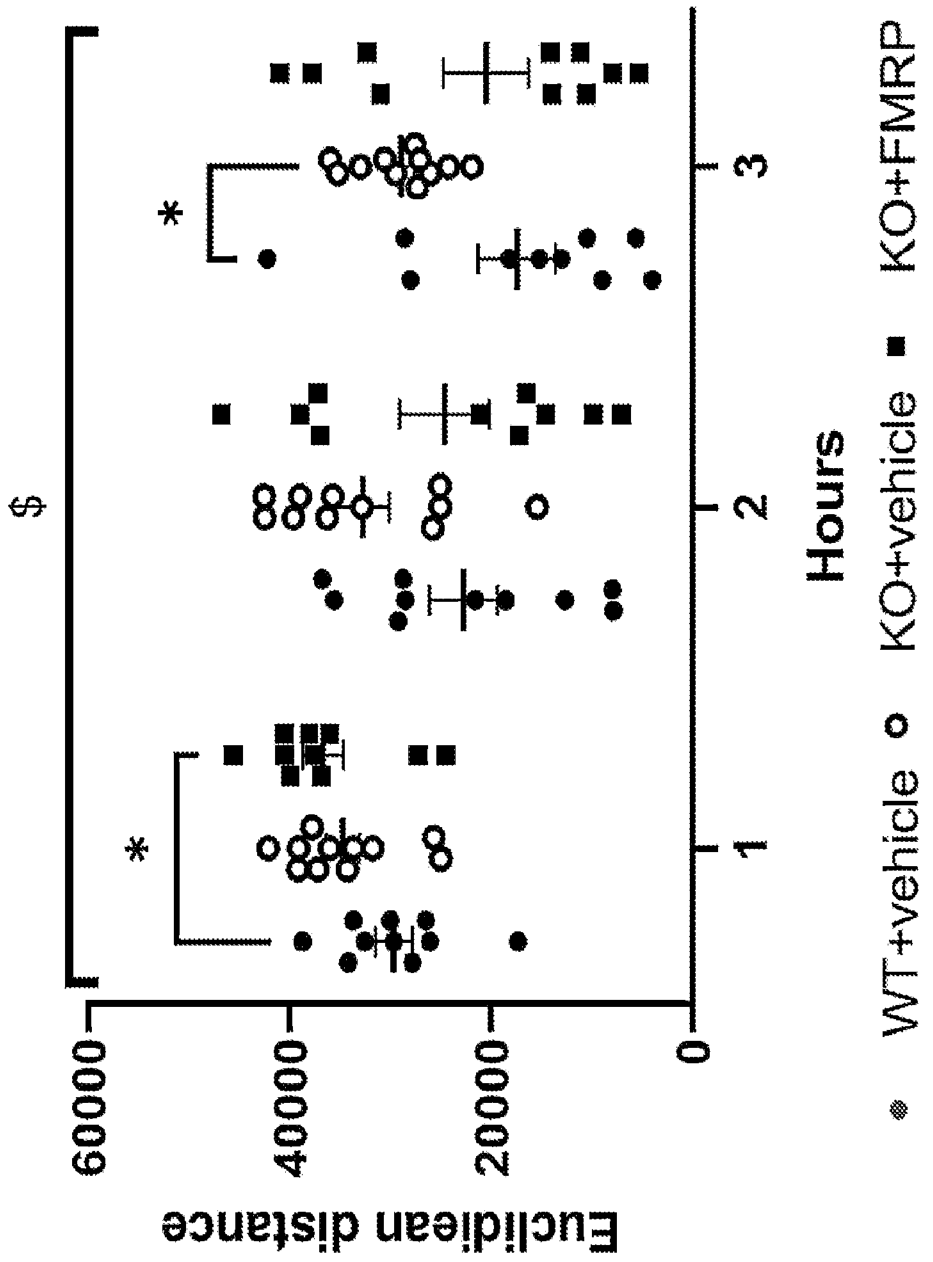

Circadian locomotor activity was assessed by video recording the mice for three days in a home cage setting and tracking the distance travelled using the neural network DeepLabCut (DLC). This method allowed for the evaluation of the activity of the mice for a longer duration in a home cage environment. To ascertain whether the results from the two methods were comparable, the activity of the first three hours after being placed into the video recording apparatus was evaluated (FIGS. 14A and 14B). As expected, significant increases in distance travelled were observed in the 1$^{st}$ hour, with significant differences between the WT+vehicle group and the KO+vehicle group in the male mice, and between the WT+vehicle groups and the KO+FMRP groups in the male and female mice, comparable to what was found in the open field test. In the subsequent 2$^{nd}$ and 3$^{rd}$ hour, the activity in all three treatment groups decreased as the mice acclimatized to the new environment. However, significantly higher activity was still found in the KO+vehicle group when compared to the WT+vehicle group in the 2$^{nd}$ hour in the male mice (FIG. 14A), and in the 3$^{rd}$ hour in the female mice (FIG. 14B), while no differences were observed between the WT+vehicle and KO+FMRP groups. This outcome suggested that AAV-FMRP treatment reduced the hyperactivity in the KO mice, which might have reflected elevated anxiety experienced in a novel environment.

Figure 14C:
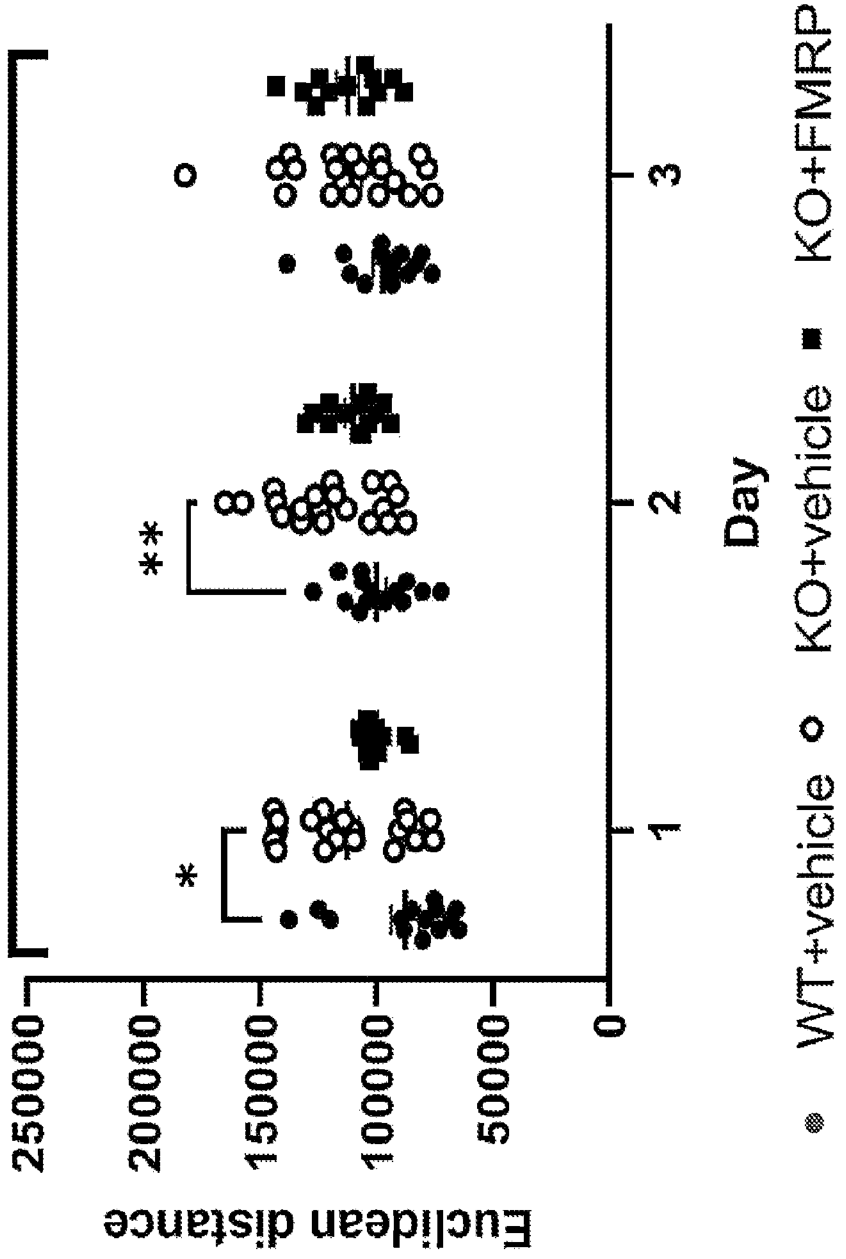
Figure 14D:
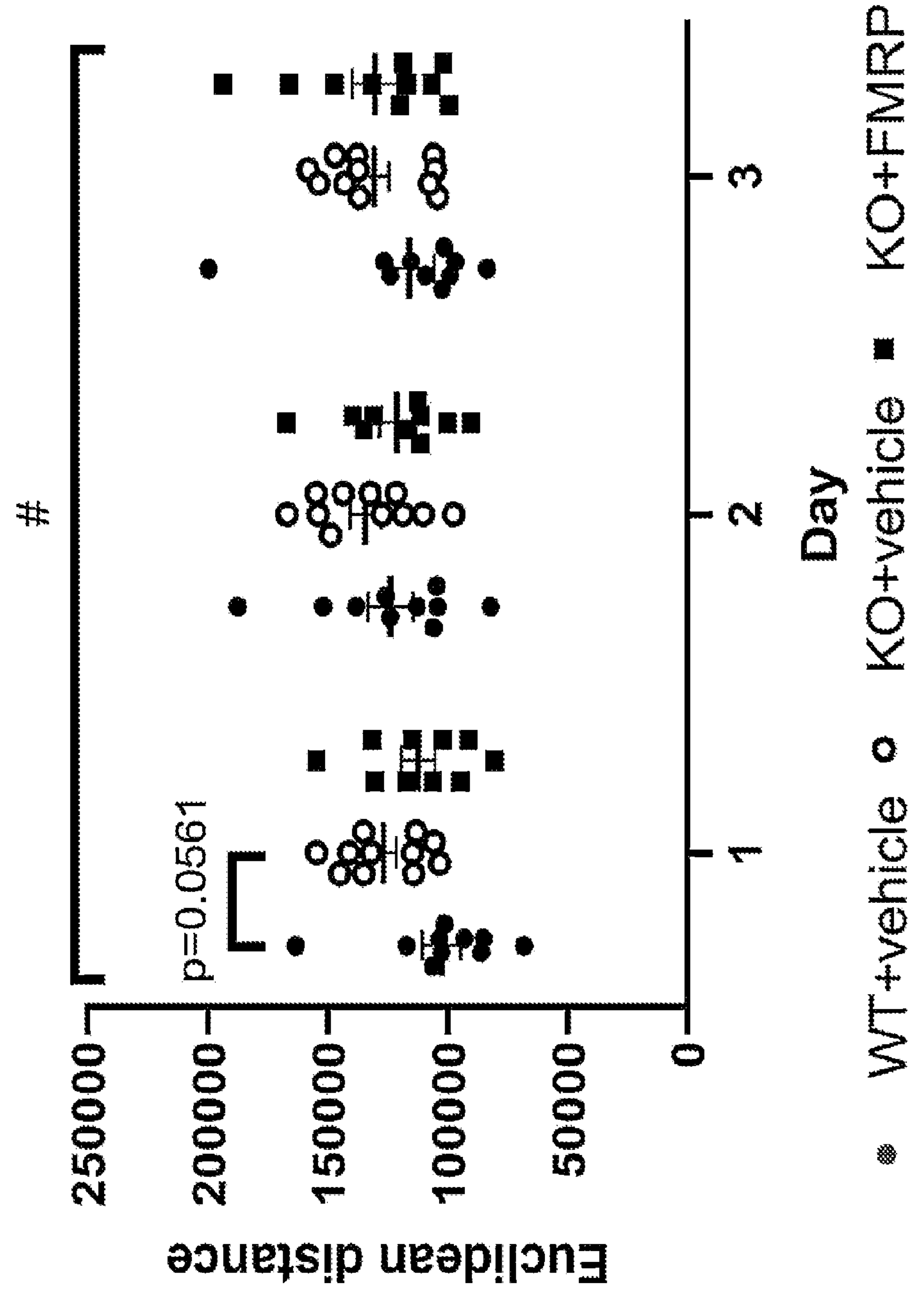
Figure 14E:
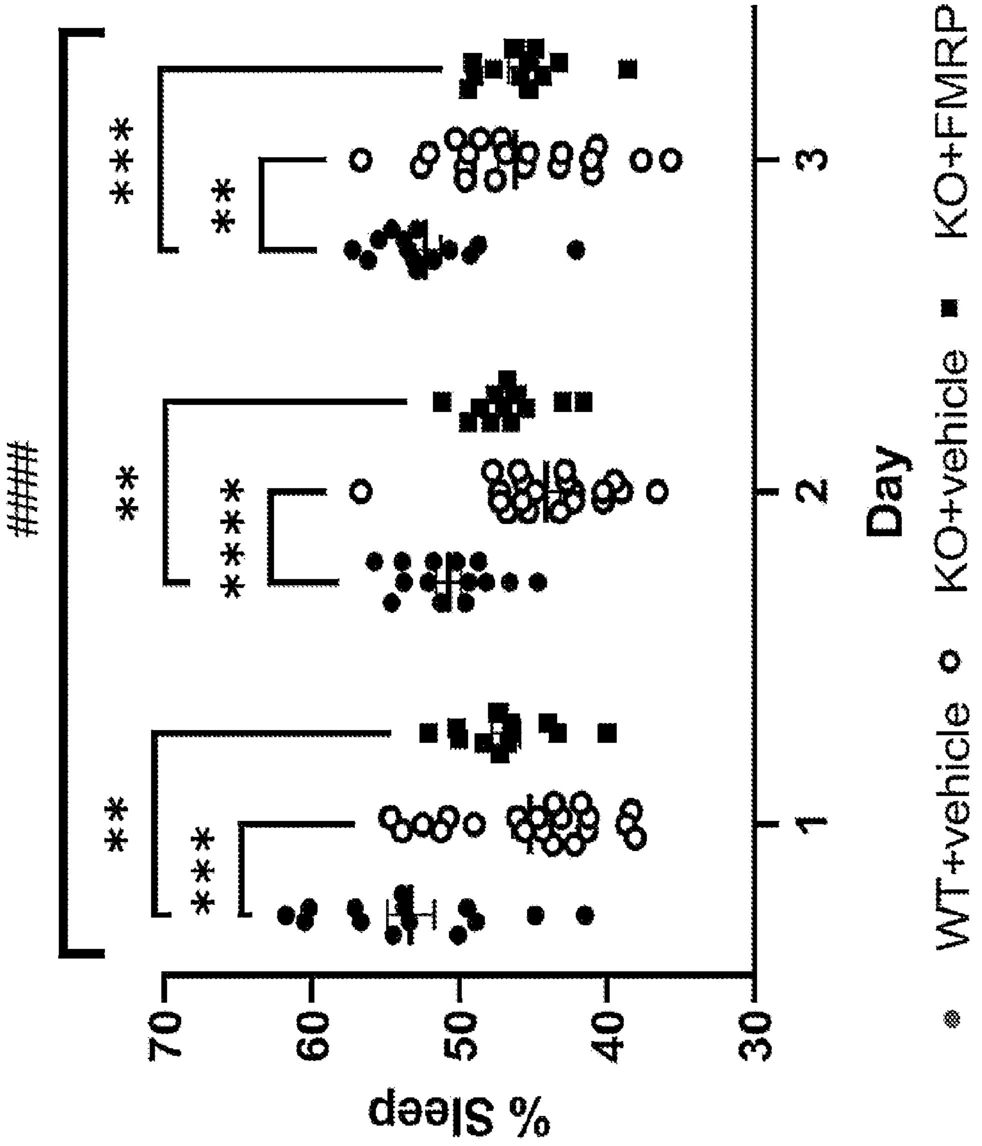
Figure 14F:
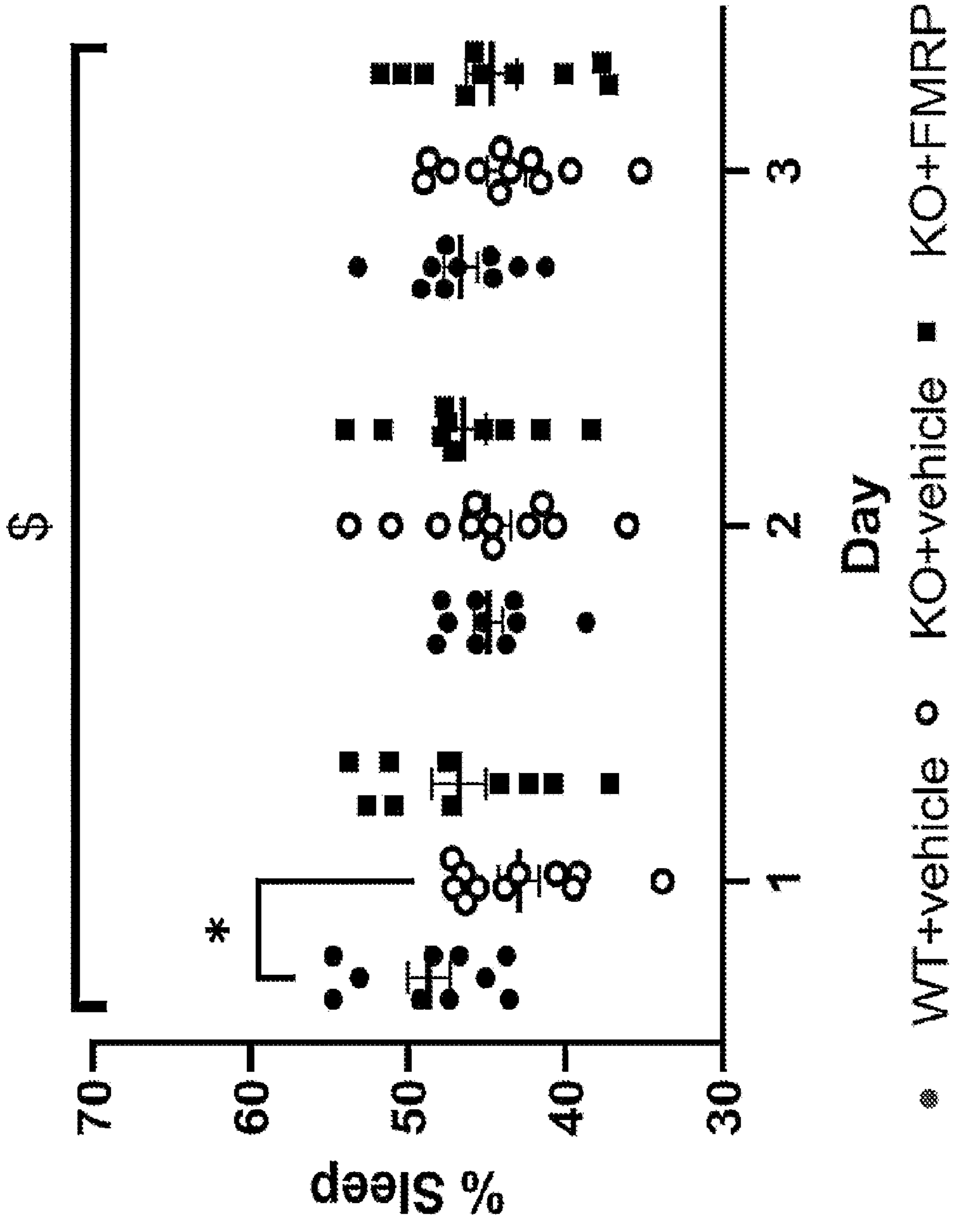

To further evaluate circadian locomotor activity, mice video recorded continuously for three days were assessed in the context of locomotor activity (distance travelled) in the light phase only and in the dark phase only (12 hr/12 hr cycle). In the dark phase in which mice are naturally more active, no differences in activity were observed among the three treatment groups in both male and female mice (data not shown). In the light phase, a significant increase in activity was observed in the male KO+vehicle group compared to the WT+vehicle group on day 1 and day 2 but not with the KO+FMRP group (FIG. 14C). In the female mice, the same trend was observed on day 1, although the difference between the KO+vehicle and WT+vehicle groups was not statistically significant ($p=0.0561$; FIG. 14D). Since mice are nocturnal animals, further analysis was performed to evaluate whether the increase in light phase activity in Fmr1KO mice was related to reduced sleep. Sleep time was assessed using an algorithm based on inactivity as described in Pack et al. (Pack, A. I., et al., 2007. Novel method for high-throughput phenotyping of sleep in mice. Physiological Genomics. 28, 232-8) and Fmr1 KO mice have been found previously to have reduced sleep using the same method (Sare, R. M., et al., 2017. Deficient Sleep in Mouse Models of Fragile X Syndrome. Front Mol Neurosci. 10, 280). In the male mice, significant decrease in sleep time was found in both KO+vehicle and KO+FMRP groups in comparison to the WT+vehicle group on all three days (FIG. 14E). In the female mice, a significant decrease in sleep was found in the KO+vehicle compared to the WT+vehicle and this difference was not observed in the KO+FMRP group (FIG. 14F). These findings suggested that the light phase hyperactivity found in the Fmr1 KO mice may be related to reduced sleep and that this deficit was improved by AAV-FMRP gene therapy treatment.

Correlation Between FMRP Expression and Efficacy

Figure 15A:
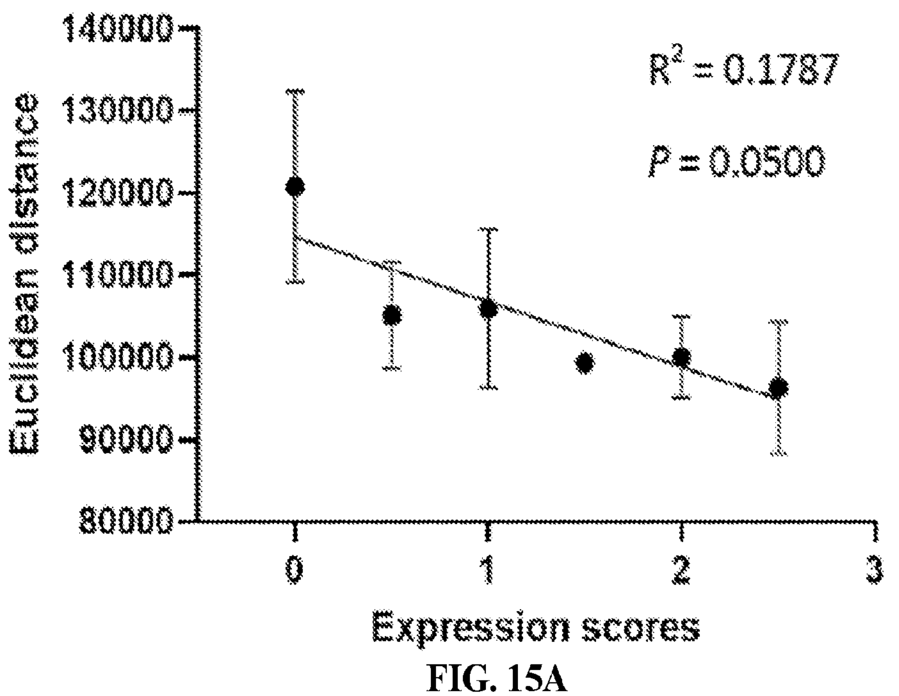
FIGS. 15A-15D show the correlation between FMRP expression level and therapeutic efficacy in light phase activity and sleep.
Figure 15B:
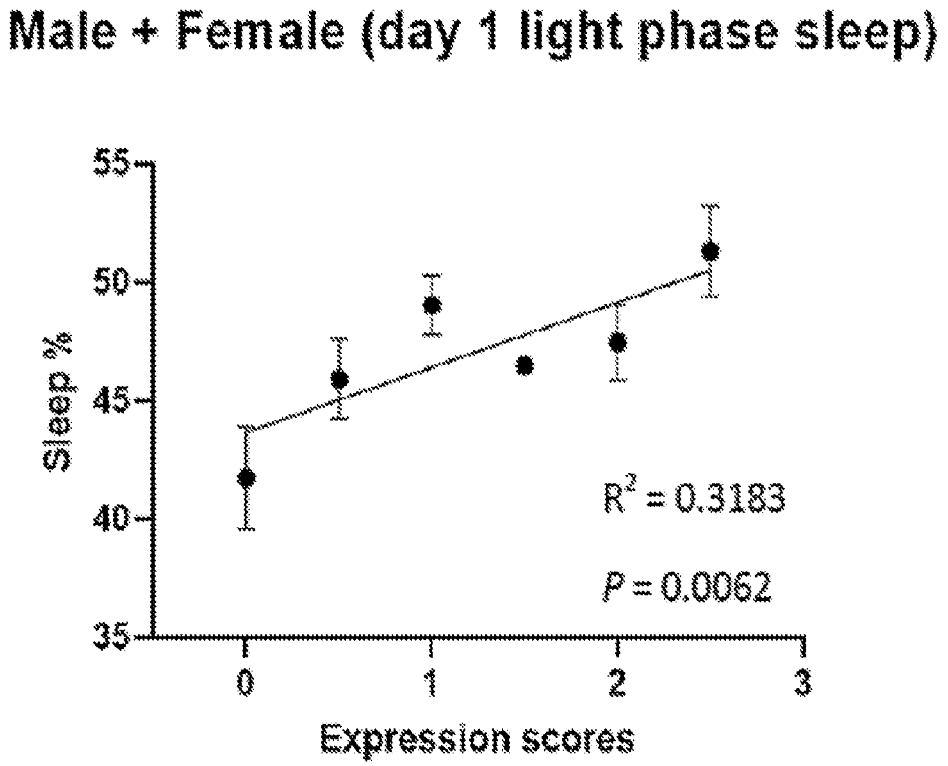

During the course of this study, more than 300 mice in the three treatment groups were injected with either vehicle or AAV-FMRP. At the end of the behavioral analyses approximately 3 months after injection, all mice in the KO+FMRP treatment group (120 mice) were collected and analyzed for brain FMRP transgene expression via tissue sectioning and immunostaining. Each mouse was scored based in the level of expression To investigate the relationship between FMRP expression and therapeutic efficacy in the context of motor hyperactivity and impaired sleep, simple linear regression was performed between the FMRP expression scores and light phase activity, and FMRP expression scores and sleep time FIGS. 15A and 15B) in KO+FMRP mice (male and female combined). This analysis was performed on the results from day 1, when the hyperactivity and sleep deficit were most prominent (FIG. 14A-14F). Light phase activity was negatively correlated to FMRP expression (FIG. 15A) while sleep time was positively correlated to FMRP expression (FIG. 15B). Both relationships were significantly non-zero by the F-test (p<0.05). These results showed that the efficacy of the AAV-FMRP treatment in reducing hyperactivity and sleep deficit was proportionally related to the level of FMRP expression in the Fmr1 KO mice.

Figure 15C:
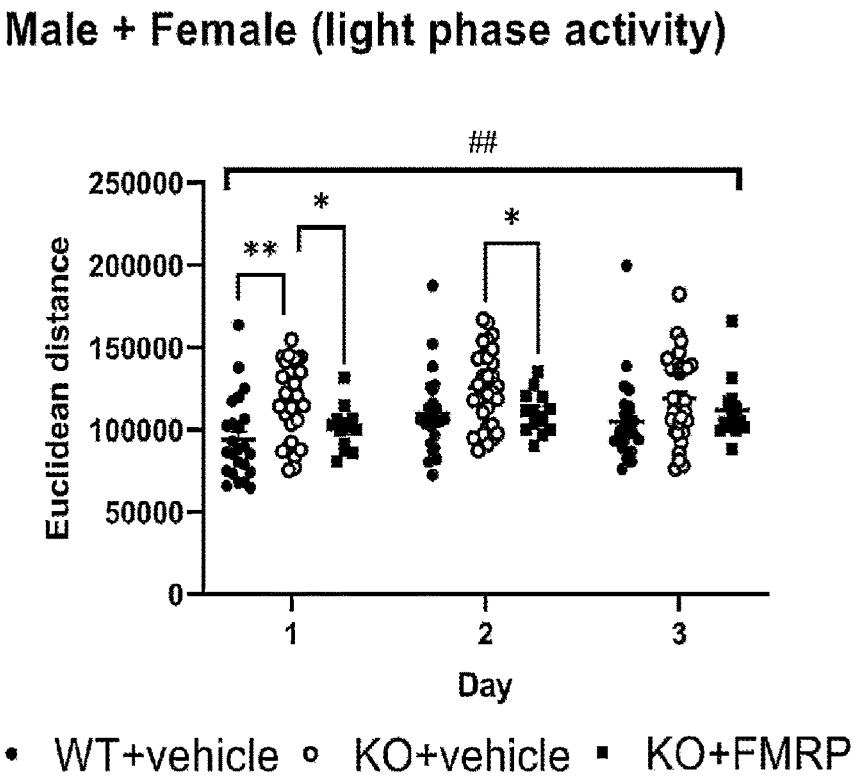
Figure 15D:
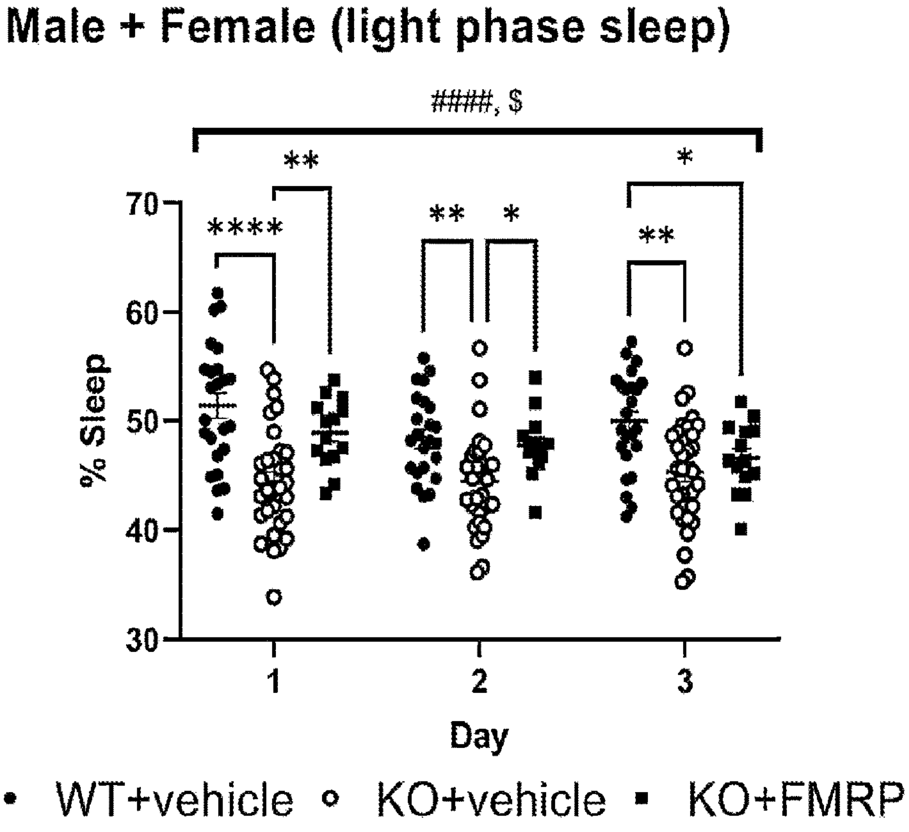

After demonstrating that FMRP expression was correlated to efficacy, male and female mice in the KO+FMRP group with no FMRP expression (score=0) were excluded and the results in light phase activity and sleep time were reanalyzed (male and female combined; FIGS. 15C and 15D). Light phase activity of the KO+vehicle group was significantly higher than WT+vehicle and KO+FMRP groups on day 1 and was also higher than the KO+FMRP group on day 2 (FIG. 15C). For sleep time, KO+vehicle group was significantly lower than both WT+vehicle and KO+FMRP groups on day 1 and 2 (FIG. 15D). Therefore, by excluding mice without FMRP expression, AAV-FMRP gene therapy was further demonstrated to have reversed the hyperactivity and sleep deficit found during the light phase in the Fmr1KO mice.

Electroencephalography

Figure 16A:
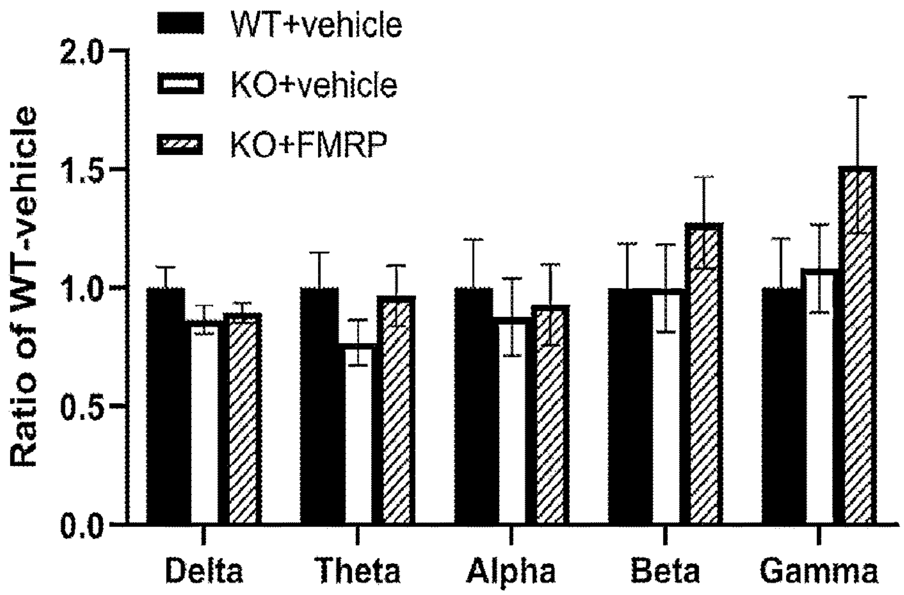
FIGS. 16A-16C show results of the EEG recordings and PCA.
Figure 16B:
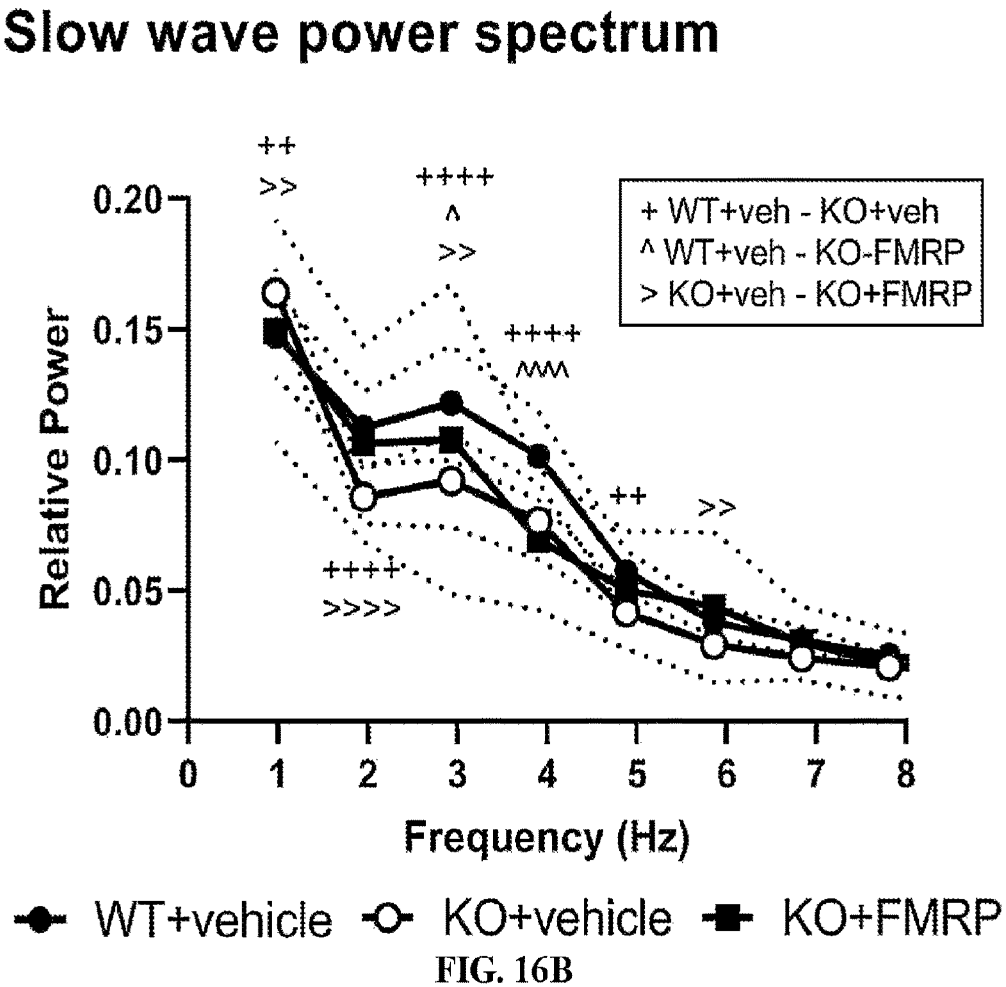
Figure 17:
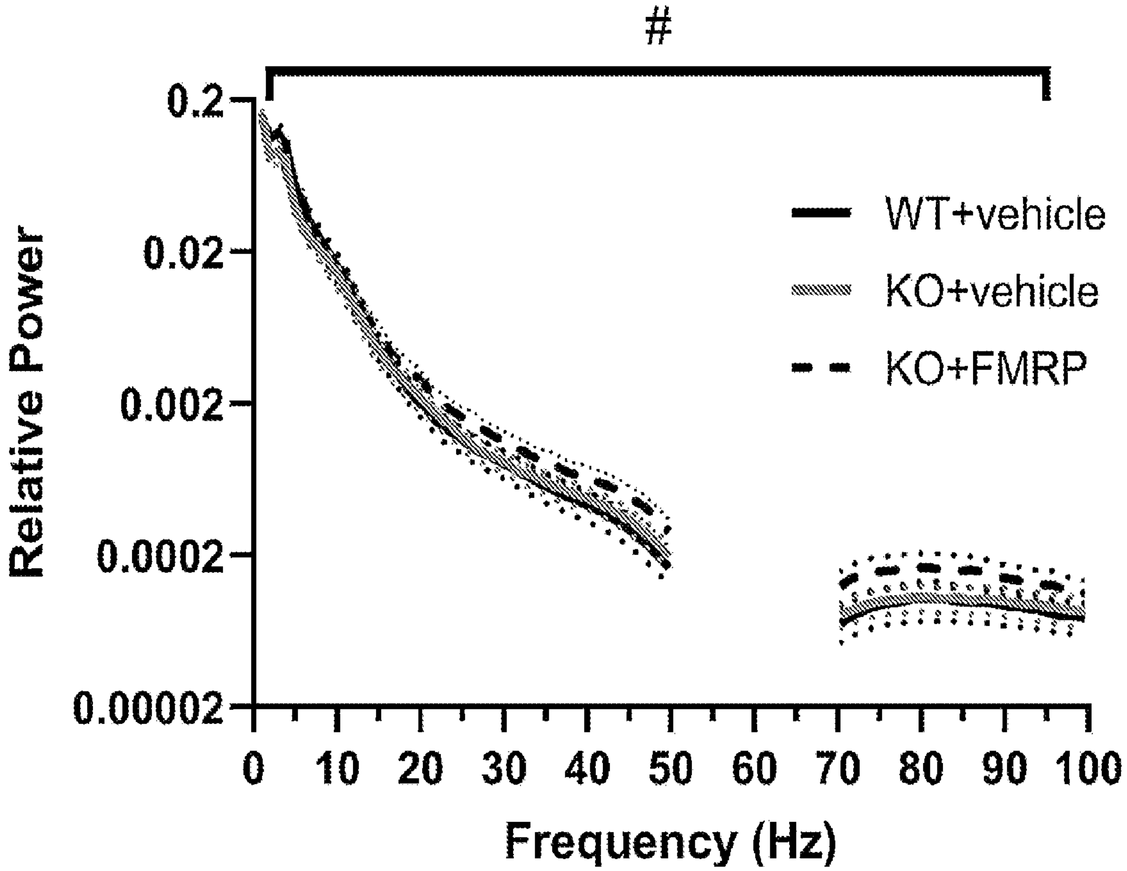
FIG. 17 shows a full power spectrum (0-100 Hz) comparison between WT+vehicle, KO+vehicle and KO+FMRP treatment groups. # denotes statistically significant difference by treatment using two-way ANOVA. WT+vehicle, n=9 males; KO+vehicle, n=16 males; KO+FMRP, n=11 males.

EEG recordings were performed in the male mice following circadian locomotor activity recording. Abnormalities in EEG patterns have been consistently reported in FXS patients and Fmr1 KO mice (Wang, J., et al., 2017. A resting EEG study of neocortical hyperexcitability and altered functional connectivity in fragile X syndrome. J Neurodev Disord. 9, 11; Lovelace, J. W., et al., 2018. Translation-relevant EEG phenotypes in a mouse model of Fragile X Syndrome. Neurobiol Dis. 115, 39-48.) and rats (Wong, H., et al., 2020. Sexually dimorphic patterns in electroencephalography power spectrum and autism-related behaviors in a rat model of fragile X syndrome. Neurobiol Dis. 146, 105118; Hooper et al., 2021). In previous study in Fmr1 KO rats, this increase was only observed in males and not in females; therefore, EEG recordings were performed only in the male mice in this study. Frequency band comparisons of EEG spectral power during immobility among the three treatment groups were shown in FIG. 16A. Higher gamma frequency band power was observed in the KO+FMRP group compared to the WT+vehicle and KO+vehicle groups, but the difference was not statistically significant. Comparison of the full power spectrum found significant difference among the three groups by treatment (2-way ANOVA; FIG. 17). Post hoc Tukey's multiple comparison test revealed a significant decrease in slow wave activity (2-5 Hz) in the KO+vehicle group compared to the WT+vehicle group. This decrease was reversed in the KO+FMRP group in the 2-3 Hz frequency range (FIG. 16B). This result was consistent with the previous study where a decrease in delta wave activity (1-3 Hz) was observed in Fmr1 KO rats during sleep and this decrease was rescued by AAV-FMRP gene therapy.

Multivariate Analysis of Track 1 Male Mice

Figure 16C:
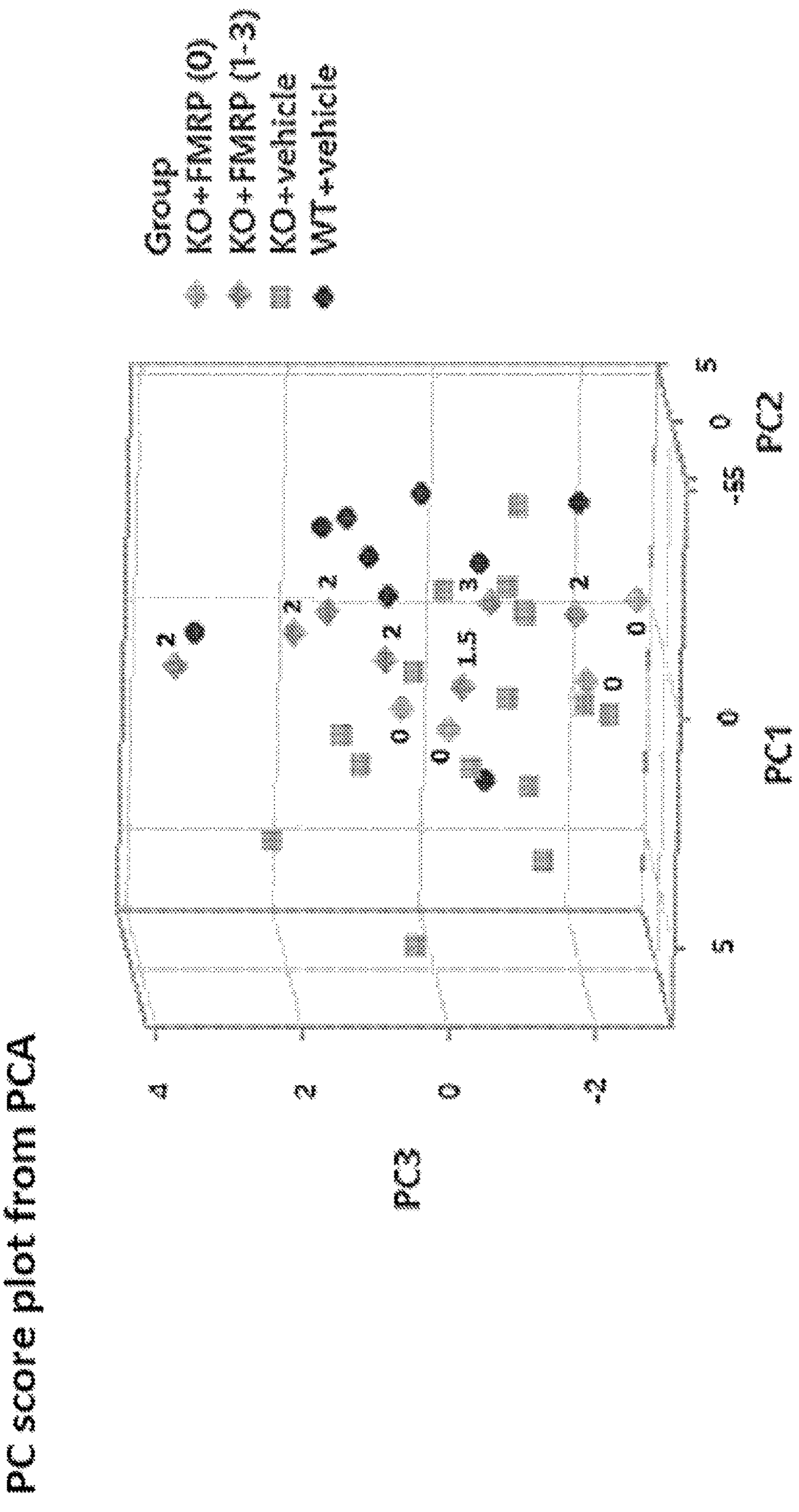

Principal component analysis (PCA) was performed on the multidimensional dataset from the male mice which underwent both circadian locomotor activity recording and EEG analysis. Three principal components were selected by parallel analysis and together they explained the majority (>75%) of the total variance. A 3D plot showing the PC1, PC2, and PC3 scores of each mouse from the three treatment groups is shown in FIG. 16C with the corresponding descriptive and inferential statistics presented in the Table 1.

TABLE 1

(D) Descriptive and inferential statistics of PCA. Mean PC1 score of WT + vehicle is significantly different (p < 0.05) from the KO + vehicle group but not the KO + FMRP group. WT + vehicle (n = 9); KO + vehicle (n 16); KO + FMRP (n = 11).

| | | | | Mean PC scores (SEM) | | | | | | |
|---|---|---|---|---|---|---|---|---|---|---|
| PC | Eigen-value | Proportion of variance | Cumulative proportion of variance | WT + V (n = 9) | KO + V (n = 16) | KO + FMRP (n = 11) | p-value (one-way ANOVA) | p-values (post hoc Tukey's test) WT + Vvs. KO + V | WT + Vvs. KO + FMRP | KO + Vvs. KO + FMRP |
| 1 | 5.168 | 0.369 | 0.369 | −1.566 (0.692) | 1.051 (0.623) | −0.248 (0.341) | 0.015 | 0.012 | 0.342 | 0.257 |
| 2 | 3.002 | 0.214 | 0.584 | 1.188 (0.541) | −0.406 (0.472) | −0.382 (0.352) | 0.055 | 0.064 | 0.098 | 0.999 |
| 3 | 2.385 | 0.170 | 0.754 | 0.583 (0.497) | −0.411 (0.313) | 0.121 (0.574) | 0.297 | 0.278 | 0.782 | 0.653 |

V: vehicle, WT: wildtype, KO: Fmr1 knockout.

TABLE 2

Component loadings of PCA.

| Variables | PC1 | PC2 | PC3 |
|---|---|---|---|
| Delta relative power | −0.1020 | 0.0504 | −0.1275 |
| Theta relative power | −0.5803 | −0.5847 | 0.2559 |
| Alpha relative power | −0.4145 | −0.6746 | 0.4757 |
| Beta relative power | −0.4269 | −0.7504 | 0.4235 |
| Gamma relative power | −0.4701 | −0.6583 | 0.2883 |
| % sleep time (day 1) | −0.7202 | 0.4092 | 0.2405 |
| % sleep time (day 2) | −0.5909 | 0.4209 | 0.4377 |
| % sleep time (day 3) | −0.7441 | 0.4786 | 0.1761 |
| Light phase activity (day 1) | 0.8190 | −0.3511 | 0.0069 |
| Light phase activity (day 2) | 0.8444 | −0.2958 | 0.0321 |
| Light phase activity (day 3) | 0.8408 | −0.3285 | 0.1550 |
| Dark phase activity (day 1) | 0.5092 | 0.2331 | 0.6708 |
| Dark phase activity (day 2) | 0.4634 | 0.3589 | 0.7396 |
| Dark phase activity (day 3) | 0.5097 | 0.3617 | 0.7154 |

The FMRP expression score of each mouse in the KO+FMRP group is indicated next to each data point in FIG. 16C. The WT+vehicle and KO+vehicle groups were neatly discriminated into two clusters, revealing the different phenotypes of the two groups. In the KO+FMRP group, the mice with no FMRP expression (expression score=0) clustered closer to the KO+vehicle group, while the mice with higher FMRP expression levels (expression score≥1) clustered closer to the WT+vehicle group. A statistically significant difference (p<0.05) was found between the mean PC1 scores of the WT+vehicle group and the KO+vehicle group but not between the WT+vehicle group and the KO+FMRP group (p>0.05) by post hoc Tukey's test (Table 1). Thus multivariate analysis using PCA revealed that AAV-FMRP gene therapy rescued the abnormal phenotype of Fmr1 KO mice and this is associated with the expression of the transgene.

SEQUENCES

SEQ ID NO: 1
Nucleic acid sequence of a pSJGK-JeT-hsaFMR1Iso17opt-SpA expression cassette comprising an optimized FMR1 open reading frame:
CTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGGGTTCGGTACCGG
GCGGAGTTAGGGCGGAGCCAATCAGCGTGCGCCGTTCCGAAAGTTGCCTTTTATGGCTGG
GCGGAGAATGGGCGGTGAACGCCGATGATTATATAAGGACGCGCCGGGTGTGGCACAGC
TAGTTCCGTCGCAGCCGGGATTTGGGTCGCGGTTCTTGTTTGTGGATCCTCCGGAAACGC
GCGCGGCCACCATGGAAGAACTGGTGGTGGAAGTGAGAGGAAGCAATGGAGCCTTCTAC
AAGGCCTTTGTGAAGGATGTGCATGAGGACTCCATTACTGTGGCTTTTGAAAACAACTGG
CAACCAGACAGACAGATTCCTTTCCATGATGTGAGATTCCCCCCTCCTGTGGGGTACAAC
AAGGACATCAATGAGTCAGATGAAGTGGAAGTGTACTCCAGAGCCAATGAGAAGGAACC
ATGTTGTTGGTGGCTTGCCAAAGTGAGAATGATCAAGGGGGAGTTCTATGTGATTGAATA
TGCAGCCTGTGATGCTACCTACAATGAAATTGTGACCATTGAGAGGCTTAGATCTGTGAA
CCCCAACAAACCAGCCACAAAGGACACCTTCCACAAGATCAAGCTGGATGTGCCTGAGG
ATCTGAGGCAGATGTGTGCCAAGGAAGCTGCCCACAAGGATTTCAAGAAAGCTGTGGGA
GCCTTCTCAGTGACTTATGACCCTGAGAATTATCAGCTGGTGATACTGAGCATCAATGAA
GTGACTTCCAAGAGAGCCCACATGCTGATTGATATGCATTTTAGAAGCCTTAGAACCAAA
CTGAGCCTCATCATGAGGAATGAGGAGGCCAGCAAGCAACTGGAAAGCTCCAGGCAGTT
GGCTTCCAGATTCCATGAACAGTTCATTGTGAGGGAAGATCTGATGGGCCTGGCAATTGG
TACTCATGGAGCCAACATCCAACAAGCCAGGAAGGTCCCAGGAGTGACTGCCATTGACC
TAGATGAAGATACTTGTACTTTCCACATTTATGGAGAAGATCAGGATGCTGTGAAGAAGG
CTAGATCCTTCCTGGAGTTTGCAGAAGATGTGATCCAGGTGCCCAGAAACCTGGTGGGA
AAGTCATTGGGAAGAATGGAAGCTGATCCAGGAAATTGTGGACAAGTCAGGTGTGGTC
AGGGTCAGAATTGAGGCAGAAAATGAAAAGAATGTGCCACAGGAGGAAGAAATCATGC
CCCCTAACTCATTGCCTTCCAACAACTCCAGGGTGGGCCCAAATGCCCCAGAAGAAAAGA
AGCATCTTGACATCAAGGAAAACTCCACCCATTTCTCACAGCCCAACAGCACCAAGGTGC
AGAGAGGAATGGTGCCTTTTGTCTTTGTGGGAACCAAGGACTCAATTGCAAATGCAACTG
TCCTGTTGGACTACCACTTGAACTACCTGAAGGAAGTGGACCAGCTGAGACTGGAGAGAT
TACAAATTGATGAACAGTTGAGGCAGATTGGAGCCAGCAGCAGGCCACCTCCTAACAGA
ACTGACAAGGAGAAGTCCTATGTGACTGATGATGGACAGGGGATGGGCAGGGGTAGCAG
ACCTTACAGAAACAGAGGACATGGCAGAAGGGGACCTGGTTACACATCAGGAACTAACT
CAGAAGCCTCCAATGCTTCAGAGACTGAATCAGACCATAGAGATGAACTGTCAGACTGG
AGCCTGGCCCCCACTGAAGAAGAAAGAGAAAGCTTCCTGAGGAGAGGAGACGGACGGC
GGCGTGGAGGGGGAGGAAGAGGACAAGGAGGAAGAGGACGTGGAGGAGGCTTCAAGGG
AAATGATGATCACAGCAGAACTGACAACAGACCCAGAAACCCCAGAGAAGCCAAGGGC
AGGACCACTGATGGAAGCCTGCAGAACACTTCCTCAGAGGGTTCCAGGCTGAGAACTGG
GAAGGATAGAAACCAGAAGAAGGAAAAGCCTGACTCAGTGGATGGCCAGCAGCCTCTGG
TCAATGGAGTCCCTTAAGCGGCCGCCTCGAGAATAAAGAGCTCAGATGCATCGATCAGA
GTGTGTTGGTTTTTTGTGTGACGCGTAGGAACCCCTAGTGATGGAGTTGGCCACTCCCTCT
CTGCGCGCTCGCTCGCTCACTGAGGCCGGGCGACCAAAGGTCGCCCGACGCCCGGGCTTT
GCCCGGGCGGCCTCAGTGAGCGAGCGAGCGCGCAGCTGGCGTAATAGCGAAGAGGCCCG
CACCGATCGCCCTTCCCAACAGTTGCGCAGCCTGAATGGCGAATGGCGATTCCGTTGCAA
TGGCTGGCGGTAATATTGTTCTGGATATTACCAGCAAGGCCGATAGTTTGAGTTCTTCTAC
TCAGGCAAGTGATGTTATTACTAATCAAAGAAGTATTGCGACAACGGTTAATTTGCGTGA
TGGACAGACTCTTTTACTCGGTGGCCTCACTGATTATAAAAACACTTCTCAGGATTCTGGC
GTACCGTTCCTGTCTAAAATCCCTTTAATCGGCCTCCTGTTTAGCTCCCGCTCTGATTCTA
ACGAGGAAAGCACGTTATACGTGCTCGTCAAAGCAACCATAGTACGCGCCCTGTAGCGG
CGCATTAAGCGCGGCGGGTGTGGTGGTTACGCGCAGCGTGACCGCTACACTTGCCAGCGC
CCTAGCGCCCGCTCCTTTCGCTTTCTTCCCTTCCTTTCTCGCCACGTTCGCCGGCTTTCCCC
GTCAAGCTCTAAATCGGGGGCTCCCTTTAGGGTTCCGATTTAGTGCTTTACGGCACCTCGA
CCCCAAAAAACTTGATTAGGGTGATGGTTCACGTAGTGGGCCATCGCCCTGATAGACGGT
TTTTCGCCCTTTGACGTTGGAGTCCACGTTCTTTAATAGTGGACTCTTGTTCCAAACTGGA
ACAACACTCAACCCTATCTCGGTCTATTCTTTTGATTTATAAGGGATTTTGCCGATTTCGG
CCTATTGGTTAAAAAATGAGCTGATTTAACAAAAATTTAACGCGAATTTTAACAAAATAT
TAACGCTTACAATTTAAATATTTGCTTATACAATCTTCCTGTTTTTGGGGCTTTTCTGATTA
TCAACCGGGGTACATATGATTGACATGCTAGTTTTACGATTACCGTTCATCGATTCTCTTG
TTTGCTCCAGACTCTCAGGCAATGACCTGATAGCCTTTGTAGAGACCTCTCAAAAATAGC
TACCCTCTCCGGCATGAATTTATCAGCTAGAACGGTTGAATATCATATTGATGGTGATTTG
ACTGTCTCCGGCCTTTCTCACCCGTTTGAATCTTTACCTACACATTACTCAGGCATTGCAT
TTAAAATATATGAGGGTTCTAAAAATTTTTATCCTTGCGTTGAAATAAAGGCTTCTCCCGC
AAAAGTATTACAGGGTCATAATGTTTTTGGTACAACCGATTTAGCTTTATGCTCTGAGGCT
TTATTGCTTAATTTTGCTAATTCTTTGCCTTGCCTGTATGATTTATTGGATGTTGGAATCGC
CTGATGCGGTATTTTCTCCTTACGCATCTGTGCGGTATTTCACACCGCATATGGTGCACTC
TCAGTACAATCTGCTCTGATGCCGCATAGTTAAGCCAGCCCCGACACCCGCCAACACCCG
CTGACGCGCCCTGACGGGCTTGTCTGCTCCCGGCATCCGCTTACAGACAAGCTGTGACCG
TCTCCGGGAGCTGCATGTGTCAGAGGTTTTCACCGTCATCACCGAAACGCGCGAGACGAA
AGGGCCTCGTGATACGCCTATTTTTATAGGTTAATGTCATGATAATAATGGTTTCTTAGAC
GTCAGGTGGCACTTTTCGGGGAAATGTGCGCGGAACCCCTATTTGTTTATTTTTCTAAATA
CATTCAAATATGTATCCGCTCATGAGACAATAACCCTGATAAATGCTTCAATAATATTGA
AAAAGGAAGAGTATGAGCCATATTCAACGGGAAACGTCTTGCTCTAGGCCGCGATTAAA
TTCCAACATGGATGCTGATTTATATGGGTATAAATGGGCTCGCGATAATGTCGGGCAATC
AGGTGCGACAATCTATCGATTGTATGGGAAGCCCGATGCGCCAGAGTTGTTTCTGAAACA
TGGCAAAGGTAGCGTTGCCAATGATGTTACAGATGAGATGGTCAGACTAAACTGGCTGA -continued

| SEQUENCES |
| --- |

CGGAATTTATGCCTCTTCCGACCATCAAGCATTTTATCCGTACTCCTGATGATGCATGGTT
ACTCACCACTGCGATCCCTGGGAAAACAGCATTCCAGGTATTAGAAGAATATCCTGATTC
AGGTGAAAATATTGTTGATGCGCTGGCAGTGTTCCTGCGCCGGTTGCATTCGATTCCTGTT
TGTAATTGTCCTTTTAACAGCGATCGCGTATTTCGTCTCGCTCAGGCGCAATCACGAATGA
ATAACGGTTTGGTTGATGCGAGTGATTTTGATGACGAGCGTAATGGCTGGCCTGTTGAAC
AAGTCTGGAAAGAAATGCATAAACTTTTGCCATTCTCACCGGATTCAGTCGTCACTCATG
GTGATTTCTCACTTGATAACCTTATTTTTGACGAGGGGAAATTAATAGGTTGTATTGATGT
TGGACGAGTCGGAATCGCAGACCGATACCAGGATCTTGCCATCCTATGGAACTGCCTCGG
TGAGTTTTCTCCTTCATTACAGAAACGGCTTTTTCAAAAATATGGTATTGATAATCCTGAT
ATGAATAAATTGCAGTTTCATTTGATGCTCGATGAGTTTTTCTAACTGTCAGACCAAGTTT
ACTCATATATACTTTAGATTGATTTAAAACTTCATTTTTAATTTAAAAGGATCTAGGTGAA
GATCCTTTTTGATAATCTCATGACCAAAATCCCTTAACGTGAGTTTTCGTTCCACTGAGCG
TCAGACCCCGTAGAAAAGATCAAAGGATCTTCTTGAGATCCTTTTTTTCTGCGCGTAATCT
GCTGCTTGCAAACAAAAAAACCACCGCTACCAGCGGTGGTTTGTTTGCCGGATCAAGAGC
TACCAACTCTTTTTCCGAAGGTAACTGGCTTCAGCAGAGCGCAGATACCAAATACTGTTC
TTCTAGTGTAGCCGTAGTTAGGCCACCACTTCAAGAACTCTGTAGCACCGCCTACATACC
TCGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTT
CGTGCACACAGCCCAGCTTGGAGCGAACGACCTACACCGAACTGAGATACCTACAGCGT
GAGCTATGAGAAAGCGCCACGCTTCCCGAAGGGAGAAAGGCGGACAGGTATCCGGTAAG
CGGCAGGGTCGGAACAGGAGAGCGCACGAGGGAGCTTCCAGGGGGAAACGCCTGGTATC
TTTATAGTCCTGTCGGGTTTCGCCACCTCTGACTTGAGCGTCGATTTTTGTGATGCTCGTC
AGGGGGGCGGAGCCTATGGAAAAACGCCAGCAACGCGGCCTTTTTACGGTTCCTGGCCTT
TTGCTGGCCTTTTGCTCACATGTTCTTTCCTGCGTTATCCCCTGATTCTGTGGATAACCGTA
TTACCGCCTTTGAGTGAGCTGATACCGCTCGCCGCAGCCGAACGACCGAGCGCAGCGAGT
CAGTGAGCGAGGAAGCGGAAGAGCGCCCAATACGCAAACCGCCTCTCCCCGCGCGTTGG
CCGATTCATTAATGCAG

SEQ ID NO: 2
Nucleic acid sequence of mITR; nucleotides 1-106 of SEQ ID NO: 1, 1-106 of SEQ ID NO: 7, and 1-106 of SEQ ID NO: 9:
CTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGG SEQ ID NO: 3
Nucleic acid sequence of Jet Promoter; nucleotides 118-281 of SEQ ID NO: 1:
GGGCGGAGTTAGGGCGGAGCCAATCAGCGTGCGCCGTTCCGAAAGTTGCCTTTTATGGC
TGGGCGGAGAATGGGCGGTGAACGCCGATGATTATATAAGGACGCGCCGGGTGTGGCA
CAGCTAGTTCCGTCGCAGCCGGGATTTGGGTCGCGGTTCTTGTTTGT SEQ ID NO: 4
Nucleic acid sequence of FMR1 codon-optimized hsaFMR1Iso17opt; nucleotides 310-2094 of SEQ ID NO: 1, 357-2141 of SEQ ID NO: 7, and 398-2182 of SEQ ID NO: 9:
ATGGAAGAACTGGTGGTGGAAGTGAGAGGAAGCAATGGAGCCTTCTACAAGGCCTTTGT
GAAGGATGTGCATGAGGACTCCATTACTGTGGCTTTTGAAAACAACTGGCAACCAGACA
GACAGATTCCTTTCCATGATGTGAGATTCCCCCCTCCTGTGGGGTACAACAAGGACATCA
ATGAGTCAGATGAAGTGGAAGTGTACTCCAGAGCCAATGAGAAGGAACCATGTTGTTGG
TGGCTTGCCAAAGTGAGAATGATCAAGGGGGAGTTCTATGTGATTGAATATGCAGCCTGT
GATGCTACCTACAATGAAATTGTGACCATTGAGAGGCTTAGATCTGTGAACCCCAACAAA
CCAGCCACAAAGGACACCTTCCACAAGATCAAGCTGGATGTGCCTGAGGATCTGAGGCA
GATGTGTGCCAAGGAAGCTGCCCACAAGGATTTCAAGAAAGCTGTGGGAGCCTTCTCAGT
GACTTATGACCCTGAGAATTATCAGCTGGTGATACTGAGCATCAATGAAGTGACTTCCAA
GAGAGCCCACATGCTGATTGATATGCATTTTAGAAGCCTTAGAACCAAACTGAGCCTCAT
CATGAGGAATGAGGAGGCCAGCAAGCAACTGGAAAGCTCCAGGCAGTTGGCTTCCAGAT
TCCATGAACAGTTCATTGTGAGGGAAGATCTGATGGGCCTGGCAATTGGTACTCATGGAG
CCAACATCCAACAAGCCAGGAAGGTCCCAGGAGTGACTGCCATTGACCTAGATGAAGAT
ACTTGTACTTTCCACATTTATGGAGAAGATCAGGATGCTGTGAAGAAGGCTAGATCCTTC
CTGGAGTTTGCAGAAGATGTGATCCAGGTGCCCAGAAACCTGGTGGGGAAAGTCATTGG
GAAGAATGGGAAGCTGATCCAGGAAATTGTGGACAAGTCAGGTGTGGTCAGGGTCAGAA
TTGAGGCAGAAAATGAAAAGAATGTGCCACAGGAGGAAGAAATCATGCCCCCTAACTCA
TTGCCTTCCAACAACTCCAGGGTGGGCCCAAATGCCCCAGAAGAAAAGAAGCATCTTGA
CATCAAGGAAAACTCCACCCATTTCTCACAGCCCAACAGCACCAAGGTGCAGAGAGGAA
TGGTGCCTTTTGTCTTTGTGGGAACCAAGGACTCAATTGCAAATGCAACTGTCCTGTTGGA
CTACCACTTGAACTACCTGAAGGAAGTGGACCAGCTGAGACTGGAGAGATTACAAATTG
ATGAACAGTTGAGGCAGATTGGAGCCAGCAGCAGGCCACCTCCTAACAGAACTGACAAG
GAGAAGTCCTATGTGACTGATGATGGACAGGGGATGGGCAGGGGTAGCAGACCTTACAG
AAACAGAGGACATGGCAGAAGGGGACCTGGTTACACATCAGGAACTAACTCAGAAGCCT
CCAATGCTTCAGAGACTGAATCAGACCATAGAGATGAACTGTCAGACTGGAGCCTGGCC
CCCACTGAAGAAGAAAGAGAAAGCTTCCTGAGGAGAGGAGACGGACGGCGGCGTGGAG
GGGGAGGAAGAGGACAAGGAGGAAGAGGACGTGGAGGAGGCTTCAAGGGAAATGATGA
TCACAGCAGAACTGACAACAGACCCAGAAACCCCAGAGAAGCCAAGGGCAGGACCACT
GATGGAAGCCTGCAGAACACTTCCTCAGAGGGTTCCAGGCTGAGAACTGGGAAGGATAG
AAACCAGAAGAAGGAAAAGCCTGACTCAGTGGATGGCCAGCAGCCTCTGGTCAATGGAG
TCCCTTAA -continued

| SEQUENCES |
| --- |

SEQ ID NO: 5
Nucleic acid sequence of SpA; nucleotides 2095-2156 of SEQ ID NO: 1, 2142-2203 of SEQ ID NO: 7, and 2183-2244 of SEQ ID NO: 9:
GCGGCCGCCTCGAGAATAAAGAGCTCAGATGCATCGATCAGAGTGTGTTGGTTTTTTGT
GTG SEQ ID NO: 6
Nucleic acid sequence of a second AAV ITR; nucleotides 2163-2331 of SEQ ID NO: 1, 2210-2378 of SEQ ID NO: 7, and 2251-2419 of SEQ ID NO: 9:
AGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGAG
CGAGCGCGCAGCTGGCGTAATAGCGAAGAGGCCCGCACCGATCGCCCTTC SEQ ID NO: 7
Nucleic acid sequence of a pSJGK-MeP229-hsaFMR1Iso 17opt-SpA expression cassette comprising an optimized FMR1 open reading frame:
CTGCGCGCTCGCTCGCTCACTGAGGCCGCCCGGGCAAAGCCCGGGCGTCGGGCGACCTT
TGGTCGCCCGGCCTCAGTGAGCGAGCGAGCGCGCAGAGAGGGAGTGGGGTTCGGTACC
CAATTGAGGGCGTCACCGCTAAGGCTCCGCCCCAGCCTGGGCTCCACAACCAATGAAG
GGTAATCTCGACAAAGAGCAAGGGGGGGGCGCGGGCGCGCAGGTGCAGCAGCACAC
AGGCTGGTCGGGAGGGCGGGGCGCGACGTCTGCCGTGCGGGGTCCCGGCATCGGTTGC
GCGCGCGCTCCCTCCTCTCGGAGAGAGGGCTGTGGTAAAACCCGTCCGGAAACGCGCG
CGGCCACCATGGAAGAACTGGTGGTGGAAGTGAGAGGAAGCAATGGAGCCTTCTACAA
GGCCTTTGTGAAGGATGTGCATGAGGACTCCATTACTGTGGCTTTTGAAAACAACTGGC
AACCAGACAGACAGATTCCTTTCCATGATGTGAGATTCCCCCCTCCTGTGGGGTACAAC
AAGGACATCAATGAGTCAGATGAAGTGGAAGTGTACTCCAGAGCCAATGAGAAGGAAC
CATGTTGTTGGTGGCTTGCCAAAGTGAGAATGATCAAGGGGGAGTTCTATGTGATTGAA
TATGCAGCCTGTGATGCTACCTACAATGAAATTGTGACCATTGAGAGGCTTAGATCTGT
GAACCCCAACAAACCAGCCACAAAGGACACCTTCCACAAGATCAAGCTGGATGTGCCT
GAGGATCTGAGGCAGATGTGTGCCAAGGAAGCTGCCCACAAGGATTTCAAGAAAGCTG
TGGGAGCCTTCTCAGTGACTTATGACCCTGAGAATTATCAGCTGGTGATACTGAGCATC
AATGAAGTGACTTCCAAGAGAGCCCACATGCTGATTGATATGCATTTTAGAAGCCTTAG
AACCAAACTGAGCCTCATCATGAGGAATGAGGAGGCCAGCAAGCAACTGGAAAGCTCC
AGGCAGTTGGCTTCCAGATTCCATGAACAGTTCATTGTGAGGGAAGATCTGATGGGCCT
GGCAATTGGTACTCATGGAGCCAACATCCAACAAGCCAGGAAGGTCCCAGGAGTGACT
GCCATTGACCTAGATGAAGATACTTGTACTTTCCACATTTATGGAGAAGATCAGGATGC
TGTGAAGAAGGCTAGATCCTTCCTGGAGTTTGCAGAAGATGTGATCCAGGTGCCCAGAA
ACCTGGTGGGGAAAGTCATTGGGAAGAATGGGAAGCTGATCCAGGAAATTGTGGACAA
GTCAGGTGTGGTCAGGGTCAGAATTGAGGCAGAAAATGAAAAGAATGTGCCACAGGAG
GAAGAAATCATGCCCCCTAACTCATTGCCTTCCAACAACTCCAGGGTGGGCCCAAATGC
CCCAGAAGAAAAGAAGCATCTTGACATCAAGGAAAACTCCACCCATTTCTCACAGCCC
AACAGCACCAAGGTGCAGAGAGGAATGGTGCCTTTTGTCTTTGTGGGAACCAAGGACT
CAATTGCAAATGCAACTGTCCTGTTGGACTACCACTTGAACTACCTGAAGGAAGTGGAC
CAGCTGAGACTGGAGAGATTACAAATTGATGAACAGTTGAGGCAGATTGGAGCCAGCA
GCAGGCCACCTCCTAACAGAACTGACAAGGAGAAGTCCTATGTGACTGATGATGGACA
GGGGATGGGCAGGGGTAGCAGACCTTACAGAAACAGAGGACATGGCAGAAGGGGACC
TGGTTACACATCAGGAACTAACTCAGAAGCCTCCAATGCTTCAGAGACTGAATCAGACC
ATAGAGATGAACTGTCAGACTGGAGCCTGGCCCCCACTGAAGAAGAAAGAGAAAGCTT
CCTGAGGAGAGGAGACGGACGGCGGCGTGGAGGGGGAGGAAGAGGACAAGGAGGAA
GAGGACGTGGAGGAGGCTTCAAGGGAAATGATGATCACAGCAGAACTGACAACAGAC
CCAGAAACCCCAGAGAAGCCAAGGGCAGGACCACTGATGGAAGCCTGCAGAACACTTC
CTCAGAGGGTTCCAGGCTGAGAACTGGGAAGGATAGAAACCAGAAGAAGGAAAAGCC
TGACTCAGTGGATGGCCAGCAGCCTCTGGTCAATGGAGTCCCTTAAGCGGCCGCCTCGA
GAATAAAGAGCTCAGATGCATCGATCAGAGTGTGTTGGTTTTTTGTGTGACGCGTAGGA
ACCCCTAGTGATGGAGTTGGCCACTCCCTCTCTGCGCGCTCGCTCGCTCACTGAGGCCG
GGCGACCAAAGGTCGCCCGACGCCCGGGCTTTGCCCGGGCGGCCTCAGTGAGCGAGCG
AGCGCGCAGCTGGCGTAATAGCGAAGAGGCCCGCACCGATCGCCCTTCCCAACAGTTG
CGCAGCCTGAATGGCGAATGGCGATTCCGTTGCAATGGCTGGCGGTAATATTGTTCTGG
ATATTACCAGCAAGGCCGATAGTTTGAGTTCTTCTACTCAGGCAAGTGATGTTATTACT
AATCAAAGAAGTATTGCGACAACGGTTAATTTGCGTGATGGACAGACTCTTTTACTCGG
TGGCCTCACTGATTATAAAAACACTTCTCAGGATTCTGGCGTACCGTTCCTGTCTAAAAT
CCCTTTAATCGGCCTCCTGTTTAGCTCCCGCTCTGATTCTAACGAGGAAAGCACGTTATA
CGTGCTCGTCAAAGCAACCATAGTACGCGCCCTGTAGCGGCGCATTAAGCGCGGCGGG
TGTGGTGGTTACGCGCAGCGTGACCGCTACACTTGCCAGCGCCCTAGCGCCCGCTCCTT
TCGCTTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAACTTG
ATTAGGGTGATGGTTCACGTAGTGGGCCATCGCCCTGATAGACGGTTTTTCGCCCTTTG
ACGTTGGAGTCCACGTTCTTTAATAGTGGACTCTTGTTCCAAACTGGAACAACACTCAA
CCCTATCTCGGTCTATTCTTTTGATTTATAAGGGATTTTGCCGATTTCGGCCTATTGGTTA
AAAAATGAGCTGATTTAACAAAAATTTAACGCGAATTTTAACAAAATATTAACGCTTAC
AATTTAAATATTTGCTTATACAATCTTCCTGTTTTTGGGGCTTTTCTGATTATCAACCGG
GGTACATATGATTGACATGCTAGTTTTACGATTACCGTTCATCGATTCTCTTGTTTGCTC
CAGACTCTCAGGCAATGACCTGATAGCCTTTGTAGAGACCTCTCAAAAATAGCTACCCT
CTCCGGCATGAATTTATCAGCTAGAACGGTTGAATATCATATTGATGGTGATTTGACTG
TCTCCGGCCTTTCTCACCCGTTTGAATCTTTACCTACACATTACTCAGGCATTGCATTTA
AAATATATGAGGGTTCTAAAAATTTTTATCCTTGCGTTGAATAAAGGCTTCTCCCGCA -continued

| SEQUENCES |
|---|

AAAGTATTACAGGGTCATAATGTTTTTGGTACAACCGATTTAGCTTTATGCTCTGAGGCT
TTATTGCTTAATTTTGCTAATTCTTTGCCTTGCCTGTATGATTTATTGGATGTTGGAATCG
CCTGATGCGGTATTTTCTCCTTACGCATCTGTGCGGTATTTCACACCGCATATGGTGCAC
TCTCAGTACAATCTGCTCTGATGCCGCATAGTTAAGCCAGCCCCGACACCCGCCAACAC
CCGCTGACGCGCCCTGACGGGCTTGTCTGCTCCCGGCATCCGCTTACAGACAAGCTGTG
ACCGTCTCCGGGAGCTGCATGTGTCAGAGGTTTTCACCGTCATCACCGAAACGCGCGAG
ACGAAAGGGCCTCGTGATACGCCTATTTTTATAGGTTAATGTCATGATAATAATGGTTT
CTTAGACGTCAGGTGGCACTTTTCGGGGAAATGTGCGCGGAACCCCTATTTGTTTATTTT
TCTAAATACATTCAAATATGTATCCGCTCATGAGACAATAACCCTGATAAATGCTTCAA
TAATATTGAAAAAGGAAGAGTATGAGCCATATTCAACGGGAAACGTCTTGCTCTAGGC
CGCGATTAAATTCCAACATGGATGCTGATTTATATGGGTATAAATGGGCTCGCGATAAT
GTCGGGCAATCAGGTGCGACAATCTATCGATTGTATGGGAAGCCCGATGCGCCAGAGTT
GTTTCTGAAACATGGCAAAGGTAGCGTTGCCAATGATGTTACAGATGAGATGGTCAGAC
TAAACTGGCTGACGGAATTTATGCCTCTTCCGACCATCAAGCATTTTATCCGTACTCCTG
ATGATGCATGGTTACTCACCACTGCGATCCCTGGGAAAACAGCATTCCAGGTATTAGAA
GAATATCCTGATTCAGGTGAAAATATTGTTGATGCGCTGGCAGTGTTCCTGCGCCGGTT
GCATTCGATTCCTGTTTGTAATTGTCCTTTTAACAGCGATCGCGTATTTCGTCTCGCTCA
GGCGCAATCACGAATGAATAACGGTTTGGTTGATGCGAGTGATTTTGATGACGAGCGTA
ATGGCTGGCCTGTTGAACAAGTCTGGAAAGAAATGCATAAACTTTTGCCATTCTCACCG
GATTCAGTCGTCACTCATGGTGATTTCTCACTTGATAACCTTATTTTTGACGAGGGGAAA
TTAATAGGTTGTATTGATGTTGGACGAGTCGGAATCGCAGACCGATACCAGGATCTTGC
CATCCTATGGAACTGCCTCGGTGAGTTTTCTCCTTCATTACAGAAACGGCTTTTTCAAAA
ATATGGTATTGATAATCCTGATATGAATAAATTGCAGTTTCATTTGATGCTCGATGAGTT
TTTCTAACTGTCAGACCAAGTTTACTCATATATACTTTAGATTGATTTAAAACTTCATTT
TTAATTTAAAAGGATCTAGGTGAAGATCCTTTTTGATAATCTCATGACCAAAATCCCTTA
ACGTGAGTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCGCTACCA
GCGGTGGTTTGTTTGCCGGATCAAGAGCTACCAACTCTTTTTCCGAAGGTAACTGGCTTC
AGCAGAGCGCAGATACCAAATACTGTTCTTCTAGTGTAGCCGTAGTTAGGCCACCACTT
CAAGAACTCTGTAGCACCGCCTACATACCTCGCTCTGCTAATCCTGTTACCAGTGGCTG
CTGCCAGTGGCGATAAGTCGTGTCTTACCGGGTTGGACTCAAGACGATAGTTACCGGAT
AAGGCGCAGCGGTCGGGCTGAACGGGGGGTTCGTGCACACAGCCCAGCTTGGAGCGAA
CGACCTACACCGAACTGAGATACCTACAGCGTGAGCTATGAGAAAGCGCCACGCTTCC
CGAAGGGAGAAAGGCGGACAGGTATCCGGTAAGCGGCAGGGTCGGAACAGGAGAGCG
CACGAGGGAGCTTCCAGGGGGAAACGCCTGGTATCTTTATAGTCCTGTCGGGTTTCGCC
ACCTCTGACTTGAGCGTCGATTTTTGTGATGCTCGTCAGGGGGGCGGAGCCTATGGAAA
AACGCCAGCAACGCGGCCTTTTTACGGTTCCTGGCCTTTTGCTGGCCTTTTGCTCACATG
TTCTTTCCTGCGTTATCCCCTGATTCTGTGGATAACCGTATTACCGCCTTTGAGTGAGCT
GATACCGCTCGCCGCAGCCGAACGACCGAGCGCAGCGAGTCAGTGAGCGAGGAAGCGG
AAGAGCGCCCAATACGCAAACCGCCTCTCCCCGCGCGTTGGCCGATTCATTAATGCAG

SEQ ID NO: 8
Nucleic acid sequence of an MeP229 promoter; nucleotides 118-342 of SEQ ID NO: 7:
CAATTGAGGGCGTCACCGCTAAGGCTCCGCCCCAGCCTGGGCTCCACAACCAATGAAGG
GTAATCTCGACAAAGAGCAAGGGGTGGGGCGCGGGCGCGCAGGTGCAGCAGCACACAG
GCTGGTCGGGAGGGCGGGGCGCGACGTCTGCCGTGCGGGGTCCCGGCATCGGTTGCGCG
CGCGCTCCCTCCTCTCGGAGAGAGGGCTGTGGTAAAACCCGTCCGGAAA SEQ ID NO: 9
Nucleic acid sequence of a pSJGK-pFMRQ(244)-hsaFMRQIso17opt-SpA expression cassette comprising an optimized FMR1 open reading frame:
CTGCGCGCTCGCTCGCTCACTGAGGCCGCCCGGGCAAAGCCCGGGCGTCGGGCGACCTT
TGGTCGCCCGGCCTCAGTGAGCGAGCGAGCGCGCAGAGAGGGAGTGGGGTTCGGTACC
CGCCGGCGCCGCCCTTCAGCCTTCCCGCCCTCCACCAAGCCCGCGCACGCCCGGCCCGC
GCGTCTGTCTTTCGACCCGGCACCCCGGCCGGTTCCCAGCAGCGCGCATGCGCGCGCTC
CCAGGCCACTTGAAGAGAGAGGGCGGGGCCGAGGGGCTGAGCCCGCGGGGGGAGGGA
ACAGCGTTGATCACGTGACGTGGTTTCAGTGTTTACACCCGCAGCGGGCCGGGGGTTCG
GCCTCAGTCAGGCGCTCAGGATCCTCCGGAAACGCGCGCGGCCACCATGGAAGAACTG
GTGGTGGAAGTGAGAGGAAGCAATGGAGCCTTCTACAAGGCCTTTGTGAAGGATGTGC
ATGAGGACTCCATTACTGTGGCTTTTGAAAACAACTGGCAACCAGACAGACAGATTCCT
TTCCATGATGTGAGATTCCCCCCTCCTGTGGGGTACAACAAGGACATCAATGAGTCAGA
TGAAGTGGAAGTGTACTCCAGAGCCAATGAGAAGGAACCATGTTGTTGGTGGCTTGCC
AAAGTGAGAATGATCAAGGGGGAGTTCTATGTGATTGAATATGCAGCCTGTGATGCTAC
CTACAATGAAATTGTGACCATTGAGAGGCTTAGATCTGTGAACCCCAACAAACCAGCCA
CAAAGGACACCTTCCACAAGATCAAGCTGGATGTGCCTGAGGATCTGAGGCAGATGTG
TGCCAAGGAAGCTGCCCACAAGGATTTCAAGAAAGCTGTGGGAGCCTTCTCAGTGACTT
ATGACCCTGAGAATTATCAGCTGGTGATACTGAGCATCAATGAAGTGACTTCCAAGAGA
GCCCACATGCTGATTGATATGCATTTTAGAAGCCTTAGAACCAAACTGAGCCTCATCAT
GAGGAATGAGGAGGCCAGCAAGCAACTGGAAAGCTCCAGGCAGTTGGCTTCCAGATTC
CATGAACAGTTCATTGTGAGGGAAGATCTGATGGGCCTGGCAATTGGTACTCATGGAGC
CAACATCCAACAAGCCAGGAAGGTCCCAGGAGTGACTGCCATTGACCTAGATGAAGAT
ACTTGTACTTTCCACATTTATGGAGAAGATCAGGATGCTGTGAAGAAGGCTAGATCCTT
CCTGGAGTTTGCAGAAGATGTGATCCAGGTGCCCAGAAACCTGGTGGGGAAAGTCATT
GGGAAGAATGGGAAGCTGATCCAGGAAATTGTGGACAAGTCAGGTGTGGTCAGGGTCA
GAATTGAGGCAGAAAATGAAAAGAATGTGCCACAGGAGGAAGAAATCATGCCCCCTAA
CTCATTGCCTTCCAACAACTCCAGGGTGGGCCCAAATGCCCCAGAAGAAAAGAAGCAT
CTTGACATCAAGGAAAACTCCACCCATTTCTCACAGCCCAACAGCACCAAGGTGCAGA -continued

| SEQUENCES |
| --- |
| GAGGAATGGTGCCTTTTGTCTTTGTGGGAACCAAGGACTCAATTGCAAATGCAACTGTC<br>CTGTTGGACTACCACTTGAACTACCTGAAGGAAGTGGACCAGCTGAGACTGGAGAGAT<br>TACAAATTGATGAACAGTTGAGGCAGATTGGAGCCAGCAGCAGGCCACCTCCTAACAG<br>AACTGACAAGGAGAAGTCCTATGTGACTGATGATGGACAGGGGATGGGCAGGGGTAGC<br>AGACCTTACAGAAACAGAGGACATGGCAGAAGGGGACCTGGTTACACATCAGGAACTA<br>ACTCAGAAGCCTCCAATGCTTCAGAGACTGAATCAGACCATAGAGATGAACTGTCAGA<br>CTGGAGCCTGGCCCCACTGAAGAAGAAAGAGAAAGCTTCCTGAGGAGAGGAGACGG<br>ACGGCGGCGTGGAGGGGGAGGAAGAGGACAAGGAGGAAGAGGACGTGGAGGAGGCTT<br>CAAGGGAAATGATGATCACAGCAGAACTGACAACAGACCCAGAAACCCCAGAGAAGC<br>CAAGGGCAGGACCACTGATGGAAGCCTGCAGAACACTTCCTCAGAGGGTTCCAGGCTG<br>AGAACTGGGAAGGATAGAAACCAGAAGAAGGAAAAGCCTGACTCAGTGGATGGCCAG<br>CAGCCTCTGGTCAATGGAGTCCCTTAAGCGGCCGCCTCGAGAATAAAGAGCTCAGATGC<br>ATCGATCAGAGTGTGTTGGTTTTTTGTGTGACGCGTAGGAACCCCTAGTGATGGAGTTG<br>GCCACTCCCTCTCTGCGCGCTCGCTCGCTCACTGAGGCCGGGCGACCAAAGGTCGCCCG<br>ACGCCCGGGCTTTGCCCGGGCGGCCTCAGTGAGCGAGCGAGCGCGCAGCTGGCGTAAT<br>AGCGAAGAGGCCCGCACCGATCGCCCTTCCCAACAGTTGCGCAGCCTGAATGGCGAAT<br>GGCGATTCCGTTGCAATGGCTGGCGGTAATATTGTTCTGGATATTACCAGCAAGGCCGA<br>TAGTTTGAGTTCTTCTACTCAGGCAAGTGATGTTATTACTAATCAAAGAAGTATTGCGA<br>CAACGGTTAATTTGCGTGATGGACAGACTCTTTTACTCGGTGGCCTCACTGATTATAAA<br>AACACTTCTCAGGATTCTGGCGTACCGTTCCTGTCTAAAATCCCTTTAATCGGCCTCCTG<br>TTTAGCTCCCGCTCTGATTCTAACGAGGAAAGCACGTTATACGTGCTCGTCAAAGCAAC<br>CATAGTACGCGCCCTGTAGCGGCGCATTAAGCGCGGCGGGTGTGGTGGTTACGCGCAG<br>CGTGACCGCTACACTTGCCAGCGCCCTAGCGCCCGCTCCTTTCGCTTTCTTCCCTTCCTT<br>TCTCGCCACGTTCGCCGGCTTTCCCCGTCAAGCTCTAAATCGGGGGCTCCCTTTAGGGTT<br>CCGATTTAGTGCTTTACGGCACCTCGACCCCAAAAAACTTGATTAGGGTGATGGTTCAC<br>GTAGTGGGCCATCGCCCTGATAGACGGTTTTTCGCCCTTTGACGTTGGAGTCCACGTTCT<br>TTAATAGTGGACTCTTGTTCCAAACTGGAACAACACTCAACCCTATCTCGGTCTATTCTT<br>TTGATTTATAAGGGATTTTGCCGATTTCGGCCTATTGGTTAAAAAATGAGCTGATTTAAC<br>AAAAATTTAACGCGAATTTTAACAAAATATTAACGCTTACAATTTAAATATTTGCTTAT<br>ACAATCTTCCTGTTTTTGGGGCTTTTCTGATTATCAACCGGGGTACATATGATTGACATG<br>CTAGTTTTACGATTACCGTTCATCGATTCTCTTGTTTGCTCCAGACTCTCAGGCAATGAC<br>CTGATAGCCTTTGTAGAGACCTCTCAAAAATAGCTACCCTCTCCGGCATGAATTTATCA<br>GCTAGAACGGTTGAATATCATATTGATGGTGATTTGACTGTCTCCGGCCTTTCTCACCCG<br>TTTGAATCTTTACCTACACATTACTCAGGCATTGCATTTAAAATATATGAGGGTTCTAAA<br>AATTTTTATCCTTGCGTTGAAATAAAGGCTTCTCCCGCAAAAGTATTACAGGGTCATAA<br>TGTTTTTGGTACAACCGATTTAGCTTTATGCTCTGAGGCTTTATTGCTTAATTTTGCTAAT<br>TCTTTGCCTTGCCTGTATGATTTATTGGATGTTGGAATCGCCTGATGCGGTATTTTCTCCT<br>TACGCATCTGTGCGGTATTTCACACCGCATATGGTGCACTCTCAGTACAATCTGCTCTGA<br>TGCCGCATAGTTAAGCCAGCCCCGACACCCGCCAACACCCGCTGACGCGCCCTGACGG<br>GCTTGTCTGCTCCCGGCATCCGCTTACAGACAAGCTGTGACCGTCTCCGGGAGCTGCAT<br>GTGTCAGAGGTTTTCACCGTCATCACCGAAACGCGCGAGACGAAAGGGCCTCGTGATA<br>CGCCTATTTTTATAGGTTAATGTCATGATAATAATGGTTTCTTAGACGTCAGGTGGCACT<br>TTTCGGGGAAATGTGCGCGGAACCCCTATTTGTTTATTTTTCTAAATACATTCAAATATG<br>TATCCGCTCATGAGACAATAACCCTGATAAATGCTTCAATAATATTGAAAAAGGAAGA<br>GTATGAGCCATATTCAACGGGAAACGTCTTGCTCTAGGCCGCGATTAAATTCCAACATG<br>GATGCTGATTTATATGGGTATAAATGGGCTCGCGATAATGTCGGGCAATCAGGTGCGAC<br>AATCTATCGATTGTATGGGAAGCCCGATGCGCCAGAGTTGTTTCTGAAACATGGCAAAG<br>GTAGCGTTGCCAATGATGTTACAGATGAGATGGTCAGACTAAACTGGCTGACGGAATTT<br>ATGCCTCTTCCGACCATCAAGCATTTTATCCGTACTCCTGATGATGCATGGTTACTCACC<br>ACTGCGATCCCTGGGAAAACAGCATTCCAGGTATTAGAAGAATATCCTGATTCAGGTGA<br>AAATATTGTTGATGCGCTGGCAGTGTTCCTGCGCCGGTTGCATTCGATTCCTGTTTGTAA<br>TTGTCCTTTTAACAGCGATCGCGTATTTCGTCTCGCTCAGGCGCAATCACGAATGAATA<br>ACGGTTTGGTTGATGCGAGTGATTTTGATGACGAGCGTAATGGCTGGCCTGTTGAACAA<br>GTCTGGAAAGAAATGCATAAACTTTTGCCATTCTCACCGGATTCAGTCGTCACTCATGG<br>TGATTTCTCACTTGATAACCTTATTTTTGACGAGGGGAAATTAATAGGTTGTATTGATGT<br>TGGACGAGTCGGAATCGCAGACCGATACCAGGATCTTGCCATCCTATGGAACTGCCTCG<br>GTGAGTTTTCTCCTTCATTACAGAAACGGCTTTTTCAAAAATATGGTATTGATAATCCTG<br>ATATGAATAAATTGCAGTTTCATTTGATGCTCGATGAGTTTTTCTAACTGTCAGACCAAG<br>TTTACTCATATATACTTTAGATTGATTTAAAACTTCATTTTTAATTTAAAAGGATCTAGG<br>TGAAGATCCTTTTTGATAATCTCATGACCAAAATCCCTTAACGTGAGTTTTCGTTCCACT<br>GAGCGTCAGACCCCGTAGAAAAGATCAAAGGATCTTCTTGAGATCCTTTTTTTCTGCGC<br>GTAATCTGCTGCTTGCAAACAAAAAAACCACCGCTACCAGCGGTGGTTTGTTTGCCGGA<br>TCAAGAGCTACCAACTCTTTTTCCGAAGGTAACTGGCTTCAGCAGAGCGCAGATACCAA<br>ATACTGTTCTTCTAGTGTAGCCGTAGTTAGGCCACCACTTCAAGAACTCTGTAGCACCG<br>CCTACATACCTCGCTCTGCTAATCCTGTTACCAGTGGCTGCTGCCAGTGGCGATAAGTC<br>GTGTCTTACCGGGTTGGACTCAAGACGATAGTTACCGGATAAGGCGCAGCGGTCGGGCT<br>GAACGGGGGGTTCGTGCACACAGCCCAGCTTGGAGCGAACGACCTACACCGAACTGAG<br>ATACCTACAGCGTGAGCTATGAGAAAGCGCCACGCTTCCCGAAGGGAGAAAGGCGGAC<br>AGGTATCCGGTAAGCGGCAGGGTCGGAACAGGAGAGCGCACGAGGGAGCTTCCAGGG<br>GGAAACGCCTGGTATCTTTATAGTCCTGTCGGGTTTCGCCACCTCTGACTTGAGCGTCGA<br>TTTTTGTGATGCTCGTCAGGGGGGCGGAGCCTATGGAAAAACGCCAGCAACGCGGCCTT<br>TTTACGGTTCCTGGCCTTTTGCTGGCCTTTTGCTCACATGTTCTTTCCTGCGTTATCCCCT<br>GATTCTGTGGATAACCGTATTACCGCCTTTGAGTGAGCTGATACCGCTCGCCGCAGCCG<br>AACGACCGAGCGCAGCGAGTCAGTGAGCGAGGAAGCGGAAGAGCGCCCAATACGCAA<br>ACCGCCTCTCCCCGCGCGTTGGCCGATTCATTAATGCAG |

SEQUENCES

SEQ ID NO: 10
Nucleic acid sequence of a pFMR1(244) promoter; nucleotides 126-369 of SEQ ID NO: 9:
CCGCCCTTCAGCCTTCCCGCCCTCCACCAAGCCCGCGCACGCCCGGCCCGCGCGTCTGTCT
TTCGACCCGGCACCCCGGCCGGTTCCCAGCAGCGCGCATGCGCGCGCTCCCAGGCCACTT
GAAGAGAGAGGGCGGGGCCGAGGGGCTGAGCCCGCGGGGGGAGGGAACAGCGTTGATC
ACGTGACGTGGTTTCAGTGTTTACACCCGCAGCGGGCCGGGGGTTCGGCCTCAGTCAGGC
GCTCA SEQ ID NO: 11
Nucleic acid sequence of a mutant AAV2 ITR:
CTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGG SEQ ID NO: 12
Nucleic acid sequence of a wildtype AAV2 ITR:
AGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGAG
CGAGCGCGCAGCTGGCGTAATAGCGAAGAGGCCCGCACCGATCGCCCTTC SEQ ID NO: 13
Nucleic acid sequence of a 5' ITR:
CTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCAC
TAGGGGTTCCT SEQ ID NO: 14
Nucleic acid sequence of a 3' ITR:
AGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGAG
CGAGCGCGCAG SEQ ID NO: 15
Nucleic acid sequence of a 5' ITR:
GGGGGGGGGGGGGGGGGGTTGGCCACTCCCTCTCTGCGCGCTCGCTCGCTCACTGAGGCCG
GGCGACCAAAGGTCGCCCGACGCCCGGGCTTTGCCCGGGCGGCCTCAGTGAGCGAGCGA
GCGCGCAGAGAGGGAGTGGCCAACTCCATCACTAGGGGTTCCTAGATCT SEQ ID NO: 16
Nucleic acid sequence of a 5' ITR:
AGATCTAGGAACCCCTAGTGATGGAGTTGGCCACTCCCTCTCTGCGCGCTCGCTCGCTCA
CTGAGGCCGCCCGGGCAAAGCCCGGGCGTCGGGCGACCTTTGGTCGCCCGGCCTCAGTG
AGCGAGCGAGCGCGCAGAGAGGGAGTGGCCAACCCCCCCCCCCCCCCCCC SEQ ID NO: 17
Nucleic acid sequence of a 3' ITR:
AGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGAG
CGAGCGCGCCAGCTGGCGTAATAGCGAAGAGGCCCGCACCGATCGCCCTTC SEQ ID NO: 18
Nucleic acid sequence of a 5' ITR:
TGCGCGCTCGCTCGCTCACTGAGGCCGCCCGGGCAAAGCCCGGGCGTCGGGCGACCTTTG
GTCGCCCGGCCTCAGTGAGCGAGCGAGCGCGCAGAGAGGGAGTG SEQ ID NO: 19
Nucleic acid sequence of a 3' ITR:
CCACTCCCTCTCTGCGCGCTCGCTCGCTCACTGAGGCCGGGCGACCAAAGGTCGCCCGAC
GCCCGGGCTTTGCCCGGGCGGCCTCAGTGAGCGAGCGAGCGCGCCA SEQ ID NO: 20
Nucleic acid sequence of a JeT + 1 promoter:
GGTACCGGGCGGAGTTAGGGCGGAGCCAATCAGCGTGCGCCGTTCCGAAAGTTGCCTTTT
ATGGCTGGGCGGAGAATGGGCGGTGAACGCCGATGATTATATAAGGACGCGCCGGGTGT
GGCACAGCTAGTTCCGTCGCAGCCGGGATTTGGGTCGCGGTTCTTGTTTGTGGATCCCTGT
GATCGTCACTTGGTAAGTCACTGACTGTCTATGCCTGGGAAAGGGTGGGCAGGAGATGG
GGCAGTGCAGGAAAAGTGGCACTATGAACCCTGCAGCCCTAGGAATGCATCTAGACAAT
TGTACTAACCTTCTTCTCTTTCCTCTCCTGACAG SEQ ID NO: 21
Nucleic acid sequence of a CBh promoter:
GGTACCGGGCGGAGTTAGGGCGGAGCCAATCAGCGTGCGCCGTTCCGAAAGTTGCCTTTT
ATGGCTGGGCGGAGAATGGGCGGTGAACGCCGATGATTATATAAGGACGCGCCGGGTGT
GGCACAGCTAGTTCCGTCGCAGCCGGGATTTGGGTCGCGGTTCTTGTTTGTGGATCCCTGT
GATCGTCACTTGGTAAGTCACTGACTGTCTATGCCTGGGAAAGGGTGGGCAGGAGATGG
GGCAGTGCAGGAAAAGTGGCACTATGAACCCTGCAGCCCTAGGAATGCATCTAGACAAT
TGTACTAACCTTCTTCTCTTTCCTCTCCTGACAG -continued

| SEQUENCES |
| --- |

SEQ ID NO: 22
Nucleic acid sequence of a U6 promoter:
GAGGGCCTATTTCCCATGATTCCTTCATATTTGCATATACGATACAAGGCTGTTAGAGAG
ATAATTGGAATTAATTTGACTGTAAACACAAAGATATTAGTACAAAATACGTGACGTAGA
AAGTAATAATTTCTTGGGTAGTTTGCAGTTTTAAAATTATGTTTTAAAATGGACTATCATA
TGCTTACCGTAACTTGAAAGTATTTCGATTTCTTGGCTTTATATATCTTGTGGAAAGGAC SEQ ID NO: 23
Nucleic acid sequence of a Synapsin promoter 1:
AGTGCAAGTGGGTTTTAGGACCAGGATGAGGCGGGGTGGGGGTGCCTACCTGACGACCG
ACCCCGACCCACTGGACAAGCACCCAACCCCCATTCCCCAAATTGCGCATCCCCTATCAG
AGAGGGGGAGGGGAAACAGGATGCGGCGAGGCGCGTGCGCACTGCCAGCTTCAGCACC
GCGGACAGTGCCTTCGCCCCCGCCTGGCGGCGCGCGCCACCGCCGCCTCAGCACTGAAGG
CGCGCTGACGTCACTCGCCGGTCCCCCGCAAACTCCCCTTCCCGGCCACCTTGGTCGCGTC
CGCGCCGCCGCCGGCCCAGCCGGACCGCACCACGCGAGGCGCGAGATAGGGGGGCACGG
GCGCGACCATCTGCGCTGCGGCGCCGGCGACTCAGCGCTGCCTCAGTCTGCGGTGGGCAG
CGGAGGAGTCGTGTCGTGCCTGAGAGCGCAG SEQ ID NO: 24
Nucleic acid sequence of a Synapsin promoter 2:
CTGCAGAGGGCCCTGCGTATGAGTGCAAGTGGGTTTTAGGACCAGGATGAGGCGGGGTG
GGGGTGCCTACCTGACGACCGACCCCGACCCACTGGACAAGCACCCAACCCCCATTCCCC
AAATTGCGCATCCCCTATCAGAGAGGGGGAGGGGAAACAGGATGCGGCGAGGCGCGTGC
GCACTGCCAGCTTCAGCACCGCGGACAGTGCCTTCGCCCCCGCCTGGCGGCGCGCGCCAC
CGCCGCCTCAGCACTGAAGGCGCGCTGACGTCACTCGCCGGTCCCCCGCAAACTCCCCTT
CCCGGCCACCTTGGTCGCGTCCGCGCCGCCGCCGGCCCAGCCGGACCGCACCACGCGAG
GCGCGAGATAGGGGGGCACGGGCGCGACCATCTGCGCTGCGGCGCCGGCGACTCAGCGC
TGCCTCAGTCTGCGGTGGGCAGCGGAGGAGTCGTGTCGTGCCTGAGAGCGCAG SEQ ID NO: 25
Nucleic acid sequence of a CBA promoter:
ACGTATTAGTCATCGCTATTACCATGGTCGAGGTGAGCCCCACGTTCTGCTTCACTCTCCC
CATCTCCCCCCCCTCCCCACCCCCAATTTTGTATTTATTTATTTTTTAATTATTTTGTGCAG
CGATGGGGGCGGGGGGGGGGGGGGGGCGCGCGCCAGGCGGGGCGGGGCGGGGCGAGGG
GCGGGGCGGGGCGAGGCGGAGAGGTGCGGCGGCAGCCAATCAGAGCGGCGCGCTCCGA
AAGTTTCCTTTTATGGCGAGGCGGCGGCGGCGGCGGCCCTATAAAAAGCGAAGCGCGCG
GCGG SEQ ID NO: 26
Nucleic acid sequence of a CMV sequence:
TACATAACTTACGGTAAATGGCCCGCCTGGCTGACCGCCCAACGACCCCCGCCCATTGAC
GTCAATAGTAACGCCAATAGGGACTTTCCATTGACGTCAATGGGTGGAGTATTTACGGTA
AACTGCCCACTTGGCAGTACATCAAGTGTATCATATGCCAAGTACGCCCCCTATTGACGT
CAATGACGGTAAATGGCCCGCCTGGCATTGTGCCCAGTACATGACCTTATGGGACTTTCC
TACTTGGCAGTACATCT SEQ ID NO: 27
Nucleic acid sequence of a CBA Exon 1:
GGAGTCGCTGCGCGCTGCCTTCGCCCCGTGCCCCGCTCCGCCGCCGCCTCGCGCCGCCCG
CCCCGGCTCTGACTGACCGCGTTACTCCCACAG SEQ ID NO: 28
Nucleic acid sequence of a CBA Intron 1:
GTGAGCGGGCGGGACGGCCCTTCTCCTCCGGGCTGTAATTAGC SEQ ID NO: 29
Nucleic acid sequence of an MVM Intron:
AAGAGGTAAGGGTTTAAGGGATGGTTGGTTGGTGGGGTATTAATGTTTAATTACCTGGAG
CACCTGCCTGAAATCACTTTTTTTCAGGTTGG SEQ ID NO: 30
Nucleic acid sequence of a Kozak sequence:
GCCACCATGG SEQ ID NO: 31
Nucleic acid sequence of a WPRE:
TCAACCTCTGGATTACAAAATTTGTGAAAGATTGACTGGTATTCTTAACTATGTTGCTCCT
TTTACGCTATGTGGATACGCTGCTTTAATGCCTTTGTATCATGCTATTGCTTCCCGTATGG
CTTTCATTTTCTCCTCCTTGTATAAATCCTGGTTGCTGTCTCTTTATGAGGAGTTGTGGCCC
GTTGTCAGGCAACGTGGCGTGGTGTGCACTGTGTTTGCTGACGCAACCCCCACTGGTTGG
GGCATTGCCACCACCTGTCAGCTCCTTTCCGGGACTTTCGCTTTCCCCCTCCCTATTGCCA
CGGCGGAACTCATCGCCGCCTGCCTTGCCCGCTGCTGGACAGGGGCTCGGCTGTTGGGCA
CTGACAATTCCGTGGTGTTGTCGGGGAAATCATCGTCCTTTCCTTGGCTGCTCGCCTGTGT
TGCCACCTGGATTCTGCGCGGGACGTCCTTCTGCTACGTCCCTTCGGCCCTCAATCCAGCG
GACCTTCCTTCCCGCGGCCTGCTGCCGGCTCTGCGGCCTCTTCCGCGTCTTCGCCTTCGCC
CTCAGACGAGTCGGATCTCCCTTTGGGCCGCCTCCCCG -continued

SEQUENCES

SEQ ID NO: 32
Nucleic acid sequence of a kanamycin resistance gene:
ATGAGCCATATTCAACGGGAAACGTCTTGCTCTAGGCCGCGATTAAATTCCAACATGGAT
GCTGATTTATATGGGTATAAATGGGCTCGCGATAATGTCGGGCAATCAGGTGCGACAATC
TATCGATTGTATGGGAAGCCCGATGCGCCAGAGTTGTTTCTGAAACATGGCAAAGGTAGC
GTTGCCAATGATGTTACAGATGAGATGGTCAGACTAAACTGGCTGACGGAATTTATGCCT
CTTCCGACCATCAAGCATTTTATCCGTACTCCTGATGATGCATGGTTACTCACCACTGCGA
TCCCTGGGAAAACAGCATTCCAGGTATTAGAAGAATATCCTGATTCAGGTGAAAATATTG
TTGATGCGCTGGCAGTGTTCCTGCGCCGGTTGCATTCGATTCCTGTTTGTAATTGTCCTTTT
AACAGCGATCGCGTATTTCGTCTCGCTCAGGCGCAATCACGAATGAATAACGGTTTGGTT
GATGCGAGTGATTTTGATGACGAGCGTAATGGCTGGCCTGTTGAACAAGTCTGGAAAGA
AATGCATAAACTTTTGCCATTCTCACCGGATTCAGTCGTCACTCATGGTGATTTCTCACTT
GATAACCTTATTTTTGACGAGGGGAAATTAATAGGTTGTATTGATGTTGGACGAGTCGGA
ATCGCAGACCGATACCAGGATCTTGCCATCCTATGGAACTGCCTCGGTGAGTTTTCTCCTT
CATTACAGAAACGGCTTTTTCAAAAATATGGTATTGATAATCCTGATATGAATAAATTGC
AGTTTCATTTGATGCTCGATGAGTTTTTCTAA SEQ ID NO: 33
Nucleic acid sequence of a resistance gene promoter:
TTCAAATATGTATCCGCTCATGAGACAAT SEQ ID NO: 34
Nucleic acid sequence of a prokaryotic promoter:
CGCGGAACCCCTATTTGTTTATTTTTCTAAATACATTCAAATATGTATCCGCTCATGAGAC
AATAACCCTGATAAATGCTTCAATAATATTGAAAAAGGAAGAGT SEQ ID NO: 35
Nucleic acid sequence of a MeCP2 promoter:
CATCTGATTCAACAATGACAGACCGATCTCTTATGGGCTTGGCACACACCATCTGCGCAT
TATAAACGTCTGCAAAGACCAAGGTTTGATATGTTGATTTTACTGTCAGCCTTAAGAGTG
CGACATCTGCTAATTTAGTGTAATAATACAATTAGTAGACCCTTTAAAACAAGTCCCTTG
GCTTGGAACAACGCCAGGCTCCTCAACAGGCAACTTTGCTACTTCTACAGAAAATGATAA
TAAAGAAATGCTGGTGAAGTCAAATGCTTATCACAATGGTGAACTACTCAGCAGGGAGG
CTCTAATAGGCGCCAAGAGCCTAGACTTCCTTAAGCGCCAGAGTCCACAAGGGCCCAGTT
AATCCTCAACATTCAAATGCTGCCCACAAAACCAGCCCCTCTGTGCCCTAGCCGCCTCTTT
TTTCCAAGTGACAGTAGAACTCCACCAATCCGCAGCTGAATGGGGTCCGCCTCTTTTCCCT
GCCTAAACAGACAGGAACTCCTGCCAATTGAGGGCGTCACCGCTAAGGCTCCGCCCCAG
CCTGGGCTCCACAACCAATGAAGGGTAATCTCGACAAAGAGCAAGGGGTGGGGCGCGGG
CGCGCAGGTGCAGCAGCACACAGGCTGGTCGGGAGGGCGGGGCGCGACGTCTGCCGTGC
GGGGTCCCGGCATCGGTTGCGCGCGCGCTCCCTCCTCTCGGAGAGAGGGCTGTGGTAAAA
CCCGTCCGGAAAAT Nucleic acid sequence of a hSyn promoter:
AGTGCAAGTGGGTTTTAGGACCAGGATGAGGCGGGGTGGGGGTGCCTACCTGACGACCG
ACCCCGACCCACTGGACAAGCACCCAACCCCCATTCCCCAAATTGCGCATCCCCTATCAG
AGAGGGGGAGGGGAAACAGGATGCGGCGAGGCGCGTGCGCACTGCCAGCTTCAGCACC
GCGGACAGTGCCTTCGCCCCCGCCTGGCGGCGCGCGCCACCGCCGCCTCAGCACTGAAGG
CGCGCTGACGTCACTCGCCGGTCCCCCGCAAACTCCCCTTCCCGGCCACCTTGGTCGCGTC
CGCGCCGCCGCCGGCCCAGCCGGACCGCACCACGCGAGGCGCGAGATAGGGGGGCACGG
GCGCGACCATCTGCGCTGCGGCGCCGGCGACTCAGCGCTGCCTCAGTCTGCGGTGGGCAG
CGGAGGAGTCGTGTCGTGCCTGAGAGCGCAGT SEQ ID NO: 37
Nucleic acid sequence of a Human FMRP Isoform 17 mRNA:
ATGGAGGAGCTGGTGGTGGAAGTGCGGGGCTCCAATGGCGCTTTCTACAAGGCATTTGTA
AAGGATGTTCATGAAGATTCAATAACAGTTGCATTTGAAAACAACTGGCAGCCTGATAGG
CAGATTCCATTTCATGATGTCAGATTCCCACCTCCTGTAGGTTATAATAAAGATATAAATG
AAAGTGATGAAGTTGAGGTGTATTCCAGAGCAAATGAAAAAGAGCCTTGCTGTTGGTGG
TTAGCTAAAGTGAGGATGATAAAGGGTGAGTTTTATGTGATAGAATATGCAGCATGTGAT
GCAACTTACAATGAAATTGTCACAATTGAACGTCTAAGATCTGTTAATCCCAACAAACCT
GCCACAAAAGATACTTTCCATAAGATCAAGCTGGATGTGCCAGAAGACTTACGGCAAAT
GTGTGCCAAAGAGGCGGCACATAAGGATTTTAAAAAGGCAGTTGGTGCCTTTTCTGTAAC
TTATGATCCAGAAAATTATCAGCTTGTCATTTTGTCCATCAATGAAGTCACCTCAAAGCG
AGCACATATGCTGATTGACATGCACTTTCGGAGTCTGCGCACTAAGTTGTCTCTGATAAT
GAGAAATGAAGAAGCTAGTAAGCAGCTGGAGAGTTCAAGGCAGCTTGCCTCGAGATTTC
ATGAACAGTTTATCGTAAGAGAAGATCTGATGGGTCTAGCTATTGGTACTCATGGTGCTA
ATATTCAGCAAGCTAGAAAAGTACCTGGGGTCACTGCTATTGATCTAGATGAAGATACCT
GCACATTTCATATTTATGGAGAGGATCAGGATGCAGTGAAAAAAGCTAGAAGCTTTCTCG
AATTTGCTGAAGATGTAATACAAGTTCCAAGGAACTTAGTAGGCAAAGTAATAGGAAAA
AATGGAAAGCTGATTCAGGAGATTGTGGACAAGTCAGGAGTTGTGAGGGTGAGGATTGA
GGCTGAAAATGAGAAAAATGTTCCACAAGAAGAGGAAATTATGCCACCAAATTCCCTTC
CTTCCAATAATTCAAGGGTTGGACCTAATGCCCCAGAAGAAAAAAAACATTTAGATATAA
AGGAAAACAGCACCCATTTTTCTCAACCTAACAGTACAAAAGTCCAGAGGGGTATGGTA
CCATTTGTTTTTGTGGGAACAAAGGACAGCATCGCTAATGCCACTGTTCTTTTGGATTATC
ACCTGAACTATTTAAAGGAAGTAGACCAGTTGCGTTTGGAGAGATTACAAATTGATGAGC
AGTTGCGACAGATTGGAGCTAGTTCTAGACCACCACCAAATCGTACAGATAAGGAAAAA -continued

SEQUENCES

AGCTATGTGACTGATGATGGTCAAGGAATGGGTCGAGGTAGTAGACCTTACAGAAATAG
GGGGCACGGCAGACGCGGTCCTGGATATACTTCAGGAACTAATTCTGAAGCATCAAATG
CTTCTGAAACAGAATCTGACCACAGAGACGAACTCAGTGATTGGTCATTAGCTCCAACAG
AGGAAGAGAGGGAGAGCTTCCTGCGCAGAGGAGACGGACGGCGGCGTGGAGGGGGAGG
AAGAGGACAAGGAGGAAGAGGACGTGGAGGAGGCTTCAAAGGAAACGACGATCACTCC
CGAACAGATAATCGTCCACGTAATCCAAGAGAGGCTAAAGGAAGAACAACAGATGGATC
CCTTCAGAATACCTCCAGTGAAGGTAGTCGGCTGCGCACGGGTAAAGATCGTAACCAGA
AGAAAGAGAAGCCAGACAGCGTGGATGGTCAGCAACCACTCGTGAATGGAGTACCCTAA

SEQ ID NO: 38
Amino acid sequence of a Human FMRP Isoform 17 protein:
MEELVVEVRGSNGAFYKAFVKDVHEDSITVAFENNWQPDRQIPFHDVRFPPPVGYNKDINES
DEVEVYSRANEKEPCCWWLAKVRMIKGEFYVIEYAACDATYNEIVTIERLRSVNPNKPATKD
TFHKIKLDVPEDLRQMCAKEAAHKDFKKAVGAFSVTYDPENYQLVILSINEVTSKRAHMLID
MHFRSLRTKLSLIMRNEEASKQLESSRQLASRFHEQFIVREDLMGLAIGTHGANIQQARKVPG
VTAIDLDEDTCTFHIYGEDQDAVKKARSFLEFAEDVIQVPRNLVGKVIGKNGKLIQEIVDKSG
VVRVRIEAENEKNVPQEEEIMPPNSLPSNNSRVGPNAPEEKKHLDIKENSTHFSQPNSTKVQR
GMVPFVFVGTKDSIANATVLLDYHLNYLKEVDQLRLERLQIDEQLRQIGASSRPPPNRTDKEK
SYVTDDGQGMGRGSRPYRNRGHGRRGPGYTSGTNSEASNASETESDHRDELSDWSLAPTEE
ERESFLRRGDGRRRGGGGRGQGGRGRGGGFKGNDDHSRTDNRPRNPREAKGRTTDGSLQNT
SSEGSRLRTGKDRNQKKEKPDSVDGQQPLVNGVP SEQ ID NO: 39
Nucleic acid sequence of a natural state FMRP:
AGAGGAGACGGACGGCGGCGTGGAGGGGGAGGAAGAGGACAAGGAGGAAGAGGACGT
GGAGGAGGCT

What is claimed is:

1. A recombinant adeno-associated virus (rAAV) vector comprising in 5' to 3' direction:
a) a first AAV ITR sequence;
b) a promoter sequence;
c) a transgene nucleic acid molecule, wherein the transgene nucleic acid molecule comprises a sequence that is at least 90% identical to the sequence set forth in SEQ ID NO: 4;
d) a polyA sequence; and
e) a second AAV ITR sequence.

2. The rAAV vector of claim 1, wherein the transgene nucleic acid molecule comprises the nucleic acid sequence set forth in SEQ ID NO:4.

3. The rAAV vector of claim 1, wherein the rAAV vector comprises SEQ ID NO: 1, 7, or 9.

4. The rAAV vector of claim 1, wherein the first AAV ITR sequence comprises the nucleic acid sequence set forth in SEQ ID NO: 2.

5. The rAAV vector of claim 1, wherein the second AAV ITR sequence comprises the nucleic acid sequence set forth in SEQ ID NO: 6.

6. The rAAV vector of claim 1,
wherein the promoter sequence comprises a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, a U6 promoter, a JetI promoter, an H1 promoter, a CAG promoter, a hybrid chicken beta-actin (CBA) promoter, an MeCP2 promoter, an EF1 promoter, a ubiquitous chicken beta-actin hybrid (CBh) promoter, a Ula promoter, a U1b promoter, an MeP418 promoter, an MeP426 promoter, a minimal MeCP2 promoter, a VMD2 promoter, an mRho promoter, EF1a promoter, Ubc promoter, human β-actin promoter, a synapsin (hSyn) promoter, TRE promoter, Ac5 promoter, Polyhedrin promoter, CaMKIIa promoter, Gal1 promoter, TEF1 promoter, GDS promoter, ADH1 promoter, Ubi promoter, or α-1-antitrypsin (hAAT) promoter.

7. The rAAV vector of claim 1, wherein the promoter sequence comprises the nucleic acid sequence set forth in SEQ ID NO:3, 8, 10, 35, or 36.

8. The rAAV vector of claim 1, wherein the polyA sequence comprises the nucleic acid sequence set forth in SEQ ID NO:5.

9. The rAAV vector of claim 1, comprising, in the 5' to 3' direction:
a) a first AAV ITR sequence comprising the nucleic acid sequence set forth in SEQ ID NO: 2;
b) a promoter sequence comprising the nucleic acid sequence set forth in SEQ ID NO: 3, 7, 10, 35, or 36;
c) a transgene nucleic acid molecule, wherein the transgene nucleic acid molecule comprises a nucleic acid sequence encoding for an FMRP polypeptide, wherein the nucleic acid sequence encoding for an FMRP polypeptide comprises the nucleic acid sequence set forth in SEQ ID NO:4;
d) a polyA sequence comprising the nucleic acid sequence set forth in SEQ ID NO: 5; and
e) a second AAV ITR sequence comprising the nucleic acid sequence set forth in SEQ ID NO:6.

10. The rAAV viral vector of claim 1, further comprising a sequence encoding an AAV capsid protein.

11. The rAAV viral vector of claim 10, wherein the AAV capsid protein is an AAV9 capsid protein.

12. A pharmaceutical composition comprising:
a) an rAAV viral vector comprising:
(i) a sequence encoding an AAV capsid protein; and
(ii) an rAAV vector comprising:
a) a first AAV ITR sequence;
b) a promoter sequence;
c) a transgene nucleic acid molecule, wherein the transgene nucleic acid molecule comprises a sequence that is at least 90% identical to the sequence set forth in SEO ID NO: 4;
d) a polyA sequence; and
e) a second AAV ITR sequence; and
at least one pharmaceutically acceptable excipient and/or additive.

* * * * *